United States Patent
Johnson et al.

(10) Patent No.: US 10,011,594 B2
(45) Date of Patent: Jul. 3, 2018

(54) 4-HYDROXY-3-(HETEROARYL) PYRIDINE-2-ONE APJ AGONISTS

(71) Applicant: BRISTOL-MYERS SQUIBB COMPANY, Princeton, NJ (US)

(72) Inventors: James A. Johnson, Pennington, NJ (US); Soong-Hoon Kim, Titusville, NJ (US); R. Michael Lawrence, Yardley, PA (US); Michael C. Myers, Newtown, PA (US); Hannguang J. Chao, Nashua, NH (US); Monique Phillips, Ewing, NJ (US); Ji Jiang, West Windsor, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 15/171,276

(22) Filed: Jun. 2, 2016

(65) Prior Publication Data
US 2016/0355507 A1  Dec. 8, 2016

Related U.S. Application Data

(60) Provisional application No. 62/170,215, filed on Jun. 3, 2015.

(51) Int. Cl.
| | |
|---|---|
| C07D 413/04 | (2006.01) |
| C07D 413/14 | (2006.01) |
| C07D 401/04 | (2006.01) |
| C07D 417/14 | (2006.01) |
| C07D 498/04 | (2006.01) |

(52) U.S. Cl.
CPC ......... *C07D 413/04* (2013.01); *C07D 401/04* (2013.01); *C07D 413/14* (2013.01); *C07D 417/14* (2013.01); *C07D 498/04* (2013.01)

(58) Field of Classification Search
USPC ........................................ 514/332, 333, 334
See application file for complete search history.

(56) References Cited

U.S. PATENT DOCUMENTS

| 5,338,740 A | 8/1994 | Carpino et al. |
|---|---|---|
| 2006/0004001 A1 | 1/2006 | Jirgensons et al. |
| 2011/0070190 A1 | 3/2011 | Broka et al. |
| 2011/0071150 A1 | 3/2011 | Alam et al. |

FOREIGN PATENT DOCUMENTS

| EP | 0 329 070 | 8/1989 |
|---|---|---|
| JP | 2001-89368 A | 4/2001 |
| JP | 2007-314516 A | 12/2007 |
| JP | 2015-147747 A | 8/2015 |
| KR | 2017009185 | 2/2017 |
| WO | WO02/068417 A2 | 9/2002 |
| WO | WO02/079143 A1 | 10/2002 |
| WO | WO03/020719 A1 | 3/2003 |
| WO | WO03/059871 A1 | 7/2003 |
| WO | WO03/059886 A1 | 7/2003 |
| WO | WO2005/004818 A2 | 1/2005 |
| WO | WO2005/097750 A1 | 1/2005 |
| WO | WO2005/097740 A1 | 10/2005 |
| WO | WO2006/002099 A2 | 1/2006 |
| WO | WO2006/019833 A1 | 2/2006 |
| WO | WO2006/048330 A1 | 5/2006 |
| WO | WO2006/123165 A2 | 11/2006 |
| WO | WO2007/023290 A1 | 3/2007 |
| WO | WO2007/087276 A1 | 8/2007 |
| WO | WO2008/016968 A2 | 2/2008 |
| WO | WO2008/019090 A2 | 2/2008 |
| WO | WO2008/025540 A1 | 3/2008 |
| WO | WO2008/070552 A2 | 6/2008 |
| WO | WO2008/116909 A1 | 10/2008 |
| WO | WO2009/093264 A2 | 7/2009 |
| WO | WO2009/126691 A1 | 10/2009 |
| WO | WO2009/146343 A1 | 12/2009 |
| WO | WO2010/002933 A1 | 1/2010 |
| WO | WO2010/050445 A1 | 5/2010 |

(Continued)

OTHER PUBLICATIONS

Cao, Jingang et al., "Targeting Drugs to APJ Receptor: The Prospect of Treatment of Hypertension and Other Cardiovascular Diseases", Current Drug Targets, vol. 16, pp. 148-155 (2015).*

Ashley, Euan et al., "The endogenous peptide apelin potently improves cardiac contractility and reduces cardiac loading in vivo", Cardiovascular Research, vol. 65, pp. 73-82 (2005).

Berry, Mark et al., "Apelin Has In Vivo Inotropic Effects on Normal and Failing Hearts", Circulation, vol. 110(suppl II), pp. II187-II-193, (2004).

Borlaug, Barry, et al., "Heart failure with preserved ejection fraction: Pathophysiology, diagnosis, and treatment", European Heart Journal, vol. 32, pp. 670-679 (2011).

Charo, David et al., "Endogenous regulation of cardiovascular function by apelin—APJ", Am J Physiol Heart Circ Physiol, vol. 297, pp. H1904-H1913 (2009).

(Continued)

*Primary Examiner* — Pancham Bakshi
(74) *Attorney, Agent, or Firm* — Hong Liu

(57) ABSTRACT

The present invention provides compounds of Formula (I):

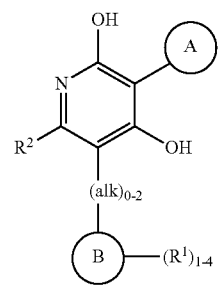

(I)

wherein all variables are as defined in the specification, and compositions comprising any of such novel compounds. These compounds are APJ agonists which may be used as medicaments.

30 Claims, No Drawings

(56) References Cited

FOREIGN PATENT DOCUMENTS

| WO | WO2011/062955 A2 | 6/2011 |
| --- | --- | --- |
| WO | WO2011/075684 A1 | 6/2011 |
| WO | WO2011/140936 A1 | 11/2011 |
| WO | WO2011/148956 A1 | 12/2011 |
| WO | WO2012/074022 A1 | 6/2012 |
| WO | WO2012/117097 A1 | 9/2012 |
| WO | WO2012/142308 A1 | 10/2012 |
| WO | WO2012/158844 A1 | 11/2012 |
| WO | WO2013/092943 A1 | 6/2013 |
| WO | WO2013/164769 A1 | 11/2013 |
| WO | WO2013/167633 A1 | 11/2013 |
| WO | WO2013/184202 A1 | 12/2013 |
| WO | WO2014/006045 A1 | 1/2014 |
| WO | WO2014/012511 A1 | 1/2014 |
| WO | WO2014/031928 A2 | 2/2014 |
| WO | WO2014/062938 A1 | 4/2014 |
| WO | WO2014/144715 A1 | 9/2014 |
| WO | WO2015/017305 A1 | 2/2015 |
| WO | WO2015/129755 A1 | 9/2015 |
| WO | WO2015/140195 A1 | 9/2015 |
| WO | WO2015/191630 A1 | 12/2015 |
| WO | WO2016/187308 A1 | 11/2016 |
| WO | WO2017/066402 A1 | 4/2017 |
| WO | WO2017/091513 A1 | 6/2017 |
| WO | WO2017/096130 A1 | 6/2017 |
| WO | WO2017/100558 A1 | 6/2017 |
| WO | WO2017/106396 A1 | 6/2017 |
| WO | WO2017/165640 A1 | 9/2017 |

OTHER PUBLICATIONS

Cheng, Xing et al., "Venous dilator effect of apelin, an endogenouse peptide ligand for the orphan APJ receptor, in conscious rats", European Journal of Pharmacology, vol. 470, pp. 171-175 (2003).

Chun, Hyung et al., "Apelin signaling antagonizes Ang II effects in mouse models of atherosclerosis", The Journal of Clinical Investigation, vol. 118(10), pp. 3343-3354 (2008).

Japp, A.G. et al., "Acute Cardiovascular Effects of Apelin in Humans" Potential Role in Patients With Chronic Heart Failure, Circulation, vol. 121, pp. 1818-1827 (2010).

Japp, A.G. et al., "The apelin—APJ system in heart failure Pathophysiologic relevance and therapeutic potential", Biochemical Pharmacology, vol. 75, pp. 1882-1892 (2008).

Kappe, Thomas et al., Monatshefte fur Chemie, vol. 114, pp. 485-493 (1983).

Kleinz, Matthias et al., "Emerging roles of apelin in biology and medicine", Pharmacology & Therapeutics, vol. 107, pp. 198-211 (2005).

Koguchi, Wataru et al., Cardioprotective Effect of Apelin-13 on Cardiac Performance and Remodeling in End-Stage Heart Failure, Circulation Journal, vol. 76, pp. 137-144 (2012).

Kuba, Keiji et al., "Impaired Heart Contractility in Apelin Gene-Deficient Mice Associated with Aging and Pressure Overload", Circ Res. vol. 101, pp. e32-e42 (2007).

Kakeya, N et al., "Studies on Prodrugs of Cephalosporins.I. Synthesis and Biological Properties of Glycyloxybenzoyloxymethyl and Glycylaminobenzoyloxymethyl Esters of 7β[2-(2-Aminothiazol-4-yl)-(Z)-2-methoxyiminoacetamido]-3-methyl-3-cephem-4-carboxylic Acid", Chem Pharm Bulletin, vol. 32(2), pp. 692-698 (1984).

Maguire, Janet et al., "[Pry$^1$]Apelin-13 Identified as the Predominant Apelin Isoform in the Human Heart, Vasoactive Mechanisms and Inotropic Action in Disease", Hypertension, vol. 54, pp. 598-604 (2009).

Pitkin, Sarah et al., "International Union of Basic and Clinical Pharmacology, LXXIV. Apelin Receptor Nomenclature, Distribution, Pharmacology, and Function" Pharmacological Reviews, vol. 62(3), pp. 331-342 (2010).

Roger, Veronique et al., "Trends in Heart Failure incidence and Survival in a Community-Based Population", JAMA, vol. 292(3), pp. 344-350 (2004).

Roger, Veronique et al., "Heart Disease and Stroke Statistics—2012 Update. A report from the American Heart Assocation", Circulation, vol. 125, pp. e2-e220, (2012).

Sarzani, Riccardo et al., "The 212A Variant of the APJ Receptor Gene for the Endogenous Inotrope Apelin is Associated With Slower Heart Failure Progression in Idiopathis Dilated Cardiomyopathy", J. of Cardiac Failure, vol. 13(7), pp. 521-529 (2007).

Scimia, Maria Cecilia et al., "APJ acts as a dual receptor in cardiac hypertrophy", Nature, vol. 488, pp. 394-398 (2012).

Siddiquee, Khandaker et al., "Apelin protects against angiotensin II-induced cardiovascular fibrosis and decreases plasminogen activator inhibitor type-1 production", J Hypertension, vol. 29, pp. 724-731 (2011).

Simpkin, James et al., "Apelin-13 and apelin-36 exhibit direct cardioprotective activity against ischemia-reperfusion injury", Basic Res Cardiol, vol. 102, pp. 518-528 (2007).

Tatemoto, K. et al., "Isolation and Characterization of a Novel Endogenous Peptide Ligand for the Human APJ Receptor", Biochemical and Biophysical Research Communications, vol. 251, pp. 471-476 (1998).

Tatemoto, K. et al., "The novel peptide apelin lowers blood pressure via a nitric oxide-dependent mechanism", Regulatory peptides, vol. 22, pp. 87-92 (2001).

Bundgaard, Hans et al., "Glycolamide Esters as Biolabile Prodrugs of Carboxylic Acid Agents:Synthesis, Stability, Bioconversion, and Physicochemical Properties", J Pharm Sci, Vo. 77(4), pp. 285 (1988).

Bundgaard, Hans, "Means to Enhance Penetration", Advanced drug delivery reviews, vol. 8 pp. 1-38 (1992).

Krogsgaard-Larsen, A Textbook of Drug Design and Development. Rautio, J. Editor, "Prodrugs and Targeted Delivery", vol. 47 Table of Contents.

Widder, K, Editor, "Methods of Enzymology", vol. 12 pp. 309-396 (1985).

* cited by examiner

4-HYDROXY-3-(HETEROARYL)PYRIDINE-2-ONE APJ AGONISTS

CROSS REFERENCE TO RELATED APPLICATIONS

This application is entitled to priority pursuant to 35 U.S.C. § 119(e) to U.S. provisional patent application No. 62/170,215, filed on Jun. 3, 2015, which is incorporated herein in its entirety.

FIELD OF THE INVENTION

The present invention provides novel 4-hydroxyl-3-(heteroaryl)pyridine-2-one compounds, and their analogues thereof, which are APJ agonists, compositions containing them, and methods of using them, for example, for the treatment or prophylaxis of heart failure, atherosclerosis, ischemic heart disease and related conditions.

BACKGROUND OF THE INVENTION

Heart failure (HF) and related complications constitute major health burden in developed countries with an estimated prevalence of 5,700,000 in the United States alone (Roger, V. L. et al., *Circulation*, 125(1):e2-e220 (2012)). Despite considerable advances in recent two decades, the prognosis remains very poor, with survival rates of only ~50% within 5-years of diagnosis (Roger, V. L. et al., *JAMA*, 292(3):344-350 (2004)). In addition to poor survival, the impaired quality of life and recurrent hospitalizations constitute clear unmet medical need for development of novel treatment options.

HF is a clinical syndrome characterized by the inability of the heart to deliver sufficient supply of blood and oxygen to meet the metabolic demands of organs in the body. Main symptoms associated with HF include shortness of breath due to pulmonary edema, fatigue, reduced tolerance to exercise and lower extremity edemas. The etiology of HF is highly complex with multiple associated risk factors and potential causes.

Among the leading causes of HF are coronary artery disease and cardiac ischemia, acute myocardial infarction, intrinsic cardiomyopathies and chronic uncontrolled hypertension. HF can develop either acutely (functional impairment post myocardial infarction) or as a chronic condition, characterized by long-term maladaptive cardiac tissue remodeling, hypertrophy and cardiac dysfunction (for example due to uncontrolled long-term hypertension). According to the diagnostic criteria and type of ventricular dysfunction, HF is classified to two major groups, HF with "reduced ejection fraction" (HFrEF) or HF with "preserved ejection fraction" (HFpEF). Both types are associated with similar signs and symptoms, but differ in the type of ventricular functional impairment (Borlaug, B. A. et al., *Eur. Heart J.*, 32(6):670-679 (2011)).

APJ receptor (APLNR) and its endogenous peptidic ligand apelin have been implicated as important modulators of cardiovascular function and candidates for therapeutic intervention in HF (for review see Japp, A. G. et al., *Biochem. Pharmacol.*, 75(10):1882-1892 (2008)).

Accumulated evidence from preclinical disease models and human heart failure patients have implicated apelin and APJ agonism as beneficial in the setting of HF. Mice lacking Apelin or APJ gene have impaired myocyte contractility (Charo, D. N. et al., *Am. J. Physiol. Heart Circ. Physiol.*, 297(5):H1904-H1913 (2009)). Apelin knockout (KO) mice develop progressive cardiac dysfunction with aging and are more susceptible to HF in the model of trans-aortic constriction (TAC) (Kuba, K. et al., *Circ. Res.*, 101(4):e32-42 (2007)). The functional impairment in chronic HF is a result of prolonged demand on the heart and is associated with maladaptive cardiac remodeling, manifested by the cardiac hypertrophy, increased inflammation and interstitial fibrosis which eventually lead to decrease in cardiac performance.

Acute administration of apelin increases cardiac output in rodents under normal conditions and also in models of heart failure (Berry, M. F., *Circulation*, 110(11 Suppl. 1):II187-II193 (2004)). Increased cardiac output is a result of direct augmentation of cardiac contractility and reduced peripheral vascular resistance in the arterial and venous beds (Ashley, E. A., *Cardiovasc. Res.*, 65(1):73-82 (2005)). Reduction in the vascular resistance leads to lower pre-load and after-load on the heart and thus lesser work load (Cheng, X. et al., *Eur. J. Pharmacol.*, 470(3):171-175 (2003)). Similar to rodent studies, acute infusion of apelin to healthy human subjects and patients with heart failure produces similar hemodynamic responses with increased cardiac output and increased vasodilatory response in peripheral and coronary arteries (Japp, A. G. et al., *Circulation*, 121(16):1818-1827 (2010)).

The mechanisms underlying inotropic action of apelin are not well understood, but appear to be distinct from clinically used $\beta_1$-adrenergic agonists (dobutamine) due to lack of increase in heart rate. The vasodilatory action of apelin is primarily mediated via endothelial nitric oxide synthase pathways (Tatemoto, K., *Regul. Pept.*, 99(2-3):87-92 (2001)). Apelin is induced under hypoxic conditions, promotes angiogenesis and has been shown to limit the infarct size in ischemia-reperfusion models (Simpkin, J. C., *Basic Res. Cardiol.*, 102(6):518-528 (2007)).

In addition to aforementioned studies evaluating acute administration of apelin, several studies have clearly demonstrated beneficial effects of prolonged administration of apelin in a number of chronic rodent models of HF, including the angiotensin II model, TAC model and rat Dahl salt-sensitive model (Siddiquee, K. et al., *J. Hypertens.*, 29(4):724-731 (2011); Scimia, M. C. et al., *Nature*, 488 (7411):394-398 (2012); Koguchi, W. et al., *Circ. J.*, 76(1): 137-144 (2012)). In these studies, prolonged apelin infusion reduced cardiac hypertrophy and cardiac fibrosis, and was associated with improvement in cardiac performance.

Genetic evidence is also emerging that polymorphisms in the APJ gene are associated with slower progression of HF (Sarzani, R. et al., *J. Card. Fail.*, 13(7):521-529 (2007)). Importantly, while expression of APJ and apelin can be reduced or vary considerably with HF progression, the cardiovascular hemodynamic effects of apelin are sustained in patients with developed HF and receiving standard of care therapy (Japp, A. G. et al., *Circulation*, 121(16):1818-1827 (2010)).

In summary, there is a significant amount of evidence to indicate that APJ receptor agonism plays a cardioprotective role in HF and would be of potential benefit to HF patients. Apelin's very short half life in circulation limits its therapeutic utility, and consequently, there is a need for APJ receptor agonists with improved pharmacokinetic and signaling profile while maintaining or enhancing the beneficial effects of endogenous APJ agonist apelin.

SUMMARY OF THE INVENTION

The present invention provides 4-hydroxylpyridine-2-one compounds, and their analogues thereof, which are useful as APJ agonists, including stereoisomers, tautomers, pharmaceutically acceptable salts, or solvates thereof.

The present invention also provides processes and intermediates for making the compounds of the present invention or stereoisomers, tautomers, pharmaceutically acceptable salts, or solvates thereof.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of multiple diseases or disorders associated with APJ, such as heart failure, coronary artery disease, cardiomyopathy, diabetes and related conditions including but not limited to acute coronary syndrome, myocardial ischemia, hypertension, pulmonary hypertension, coronary vasospasm, cerebral vasospasm, ischemia/reperfusion injury, angina, renal disease, metabolic syndrome and insulin resistance.

The compounds of the invention may be used in therapy.

The compounds of the invention may be used for the manufacture of a medicament for the treatment and/or prophylaxis of multiple diseases or disorders associated with APJ.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

I. Compounds of the Invention

In a first aspect, the present disclosure provides, inter alia, a compound of Formula (I):

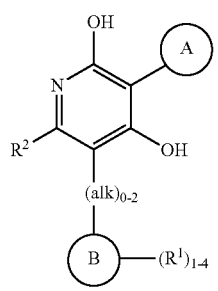

or a stereoisomer, a tautomer, a pharmaceutically acceptable salt, or a solvate thereof, wherein:
alk is $C_{1-6}$ alkyl substituted with 0-5 $R^e$;
ring A is independently selected from:

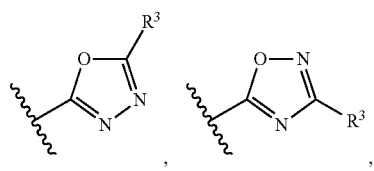

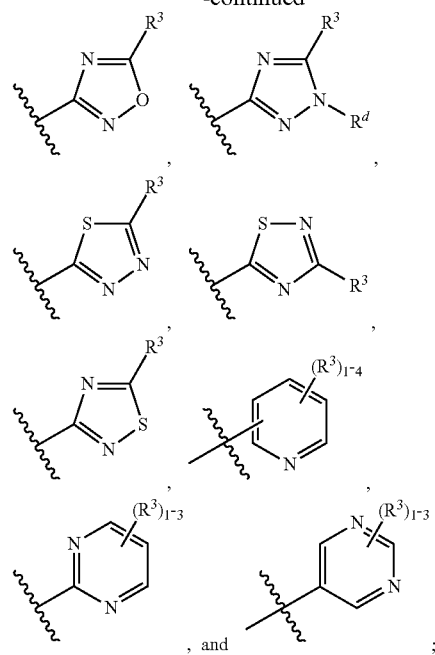

ring B is independently selected from:

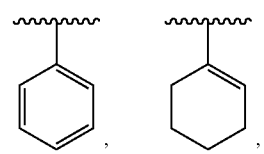 [SMILES: *c1ccccc1 ; *C1=CCCCC1]

and 6-membered heteroaryl;

$R^1$ is independently selected from: halogen, $NO_2$, —$(CH_2)_nOR^b$, —$(CH_2)_nS(O)_pR_c$, —$(CH_2)_nC(=O)R^b$, —$(CH_2)_nNR^aR^a$, —$(CH_2)_nCN$, —$(CH_2)_nC(=O)NR^aR^a$, —$(CH_2)_nNR^aC(=O)R^b$, —$(CH_2)_nNR^aC(=O)NR^aR^a$, —$(CH_2)_nNR^aC(=O)OR^b$, —$(CH_2)_n$ $OC(=O)NR^aR^a$, —$(CH_2)_nC(=O)OR^b$, —$(CH_2)_nS(O)_pNR^aR^a$, —$(CH_2)_nNR^aS(O)_pNR^aR^a$, —$(CH_2)_nNR^aS(O)_pR^c$, $C_{1-4}$ alkyl substituted with 0-3 $R^e$, —$(CH_2)_n$—$C_{3-6}$ carbocyclyl substituted with 0-3 $R^e$, and —$(CH_2)_n$-heterocyclyl substituted with 0-3 $R^e$;

$R^2$ is independently selected from: $C_{1-5}$ alkyl substituted with 0-3 $R^e$; $C_{1-5}$ alkenyl substituted with 0-3 $R^e$, and $C_{1-6}$ cycloalkyl substituted with 0-3 $R^e$; wherein the carbon atom except the one attached to the ring of $C_{1-5}$ alkyl and the groups attached thereto may be replaced by O, N, and S;

$R^3$ is independently selected from:
(1) —$(CR^4R^4)_nC(=O)OC_{1-4}$ alkyl substituted with 0-5 $R^e$,
(2) —$(CR^4R^4)_nNR^aR^a$,
(3) —$(CR^4R^4)_nC(=O)NR^aR^a$,
(4) —$(CR^4R^4)_nNR^aC(=O)$ $C_{1-4}$alkyl substituted with 0-5 $R^e$,
(5) —$(CR^4R^4)_nNR^aC(=O)(CR^4R^4)_n\prime\prime OC_{1-4}$alkyl substituted with 0-5 $R^e$,
(6) —$(CR^4R^4)_n$—$R^5$,
(7) —$(CR^4R^4)_n$—$OR^5$, and
(8) —$(CR^4R^4)_nNR^aC(=O)(CR^4R^4)_nR^5$;

R⁴ is independently selected from: H, halogen, NR$^a$R$^a$, OC$_{1-4}$ alkyl, and C$_{1-4}$ alkyl; or R⁴ and R⁴ together with the carbon atom to which they are both attached form C$_{3-6}$ cycloalkyl substituted with 0-5 R$^e$;

R⁵ is independently selected from: —(CH$_2$)$_n$—C$_{3-10}$ carbocycle and —(CH$_2$)$_n$-heterocycle, each substituted with 0-3 R⁶;

R⁶ is independently selected from: H, halogen, =O, —(CH$_2$)$_n$OR$^b$, (CH$_2$)$_n$S(O)$_p$R$^c$, —(CH$_2$)$_n$C(=O)R$^b$, —(CH$_2$)$_n$NR$^a$R$^a$, —(CH$_2$)$_n$CN, —(CH$_2$)$_n$C(=O)NR$^a$R$^a$, —(CH$_2$)$_n$NR$^a$C(=O)R$^b$, —(CH$_2$)$_n$NR$^a$C(=O)NR$^a$R$^a$, —(CH$_2$)$_n$NR$^a$C(=O)OR$^b$, —(CH$_2$)$^n$ OC(=O)NR$^a$R$^a$, —(CH$_2$)$_n$C(=O)OR$^b$, —(CH$_2$)$_n$S(O)$_p$NR$^a$R$^a$, —(CH$_2$)$_n$NR$^a$S(O)$_p$NR$^a$R$^a$, —(CH$_2$)$_n$NR$^a$S(O)$_p$R$^c$, C$_{1-5}$ alkyl substituted with 0-3 R$^e$, (CH$_2$)$_n$—C$_{3-6}$ carbocyclyl substituted with 0-3 R$^e$, and —(CH$_2$)$_n$-heterocyclyl substituted with 0-3 R$^e$;

R$^a$ is independently selected from H, C$_{1-6}$ alkyl substituted with 0-5 R$^e$, C$_{2-6}$ alkenyl substituted with 0-5 R$^e$, C$_{2-6}$ alkynyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$; or R$^a$ and R$^a$ together with the nitrogen atom to which they are both attached form a heterocyclic ring substituted with 0-5 R$^e$;

R$^b$ is independently selected from H, C$_{1-6}$ alkyl substituted with 0-5 R$^e$, C$_{2-6}$ alkenyl substituted with 0-5 R$^e$, C$_{2-6}$ alkynyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$;

R$^c$ is independently selected from C$_{1-6}$ alkyl substituted with 0-5 R$^e$, C$_{2-6}$alkenyl substituted with 0-5 R$^e$, C$_{2-6}$alkynyl substituted with 0-5 R$^e$, C$_{3-6}$carbocyclyl, and heterocyclyl;

R$^d$ is independently selected from H and C$_{1-4}$alkyl substituted with 0-5 R$^e$;

R$^e$ is independently selected from C$_{1-6}$ alkyl substituted with 0-5 R$_f$, C$_{2-6}$ alkenyl, C$_{2-6}$ alkynyl, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, CO$_2$H, —(CH$_2$)$_n$OR$^f$, S(O)$_p$R$^f$, C(=O)NR$^f$R$^f$, NR$^f$C(=O)R$^f$, S(O)$_p$NR$^f$R$^f$, NR$^f$S(O)$_p$R$^f$, NR$^f$C(=O)OR$^f$, OC(=O)NR$^f$R$^f$ and —(CH$_2$)$_n$NR$^f$R$^f$;

R$^f$ is independently selected from H, F, Cl, Br, CN, OH, C$_{1-5}$alkyl (optimally substituted with halogen and OH), C$_{3-6}$ cycloalkyl, and phenyl, or R$^f$ and R$^f$ together with the nitrogen atom to which they are both attached form a heterocyclic ring optionally substituted with C$_{1-4}$alkyl;

n is independently selected from zero, 1, 2, and 3; and
p is independently selected from zero, 1, and 2.

In a second aspect, the present disclosure provides a compound of Formula (II):

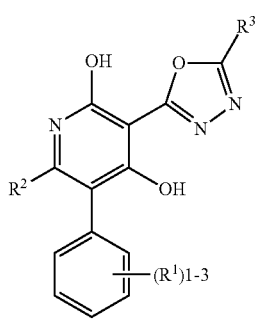

(II)

or a stereoisomer, a tautomer, a pharmaceutically acceptable salt, or a solvate thereof, within the scope of the first aspect, wherein:

R¹ is independently selected from: F, Cl, Br, NO$_2$, —(CH$_2$)$_n$OR$^b$, —(CH$_2$)$_n$C(=O)R$^b$, —(CH$_2$)$_n$NR$^a$R$^a$, —(CH$_2$)$_n$C(=O)NR$^a$R$^a$, —(CH$_2$)$_n$ NR$^a$C(=O)R$^b$, C$_{1-4}$ alkyl substituted with 0-3 R$^e$ and C$_{3-6}$ cycloalkyl substituted with 0-3 R$^e$;

R² is independently selected from: C$_{1-5}$ alkyl substituted with 0-3 R$^e$; C$_{1-5}$ alkenyl, and C$_{1-6}$ cycloalkyl; wherein the carbon atom except the one attached to the ring of C$_{1-5}$ alkyl and the groups attached thereto are replaced by O, N, and S;

R³ is independently selected from:

(1) —(CR⁴R⁴)$_n$C(=O)OC$_{1-4}$ alkyl substituted with 0-5 R$^e$, (2) —(CR⁴R⁴)$_n$NR$^a$R$^a$, (3) —(CR⁴R⁴)$_n$C(=O)NR$^a$R$^a$, (4) —(CR⁴R⁴)$_n$NR$^a$C(=O) C$_{1-4}$alkyl substituted with 0-5 R$^e$, (5) —(CR⁴R⁴)$_n$NR$^a$C(=O)(CR⁴R⁴)$_n$OC$_{1-4}$alkyl substituted with 0-5 R$^e$, (6) —(CR⁴R⁴)$_n$—R⁵, (7) —(CR⁴R⁴)$_n$—OR⁵, and (8) —(CR⁴R⁴)$_n$NR$^a$C(=O)(CR⁴R⁴)$_n$R⁵;

R⁴ is independently selected from: H, F, Cl, NR$^a$R$^a$, OC$_{1-4}$ alkyl, and C$_{1-4}$ alkyl; or R⁴ and R⁴ together with the carbon atom to which they are both attached form C$_{3-6}$ cycloalkyl substituted with 0-5 R$^e$;

R⁵ is independently selected from: —(CH$_2$)$_n$-aryl, —(CH$_2$)$_n$—C$_{3-6}$ cycloalkyl and —(CH$_2$)$_n$-heterocycle, each substituted with 0-3 R⁶;

R⁶ is independently selected from: H, F, Cl, Br, —OR$^b$, =O, —(CH$_2$)$_n$C(=O)R$^b$, —(CH$_2$)$_n$C(=O)OR$^b$, —(CH$_2$)$_n$NR$^a$R$^a$, CN, —(CH$_2$)$_n$C(=O)NR$^a$R$^a$, C$_{1-4}$ alkyl substituted with 0-3 R$^e$, (CH$_2$)$_n$—C$_{3-6}$ carbocyclyl substituted with 0-3 R$^e$, and —(CH$_2$)$_n$-heterocyclyl substituted with 0-3 R$^e$;

R$^a$ is independently selected from H, C$_{1-6}$ alkyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$; or R$^a$ and R$^a$ together with the nitrogen atom to which they are both attached form a heterocyclic ring substituted with 0-5 R$^e$;

R$^b$ is independently selected from H, C$_{1-6}$ alkyl substituted with 0-5 R$^e$, C$_{2-6}$ alkenyl substituted with 0-5 R$^e$, C$_{2-6}$ alkynyl substituted with 0-5 R$^e$, —(CH$_2$)$_n$—C$_{3-10}$ carbocyclyl substituted with 0-5 R$^e$, and —(CH$_2$)$_n$-heterocyclyl substituted with 0-5 R$^e$;

R$^e$ is independently selected from C$_{1-6}$ alkyl substituted with 0-5 R$_f$, C$_{2-6}$ alkenyl, C$_{2-6}$ alkynyl, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, CO$_2$H, —(CH$_2$)$_n$OR$_f$, S(O)$_p$R$^f$, C(=O)NR$^f$R$^f$, NR$^f$C(=O)R$^f$, S(O)$_p$NR$^f$R$^f$, NR$^f$S(O)$_p$R$^f$, NR$^f$C(=O)OR$^f$, OC(=O)NR$^f$R$^f$ and —(CH$_2$)$_n$NR$^f$R$^f$;

R$^f$ is independently selected from H, F, Cl, Br, CN, OH, C$_{1-5}$alkyl (optimally substituted with halogen and OH), C$_{3-6}$ cycloalkyl, and phenyl;

n is independently selected from zero, 1, 2, and 3; and
p is independently selected from zero, 1, and 2.

In a third aspect, the present disclosure provides a compound of Formula (III):

(III)

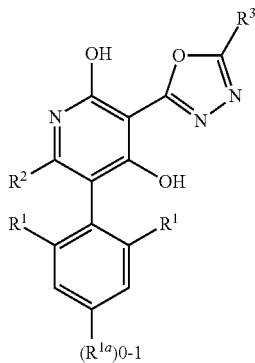

or a stereoisomer, a tautomer, a pharmaceutically acceptable salt, or a solvate thereof, within the scope of the first or second aspect, wherein:

$R^1$ is independently selected from: F, Cl, OH, and $OC_{1-4}$ alkyl;

$R^{1a}$ is independently selected from: F, Cl, and $C_{1-2}$ alkyl;

$R^2$ is independently selected from: $C_{1-5}$ alkyl substituted with 0-3 $R^e$; $C_{1-5}$ alkenyl, and $C_{1-6}$ cycloalkyl and $CH_2O(CH_2)_{1-3}CH_3$;

$R^3$ is independently selected from:
  (1) $-(CR^4R^4)_nC(=O)OC_{1-4}$ alkyl substituted with 0-5 $R^e$,
  (2) $-(CR^4R^4)_nNR^aR^a$,
  (3) $-(CR^4R^4)_nC(=O)NR^aR^a$,
  (4) $-(CR^4R^4)_nNR^aC(=O) C_{1-4}$ alkyl substituted with 0-5 $R^e$,
  (5) $-(CR^4R^4)_nNR^aC(=O)(CR^4R^4)_nOC_{1-4}$ alkyl substituted with 0-5 $R^e$,
  (6) $-(CR^4R^4)_n-R^5$,
  (7) $-(CR^4R^4)_n-OR^5$, and
  (8) $-(CR^4R^4)_nNR^aC(=O)(CR^4R^4)_nR^5$;

$R^4$ is independently selected from: H, F, Cl, $NR^aR^a$, $OC_{1-4}$ alkyl, and $C_{1-4}$ alkyl; or $R^4$ and $R^4$ together with the carbon atom to which they are both attached form $C_{3-6}$ cycloalkyl substituted with 0-5 $R^e$;

$R^5$ is independently selected from: $-(CH_2)_n$-aryl, $-(CH_2)_n-C_{3-6}$ cycloalkyl and $-(CH_2)_n$-heterocycle, each substituted with 0-3 $R^6$;

$R^6$ is independently selected from: H, F, Cl, Br, $-OR^b$, $=O$, $-(CH_2)_nC(=O)R^b$, $-(CH_2)_nC(=O)OR^b$, $-(CH_2)_nNR^aR^a$, CN, $-(CH_2)_nC(=O)NR^aR^a$, $C_{1-4}$ alkyl substituted with 0-3 $R^e$, $(CH_2)_n-C_{3-6}$ carbocyclyl substituted with 0-3 $R^e$, and $-(CH_2)_n$-heterocyclyl substituted with 0-3 $R^e$;

$R^a$ is independently selected from H, $C_{1-6}$ alkyl substituted with 0-5 $R^e$, $-(CH_2)_n-C_{3-10}$ carbocyclyl substituted with 0-5 $R^e$, and $-(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$ is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, $-(CH_2)_n-C_{3-10}$carbocyclyl substituted with 0-5 $R^e$, and $-(CH_2)_n$-heterocyclyl substituted with 0-5 $R^e$;

$R^e$ is independently selected from $C_{1-6}$ alkyl (optionally substituted with F and Cl), OH, $OCH_3$, $OCF_3$, $-(CH_2)_n-C_{3-6}$ cycloalkyl, $-(CH_2)_n-C_{4-6}$ heterocyclyl, $-(CH_2)_n$-aryl, $-(CH_2)_n$-heteroaryl, F, Cl, Br, CN, $NO_2$, $=O$, $CO_2H$; and n is independently selected from zero, 1, 2, and 3.

In a fourth aspect, the present disclosure provides a compound of Formula (III), or a stereoisomer, a tautomer, a pharmaceutically acceptable salt, or a solvate thereof, within the scope of any of the first, second and third aspects, wherein:

$R^3$ is independently selected from:
  (1) $-(CR^4R^4)_n-R^5$,
  (2) $-(CR^4R^4)_n-OR^5$, and
  (3) $-(CR^4R^4)_nNR^aC(=O)(CR^4R^4)_nR^5$;

$R^4$ is independently selected from: H, F, Cl, $N(CH_3)_2$, $OCH_3$, and $CH_3$; or $R^4$ and $R^4$ together with the carbon atom to which they are both attached form cyclopropyl;

$R^5$ is independently selected from:

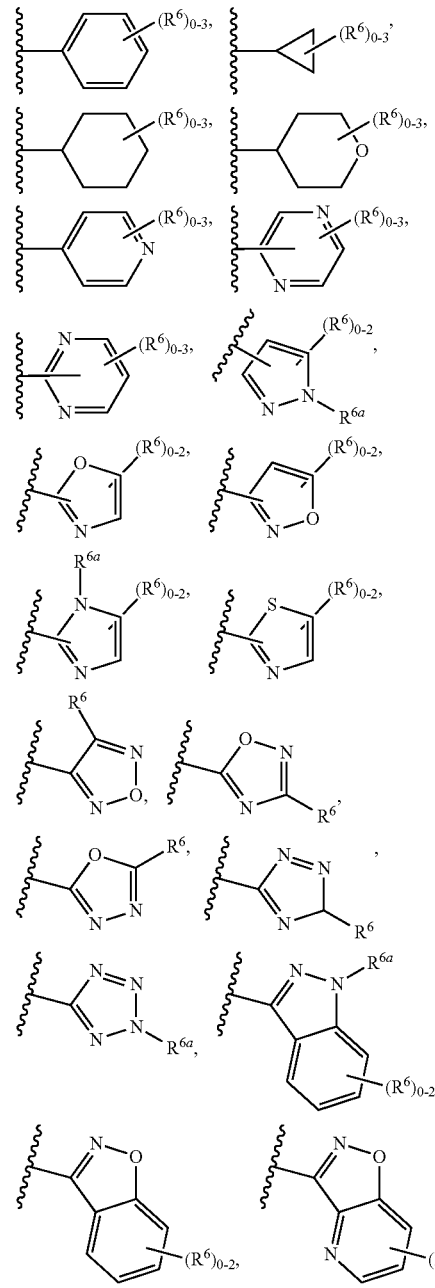

-continued

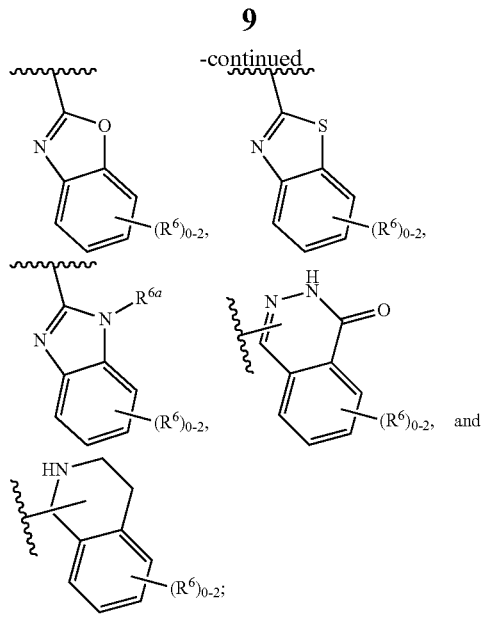

$R^6$ is independently selected from: H, F, Cl, Br, —OCH$_3$, —OCF$_3$, =O, CN, CH$_3$, CF$_3$—(CH$_2$)$_n$-aryl, —(CH$_2$)$_n$—C$_{3-6}$ cycloalkyl substituted with 0-3 R$^e$, and —(CH$_2$)$_n$-heterocyclyl substituted with 0-3 R$^e$;

$R^{6a}$ is independently selected from: H, CH$_3$, aryl substituted with 0-3 R$^e$, and heterocyclyl substituted with 0-3 R$^e$;

$R^a$ is independently selected from H, C$_{1-6}$ alkyl substituted with 0-5 R$^e$, —(CH$_2$)$_n$—C$_{3-10}$ carbocyclyl substituted with 0-5 R$^e$, and —(CH$_2$)$_n$-heterocyclyl substituted with 0-5 R$^e$;

$R^e$ is independently selected from C$_{1-6}$ alkyl (optionally substituted with F and Cl), OH, OCH$_3$, OCF$_3$, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, CO$_2$H; and n is independently selected from zero, 1, 2, and 3.

In a fifth aspect, the present disclosure provides a compound of Formula (III), or a stereoisomer, a tautomer, a pharmaceutically acceptable salt, or a solvate thereof, within the scope of any of the first, second and third aspects, wherein:

$R^3$ is independently selected from:
(1) —(CR$^4$R$^4$)$_n$NR$^a$R$^a$,
(2) —(CR$^4$R$^4$)$_n$C(=O)NR$^a$R$^a$, $R^4$ is independently selected from: H, F, Cl, N(CH$_3$)$_2$, OCH$_3$, and CH$_3$; or R$^4$ and R$^4$ together with the carbon atom to which they are both attached form C$_{3-6}$ cycloalkyl substituted with 0-5 R$^e$;

$R^6$ is independently selected from: H, F, Cl, Br, —OCH$_3$, —OCF$_3$, =O, CN, CH$_3$, CF$_3$—(CH$_2$)$_n$-aryl, —(CH$_2$)$_n$—C$_{3-6}$ cycloalkyl substituted with 0-3 R$^e$, and —(CH$_2$)$_n$-heterocyclyl substituted with 0-3 R$^e$;

$R^{6a}$ is independently selected from: H, CH$_3$, aryl substituted with 0-3 R$^e$, and heterocyclyl substituted with 0-3 R$^e$;

$R^a$ and $R^a$ together with the nitrogen atom to which they are both attached form a heterocyclic ring substituted with 0-5 R$^e$, wherein the heterocyclic ring is selected from:

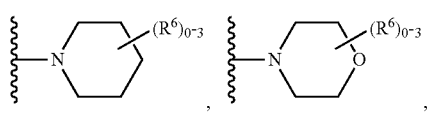

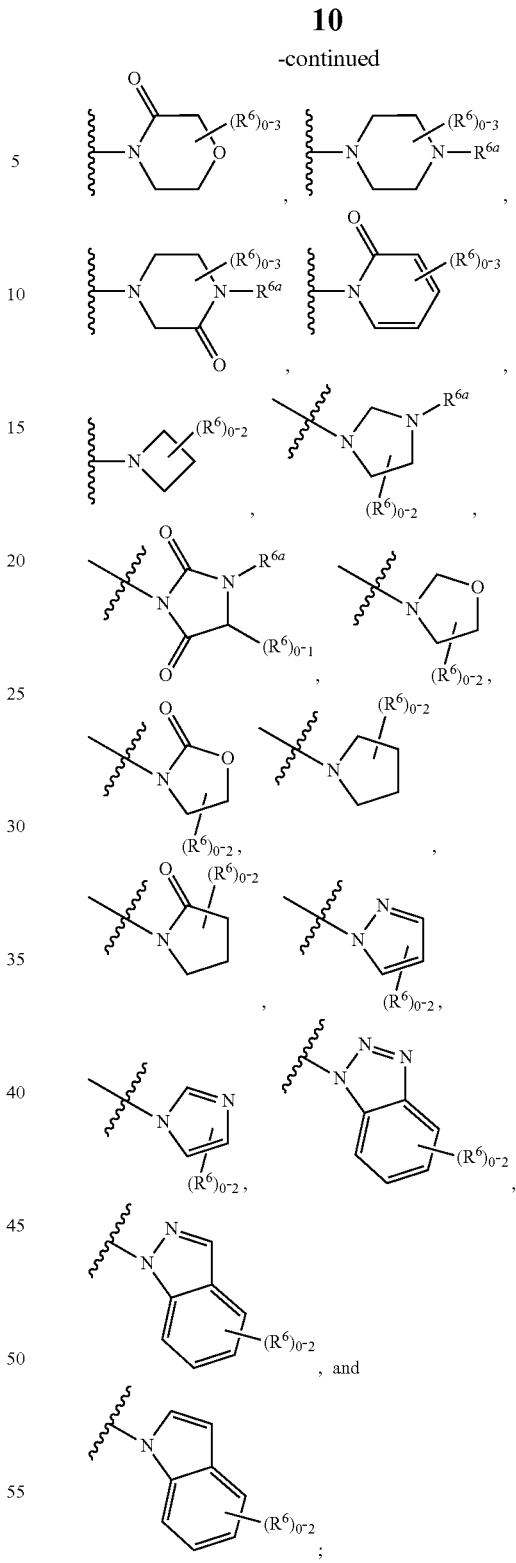

$R^e$ is independently selected from C$_{1-6}$ alkyl (optionally substituted with F and Cl), OH, OCH$_3$, OCF$_3$, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, CO$_2$H; and n is independently selected from zero, 1, 2, and 3.

In a sixth aspect, the present disclosures provides a compound of Formula (III), or a stereoisomer, a tautomer, a pharmaceutically acceptable salt, or a solvate thereof, within the scope of any of the first, second and third aspects, wherein:

$R^1$ is independently selected from: F, Cl, OH, and $OC_{1-4}$ alkyl;

$R^{1a}$ is independently selected from: F, Cl, and $C_{1-2}$ alkyl;

$R^2$ is independently selected from: $C_{1-5}$ alkyl substituted with 0-3 $R^e$; $C_{1-5}$ alkenyl, and $C_{1-6}$ cycloalkyl; and $CH_2O(CH_2)_{1-3}CH_3$;

$R^3$ is independently selected from:
(1) $-(CH_2)_nC(=O)OC_{1-4}$ alkyl substituted with 0-3 $R^e$,
(2) $-(CH_2)_nNR^aR^a$,
(3) $-(CH_2)_nC(=O)NR^aR^a$,
(4) $-(CH_2)_nNR^aC(=O)$ $C_{1-4}$alkyl substituted with 0-3 $R^e$, and
(5) $-(CH_2)_nNR^aC(=O)(CR^4R^4)_nOC_{1-4}$alkyl substituted with 0-3 $R^e$;

$R^4$ is independently selected from: H, F, Cl, $NR^aR^a$, $OC_{1-4}$ alkyl, and $C_{1-4}$ alkyl;

$R^5$ is independently selected from: $-(CH_2)_n$-aryl, $-(CH_2)_n-C_{3-6}$ cycloalkyl and $-(CH_2)_n$-heterocycle, each substituted with 0-3 $R^6$;

$R^6$ is independently selected from: H, F, Cl, Br, $-OCH_3$, $-OCF_3$, =O, CN, $CH_3$, $CF_3-(CH_2)_n$-aryl, $-(CH_2)_n-C_{3-6}$ cycloalkyl substituted with 0-3 $R^e$, and $-(CH_2)_n$-heterocyclyl substituted with 0-3 $R^e$;

$R^a$ is independently selected from H, $C_{1-6}$ alkyl substituted with 0-5 $R^e$, $-(CH_2)_n-C_{3-10}$carbocyclyl substituted with 0-5 $R^e$, and $-(CH_2)_n$-heterocyclyl substituted with 0-5 $R^e$;

$R^e$ is independently selected from $C_{1-6}$ alkyl (optionally substituted with F and Cl), OH, $OCH_3$, $OCF_3$, $-(CH_2)_n-C_{3-6}$ cycloalkyl, $-(CH_2)_n-C_{4-6}$ heterocyclyl, $-(CH_2)_n$-aryl, $-(CH_2)_n$-heteroaryl, F, Cl, Br, CN, $NO_2$, =O, $CO_2H$; and n is independently selected from zero, 1, 2, and 3.

In a seventh aspect, the present disclosures provides a compound of Formula (IV):

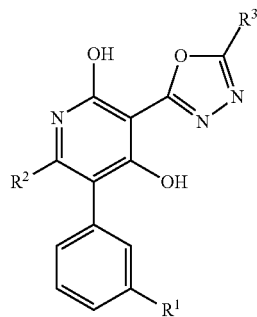

(IV)

or a stereoisomer, a tautomer, a pharmaceutically acceptable salt, or a solvate thereof, within the scope of the first and second aspects, wherein:

$R^1$ is independently selected from: $-CH_2OH$, $-OCH_3$, $-OCF_3$, $OCH_2Ph$, $-C(=O)NR^aR^a$, $-NR^aR^a$, $CH_3$, $CH_2CH_3$, $CH(CH_3)_2$, and cyclopropyl;

$R^2$ is independently selected from: $C_{1-4}$ alkyl substituted with 0-3 $R^e$; $C_{2-4}$ alkenyl, $C_{1-6}$ cycloalkyl, and $CH_2O(CH_2)_{1-3}CH_3$;

$R^3$ is independently selected from:
(1) $-(CR^4R^4)_nC(=O)OC_{1-4}$ alkyl substituted with 0-3 $R^e$,
(2) $-(CR^4R^4)_nNR^aR^a$,
(3) $-(CR^4R^4)_nC(=O)NR^aR^a$,
(4) $-(CR^4R^4)_nNR^aC(=O)$ $C_{1-4}$alkyl substituted with 0-3 $R^e$,
(5) $-(CR^4R^4)_nNR^aC(=O)(CR^4R^4)_nOC_{1-4}$alkyl substituted with 0-3 $R^e$,
(6) $-(CR^4R^4)_n-R^5$,
(7) $-(CR^4R^4)_n-OR^5$, and
(8) $-(CR^4R^4)_nNR^aC(=O)(CR^4R^4)_nR^5$;

$R^4$ is independently selected from: H, F, Cl, $NR^aR^a$, $OC_{1-4}$ alkyl, and $C_{1-4}$ alkyl;

$R^5$ is independently selected from: aryl, $C_{3-6}$ cycloalkyl and heterocycle, each substituted with 0-3 $R^6$;

$R^6$ is independently selected from: H, F, Cl, Br, $-OR^b$, =O, $-(CH_2)_nC(=O)R^b$, $-(CH_2)_nC(=O)OR^b$, $-(CH_2)_nNR^aR^a$, CN, $-(CH_2)_nC(=O)NR^aR^a$, $C_{1-4}$ alkyl substituted with 0-3 $R^e$, $(CH_2)_n-C_{3-6}$ carbocyclyl substituted with 0-3 $R^e$, and $-(CH_2)_n$-heterocyclyl substituted with 0-3 $R^e$;

$R^a$ is independently selected from H, $C_{1-6}$ alkyl substituted with 0-5 $R^e$, $-(CH_2)_n-C_{3-10}$carbocyclyl substituted with 0-5 $R^e$, and $-(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$ is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, $-(CH_2)_n-C_{3-10}$carbocyclyl substituted with 0-5 $R^e$, and $-(CH_2)_n$-heterocyclyl substituted with 0-5 $R^e$;

$R^e$ is independently selected from $C_{1-6}$ alkyl (optionally substituted with F and Cl), OH, $OCH_3$, $OCF_3$, $-(CH_2)_n-C_{3-6}$ cycloalkyl, $-(CH_2)_n-C_{4-6}$ heterocyclyl, $-(CH_2)_n$-aryl, $-(CH_2)_n$-heteroaryl, F, Cl, Br, CN, $NO_2$, =O, $CO_2H$; and n is independently selected from zero, 1, 2, and 3.

In an eighth aspect, the present invention provides a compound selected from the exemplified examples or a stereoisomer, a tautomer, a pharmaceutically acceptable salt, or a solvate thereof.

In another aspect, the present invention provides compounds of Formula (I):

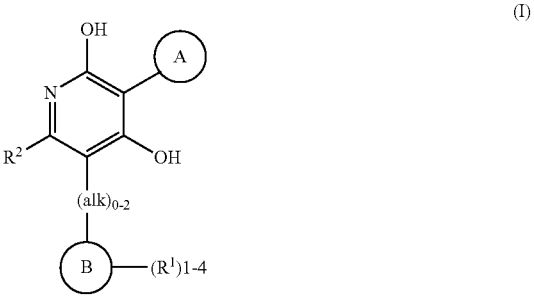

(I)

or stereoisomers, enantiomers, diastereoisomers, tautomers, pharmaceutically acceptable salts, solvates, or prodrugs thereof, wherein:

alk is $C_{1-6}$ alkyl substituted with 0-5 $R^e$;
ring A is independently selected from:

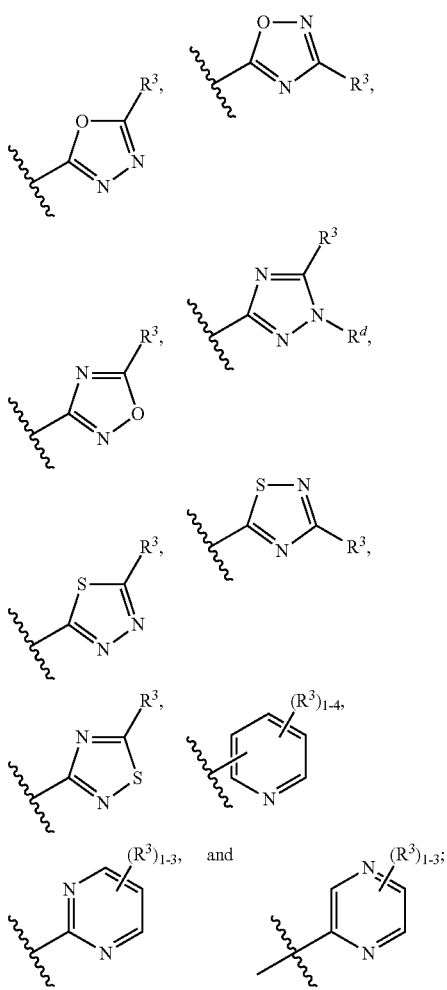

ring B is independently selected from:

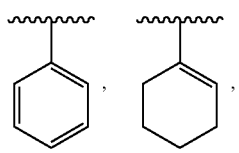

and 6-membered heteroaryl;

$R^1$ is independently selected from: H, halogen, $NO_2$, —$(CH_2)_nOR^b$, $(CH_2)_nS(O)_pR^c$, —$(CH_2)_nC(=O)R^b$, —$(CH_2)_nNR^aR^a$, —$(CH_2)_nCN$, —$(CH_2)_nC(=O)NR^aR^a$, —$(CH_2)_nNR^aC(=O)R^b$, —$(CH_2)_nNR^aC(=O)NR^aR^a$, —$(CH_2)_nNR^aC(=O)OR^b$, —$(CH_2)_n$ $OC(=O)NR^aR^a$, —$(CH_2)_nC(=O)OR^b$, —$(CH_2)_nS(O)_pNR^aR^a$, —$(CH_2)_nNR^aS(O)_pNR^aR^a$, —$(CH_2)_nNR^aS(O)_pR^c$, $C_{1-4}$ alkyl substituted with 0-3 $R^e$, —$(CH_2)_n$—$C_{3-6}$ carbocyclyl substituted with 0-3 $R^e$, and —$(CH_2)_n$-heterocyclyl substituted with 0-3 $R^e$;

$R^2$ is independently selected from: $C_{1-5}$ alkyl substituted with 0-3 $R^e$; $C_{1-5}$ alkenyl substituted with 0-3 $R^e$, and $C_{1-6}$ cycloalkyl substituted with 0-3 $R^e$; provided when $R^2$ is $C_{1-5}$ alkyl, the carbon atom except the one attached directly to the pyridine ring may be replaced by O, N, and S;

$R^3$ is independently selected from:
(1) —$(CR^4R^4)_rC(=O)OC_{1-4}$ alkyl substituted with 0-5 $R^e$,
(2) —$(CR^4R^4)_rNR^aR^a$,
(3) —$(CR^4R^4)_rC(=O)NR^aR^a$,
(4) —$(CR^4R^4)_rNR^aC(=O)C_{1-4}$alkyl substituted with 0-5 $R^e$,
(5) —$(CR^4R^4)_rNR^aC(=O)(CR^4R^4)_nOC_{1-4}$alkyl substituted with 0-5 $R^e$,
(6) —$(CR^4R^4)_r$—$R^5$,
(7) —$(CR^4R^4)_r$—$OR^5$,
(8) —$(CR^4R^4)_rNR^aC(=O)(CR^4R^4)_nR^5$, and
(9) —$(CR^4R^4)_rC(=O)NR^a(CR^4R^4)_nR^5$;

$R^4$ is independently selected from: H, halogen, $NR^aR^a$, $OC_{1-4}$ alkyl, and $C_{1-4}$ alkyl; or $R^4$ and $R^4$ together with the carbon atom to which they are both attached form $C_{3-6}$ cycloalkyl substituted with 0-5 $R^e$;

$R^5$ is independently selected from: —$(CH_2)_n$—$C_{3-10}$ carbocycle and —$(CH_2)_n$-heterocycle, each substituted with 0-3 $R^6$;

$R^6$ is independently selected from: H, halogen, =O, —$(CH_2)_nOR^b$, $(CH_2)_nS(O)_pR^c$, —$(CH_2)_nC(=O)R^b$, —$(CH_2)_nNR^aR^a$, —$(CH_2)_nCN$, —$(CH_2)_nC(=O)NR^aR^a$, —$(CH_2)_nNR^aC(=O)R^b$, —$(CH_2)_nNR^aC(=O)NR^aR^a$, —$(CH_2)_nNR^aC(=O)OR^b$, —$(CH_2)_n$ $OC(=O)NR^aR^a$, —$(CH_2)_nC(=O)OR^b$, —$(CH_2)_nS(O)_pNR^aR^a$, —$(CH_2)_nNR^aS(O)_pNR^aR^a$, —$(CH_2)_nNR^aS(O)_pR^c$, $C_{1-5}$ alkyl substituted with 0-3 $R^e$, $(CH_2)_n$—$C_{3-6}$ carbocyclyl substituted with 0-3 $R^e$, and —$(CH_2)_n$-heterocyclyl substituted with 0-3 $R^e$;

$R^a$ is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$ is independently selected from H, $C_1$-6 alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$;

$R^c$ is independently selected from $C_{1-6}$ alkyl substituted with 0-5 $R^e$, $C_{2-6}$alkenyl substituted with 0-5 $R^e$, $C_{2-6}$alkynyl substituted with 0-5 $R^e$, $C_{3-6}$carbocyclyl, and heterocyclyl;

$R^d$ is independently selected from H and $C_{1-4}$alkyl substituted with 0-5 $R^e$; $R^e$ is independently selected from $C_{1-6}$ alkyl substituted with 0-5 $R_f$, $C_{2-6}$ alkenyl, $C_{2-6}$ alkynyl, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, $NO_2$, =O, $CO_2H$, —$(CH_2)_nOR_f$, $S(O)_pR^f$, $C(=O)NR^fR^f$, $NR^fC(=O)R^f$, $S(O)_pNR^fR^f$, $NR^fS(O)_pR^f$, $NR^fC(=O)$ $OR^f$, $OC(=O)NR^fR^f$ and —$(CH_2)_nNR^fR^f$, $R^f$ is independently selected from H, F, Cl, Br, CN, OH, $C_{1-5}$alkyl (optimally substituted with halogen and OH), $C_{3-6}$ cycloalkyl, and phenyl, or $R^f$ and $R^f$ together with the nitrogen atom to which they are both attached form a heterocyclic ring optionally substituted with $C_{1-4}$alkyl;

n is independently selected from zero, 1, 2, and 3;
r is independently selected from zero, 1, 2, and 3; and
p is independently selected from zero, 1, and 2.

In another aspect, the present invention provides compounds of Formula (I), or stereoisomers, enantiomers, diastereoisomers, tautomers, pharmaceutically acceptable salts, solvates, or prodrugs thereof, wherein:
alk is $C_{1-6}$ alkyl substituted with 0-5 $R^e$;
ring A is independently selected from:

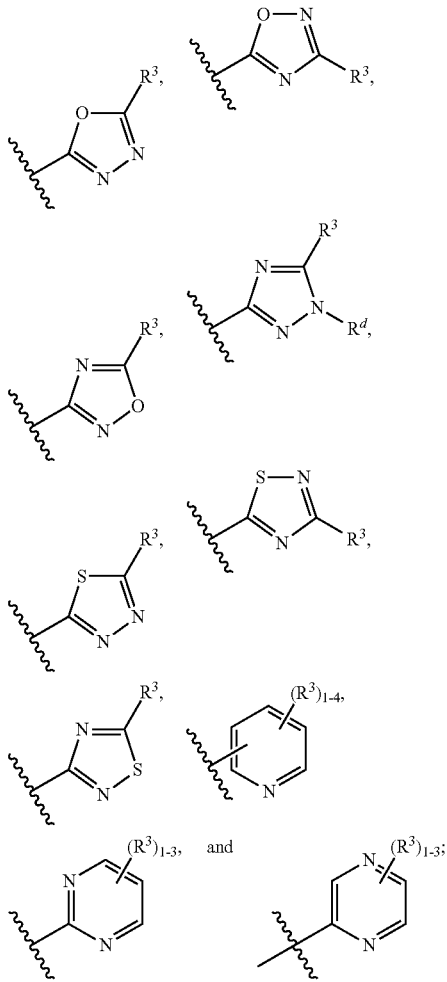

ring B is independently selected from:

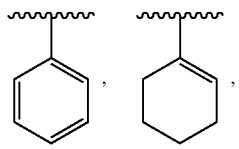

and 6-membered heteroaryl;
$R^1$ is independently selected from: H, halogen, $NO_2$, —$(CH_2)_nOR^b$, $(CH_2)_nS(O)_pR^c$, —$(CH_2)_nC(=O)R^b$, —$(CH_2)_nNR^aR^a$, —$(CH_2)_nCN$, —$(CH_2)_nC(=O)NR^aR^a$, —$(CH_2)_nNR^aC(=O)R^b$, —$(CH_2)_nNR^aC(=O)NR^aR^a$, —$(CH_2)_nNR^aC(=O)OR^b$, —$(CH_2)_n$ $OC(=O)NR^aR^a$, —$(CH_2)_nC(=O)OR^b$, —$(CH_2)_nS(O)_pNR^aR^a$, —$(CH_2)_nNR^aS(O)_pNR^aR^a$, —$(CH_2)_nNR^aS(O)_pR^c$, $C_{1-4}$ alkyl substituted with 0-3 $R^e$, —$(CH_2)_n$—$C_{3-6}$ carbocyclyl substituted with 0-3 $R^e$, and —$(CH_2)_n$-heterocyclyl substituted with 0-3 $R^e$;
$R^2$ is independently selected from: $C_{1-5}$ alkyl substituted with 0-3 $R^e$; $C_{1-5}$ alkenyl substituted with 0-3 $R^e$, and $C_{1-6}$ cycloalkyl substituted with 0-3 $R^e$; provided when $R^2$ is $C_{1-5}$ alkyl, the carbon atom except the one attached directly to the pyridine ring may be replaced by O, N, and S;
$R^3$ is independently selected from:
(1) —$(CR^4R^4)_rC(=O)OC_{1-4}$ alkyl substituted with 0-5 $R^e$,
(2) —$(CR^4R^4)_rNR^aR^a$,
(3) —$(CR^4R^4)_rC(=O)NR^aR^a$,
(4) —$(CR^4R^4)_rNR^aC(=O)C_{1-4}$alkyl substituted with 0-5 $R^e$,
(5) —$(CR^4R^4)_rNR^aC(=O)(CR^4R^4)_nOC_{1-4}$alkyl substituted with 0-5 $R^e$,
(6) —$(CR^4R^4)_r$—$R^5$,
(7) —$(CR^4R^4)_r$—$OR^5$,
(8) —$(CR^4R^4)_rNR^aC(=O)(CR^4R^4)_nR^5$, and
(9) —$(CR^4R^4)_rC(=O)NR^a(CR^4R^4)_nR^5$;
$R^4$ is independently selected from: H, halogen, $NR^aR^a$, $OC_{1-4}$ alkyl, and $C_{1-4}$ alkyl; or $R^4$ and $R^4$ together with the carbon atom to which they are both attached form $C_{3-6}$ cycloalkyl substituted with 0-5 $R^e$;
$R^5$ is independently selected from: —$(CH_2)_n$—$C_{3-10}$ carbocycle and —$(CH_2)_n$-heterocycle, each substituted with 0-3 $R^6$;
$R^6$ is independently selected from: H, halogen, =O, —$(CH_2)_nOR^b$, $(CH_2)_nS(O)_pR^c$, —$(CH_2)_nC(=O)R^b$, —$(CH_2)_nNR^aR^a$, —$(CH_2)_nCN$, —$(CH_2)_nC(=O)NR^aR^a$, —$(CH_2)_nNR^aC(=O)R^b$, —$(CH_2)_nNR^aC(=O)NR^aR^a$, —$(CH_2)_nNR^aC(=O)OR^b$, —$(CH_2)_n$ $OC(=O)NR^aR^a$, —$(CH_2)_nC(=O)OR^b$, —$(CH_2)_nS(O)_pNR^aR^a$, —$(CH_2)_nNR^aS(O)_pNR^aR^a$, —$(CH_2)_nNR^aS(O)_pR^c$, $C_{1-5}$ alkyl substituted with 0-3 $R^e$, —$(CH_2)_n$—$C_{3-6}$ carbocyclyl substituted with 0-3 $R^e$, and —$(CH_2)_n$-heterocyclyl substituted with 0-3 $R^e$;
$R^a$ is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;
$R^b$ is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$;
$R^c$ is independently selected from $C_{1-6}$ alkyl substituted with 0-5 $R^e$, $C_{2-6}$alkenyl substituted with 0-5 $R^e$, $C_{2-6}$alkynyl substituted with 0-5 $R^e$, $C_{3-6}$carbocyclyl, and heterocyclyl;
$R^d$ is independently selected from H and $C_{1-4}$alkyl substituted with 0-5 $R^e$;
$R^e$ is independently selected from $C_{1-6}$ alkyl substituted with 0-5 $R_f$, $C_{2-6}$ alkenyl, $C_{2-6}$ alkynyl, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, $NO_2$, =O, $CO_2H$, —$(CH_2)_nOR_f$, $S(O)_pR^f$, $C(=O)NR^fR^f$, $NR^fC(=O)R^f$, $S(O)_pNR^fR^f$, $NR^fS(O)_pR^f$, $NR^fC(=O)OR^f$, $OC(=O)NR^fR^f$ and —$(CH_2)_nNR^fR^f$,
$R^f$ is independently selected from H, F, Cl, Br, CN, OH, $C_{1-5}$alkyl (optimally substituted with halogen and OH), $C_{3-6}$ cycloalkyl, and phenyl, or $R^f$ and $R^f$ together with the nitrogen atom to which they are both attached form a heterocyclic ring optionally substituted with $C_{1-4}$alkyl;
n is independently selected from zero, 1, 2, and 3;
r is independently selected from zero, 1, 2, and 3; and
p is independently selected from zero, 1, and 2.

In another aspect, the present invention provides compounds of Formula (II):

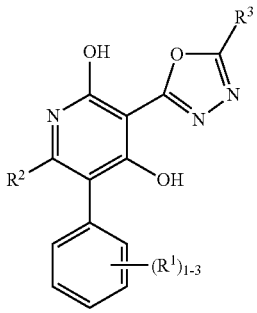

(II)

or stereoisomers, enantiomers, diastereoisomers, tautomers, pharmaceutically acceptable salts, solvates, or prodrugs thereof, wherein:

$R^1$ is independently selected from: F, Cl, Br, $NO_2$, —$(CH_2)_nOR^b$, —$(CH_2)_nC(=O)R^b$, —$(CH_2)_nNR^aR^a$, —$(CH_2)_nC(=O)NR^aR^a$, —$(CH_2)_n$ $NR^aC(=O)R^b$, $C_{1-4}$ alkyl substituted with 0-3 $R^e$ and $C_{3-6}$ cycloalkyl substituted with 0-3 $R^e$;

$R^2$ is independently selected from: $C_{1-5}$ alkyl substituted with 0-3 $R^e$; $C_{1-5}$ alkenyl, and $C_{1-6}$ cycloalkyl; provided when $R^2$ is $C_{1-5}$ alkyl, the carbon atom except the one attached directly to the pyridine ring may be replaced by O, N, and S;

$R^3$ is independently selected from:
(1) —$(CR^4R^4)_rC(=O)OC_{1-4}$ alkyl substituted with 0-5 $R^e$,
(2) —$(CR^4R^4)_rNR^aR^a$,
(3) —$(CR^4R^4)_rC(=O)NR^aR^a$,
(4) —$(CR^4R^4)_rNR^aC(=O)C_{1-4}$alkyl substituted with 0-5 $R^e$,
(5) —$(CR^4R^4)_rNR^aC(=O)(CR^4R^4)_nOC_{1-4}$alkyl substituted with 0-5 $R^e$,
(6) —$(CR^4R^4)_r$—$R^5$,
(7) —$(CR^4R^4)_r$—$OR^5$,
(8) —$(CR^4R^4)_rNR^aC(=O)(CR^4R^4)_nR^5$, and
(9) —$(CR^4R^4)_rC(=O)NR^a(CR^4R^4)_nR^5$;

$R^4$ is independently selected from: H, F, Cl, $NR^aR^a$, $OC_{1-4}$ alkyl, and $C_{1-4}$ alkyl; or $R^4$ and $R^4$ together with the carbon atom to which they are both attached form $C_{3-6}$ cycloalkyl substituted with 0-5 $R^e$;

$R^5$ is independently selected from: —$(CH_2)_n$-aryl, —$(CH_2)_n$—$C_{3-6}$ cycloalkyl and —$(CH_2)_n$-heterocycle, each substituted with 0-3 $R^6$;

$R^6$ is independently selected from: H, F, Cl, Br, —$OR^b$, =O, —$(CH_2)_nC(=O)R^b$, —$(CH_2)_nC(=O)OR^b$, —$(CH_2)_nNR^aR^a$, CN, —$(CH_2)_nC(=O)NR^aR^a$, —$(CH_2)_nS(O)_pNR^aR^a$, $C_{1-4}$ alkyl substituted with 0-3 $R^e$, $(CH_2)_n$—$C_{3-6}$ carbocyclyl substituted with 0-3 $R^e$, and —$(CH_2)_n$-heterocyclyl substituted with 0-3 $R^e$;

$R^a$ is independently selected from H, $C_{1-6}$ alkyl substituted with 0-5 $R^e$, —$(CH_2)_n$—$C_{3-10}$ carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$ is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$;

$R^e$ is independently selected from $C_{1-6}$ alkyl substituted with 0-5 $R_f$, $C_{2-6}$ alkenyl, $C_{2-6}$ alkynyl, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, $NO_2$, =O, $CO_2H$, —$(CH_2)_nOR_f$, $S(O)_pR^f$, $C(=O)NR^fR^f$, $NR^fC(=O)R^f$, $S(O)_pNR^fR^f$, $NR^fS(O)_pR^f$, $NR^fC(=O)OR^f$, $OC(=O)NR^fR^f$ and —$(CH_2)_nNR^fR^f$;

$R^f$ is independently selected from H, F, Cl, Br, CN, OH, $C_{1-5}$alkyl (optimally substituted with halogen and OH), $C_{3-6}$ cycloalkyl, and phenyl;

n is independently selected from zero, 1, 2, and 3;
r is independently selected from 1, 2, and 3; and
p is independently selected from zero, 1, and 2.

In another aspect, the present invention provides compounds of Formula (III):

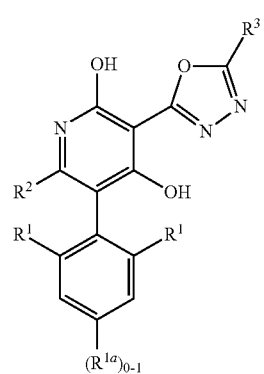

(III)

or stereoisomers, enantiomers, diastereoisomers, tautomers, pharmaceutically acceptable salts, solvate, or prodrugs thereof, wherein:

$R^1$ is independently selected from: F, Cl, OH, and $OC_{1-4}$ alkyl;

$R^{1a}$ is independently selected from: F, Cl, and $C_{1-2}$ alkyl;

$R^2$ is independently selected from: $C_{1-5}$ alkyl substituted with 0-3 $R^e$; $C_{1-5}$ alkenyl, and $C_{1-6}$ cycloalkyl and $CH_2O(CH_2)_{1-3}CH_3$;

$R^3$ is independently selected from:
(1) —$(CR^4R^4)_rC(=O)OC_{1-4}$ alkyl substituted with 0-5 $R^e$,
(2) —$(CR^4R^4)_rNR^aR^a$,
(3) —$(CR^4R^4)_rC(=O)NR^aR^a$,
(4) —$(CR^4R^4)_rNR^aC(=O)$ $C_{1-4}$alkyl substituted with 0-5 $R^e$,
(5) —$(CR^4R^4)_rNR^aC(=O)(CR^4R^4)_nOC_{1-4}$alkyl substituted with 0-5 $R^e$,
(6) —$(CR^4R^4)_r$—$R^5$,
(7) —$(CR^4R^4)_r$—$OR^5$, and
(8) —$(CR^4R^4)_rNR^aC(=O)(CR^4R^4)_nR^5$, and
(9) —$(CR^4R^4)_rC(=O)NR^a(CR^4R^4)_nR^5$;

$R^4$ is independently selected from: H, F, Cl, $NR^aR^a$, $OC_{1-4}$ alkyl, and $C_{1-4}$ alkyl; or $R^4$ and $R^4$ together with the carbon atom to which they are both attached form $C_{3-6}$ cycloalkyl substituted with 0-5 $R^e$;

$R^5$ is independently selected from: —$(CH_2)_n$-aryl, —$(CH_2)_n$—$C_{3-6}$ cycloalkyl and —$(CH_2)_n$-heterocycle, each substituted with 0-3 $R^6$;

$R^6$ is independently selected from: H, F, Cl, Br, —$OR^b$, =O, —$(CH_2)_nC(=O)R^b$, —$(CH_2)_nC(=O)OR^b$, —$(CH_2)_nNR^aR^a$, CN, —$(CH_2)_nC(=O)NR^aR^a$, —$(CH_2)_nS(O)_pNR^aR^a$, $C_{1-4}$ alkyl substituted with 0-3 $R^e$, $(CH_2)_n$—$C_{3-6}$ carbocyclyl substituted with 0-3 $R^e$, and —$(CH_2)_n$-heterocyclyl substituted with 0-3 $R^e$;

$R^a$ is independently selected from H, $C_{1-6}$ alkyl substituted with 0-5 $R^e$, —$(CH_2)_n$—$C_{3-10}$ carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$ is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$ carbocyclyl substituted with 0-5 $R^e$, and —$(CH_2)_n$-heterocyclyl substituted with 0-5 $R^e$;

$R^e$ is independently selected from $C_{1-6}$ alkyl (optionally substituted with F and Cl), OH, $OCH_3$, $OCF_3$, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, $NO_2$, =O, $CO_2H$; d n is independently selected from zero, 1, 2, and 3; and
r is independently selected from 1, 2, and 3.

In another aspect, the present invention provides compounds of Formula (IIIa):

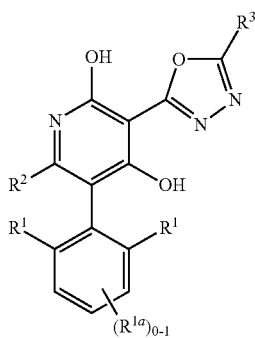

(IIIa)

or stereoisomers, enantiomers, diastereoisomers, tautomers, pharmaceutically acceptable salts, solvate, or prodrugs thereof, wherein:

$R^1$ is independently selected from: F, Cl, OH, and $OC_{1-4}$ alkyl;

$R^{1a}$ is independently selected from: F, Cl, and $C_{1-2}$ alkyl;

$R^2$ is independently selected from: $C_{1-5}$ alkyl substituted with 0-3 $R^e$; $C_{1-5}$ alkenyl, and $C_{1-6}$ cycloalkyl and $CH_2O(CH_2)_{1-3}CH_3$;

$R^3$ is independently selected from:
(1) —$(CR^4R^4)_rC(=O)OC_{1-4}$ alkyl substituted with 0-5 $R^e$,
(2) —$(CR^4R^4)_rNR^aR^a$,
(3) —$(CR^4R^4)_rC(=O)NR^aR^a$,
(4) —$(CR^4R^4)_rNR^aC(=O)$ $C_{1-4}$alkyl substituted with 0-5 $R^e$,
(5) —$(CR^4R^4)_rNR^aC(=O)(CR^4R^4)_nOC_{1-4}$alkyl substituted with 0-5 $R^e$,
(6) —$(CR^4R^4)_r$—$R^5$,
(7) —$(CR^4R^4)_r$—$OR^5$, and
(8) —$(CR^4R^4)_rNR^aC(=O)(CR^4R^4)_nR^5$, and
(9) —$(CR^4R^4)_rC(=O)NR^a(CR^4R^4)_nR^5$;

$R^4$ is independently selected from: H, F, Cl, $NR^aR^a$, $OC_{1-4}$ alkyl, and $C_{1-4}$ alkyl; or $R^4$ and $R^4$ together with the carbon atom to which they are both attached form $C_{3-6}$ cycloalkyl substituted with 0-5 $R^e$;

$R^5$ is independently selected from: —$(CH_2)_n$-aryl, —$(CH_2)_n$—$C_{3-6}$ cycloalkyl and —$(CH_2)_n$-heterocycle, each substituted with 0-3 $R^6$;

$R^6$ is independently selected from: H, F, Cl, Br, —$OR^b$, =O, —$(CH_2)_nC(=O)R^b$, —$(CH_2)_nC(=O)OR^b$, —$(CH_2)_nNR^aR^a$, CN, —$(CH_2)_nC(=O)NR^aR^a$, —$(CH_2)_nS(O)_pNR^aR^a$, $C_{1-4}$ alkyl substituted with 0-3 $R^e$, $(CH_2)_n$—$C_{3-6}$ carbocyclyl substituted with 0-3 $R^e$, and —$(CH_2)_n$-heterocyclyl substituted with 0-3 $R^e$;

$R^a$ is independently selected from H, $C_{1-6}$ alkyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$ is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$;

$R^e$ is independently selected from $C_{1-6}$ alkyl (optionally substituted with F and Cl), OH, $OCH_3$, $OCF_3$, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, $NO_2$, =O, $CO_2H$; d n is independently selected from zero, 1, 2, and 3; and
r is independently selected from 1, 2, and 3.

In another aspect, the present invention provides compounds of Formula (III), or stereoisomers, enantiomers, diastereoisomers, tautomers, pharmaceutically acceptable salts, solvate, or prodrugs thereof, wherein:

$R^3$ is independently selected from:
(1) —$(CR^4R^4)_r$—$R^5$,
(2) —$(CR^4R^4)_r$—$OR^5$,
(3) —$(CR^4R^4)_rNR^aC(=O)(CR^4R^4)_nR^5$, and
(4) —$(CR^4R^4)_rC(=O)NR^a(CR^4R^4)_nR^5$;

$R^4$ is independently selected from: H, F, Cl, $N(CH_3)_2$, $OCH_3$, and $CH_3$; or $R^4$ and $R^4$ together with the carbon atom to which they are both attached form cyclopropyl;

$R^5$ is independently selected from:

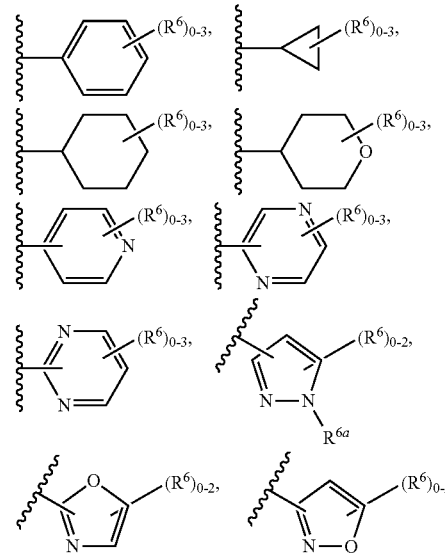

-continued

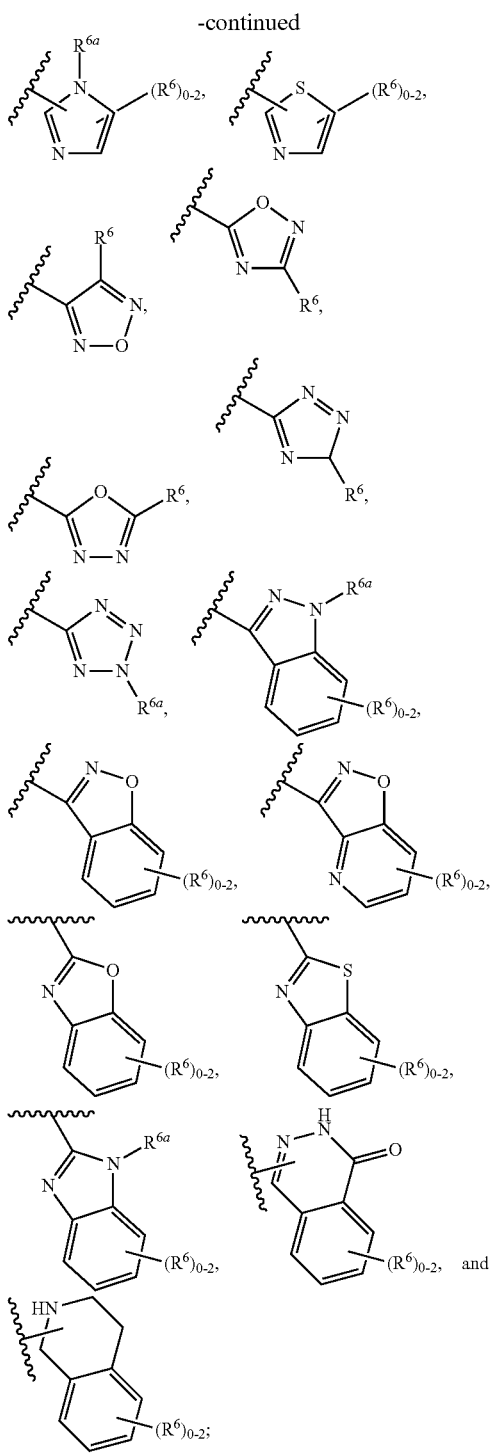

R[6] is independently selected from: H, F, Cl, Br, —OCH$_3$, —OCF$_3$, =O, —NR$^a$R$^a$, CN, —S(O)$_2$NH$_2$, CH$_3$, CF$_3$—(CH$_2$)$_n$-aryl, —(CH$_2$)$_n$—C$_{3-6}$ cycloalkyl substituted with 0-3 R$^e$, and —(CH$_2$)$_n$-heterocyclyl substituted with 0-3 R$^e$;

R$^{6a}$ is independently selected from: H, CH$_3$, aryl substituted with 0-3 R$^e$, and heterocyclyl substituted with 0-3 R$^e$;

R$^a$ is independently selected from H, C$_{1-6}$ alkyl substituted with 0-5 R$^e$, —(CH$_2$)$_n$—C$_{3-10}$ carbocyclyl substituted with 0-5 R$^e$, and —(CH$_2$)$_n$-heterocyclyl substituted with 0-5 R$^e$;

R$^e$ is independently selected from C$_{1-6}$ alkyl (optionally substituted with F and Cl), OH, OCH$_3$, OCF$_3$, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, CO$_2$H;

n is independently selected from zero, 1, 2, and 3;
r is independently selected from 1, 2, and 3; and
other variables are as defined in Formula (III).

In another aspect, the present invention provides compounds of Formula (III), or stereoisomers, enantiomers, diastereoisomers, tautomers, pharmaceutically acceptable salts, solvate, or prodrugs thereof, wherein:

R$^3$ is independently selected from:
(1) —(CR$^4$R$^4$)$_r$NR$^a$R$^a$, and
(2) —(CR$^4$R$^4$)$_r$C(=O)NR$^a$R$^a$, R$^4$ is independently selected from: H, F, Cl, N(CH$_3$)$_2$, OCH$_3$, and CH$_3$; or R$^4$ and R$^4$ together with the carbon atom to which they are both attached form C$_{3-6}$ cycloalkyl substituted with 0-5 R$^e$;

R$^6$ is independently selected from: H, F, Cl, Br, —OCH$_3$, —OCF$_3$, =O, CN, —NR$^a$R$^a$, —S(O)$_2$NH$_2$, —CH$_3$, CF$_3$—(CH$_2$)$_n$-aryl, —(CH$_2$)$_n$—C$_{3-6}$ cycloalkyl substituted with 0-3 R$^e$, and —(CH$_2$)$_n$-heterocyclyl substituted with 0-3 R$^e$;

R$^{6a}$ is independently selected from: H, CH$_3$, aryl substituted with 0-3 R$^e$, and heterocyclyl substituted with 0-3 R$^e$;

R$^a$ and R$^a$ together with the nitrogen atom to which they are both attached form a heterocyclic ring substituted with 0-5 R$^e$, wherein the heterocyclic ring is selected from:

-continued

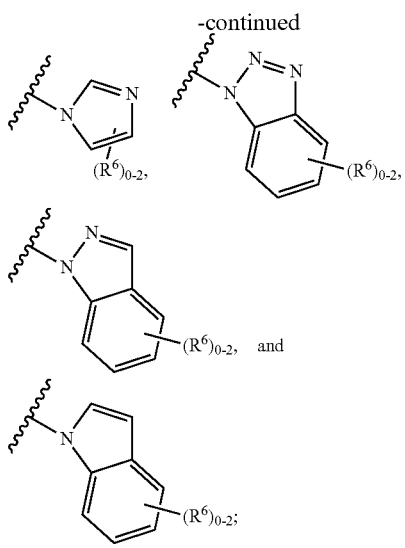

$R^e$ is independently selected from $C_{1-6}$ alkyl (optionally substituted with F and Cl), OH, OCH$_3$, OCF$_3$, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, CO$_2$H;

n is independently selected from zero, 1, 2, and 3;
r is independently selected from 1, 2, and 3, and
other variables are as defined in Formula (III).

In another aspect, the present invention provides compounds of Formula (III), or stereoisomers, enantiomers, diastereoisomers, tautomers, pharmaceutically acceptable salts, solvate, or prodrugs thereof, wherein:

$R^1$ is independently selected from: F, Cl, OH, and OC$_{1-4}$ alkyl;
$R^{1a}$ is independently selected from: F, Cl, and C$_{1-2}$ alkyl;
$R^2$ is independently selected from: C$_{1-5}$ alkyl substituted with 0-3 R$^e$; C$_{1-5}$ alkenyl, and C$_{1-6}$ cycloalkyl; and CH$_2$O(CH$_2$)$_{1-3}$CH$_3$;
$R^3$ is independently selected from:
(1) —(CH$_2$)$_r$C(=O)OC$_{1-4}$ alkyl substituted with 0-3 R$^e$,
(2) —(CH$_2$)$_r$NR$^a$R$^a$,
(3) —(CH$_2$)$_r$C(=O)NR$^a$R$^a$,
(4) —(CH$_2$)$_r$NR$^a$C(=O)C$_{1-4}$alkyl substituted with 0-3 R$^e$, and
(5) —(CH$_2$)$_r$NR$^a$C(=O)(CR$^4$R$^4$)$_n$OC$_{1-4}$alkyl substituted with 0-3 R$^e$;
$R^4$ is independently selected from: H, F, Cl, NR$^a$R$^a$, OC$_{1-4}$ alkyl, and C$_{1-4}$ alkyl;
$R^5$ is independently selected from: —(CH$_2$)$_n$-aryl, —(CH$_2$)$_n$—C$_{3-6}$ cycloalkyl and —(CH$_2$)$_n$-heterocycle, each substituted with 0-3 R$^6$;
$R^6$ is independently selected from: H, F, Cl, Br, —OCH$_3$, —OCF$_3$, =O, CN, —NR$^a$R$^a$, —S(O)$_2$NH$_2$, CH$_3$, CF$_3$— (CH$_2$)$_n$-aryl, —(CH$_2$)$_n$—C$_{3-6}$ cycloalkyl substituted with 0-3 R$^e$, and —(CH$_2$)$_n$-heterocyclyl substituted with 0-3 R$^e$;
$R^a$ is independently selected from H, C$_{1-6}$ alkyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$;
$R^e$ is independently selected from C$_{1-6}$ alkyl (optionally substituted with F and Cl), OH, OCH$_3$, OCF$_3$, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, CO$_2$H;

n is independently selected from zero, 1, 2, and 3; and
r is independently selected from 1, 2, and 3; and
other variables are as defined in Formula (III).

In another aspect, the present invention provides compounds of Formula (IVa):

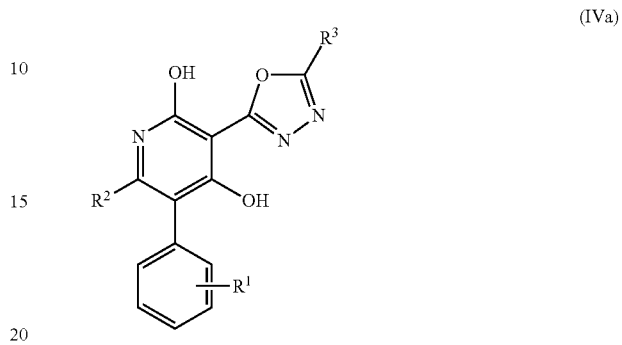

(IVa)

or stereoisomers, enantiomers, diastereoisomers, tautomers, pharmaceutically acceptable salts, solvate, or prodrugs thereof, wherein:

$R^1$ is independently selected from: —CH$_2$OH, —OCH$_3$, —OCF$_3$, OCH$_2$Ph, —C(=O)NR$^a$R$^a$, NR$^a$R$^a$, CH$_3$, CH$_2$CH$_3$, CH(CH$_3$)$_2$, and cyclopropyl;
$R^2$ is independently selected from: C$_{1-4}$ alkyl substituted with 0-3 R$^e$; C$_{2-4}$ alkenyl, C$_{1-6}$ cycloalkyl, and CH$_2$O(CH$_2$)$_{1-3}$CH$_3$;
$R^3$ is independently selected from:
(1) —(CR$^4$R$^4$)$_r$C(=O)OC$_{1-4}$ alkyl substituted with 0-3 R$^e$,
(2) —(CR$^4$R$^4$)$_r$NR$^a$R$^a$,
(3) —(CR$^4$R$^4$)$_r$C(=O)NR$^a$R$^a$,
(4) —(CR$^4$R$^4$)$_r$NR$^a$C(=O)C$_{1-4}$alkyl substituted with 0-3 R$^e$,
(5) —(CR$^4$R$^4$)$_r$NR$^a$C(=O)(CR$^4$R$^4$)$_n$OC$_{1-4}$alkyl substituted with 0-3 R$^e$,
(6) —(CR$^4$R$^4$)$_r$—R$^5$,
(7) —(CR$^4$R$^4$)$_r$—OR$^5$,
(8) —(CR$^4$R$^4$)$_r$NR$^a$C(=O)(CR$^4$R$^4$)$_n$R$^5$, and
(9) —(CR$^4$R$^4$)$_r$C(=O)NR$^a$(CR$^4$R$^4$)$_n$R$^5$;
$R^4$ is independently selected from: H, F, Cl, NR$^a$R$^a$, OC$_{1-4}$ alkyl, and C$_{1-4}$ alkyl;
$R^5$ is independently selected from: aryl, C$_{3-6}$ cycloalkyl and heterocycle, each substituted with 0-3 R$^6$;
$R^6$ is independently selected from: H, F, Cl, Br, —OR$^b$, =O, —(CH$_2$)$_n$C(=O)R$^b$, —(CH$_2$)$_n$C(=O)OR$^b$, —(CH$_2$)$_n$NR$^a$R$^a$, CN, —(CH$_2$)$_n$C(=O)NR$^a$R$^a$, C$_{1-4}$ alkyl substituted with 0-3 R$^e$, (CH$_2$)$_n$—C$_{3-6}$ carbocyclyl substituted with 0-3 R$^e$, and —(CH$_2$)$_n$-heterocyclyl substituted with 0-3 R$^e$;
$R^a$ is independently selected from H, C$_{1-6}$ alkyl substituted with 0-5 R$^e$, —(CH$_2$)$_n$—C$_{3-10}$ carbocyclyl substituted with 0-5 R$^e$, and —(CH$_2$)$_n$-heterocyclyl substituted with 0-5 R$^e$; or R$^a$ and R$^a$ together with the nitrogen atom to which they are both attached form a heterocyclic ring substituted with 0-5 R$^e$;
$R^b$ is independently selected from H, C$_{1-6}$ alkyl substituted with 0-5 R$^e$, C$_{2-6}$ alkenyl substituted with 0-5 R$^e$, C$_{2-6}$ alkynyl substituted with 0-5 R$^e$, —(CH$_2$)$_n$—C$_{3-10}$ carbocyclyl substituted with 0-5 R$^e$, and —(CH$_2$)$_n$-heterocyclyl substituted with 0-5 R$^e$;
$R^e$ is independently selected from C$_{1-6}$ alkyl (optionally substituted with F and Cl), OH, OCH$_3$, OCF$_3$, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, CO$_2$H;
n is independently selected from zero, 1, 2, and 3; and
r is independently selected from 1, 2, and 3.
In another aspect, the present invention provides compounds of Formula (V):

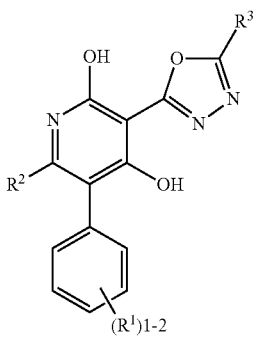

(V)

or stereoisomers, enantiomers, diastereoisomers, tautomers, pharmaceutically acceptable salts, solvate, or prodrugs thereof, wherein:
R$^1$ is independently selected from: —CH$_2$OH, —OCH$_3$, —OCF$_3$, CH$_3$, CH$_2$CH$_3$, CH(CH$_3$)$_2$, and cyclopropyl;
R$^2$ is independently selected from: C$_{1-4}$ alkyl substituted with 0-3 R$^e$; C$_{2-4}$ alkenyl, C$_{1-6}$ cycloalkyl, and CH$_2$O(CH$_2$)$_{1-3}$CH$_3$;
R$^3$ is independently selected from:
 (1) —CH$_2$C(=O)OC$_{1-4}$ alkyl substituted with 0-3 R$^e$,
 (2) —CH$_2$NR$^a$R$^a$,
 (3) —CH$_2$C(=O)NR$^a$R$^a$,
 (4) —CH$_2$NHC(=O)C$_{1-4}$alkyl substituted with 0-3 R$^e$,
 (5) —CH$_2$NR$^a$C(=O)(CH$_2$)$_{0-2}$OC$_{1-4}$alkyl substituted with 0-3 R$^e$,
 (6) —CH$_2$—R$^5$,
 (7) —CH$_2$—OR$^5$,
 (8) —CH$_2$NR$^a$C(=O)(CH$_2$)$_{0-2}$R$^5$, and
 (9) —CH$_2$C(=O)NR$^a$(CH$_2$)$_{0-2}$R$^5$;
R$^5$ is independently selected from: aryl, C$_{3-6}$ cycloalkyl and heterocycle, each substituted with 0-3 R$^6$;
R$^6$ is independently selected from: H, F, Cl, Br, —OR$^b$, =O, —(CH$_2$)$_n$C(=O)R$^b$, —(CH$_2$)$_n$C(=O)OR$^b$, —(CH$_2$)$_n$NR$^a$R$^a$, CN, —(CH$_2$)$_n$C(=O)NR$^a$R$^a$, —S(O)$_2$NH$_2$, C$_{1-4}$ alkyl substituted with 0-3 R$^e$, (CH$_2$)$_n$—C$_{3-6}$ carbocyclyl substituted with 0-3 R$^e$, and —(CH$_2$)$_n$-heterocyclyl substituted with 0-3 R$^e$;
R$^a$ is independently selected from H, C$_{1-6}$ alkyl substituted with 0-5 R$^e$, —(CH$_2$)$_n$—C$_{3-10}$ carbocyclyl substituted with 0-5 R$^e$, and —(CH$_2$)$_n$-heterocyclyl substituted with 0-5 R$^e$; or R$^a$ and R$^a$ together with the nitrogen atom to which they are both attached form a heterocyclic ring substituted with 0-5 R$^e$;
R$^b$ is independently selected from H, C$_{1-6}$ alkyl substituted with 0-5 R$^e$, C$_{2-6}$ alkenyl substituted with 0-5 R$^e$, C$_{2-6}$ alkynyl substituted with 0-5 R$^e$, —(CH$_2$)$_n$—C$_{3-10}$ carbocyclyl substituted with 0-5 R$^e$, and —(CH$_2$)$_n$-heterocyclyl substituted with 0-5 R$^e$;
R$^e$ is independently selected from C$_{1-6}$ alkyl (optionally substituted with F and Cl), OH, OCH$_3$, OCF$_3$, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, CO$_2$H;
n is independently selected from zero, 1, 2, and 3.

In another aspect, the present invention provides compounds of Formula (V), or stereoisomers, enantiomers, diastereoisomers, tautomers, pharmaceutically acceptable salts, solvate, or prodrugs thereof, wherein:
R$^3$ is independently selected from:
 (1) —CH$_2$—R$^5$,
 (2) —CH$_2$—OR$^5$,
 (3) —CH$_2$—NHC(=O)(CH$_2$)$_{0-1}$R$^5$, and
 (4) —CH$_2$—C(=O)NH(CH$_2$)$_{0-1}$R$^5$;
R$^5$ is independently selected from:

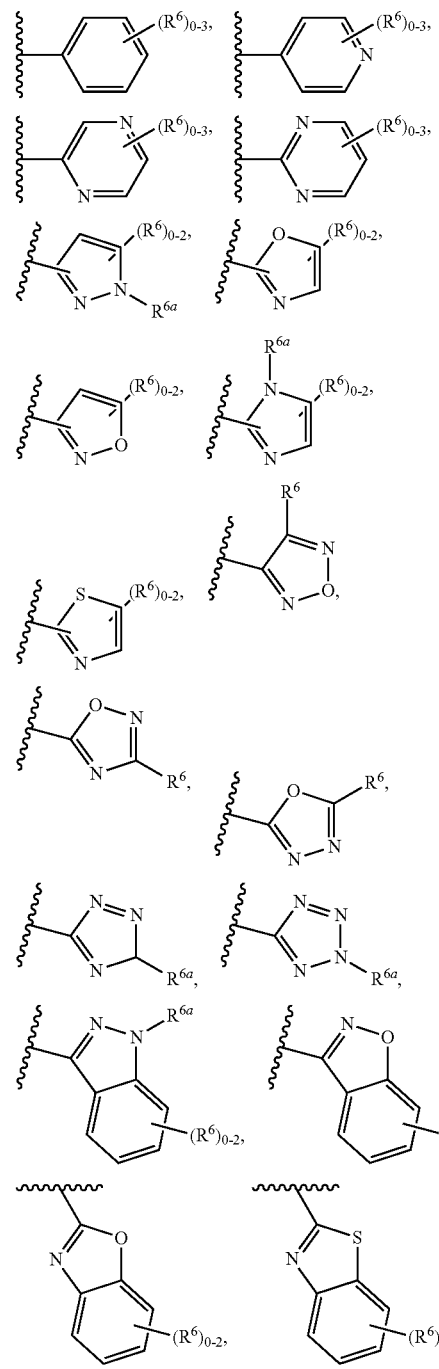

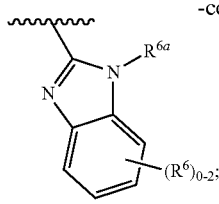

R⁶ is independently selected from: H, F, Cl, Br, —OCH₃, —OCF₃, =O, CN, CH₃, CF₃ —(CH₂)ₙ-aryl, —(CH₂)ₙ— C₃₋₆ cycloalkyl substituted with 0-3 Rᵉ, and —(CH₂)ₙ-heterocyclyl substituted with 0-3 Rᵉ;

R⁶ᵃ is independently selected from: H, CH₃, aryl substituted with 0-3 Rᵉ, and heterocyclyl substituted with 0-3 Rᵉ;

Rᵃ is independently selected from H, C₁₋₆ alkyl substituted with 0-5 Rᵉ, —(CH₂)ₙ—C₃₋₁₀ carbocyclyl substituted with 0-5 Rᵉ, and —(CH₂)ₙ-heterocyclyl substituted with 0-5 Rᵉ.

Rᵉ is independently selected from C₁₋₆ alkyl (optionally substituted with F and Cl), OH, OCH₃, OCF₃, —(CH₂)ₙ—C₃₋₆ cycloalkyl, —(CH₂)ₙ—C₄₋₆ heterocyclyl, —(CH₂)ₙ-aryl, —(CH₂)ₙ-heteroaryl, F, Cl, Br, CN, NO₂, =O, CO₂H;

n is independently selected from zero, 1, 2, and 3.

In another aspect, the present invention provides compounds of Formula (VI):

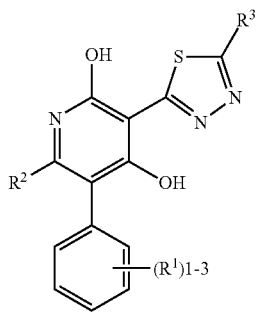

(VI)

or stereoisomers, enantiomers, diastereoisomers, tautomers, pharmaceutically acceptable salts, solvate, or prodrugs thereof, wherein:

R¹ is independently selected from: F, Cl, Br, NO₂, —(CH₂)ₙORᵇ, —(CH₂)ₙC(=O)Rᵇ, —(CH₂)ₙNRᵃRᵃ, —(CH₂)ₙC(=O)NRᵃRᵃ, —(CH₂)ₙ NRᵃC(=O)Rᵇ, C₁₋₄ alkyl substituted with 0-3 Rᵉ and C₃₋₆ cycloalkyl substituted with 0-3 Rᵉ;

R² is independently selected from: C₁₋₅ alkyl substituted with 0-3 Rᵉ; C₁₋₅ alkenyl, and C₁₋₆ cycloalkyl; wherein when R² is independently selected from: C₁₋₅ alkyl, the carbon atom except the one attached directly to the pyridine ring may be replaced by O, N, and S;

R³ is independently selected from:
(1) —CH₂C(=O)OC₁₋₄ alkyl substituted with 0-5 Rᵉ,
(2) —CH₂NRᵃRᵃ,
(3) —CH₂C(=O)NRᵃRᵃ,
(4) —CH₂NRᵃC(=O)C₁₋₄alkyl substituted with 0-5 Rᵉ,
(5) —CH₂NRᵃC(=O)(CH₂)ₙOC₁₋₄alkyl substituted with 0-5 Rᵉ,
(6) —CH₂—R⁵,
(7) —CH₂—OR⁵,
(8) —CH₂NRᵃC(=O)(CH₂)ₙR⁵, and
(9) —CH₂C(=O)NRᵃ(CH₂)ₙR⁵

R⁵ is independently selected from: —(CH₂)ₙ-aryl, —(CH₂)ₙ—C₃₋₆ cycloalkyl and —(CH₂)ₙ-heterocycle, each substituted with 0-3 R⁶;

R⁶ is independently selected from: H, F, Cl, Br, —ORᵇ, =O, —(CH₂)ₙC(=O)Rᵇ, —(CH₂)ₙC(=O)ORᵇ, —(CH₂)ₙNRᵃRᵃ, CN, —(CH₂)ₙC(=O)NRᵃRᵃ, C₁₋₄ alkyl substituted with 0-3 Rᵉ, (CH₂)ₙ—C₃₋₆ carbocyclyl substituted with 0-3 Rᵉ, and —(CH₂)ₙ-heterocyclyl substituted with 0-3 Rᵉ;

Rᵃ is independently selected from H, C₁₋₆ alkyl substituted with 0-5 Rᵉ, —(CH₂)ₙ—C₃₋₁₀carbocyclyl substituted with 0-5 Rᵉ, and —(CH₂)ₙ-heterocyclyl substituted with 0-5 Rᵉ; or Rᵃ and Rᵃ together with the nitrogen atom to which they are both attached form a heterocyclic ring substituted with 0-5 Rᵉ;

Rᵇ is independently selected from H, C₁-6 alkyl substituted with 0-5 Rᵉ, C₂₋₆ alkenyl substituted with 0-5 Rᵉ, C₂₋₆ alkynyl substituted with 0-5 Rᵉ, —(CH₂)ₙ—C₃₋₁₀carbocyclyl substituted with 0-5 Rᵉ, and —(CH₂)ₙ-heterocyclyl substituted with 0-5 Rᵉ;

Rᵉ is independently selected from C₁₋₆ alkyl substituted with 0-5 Rf, C₂₋₆ alkenyl, C₂₋₆ alkynyl, —(CH₂)ₙ—C₃₋₆ cycloalkyl, —(CH₂)ₙ—C₄₋₆ heterocyclyl, —(CH₂)ₙ-aryl, —(CH₂)ₙ-heteroaryl, F, Cl, Br, CN, NO₂, =O, CO₂H, —(CH₂)ₙORf, S(O)ₚRf, C(=O)NRfRf, NRfC(=O)Rf, S(O)ₚNRfRf, NRfS(O)ₚRf, NRfC(=O)ORf, OC(=O) NRfRf and —(CH₂)ₙNRfRf;

Rf is independently selected from H, F, Cl, Br, CN, OH, C₁₋₅alkyl (optimally substituted with halogen and OH), C₃₋₆ cycloalkyl, and phenyl;

n is independently selected from zero, 1, 2, and 3; and p is independently selected from zero, 1, and 2.

In one non-limiting embodiment, ring A is

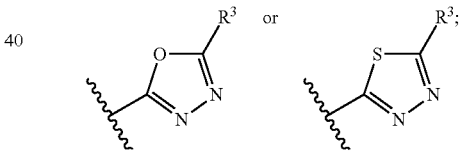

ring B is

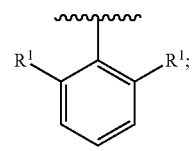

R¹ is OC₁₋₄ alkyl; R² is independently selected from: C₁₋₅ alkyl substituted with 0-3 Rᵉ; C₁₋₅ alkenyl, and C₁₋₆ cycloalkyl; provided when R² is C₁₋₅ alkyl, the carbon atom except the one attached directly to the pyridine ring may be replaced by O, N, and S; R³ is CH₂—R⁵; R⁵ is aryl, C₃₋₆ cycloalkyl and heteroaryl, each substituted with 0-3 R⁶; R⁶ is independently selected from: H, F, Cl, Br, —ORᵇ, =O, —(CH₂)ₙC(=O)Rᵇ, —(CH₂)ₙC(=O)ORᵇ, —(CH₂)ₙ NRᵃRᵃ, CN, —(CH₂)ₙC(=O)NRᵃRᵃ, —S(O)₂NH₂, C₁₋₄ alkyl substituted with 0-3 Rᵉ, (CH₂)ₙ—C₃₋₆ carbocyclyl substituted with 0-3 Rᵉ, and —(CH₂)ₙ-heterocyclyl substituted with 0-3 Rᵉ; Rᵃ is independently selected from H, C₁₋₆ alkyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$; or R$^a$ and R$^a$ together with the nitrogen atom to which they are both attached form a heterocyclic ring substituted with 0-5 R$^e$; R$^b$ is independently selected from H, C$_{1-6}$ alkyl substituted with 0-5 R$^e$, C$_{2-6}$ alkenyl substituted with 0-5 R$^e$, C$_{2-6}$ alkynyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$; R$^e$ is independently selected from C$_{1-6}$ alkyl (optionally substituted with F and Cl), OH, OCH$_3$, OCF$_3$, —(CH$_2$)$_n$—C$_{3-6}$ cycloalkyl, —(CH$_2$)$_n$—C$_{4-6}$heterocyclyl, —(CH$_2$)$_n$-aryl, —(CH$_2$)$_n$-heteroaryl, F, Cl, Br, CN, NO$_2$, =O, CO$_2$H; n is independently selected from zero, 1, 2, and 3.

In another non-limiting embodiment, ring A is

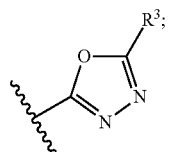

ring B is

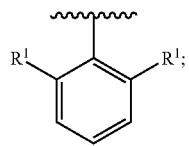

R$^1$ is OC$_{1-4}$ alkyl; R$^2$ is independently selected from C$_{1-5}$ alkyl substituted with 0-3 R$^e$; and C$_{1-6}$ cycloalkyl; provided when R$^2$ is C$_{1-5}$ alkyl, the carbon atom except the one attached directly to the pyridine ring may be replaced by O; R$^3$ is CH$_2$—R$^5$; R$^5$ is aryl, C$_{3-6}$ cycloalkyl and heteroaryl, each substituted with 0-3 R$^6$; R$^6$ is independently selected from: H, F, Cl, Br, —OR$^b$, =O, —(CH$_2$)$_n$C(=O)R$^b$, —(CH$_2$)$_n$C(=O)OR$^b$, —(CH$_2$)$_n$NR$^a$R$^a$, CN, —(CH$_2$)$_n$C(=O)NR$^a$R$^a$, —S(O)$_2$NH$_2$, C$_{1-4}$ alkyl substituted with 0-3 R$^e$, (CH$_2$)$_n$—C$_{3-6}$ carbocyclyl substituted with 0-3 R$^e$, and —(CH$_2$)$_n$-heterocyclyl substituted with 0-3 R$^e$; R$^a$ is independently selected from H, C$_{1-6}$ alkyl substituted with 0-5 R$^e$, (CH$_2$)$_n$—C$_{3-10}$carbocyclyl substituted with 0-5 R$^e$, and —(CH$_2$)$_n$-heterocyclyl substituted with 0-5 R$^e$; or R$^a$ and R$^a$ together with the nitrogen atom to which they are both attached form a heterocyclic ring substituted with 0-5 R$^e$; R$^b$ is independently selected from H, C$_{1-6}$ alkyl substituted with 0-5 R$^e$, C$_{2-6}$ alkenyl substituted with 0-5 R$^e$, C$_{2-6}$ alkynyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$; R$^e$ is independently selected from C$_{1-6}$ alkyl (optionally substituted with F and Cl), OH, OCH$_3$, OCF$_3$, —(CH$_2$)$_n$—C$_{3-6}$ cycloalkyl, —(CH$_2$)$_n$—C$_{4-6}$heterocyclyl, —(CH$_2$)$_n$-aryl, —(CH$_2$)$_n$-heteroaryl, F, Cl, Br, CN, NO$_2$, =O, CO$_2$H; n is independently selected from zero, 1, 2, and 3.

In another non-limiting embodiment, ring A is

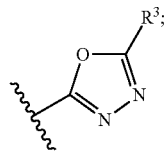

ring B is

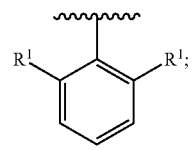

R$^1$ is OC$_{1-4}$ alkyl; R$^2$ is independently selected from: C$_{1-4}$ alkyl substituted with 0-3 R$^e$; C$_{2-4}$ alkenyl, C$_{1-6}$ cycloalkyl, and CH$_2$O(CH$_2$)$_{1-3}$CH$_3$; R$^3$ is CH$_2$—R$^5$; R$^5$ is aryl or heteroaryl selected from

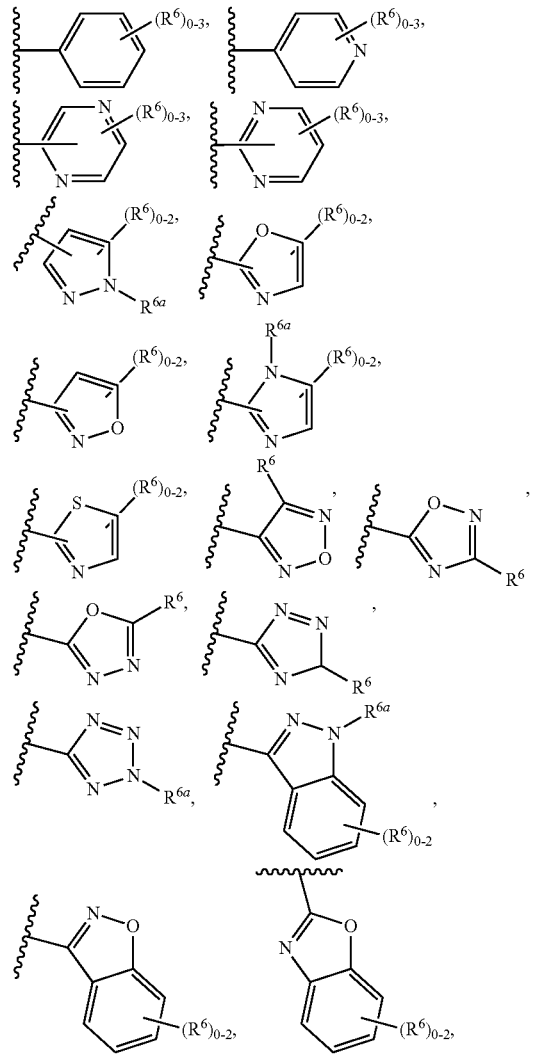

-continued

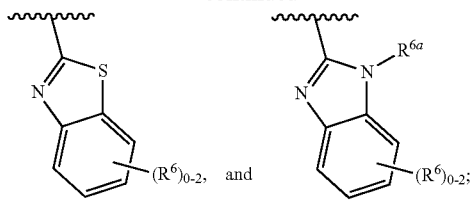

$R^6$ is independently selected from: H, F, Cl, Br, —OCH$_3$, —OCF$_3$, =O, CN, CH$_3$, CF$_3$—(CH$_2$)$_n$-aryl, —(CH$_2$)$_n$—C$_{3-6}$ cycloalkyl substituted with 0-3 R$^e$, and —(CH$_2$)$_n$-heterocyclyl substituted with 0-3 R$^e$; R$^{6a}$ is independently selected from: H, CH$_3$, R$^e$ is independently selected from C$_{1-6}$ alkyl (optionally substituted with F and Cl), OH, OCH$_3$, OCF$_3$, F, Cl, Br, CN, NO$_2$; n is independently selected from zero, 1, 2, and 3.

In another non-limiting embodiment, ring A is

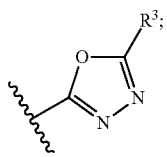

ring B is

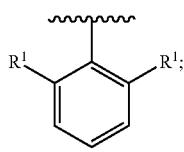

$R^1$ is OC$_{1-4}$ alkyl; $R^2$ is independently selected from: C$_{1-4}$ alkyl substituted with 0-3 R$^e$; C$_{2-4}$ alkenyl, C$_{1-6}$ cycloalkyl, and CH$_2$O(CH$_2$)$_{1-3}$CH$_3$; $R^3$ is CH$_2$—R$^5$; $R^5$ is aryl or heteroaryl selected from

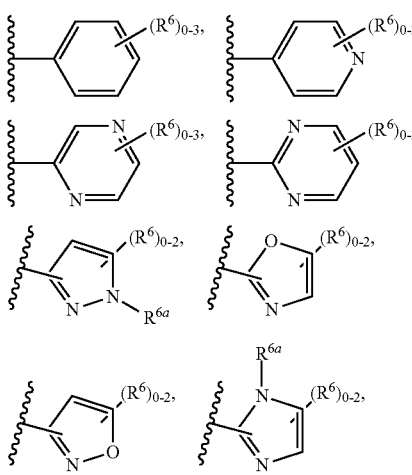

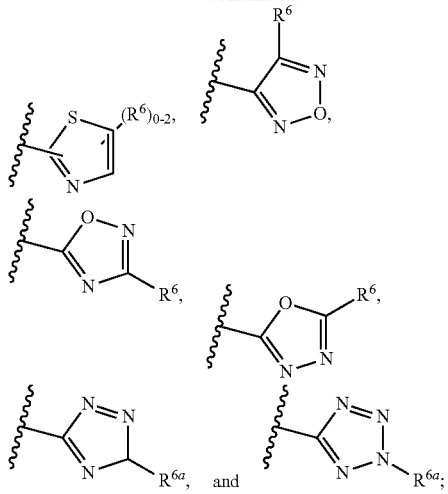

$R^6$ is independently selected from: H, F, Cl, Br, —OCH$_3$, —OCF$_3$, =O, CN, CH$_3$, CF$_3$—(CH$_2$)$_n$-aryl, —(CH$_2$)$_n$—C$_{3-6}$ cycloalkyl substituted with 0-3 R$^e$, and —(CH$_2$)$_n$-heterocyclyl substituted with 0-3 R$^e$; R$^{6a}$ is independently selected from: H, CH$_3$, R$^e$ is independently selected from C$_{1-6}$ alkyl (optionally substituted with F and Cl), OH, OCH$_3$, OCF$_3$, F, Cl, Br, CN, NO$_2$; n is independently selected from zero, 1, 2, and 3.

In another non-limiting embodiment, ring A is

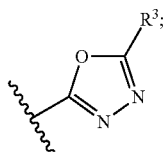

ring B is

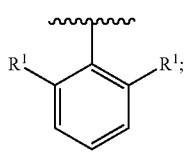

$R^1$ is OC$_{1-4}$ alkyl; $R^2$ is C$_{1-4}$ alkyl or CH$_2$O(CH$_2$)$_{1-3}$CH$_3$; $R^3$ is CH$_2$—R$^5$; $R^5$ is aryl or heteroaryl selected from

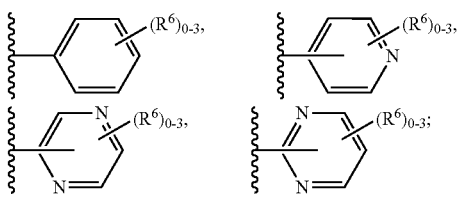

$R^6$ is independently selected from: H, F, Cl, Br, —OCH$_3$, —OCF$_3$, CN, CH$_3$, and CF$_3$.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention.

Furthermore, any elements (including individual variable definitions) of an embodiment are meant to be combined with any and all other elements from any of the embodiments to describe additional embodiments. The present invention also provides a pharmaceutical composition comprising a compound of formula I, or an enantiomer, diastereomer, or a pharmaceutically-acceptable salt, and a pharmaceutically acceptable carrier therefore.

In another embodiment, the compounds of the present invention have $EC_{50}$ values ≤10 µM, using the APJ hcAMP assay disclosed herein, preferably, $EC_{50}$ values ≤5 µM, more preferably, $EC_{50}$ values ≤1 µM, even more preferably, $EC_{50}$ values ≤0.5 µM, even more preferably, $EC_{50}$ values ≤0.1 µM, even more preferably, $EC_{50}$ values ≤0.01 µM.

In another aspect, the present invention provides compounds selected from any subset list of compounds exemplified in the present application.

In another aspect, the present invention provides compounds selected from the subset in which the APJ hcAMP $EC_{50}$ potency range is A.

In another aspect, the present invention provides compounds selected from the subset in which the APJ hcAMP $EC_{50}$ potency range is B.

In another aspect, the present invention provides compounds selected from the subset in which the APJ hcAMP $EC_{50}$ potency range is C.

In another aspect, the present invention provides a compound selected from
3-(5-benzyl-1,3,4-oxadiazol-2-yl)-6-butyl-5-(2,6-dimethoxyphenyl)pyridine-2,4-diol,
3-(5-benzyl-1,3,4-oxadiazol-2-yl)-6-butyl-5-(2,6-dimethoxy-4-methylphenyl)pyridine-2,4-diol,
6-butyl-5-(2,6-dimethoxyphenyl)-3-[5-(pyridin-4-ylmethyl)-1,3,4-oxadiazol-2-yl]pyridine-2,4-diol,
6-butyl-5-(2,6-dimethoxyphenyl)-3-[5-(2-phenylethyl)-1,3,4-oxadiazol-2-yl]pyridine-2,4-diol,
6-butyl-3-{5-[(2-chlorophenyl)methyl]-1,3,4-oxadiazol-2-yl}-5-(2,6-dimethoxyphenyl)pyridine-2,4-diol,
6-butyl-5-(2,6-dimethoxyphenyl)-3-{5-[(2-methoxyphenyl)methyl]-1,3,4-oxadiazol-2-yl}pyridine-2,4-diol,
6-butyl-5-(2,6-dimethoxyphenyl)-3-{5-[(3-methoxyphenyl)methyl]-1,3,4-oxadiazol-2-yl}pyridine-2,4-diol,
6-butyl-3-{5-[(4-chlorophenyl)methyl]-1,3,4-oxadiazol-2-yl}-5-(2,6-dimethoxyphenyl)pyridine-2,4-diol,
6-butyl-5-(2,6-dimethoxyphenyl)-3-{5-[(4-methoxyphenyl)methyl]-1,3,4-oxadiazol-2-yl}pyridine-2,4-diol,
6-butyl-3-[5-(3-chiorophenyl)-1,3,4-oxadiazol-2-yl]-5-(2,6-dimethoxyphenyl)pyridine-2,4-diol,
6-butyl-3-[5-(2-chiorophenyl)-1,3,4-oxadiazol-2-yl]-5-(2,6-dimethoxyphenyl)pyridine-2,4-diol,
6-butyl-5-(2,6-dimethoxyphenyl)-3-[5-(pyrazin-2-yl)-1,3,4-oxadiazol-2-yl]pyridine-2,4-diol,
6-butyl-5-(2,6-dimethoxyphenyl)-3-[5-(1-phenylcyclopropyl)-1,3,4-oxadiazol-2-yl]pyridine-2,4-diol,
6-butyl-3-(5-cyclopropyl-1,3,4-oxadiazol-2-yl)-5-(2,6-dimethoxyphenyl)pyridine-2,4-diol,
6-butyl-5-(2,6-dimethoxyphenyl)-3-[5-(2-phenylpropan-2-yl)-1,3,4-oxadiazol-2-yl]pyridine-2,4-diol,
6-butyl-5-(2,6-dimethoxyphenyl)-3-[5-(pyridin-3-yl)-1,3,4-oxadiazol-2-yl]pyridine-2,4-diol,
6-butyl-5-(2,6-dimethoxyphenyl)-3-[5-(phenoxymethyl)-1,3,4-oxadiazol-2-yl]pyridine-2,4-diol,
3-(5-benzyl-1,3,4-oxadiazol-2-yl)-6-(but-3-en-1-yl)-5-(2,6-dimethoxyphenyl)pyridine-2,4-diol,
6-butyl-5-(2,6-dimethoxyphenyl)-3-[5-(5-methyl-1H-pyrazol-3-yl)-1,3,4-oxadiazol-2-yl]pyridine-2,4-diol,
3-[5-(1,2-benzoxazol-3-ylmethyl)-1,3,4-oxadiazol-2-yl]-6-butyl-5-(2, 6-dimethoxyphenyl)pyridine-2,4-diol,
6-butyl-5-(2,6-dimethoxyphenyl)-3-[5-(pyrazin-2-ylmethyl)-1,3,4-oxadiazol-2-yl]pyridine-2,4-diol,
6-butyl-5-(2,6-dimethoxyphenyl)-3-[5-(pyrimidin-5-ylmethyl)-1,3,4-oxadiazol-2-yl]pyridine-2,4-diol,
6-butyl-3-{5-[(3-chlorophenyl)methyl]-1,3,4-oxadiazol-2-yl}-5-(2, 6-dimethoxyphenyl)pyridine-2,4-diol,
6-butyl-3-{5-[difluoro(phenyl)methyl]-1,3,4-oxadiazol-2-yl}-5-(2,6-dimethoxyphenyl)pyridine-2,4-diol,
3-[5-(1,3-benzoxazol-2-ylmethyl)-1,3,4-oxadiazol-2-yl]-6-butyl-5-(2,6-dimethoxyphenyl)pyridine-2,4-diol,
3-[5-(1,2-benzoxazol-3-ylmethyl)-1,3,4-oxadiazol-2-yl]-6-butyl-5-(2,6-dimethoxy-4-methylphenyl)pyridine-2,4-diol,
3-[5-(1,2-benzoxazol-3-ylmethyl)-1,3,4-oxadiazol-2-yl]-6-(but-3-en-1-yl)-5-(2,6-dimethoxyphenyl)pyridine-2,4-diol,
6-butyl-5-(2,6-dimethoxyphenyl)-3-{5-[2-(5-phenyl-1,3-oxazol-2-yl)ethyl]-1,3,4-oxadiazol-2-yl}pyridine-2,4-diol,
6-butyl-5-(2,6-dimethoxyphenyl)-3-{5-[2-(1-methyl-1H-imidazol-2-yl)ethyl]-1,3,4-oxadiazol-2-yl}pyridine-2,4-diol,
6-butyl-3-{5-[(6-chloropyridin-3-yl)methyl]-1,3,4-oxadiazol-2-yl}-5-(2,6-dimethoxyphenyl)pyridine-2,4-diol,
6-butyl-3-{5-[2-(4-chlorophenyl)propan-2-yl]-1,3,4-oxadiazol-2-yl}-5-(2,6-dimethoxyphenyl)pyridine-2,4-diol,
6-butyl-5-(2,6-dimethoxyphenyl)-3-{5-[(4-fluorophenyl)methyl]-1,3,4-oxadiazol-2-yl}pyridine-2,4-diol,
6-butyl-3-{5-[(3,4-dichlorophenyl)methyl]-1,3,4-oxadiazol-2-yl}-5-(2,6-dimethoxyphenyl)pyridine-2,4-diol,
6-butyl-5-(2,6-dimethoxyphenyl)-3-(5-{[4-fluoro-3-(trifluoromethyl)phenyl]methyl}-1,3,4-oxadiazol-2-yl)pyridine-2,4-diol,
6-butyl-3-{5-[(2,4-dichlorophenyl)methyl]-1,3,4-oxadiazol-2-yl}-5-(2,6-dimethoxyphenyl)pyridine-2,4-diol,
6-butyl-5-(2,6-dimethoxyphenyl)-3-{5-[(3,5-dimethyl-1H-pyrazol-4-yl)methyl]-1,3,4-oxadiazol-2-yl}pyridine-2,4-diol,
4-({5-[6-butyl-5-(2,6-dimethoxyphenyl)-2,4-dihydroxypyridin-3-yl]-1,3,4-oxadiazol-2-yl}methyl)benzonitrile,
6-butyl-3-{5-[(3,4-difluorophenyl)methyl]-1,3,4-oxadiazol-2-yl}-5-(2,6-dimethoxyphenyl)pyridine-2,4-diol,
6-butyl-3-(5-{[2-(4-chlorophenyl)-1,3-thiazol-4-yl]methyl}-1,3,4-oxadiazol-2-yl)-5-(2,6-dimethoxyphenyl)pyridine-2,4-diol,
6-butyl-3-{5-[1-(4-chlorophenyl)ethyl]-1,3,4-oxadiazol-2-yl}-5-(2,6-dimethoxyphenyl)pyridine-2,4-diol,
6-butyl-5-(2,6-dimethoxyphenyl)-3-{5-[(4-methyl-1,2,5-oxadiazol-3-yl)methyl]-1,3,4-oxadiazol-2-yl}pyridine-2,4-diol,
6-butyl-5-(2,6-dimethoxyphenyl)-3-[5-(4-fluorophenoxymethyl)-1,3,4-oxadiazol-2-yl]pyridine-2,4-diol,
6-butyl-5-(2,6-dimethoxyphenyl)-3-[5-(1H-indazol-3-ylmethyl)-1,3,4-oxadiazol-2-yl]pyridine-2,4-diol,
4-({5-[6-butyl-5-(2,6-dimethoxyphenyl)-2,4-dihydroxypyridin-3-yl]-1,3,4-oxadiazol-2-yl}methyl)-1,2-dihydrophthalazin-1-one,
6-butyl-5-(2,6-dimethoxyphenyl)-3-{5-[methoxy(phenyl)methyl]-1,3,4-oxadiazol-2-yl}pyridine-2,4-diol, 6-butyl-5-(2,6-dimethoxyphenyl)-3-{5-[(2-phenyl-1,3-thiazol-4-yl)methyl]-1,3,4-oxadiazol-2-yl}pyridine-2,4-diol,
3-{5-[2-(1,3-benzoxazol-2-yl)ethyl]-1,3,4-oxadiazol-2-yl}-6-butyl-5-(2,6-dimethoxyphenyl)pyridine-2,4-diol,
6-butyl-5-(2,6-dimethoxyphenyl)-3-{5-[(4-fluoro-3-methoxyphenyl)methyl]-1,3,4-oxadiazol-2-yl}pyridine-2,4-diol,
6-butyl-5-(2,6-dimethoxyphenyl)-3-[5-(1,3-thiazol-5-ylmethyl)-1,3,4-oxadiazol-2-yl]pyridine-2,4-diol,
6-butyl-3-[5-(3,4-dichlorophenoxymethyl)-1,3,4-oxadiazol-2-yl]-5-(2,6-dimethoxyphenyl)pyridine-2,4-diol,
6-butyl-5-(2,6-dimethoxyphenyl)-3-{5-[(3-methyl-1,2-oxazol-5-yl)methyl]-1,3,4-oxadiazol-2-yl}pyridine-2,4-diol,
6-butyl-5-(2,6-dimethoxyphenyl)-3-(5-{2-[3-(pyrazin-2-yl)-1,2,4-oxadiazol-5-yl]ethyl}-1,3,4-oxadiazol-2-yl)pyridine-2,4-diol,
6-butyl-3-[5-(4-chlorophenoxymethyl)-1,3,4-oxadiazol-2-yl]-5-(2,6-dimethoxyphenyl)pyridine-2,4-diol,
6-butyl-3-{5-[2-(4-chlorophenyl)-2-methylpropyl]-1,3,4-oxadiazol-2-yl}-5-(2,6-dimethoxyphenyl)pyridine-2,4-diol,
6-butyl-5-(2,6-dimethoxyphenyl)-3-(5-{[3-(pyridin-2-yl)-1,2,4-oxadiazol-5-yl]methyl}-1,3,4-oxadiazol-2-yl)pyridine-2,4-diol,
6-butyl-5-(2,6-dimethoxyphenyl)-3-(5-{[4-(trifluoromethoxy)phenyl]methyl}-1,3,4-oxadiazol-2-yl)pyridine-2,4-diol,
6-butyl-5-(2,6-dimethoxyphenyl)-3-(5-{[3-fluoro-5-(trifluoromethyl)phenyl]methyl}-1,3,4-oxadiazol-2-yl)pyridine-2,4-diol,
6-butyl-5-(2,6-dimethoxyphenyl)-3-{5-[2-(1-methyl-1H-1,3-benzodiazol-2-yl)ethyl]-1,3,4-oxadiazol-2-yl}pyridine-2,4-diol,
6-butyl-3-{5-[(2-chloropyridin-4-yl)methyl]-1,3,4-oxadiazol-2-yl}-5-(2,6-dimethoxyphenyl)pyridine-2,4-diol,
6-butyl-5-(2,6-dimethoxyphenyl)-3-(5-{2-[3-(4-methoxyphenyl)-1,2,4-oxadiazol-5-yl]ethyl}-1,3,4-oxadiazol-2-yl)pyridine-2,4-diol,
6-butyl-5-(2,6-dimethoxyphenyl)-3-[5-(1,2,3,4-tetrahydroisoquinolin-1-yl)-1,3,4-oxadiazol-2-yl]pyridine-2,4-diol,
6-butyl-3-{5-[2-(3,4-dichlorophenyl)propan-2-yl]-1,3,4-oxadiazol-2-yl}-5-(2,6-dimethoxyphenyl)pyridine-2,4-diol,
6-butyl-5-(2,6-dimethoxyphenyl)-3-{5-[(2-methyl-2H-1,2,3,4-tetrazol-5-yl)methyl]-1,3,4-oxadiazol-2-yl}pyridine-2,4-diol,
6-butyl-5-(2,6-dimethoxyphenyl)-3-[5-(2-methyl-1-phenylpropan-2-yl)-1,3,4-oxadiazol-2-yl]pyridine-2,4-diol,
6-butyl-5-(2,6-dimethoxyphenyl)-3-{5-[4-(trifluoromethyl)phenoxymethyl]-1,3,4-oxadiazol-2-yl}pyridine-2,4-diol,
6-butyl-5-(2,6-dimethoxyphenyl)-3-{5-[(5-phenyl-4H-1,2,4-triazol-3-yl)methyl]-1,3,4-oxadiazol-2-yl}pyridine-2,4-diol,
6-butyl-3-[5-(cyclohexylmethyl)-1,3,4-oxadiazol-2-yl]-5-(2,6-dimethoxyphenyl)pyridine-2,4-diol,
6-butyl-3-{5-[2-(4-chlorophenyl)ethyl]-1,3,4-oxadiazol-2-yl}-5-(2, 6-dimethoxyphenyl)pyridine-2,4-diol,
6-butyl-5-(2,6-dimethoxyphenyl)-3-[5-(oxan-4-ylmethyl)-1,3,4-oxadiazol-2-yl]pyridine-2,4-diol,
6-butyl-3-{5-[(3-chloro-4-fluorophenyl)methyl]-1,3,4-oxadiazol-2-yl}-5-(2,6-dimethoxyphenyl)pyridine-2,4-diol,
6-butyl-3-{5-[(4-chloro-3-fluorophenyl)methyl]-1,3,4-oxadiazol-2-yl}-5-(2,6-dimethoxyphenyl)pyridine-2,4-diol,
6-butyl-5-(2,6-dimethoxyphenyl)-3-{5-[2-(1,3-thiazol-2-yl)ethyl]-1,3,4-oxadiazol-2-yl}pyridine-2,4-diol,
6-butyl-5-(2,6-dimethoxyphenyl)-3-(5-{[3-(trifluoromethyl)phenyl]methyl}-1,3,4-oxadiazol-2-yl)pyridine-2,4-diol,
6-butyl-3-{5-[2-(3,4-difluorophenyl)ethyl]-1,3,4-oxadiazol-2-yl}-5-(2,6-dimethoxyphenyl)pyridine-2,4-diol,
6-butyl-5-(2,6-dimethoxyphenyl)-3-(5-{2-[4-(trifluoromethyl)phenyl]ethyl}-1,3,4-oxadiazol-2-yl)pyridine-2,4-diol,
6-butyl-3-[5-(3,4-difluorophenoxymethyl)-1,3,4-oxadiazol-2-yl]-5-(2,6-dimethoxyphenyl)pyridine-2,4-diol,
6-butyl-5-(2,6-dimethoxyphenyl)-3-{5-[2-(3-phenyl-1,2,4-oxadiazol-5-yl)ethyl]-1,3,4-oxadiazol-2-yl}pyridine-2,4-diol,
6-butyl-5-(2,6-dimethoxyphenyl)-3-{5-[(1-phenyl-1H-pyrazol-4-yl)methyl]-1,3,4-oxadiazol-2-yl}pyridine-2,4-diol,
6-butyl-5-(2,6-dimethoxyphenyl)-3-{5-[(2-methyl-1,3-thiazol-4-yl)methyl]-1,3,4-oxadiazol-2-yl}pyridine-2,4-diol,
6-butyl-5-(2,6-dimethoxyphenyl)-3-(5-{[4-(trifluoromethyl)phenyl]methyl}-1,3,4-oxadiazol-2-yl)pyridine-2,4-diol,
6-butyl-5-(2,6-dimethoxyphenyl)-3-{5-[2-(pyrimidin-2-yl)ethyl]-1,3,4-oxadiazol-2-yl}pyridine-2,4-diol,
3-{5-[2-(1,3-benzothiazol-2-yl)ethyl]-1,3,4-oxadiazol-2-yl}-6-butyl-5-(2,6-dimethoxyphenyl)pyridine-2,4-diol,
6-butyl-5-(2,6-dimethoxyphenyl)-3-(5-{2-[3-(pyridin-2-yl)-1,2,4-oxadiazol-5-yl]ethyl}-1,3,4-oxadiazol-2-yl)pyridine-2,4-diol,
6-butyl-5-(2,6-dimethoxyphenyl)-3-{5-[(5-methyl-2-phenyl-1,3-thiazol-4-yl)methyl]-1,3,4-oxadiazol-2-yl}pyridine-2,4-diol,
6-butyl-3-{5-[2-(3,4-dichlorophenyl)ethyl]-1,3,4-oxadiazol-2-yl}-5-(2,6-dimethoxyphenyl)pyridine-2,4-diol,
3-[5-(1,2-benzoxazol-3-ylmethyl)-1,3,4-oxadiazol-2-yl]-6-butyl-5-(2,6-dichlorophenyl)pyridine-2,4-diol,
6-butyl-3-{5-[(4-chlorophenyl)methyl]-1,3,4-oxadiazol-2-yl}-5-(2,6-dichlorophenyl)pyridine-2,4-diol,
6-butyl-5-(2,6-dimethoxyphenyl)-3-{5-[(dimethylamino)(4-fluorophenyl)methyl]-1,3,4-oxadiazol-2-yl}pyridine-2,4-diol,
3-[5-(1,2-benzoxazol-3-ylmethyl)-1,3,4-oxadiazol-2-yl]-5-(2,6-dimethoxyphenyl)-6-(ethoxymethyl)pyridine-2,4-diol,
3-{5-[(4-chlorophenyl)methyl]-1,3,4-oxadiazol-2-yl}-5-(2,6-dimethoxyphenyl)-6-(ethoxymethyl)pyridine-2,4-diol,
6-butyl-5-(2,6-dimethoxyphenyl)-3-{5-[(5-methyl-2-phenyl-1,3-oxazol-4-yl)methyl]-1,3,4-oxadiazol-2-yl}pyridine-2,4-diol,
3-[5-(1,2-benzoxazol-3-ylmethyl)-1,3,4-oxadiazol-2-yl]-6-cyclopropyl-5-(2,6-dimethoxyphenyl)pyridine-2,4-diol,
3-{5-[(4-chlorophenyl)methyl]-1,3,4-oxadiazol-2-yl}-6-cyclopropyl-5-(2,6-dimethoxyphenyl)pyridine-2,4-diol,
6-cyclopropyl-5-(2,6-dimethoxyphenyl)-3-{5-[(2-methyl-1,3-thiazol-4-yl)methyl]-1,3,4-oxadiazol-2-yl}pyridine-2,4-diol,
6-cyclopropyl-5-(2,6-dimethoxyphenyl)-3-(5-{[3-(pyridin-2-yl)-1,2,4-oxadiazol-5-yl]methyl}-1,3,4-oxadiazol-2-yl)pyridine-2,4-diol,
ethyl 2-{5-[6-butyl-5-(2,6-dimethoxyphenyl)-2,4-dihydroxypyridin-3-yl]-1,3,4-oxadiazol-2-yl}acetate,
6-butyl-5-(2,6-dimethoxyphenyl)-3-{5-[(1,3-dimethyl-1H-pyrazol-5-yl)methyl]-1,3,4-oxadiazol-2-yl}pyridine-2,4-diol,
3-({5-[6-butyl-5-(2,6-dimethoxyphenyl)-2,4-dihydroxypyridin-3-yl]-1,3,4-oxadiazol-2-yl}methyl)-1-methylimidazolidine-2,4-dione, 6-butyl-5-(2,6-dimethoxyphenyl)-3-{5-[(3-fluorophenyl)methyl]-1,3,4-oxadiazol-2-yl}pyridine-2,4-diol,
6-butyl-5-(2,6-dimethoxyphenyl)-3-[5-(piperidin-1-ylmethyl)-1,3,4-oxadiazol-2-yl]pyridine-2,4-diol,
6-butyl-5-(2,6-dimethoxyphenyl)-3-(5-{[3-(pyridin-3-yl)-1,2,4-oxadiazol-5-yl]methyl}-1,3,4-oxadiazol-2-yl)pyridine-2,4-diol,
6-butyl-5-(2,6-dimethoxyphenyl)-3-{5-[(1-methyl-1H-pyrazol-4-yl)methyl]-1,3,4-oxadiazol-2-yl}pyridine-2,4-diol,
6-butyl-3-{5-[(4-chloro-2-fluorophenyl)methyl]-1,3,4-oxadiazol-2-yl}-5-(2, 6-dimethoxyphenyl)pyridine-2,4-diol,
6-butyl-5-(2,6-dimethoxyphenyl)-3-(5-{[3-(pyridin-4-yl)-1,2,4-oxadiazol-5-yl]methyl}-1,3,4-oxadiazol-2-yl)pyridine-2,4-diol,
1-({5-[6-butyl-5-(2,6-dimethoxyphenyl)-2,4-dihydroxypyridin-3-yl]-1,3,4-oxadiazol-2-yl}methyl)pyrrolidin-2-one,
5-(2,6-dimethoxyphenyl)-6-(ethoxymethyl)-3-{5-[(2-methyl-1,3-thiazol-4-yl)methyl]-1,3,4-oxadiazol-2-yl}pyridine-2,4-diol,
5-(2,6-dimethoxyphenyl)-6-(ethoxymethyl)-3-(5-{[5-(pyridin-2-yl)-1,2,4-oxadiazol-3-yl]methyl}-1,3,4-oxadiazol-2-yl)pyridine-2,4-diol,
3-{5-[(3-benzyl-1,2,4-oxadiazol-5-yl)methyl]-1,3,4-oxadiazol-2-yl}-6-butyl-5-(2,6-dimethoxyphenyl)pyridine-2,4-diol,
6-butyl-3-{5-[(3-cyclopropyl-1,2,4-oxadiazol-5-yl)methyl]-1,3,4-oxadiazol-2-yl}-5-(2,6-dimethoxyphenyl)pyridine-2,4-diol,
3-{5-[(6-chloropyridin-3-yl)methyl]-1,3,4-oxadiazol-2-yl}-5-(2, 6-dimethoxyphenyl)-6-(ethoxymethyl)pyridine-2,4-diol,
6-butyl-5-(2,6-dimethoxyphenyl)-3-{5-[(3-phenyl-1,2,4-oxadiazol-5-yl)methyl]-1,3,4-oxadiazol-2-yl}pyridine-2,4-diol,
1-({5-[5-(2,6-dimethoxyphenyl)-6-(ethoxymethyl)-2,4-dihydroxypyridin-3-yl]-1,3,4-oxadiazol-2-yl}methyl)pyrrolidin-2-one,
3-({5-[6-butyl-5-(2,6-dimethoxyphenyl)-2,4-dihydroxypyridin-3-yl]-1,3,4-oxadiazol-2-yl}methyl)imidazolidine-2,4-dione,
1-({5-[6-butyl-5-(2,6-dimethoxyphenyl)-2,4-dihydroxypyridin-3-yl]-1,3,4-oxadiazol-2-yl}methyl)-1,2-dihydropyridin-2-one,
6-butyl-5-(2,6-dimethoxyphenyl)-3-[5-(1H-imidazol-1-ylmethyl)-1,3,4-oxadiazol-2-yl]pyridine-2,4-diol,
3-({5-[6-butyl-5-(2,6-dimethoxyphenyl)-2,4-dihydroxypyridin-3-yl]-1,3,4-oxadiazol-2-yl}methyl)-1,3-oxazolidin-2-one,
4-({5-[6-butyl-5-(2,6-dimethoxyphenyl)-2,4-dihydroxypyridin-3-yl]-1,3,4-oxadiazol-2-yl}methyl)morpholin-3-one,
tert-butyl 2-{5-[6-butyl-5-(2,6-dimethoxyphenyl)-2,4-dihydroxypyridin-3-yl]-1,3,4-oxadiazol-2-yl}acetate,
1-({5-[5-(2,6-dimethoxyphenyl)-6-(ethoxymethyl)-2,4-dihydroxypyridin-3-yl]-1,3,4-oxadiazol-2-yl}methyl)-1,2-dihydropyridin-2-one,
tert-butyl N-({5-[6-butyl-5-(2,6-dimethoxyphenyl)-2,4-dihydroxypyridin-3-yl]-1,3,4-oxadiazol-2-yl}methyl)carbamate,
tert-butyl N-({5-[6-butyl-5-(2,6-dimethoxyphenyl)-2,4-dihydroxypyridin-3-yl]-1,3,4-oxadiazol-2-yl}methyl)-N-methylcarbamate,
3-{5-[(4-chloro-3-fluorophenyl)methyl]-1,3,4-oxadiazol-2-yl}-5-(2,6-dimethoxyphenyl)-6-(ethoxymethyl)pyridine-2,4-diol,
3-{5-[(4-chloro-2-fluorophenyl)methyl]-1,3,4-oxadiazol-2-yl}-5-(2,6-dimethoxyphenyl)-6-(ethoxymethyl)pyridine-2,4-diol,
5-(2,6-dimethoxyphenyl)-6-(ethoxymethyl)-3-{5-[(5-fluoropyridin-2-yl)methyl]-1,3,4-oxadiazol-2-yl}pyridine-2,4-diol,
5-(2,6-dimethoxyphenyl)-6-(ethoxymethyl)-3-[5-(1H-imidazol-1-ylmethyl)-1,3,4-oxadiazol-2-yl]pyridine-2,4-diol,
5-(2,6-dimethoxyphenyl)-6-(ethoxymethyl)-3-{5-[(3-fluoro-4-methylphenyl)methyl]-1,3,4-oxadiazol-2-yl}pyridine-2,4-diol,
3-{5-[(5-chloropyridin-2-yl)methyl]-1,3,4-oxadiazol-2-yl}-5-(2,6-dimethoxyphenyl)-6-(ethoxymethyl)pyridine-2,4-diol,
5-(2,6-dimethoxyphenyl)-6-(ethoxymethyl)-3-{5-[(3-phenyl-1H-pyrazol-1-yl)methyl]-1,3,4-oxadiazol-2-yl}pyridine-2,4-diol,
5-(2,6-dimethoxyphenyl)-6-(ethoxymethyl)-3-(5-{[3-(trifluoromethyl)-1H-pyrazol-1-yl]methyl}-1,3,4-oxadiazol-2-yl)pyridine-2,4-diol,
5-(2,6-dimethoxyphenyl)-6-(ethoxymethyl)-3-{5-[(1-methyl-1H-pyrazol-4-yl)methyl]-1,3,4-oxadiazol-2-yl}pyridine-2,4-diol,
5-(2,6-dimethoxyphenyl)-6-(ethoxymethyl)-3-{5-[(6-fluoropyridin-3-yl)methyl]-1,3,4-oxadiazol-2-yl}pyridine-2,4-diol,
5-(2,6-dimethoxyphenyl)-6-(ethoxymethyl)-3-[5-(1H-indazol-3-ylmethyl)-1,3,4-oxadiazol-2-yl]pyridine-2,4-diol,
3-[5-(1H-1,2,3-benzotriazol-1-ylmethyl)-1,3,4-oxadiazol-2-yl]-5-(2,6-dimethoxyphenyl)-6-(ethoxymethyl)pyridine-2,4-diol,
5-(2,6-dimethoxyphenyl)-6-(ethoxymethyl)-3-[5-(1H-indazol-1-ylmethyl)-1,3,4-oxadiazol-2-yl]pyridine-2,4-diol,
5-(2,6-dimethoxyphenyl)-6-(ethoxymethyl)-3-{5-[(4-fluorophenyl)methyl]-1,3,4-oxadiazol-2-yl}pyridine-2,4-diol,
5-(2,6-dimethoxyphenyl)-6-(ethoxymethyl)-3-[5-(1H-indol-1-ylmethyl)-1,3,4-oxadiazol-2-yl]pyridine-2,4-diol,
6-butyl-5-(3-ethylphenyl)-4-hydroxy-3-{5-[(2-methyl-1,3-thiazol-4-yl)methyl]-1,3,4-oxadiazol-2-yl}-1,2-dihydropyridin-2-one,
3-[5-(1,2-benzoxazol-3-ylmethyl)-1,3,4-oxadiazol-2-yl]-6-butyl-5-phenylpyridine-2,4-diol,
6-butyl-3-{5-[(3,4-difluorophenyl)methyl]-1,3,4-oxadiazol-2-yl}-5-(3-methoxyphenyl)pyridine-2,4-diol,
6-butyl-3-{5-[(3,4-difluorophenyl)methyl]-1,3,4-oxadiazol-2-yl}-5-(3-ethylphenyl)pyridine-2,4-diol,
6-butyl-3-{5-[(3,4-difluorophenyl)methyl]-1,3,4-oxadiazol-2-yl}-5-[3-(trifluoromethoxy)phenyl]pyridine-2,4-diol,
5-[3-(benzyloxy)phenyl]-6-butyl-3-{5-[(3,4-difluorophenyl)methyl]-1,3,4-oxadiazol-2-yl}pyridine-2,4-diol,
6-butyl-3-{5-[(3,4-difluorophenyl)methyl]-1,3,4-oxadiazol-2-yl}-5-[3-(hydroxymethyl)phenyl]pyridine-2,4-diol,
6-butyl-5-(cyclohex-1-en-1-yl)-3-{5-[(3,4-difluorophenyl)methyl]-1,3,4-oxadiazol-2-yl}pyridine-2,4-diol,
6-butyl-3-{5-[(3,4-difluorophenyl)methyl]-1,3,4-oxadiazol-2-yl}-5-[3-(propan-2-yl)phenyl]pyridine-2,4-diol,
6-butyl-3-{5-[(3,4-difluorophenyl)methyl]-1,3,4-oxadiazol-2-yl}-5-[3-(methoxymethyl)phenyl]pyridine-2,4-diol,
3-(2-butyl-5-{5-[(3,4-difluorophenyl)methyl]-1,3,4-oxadiazol-2-yl}-4,6-dihydroxypyridin-3-yl)-N-(propan-2-yl)benzamide,
6-butyl-4-hydroxy-3-{5-[(2-methyl-1,3-thiazol-4-yl)methyl]-1,3,4-oxadiazol-2-yl}-5-[3-(propan-2-yl)phenyl]-1,2-dihydropyridin-2-one, 3-(2-butyl-4-hydroxy-5-{5-[(2-methyl-1,3-thiazol-4-yl) methyl]-1,3,4-oxadiazol-2-yl}-6-oxo-1,6-dihydropyridin-3-yl)-N-(propan-2-yl)benzamide, 6-butyl-5-(3-cyclopropylphenyl)-4-hydroxy-3-{5-[(2-methyl-1,3-thiazol-4-yl)methyl]-1,3,4-oxadiazol-2-yl}-1,2-dihydropyridin-2-one, 6-butyl-4-hydroxy-5-(3-methoxyphenyl)-3-{5-[(2-methyl-1,3-thiazol-4-yl)methyl]-1,3,4-oxadiazol-2-yl}-1,2-dihydropyridin-2-one, 6-butyl-4-hydroxy-5-[3-(hydroxymethyl)phenyl]-3-{5-[(2-methyl-1,3-thiazol-4-yl)methyl]-1,3,4-oxadiazol-2-yl}-1,2-dihydropyridin-2-one, 6-butyl-4-hydroxy-3-{5-[(2-methyl-1,3-thiazol-4-yl)methyl]-1,3,4-oxadiazol-2-yl}-5-[3-(pyrrolidin-1-yl)phenyl]-1,2-dihydropyridin-2-one, 6-butyl-5-(2,6-dimethoxyphenyl)-3-{5-[(methylamino)methyl]-1,3,4-oxadiazol-2-yl}pyridine-2,4-diol, N-({5-[6-butyl-5-(2,6-dimethoxyphenyl)-2,4-dihydroxypyridin-3-yl]-1,3,4-oxadiazol-2-yl}methyl)-N-methyl-2-phenylacetamide, N-({5-[6-butyl-5-(2,6-dimethoxyphenyl)-2,4-dihydroxypyridin-3-yl]-1,3,4-oxadiazol-2-yl}methyl)-3-chloro-N-methylbenzamide, N-({5-[6-butyl-5-(2,6-dimethoxyphenyl)-2,4-dihydroxypyridin-3-yl]-1,3,4-oxadiazol-2-yl}methyl)-N-methylpyridine-2-carb oxamide, N-({5-[6-butyl-5-(2,6-dimethoxyphenyl)-2,4-dihydroxypyridin-3-yl]-1,3,4-oxadiazol-2-yl}methyl)-2-methoxyacetamide, N-({5-[6-butyl-5-(2,6-dimethoxyphenyl)-2,4-dihydroxypyridin-3-yl]-1,3,4-oxadiazol-2-yl}methyl)-N-methylpyridine-4-carb oxamide, N-({5-[6-butyl-5-(2,6-dimethoxyphenyl)-2,4-dihydroxypyridin-3-yl]-1,3,4-oxadiazol-2-yl}methyl)pyridine-3-carboxamide, N-({5-[6-butyl-5-(2,6-dimethoxyphenyl)-2,4-dihydroxypyridin-3-yl]-1,3,4-oxadiazol-2-yl}methyl)-2-chloro-N-methylbenzamide, N-({5-[6-butyl-5-(2,6-dimethoxyphenyl)-2,4-dihydroxypyridin-3-yl]-1,3,4-oxadiazol-2-yl}methyl)-3-chlorobenzamide, N-({5-[6-butyl-5-(2,6-dimethoxyphenyl)-2,4-dihydroxypyridin-3-yl]-1,3,4-oxadiazol-2-yl}methyl)-4-chlorobenzamide, N-({5-[6-butyl-5-(2,6-dimethoxyphenyl)-2,4-dihydroxypyridin-3-yl]-1,3,4-oxadiazol-2-yl}methyl)pyridine-4-carboxamide, N-({5-[6-butyl-5-(2,6-dimethoxyphenyl)-2,4-dihydroxypyridin-3-yl]-1,3,4-oxadiazol-2-yl}methyl)-N-methylpyridine-3-carb oxamide, N-({5-[6-butyl-5-(2,6-dimethoxyphenyl)-2,4-dihydroxypyridin-3-yl]-1,3,4-oxadiazol-2-yl}methyl)-2-phenyl acetamide, N-({5-[6-butyl-5-(2,6-dimethoxyphenyl)-2,4-dihydroxypyridin-3-yl]-1,3,4-oxadiazol-2-yl}methyl)-2,2-dimethylpropanamide, N-({5-[6-butyl-5-(2,6-dimethoxyphenyl)-2,4-dihydroxypyridin-3-yl]-1,3,4-oxadiazol-2-yl}methyl)pyridine-2-carboxamide, N-({5-[6-butyl-5-(2,6-dimethoxyphenyl)-2,4-dihydroxypyridin-3-yl]-1,3,4-oxadiazol-2-yl}methyl)-N,2,2-trimethylpropanamide, 3-[5-(aminomethyl)-1,3,4-oxadiazol-2-yl]-6-butyl-5-(2,6-dimethoxyphenyl)pyridine-2,4-diol, N-({5-[6-butyl-5-(2,6-dimethoxyphenyl)-2,4-dihydroxypyridin-3-yl]-1,3,4-oxadiazol-2-yl}methyl)benzamide, N-({5-[6-butyl-5-(2,6-dimethoxyphenyl)-2,4-dihydroxypyridin-3-yl]-1,3,4-oxadiazol-2-yl}methyl)-N-methylbenzamide, N-({5-[5-(2,6-dimethoxyphenyl)-6-(ethoxymethyl)-2,4-dihydroxypyridin-3-yl]-1,3,4-oxadiazol-2-yl}methyl)benzamide, N-({5-[6-butyl-5-(2,6-dimethoxyphenyl)-2,4-dihydroxypyridin-3-yl]-1,3,4-oxadiazol-2-yl}methyl)-3-methylbutanamide, N-({5-[6-butyl-5-(2,6-dimethoxyphenyl)-2,4-dihydroxypyridin-3-yl]-1,3,4-oxadiazol-2-yl}methyl)acetamide, N-({5-[6-butyl-5-(2,6-dimethoxyphenyl)-2,4-dihydroxypyridin-3-yl]-1,3,4-oxadiazol-2-yl}methyl)-2,2,2-trifluoroacetamide, 2-{5-[6-butyl-5-(2,6-dimethoxyphenyl)-2,4-dihydroxypyridin-3-yl]-1,3,4-oxadiazol-2-yl}-N,N-diethyl acetamide, 2-{5-[6-butyl-5-(2,6-dimethoxyphenyl)-2,4-dihydroxypyridin-3-yl]-1,3,4-oxadiazol-2-yl}-N-(pyridin-2-ylmethyl)acetamide, 2-{5-[6-butyl-5-(2,6-dimethoxyphenyl)-2,4-dihydroxypyridin-3-yl]-1,3,4-oxadiazol-2-yl}-N-methylacetamide, 2-{5-[6-butyl-5-(2,6-dimethoxyphenyl)-2,4-dihydroxypyridin-3-yl]-1,3,4-oxadiazol-2-yl}acetamide, 2-{5-[6-butyl-5-(2,6-dimethoxyphenyl)-2,4-dihydroxypyridin-3-yl]-1,3,4-oxadiazol-2-yl}-N-(propan-2-yl)acetamide, 2-{5-[6-butyl-5-(2,6-dimethoxyphenyl)-2,4-dihydroxypyridin-3-yl]-1,3,4-oxadiazol-2-yl}-N,N-dimethylacetamide, 2-{5-[6-butyl-5-(2,6-dimethoxyphenyl)-2,4-dihydroxypyridin-3-yl]-1,3,4-oxadiazol-2-yl}-N-(4-methoxyphenyl)acetamide, 4-(2-{5-[6-butyl-5-(2,6-dimethoxyphenyl)-2,4-dihydroxypyridin-3-yl]-1,3,4-oxadiazol-2-yl}acetyl)piperazin-2-one, 2-{5-[6-butyl-5-(2,6-dimethoxyphenyl)-2,4-dihydroxypyridin-3-yl]-1,3,4-oxadiazol-2-yl}-1-(4-methylpiperazin-1-yl)ethan-1-one, N-benzyl-2-{5-[6-butyl-5-(2,6-dimethoxyphenyl)-2,4-dihydroxypyridin-3-yl]-1,3,4-oxadiazol-2-yl}acetamide, 2-{5-[6-butyl-5-(2,6-dimethoxyphenyl)-2,4-dihydroxypyridin-3-yl]-1,3,4-oxadiazol-2-yl}-N-ethylacetamide, 2-{5-[6-butyl-5-(2,6-dimethoxyphenyl)-2,4-dihydroxypyridin-3-yl]-1,3,4-oxadiazol-2-yl}-N-cyclopropylacetamide, 2-{5-[6-butyl-5-(2,6-dimethoxyphenyl)-2,4-dihydroxypyridin-3-yl]-1,3,4-oxadiazol-2-yl}-N-propylacetamide, 2-{5-[6-butyl-5-(2,6-dimethoxyphenyl)-2,4-dihydroxypyridin-3-yl]-1,3,4-oxadiazol-2-yl}-N-(2-fluoroethyl)acetamide, 2-{5-[6-butyl-5-(2,6-dimethoxyphenyl)-2,4-dihydroxypyridin-3-yl]-1,3,4-oxadiazol-2-yl}-N-(2,2-difluoroethyl)acetamide, 2-{5-[6-butyl-5-(2,6-dimethoxyphenyl)-2,4-dihydroxypyridin-3-yl]-1,3,4-oxadiazol-2-yl}-N-(2,2,2-trifluoroethyl)acetamide, 2-{5-[6-butyl-5-(2,6-dimethoxyphenyl)-2,4-dihydroxypyridin-3-yl]-1,3,4-oxadiazol-2-yl}-N-(2-methoxyethyl)acetamide, 2-{5-[6-butyl-5-(2,6-dimethoxyphenyl)-2,4-dihydroxypyridin-3-yl]-1,3,4-oxadiazol-2-yl}-1-(pyrrolidin-1-yl)ethan-1-one, 2-{5-[6-butyl-5-(2,6-dimethoxyphenyl)-2,4-dihydroxypyridin-3-yl]-1,3,4-oxadiazol-2-yl}-1-(piperidin-1-yl)ethan-1-one, 2-{5-[6-butyl-5-(2,6-dimethoxyphenyl)-2,4-dihydroxypyridin-3-yl]-1,3,4-oxadiazol-2-yl}-1-(morpholin-4-yl)ethan-1-one, N-butyl-2-{5-[6-butyl-5-(2,6-dimethoxyphenyl)-2,4-dihydroxypyridin-3-yl]-1,3,4-oxadiazol-2-yl}acetamide,
2-{5-[6-butyl-5-(2,6-dimethoxyphenyl)-2,4-dihydroxypyridin-3-yl]-1,3,4-oxadiazol-2-yl}-N-pentylacetamide,
2-{5-[6-butyl-5-(2,6-dimethoxyphenyl)-2,4-dihydroxypyridin-3-yl]-1,3,4-oxadiazol-2-yl}-1-(3-fluoroazetidin-1-yl)ethan-1-one,
2-{5-[6-butyl-5-(2,6-dimethoxyphenyl)-2,4-dihydroxypyridin-3-yl]-1,3,4-oxadiazol-2-yl}-1-(3,3-difluoroazetidin-1-yl)ethan-1-one,
2-{5-[6-butyl-5-(2,6-dimethoxyphenyl)-2,4-dihydroxypyridin-3-yl]-1,3,4-oxadiazol-2-yl}-N-(1,3-thiazol-2-yl)acetamide,
3-(3-benzyl-1,2,4-oxadiazol-5-yl)-6-butyl-5-(2,6-dimethoxyphenyl)pyridine-2,4-diol,
6-butyl-3-{3-[(4-chlorophenyl)methyl]-1,2,4-oxadiazol-5-yl}-5-(2, 6-dimethoxyphenyl)pyridine-2,4-diol,
3-(5-benzyl-4H-1,2,4-triazol-3-yl)-6-butyl-5-(2,6-dimethoxyphenyl)pyridine-2,4-diol,
6-butyl-3-(5-{[5-(4-chlorophenyl)-1,3,4-oxadiazol-2-yl]methyl}-1,3,4-oxadiazol-2-yl)-5-(2,6-dimethoxyphenyl)pyridine-2,4-diol,
6-butyl-5-(2,6-dimethoxyphenyl)-3-(5-{[5-(pyridin-4-yl)-1,3,4-oxadiazol-2-yl]methyl}-1,3,4-oxadiazol-2-yl)pyridine-2,4-diol,
6-butyl-5-(2,6-dimethoxyphenyl)-3-(5-{[5-(pyridin-2-yl)-1,3,4-oxadiazol-2-yl]methyl}-1,3,4-oxadiazol-2-yl)pyridine-2,4-diol,
6-butyl-3-(5-{[5-(2-chlorophenyl)-1,3,4-oxadiazol-2-yl]methyl}-1,3,4-oxadiazol-2-yl)-5-(2,6-dimethoxyphenyl)pyridine-2,4-diol,
3-{5-[(5-benzyl-1,3,4-oxadiazol-2-yl)methyl]-1,3,4-oxadiazol-2-yl}-6-butyl-5-(2,6-dimethoxyphenyl)pyridine-2,4-diol,
6-butyl-3-(5-{[5-(3-chlorophenyl)-1,3,4-oxadiazol-2-yl]methyl}-1,3,4-oxadiazol-2-yl)-5-(2,6-dimethoxyphenyl)pyridine-2,4-diol,
6-butyl-5-(2,6-dimethoxyphenyl)-3-(5-{[5-(pyridin-3-yl)-1,3,4-oxadiazol-2-yl]methyl}-1,3,4-oxadiazol-2-yl)pyridine-2,4-diol,
1-({5-[6-(ethoxymethyl)-5-(4-fluoro-2,6-dimethoxyphenyl)-2,4-dihydroxypyridin-3-yl]-1,3,4-oxadiazol-2-yl}methyl)-1,2-dihydropyridin-2-one,
3-[5-(1,2-benzoxazol-3-ylmethyl)-1,3,4-oxadiazol-2-yl]-6-(ethoxymethyl)-5-(4-fluoro-2,6-dimethoxyphenyl)pyridine-2,4-diol,
3-{5-[(4-chlorophenyl)methyl]-1,3,4-oxadiazol-2-yl}-6-(ethoxymethyl)-5-(4-fluoro-2,6-dimethoxyphenyl)pyridine-2,4-diol,
1-({5-[6-(ethoxymethyl)-5-(4-fluoro-2,6-dimethoxyphenyl)-2,4-dihydroxypyridin-3-yl]-1,3,4-oxadiazol-2-yl}methyl)pyrrolidin-2-one,
3-{5-[(6-chloropyridin-3-yl)methyl]-1,3,4-oxadiazol-2-yl}-6-(ethoxymethyl)-5-(4-fluoro-2,6-dimethoxyphenyl)pyridine-2,4-diol,
3-{5-[(4-chlorophenyl)methyl]-1,3,4-oxadiazol-2-yl}-5-(3,5-dimethoxypyridin-4-yl)-6-(ethoxymethyl)pyridine-2,4-diol,
6-butyl-3-{5-[(4-chlorophenyl)methyl]-1,3,4-oxadiazol-2-yl}-5-(3-fluoro-2, 6-dimethoxyphenyl)pyridine-2,4-diol,
3-[5-(1,2-benzoxazol-3-ylmethyl)-1,3,4-oxadiazol-2-yl]-6-butyl-5-(3-fluoro-2,6-dimethoxyphenyl)pyridine-2,4-diol,
3-{5-[(4-chlorophenyl)methyl]-1,3,4-oxadiazol-2-yl}-6-(ethoxymethyl)-5-(2-hydroxy-6-methoxyphenyl)pyridine-2,4-diol,
3-[5-(1,2-benzoxazol-3-ylmethyl)-1,3,4-oxadiazol-2-yl]-6-butyl-5-(2, 6-dimethylphenyl)pyridine-2,4-diol,
3-[5-(1,2-benzoxazol-3-ylmethyl)-1,3,4-oxadiazol-2-yl]-6-butyl-5-(2,4,6-trimethylphenyl)pyridine-2,4-diol,
3-[5-(1,2-benzoxazol-3-ylmethyl)-1,3,4-oxadiazol-2-yl]-6-butyl-5-(2, 6-diethylphenyl)pyridine-2,4-diol,
6-butyl-5-(2,6-dimethoxyphenyl)-3-(5-{[1,2]oxazolo[4,5-b]pyridin-3-ylmethyl}-1,3,4-oxadiazol-2-yl)pyridine-2,4-diol,
5-(2,6-dimethoxyphenyl)-6-(ethoxymethyl)-3-(5-{[1,2]oxazolo[4,5-b]pyridin-3-ylmethyl}-1,3,4-oxadiazol-2-yl)pyridine-2,4-diol,
3-{5-[(4-chlorophenyl)methyl]-1,3,4-oxadiazol-2-yl}-5-(2, 6-dihydroxyphenyl)-6-(ethoxymethyl)pyridine-2,4-diol,
3-{5-[(5-chloropyridin-2-yl)methyl]-1,3,4-oxadiazol-2-yl}-5-(2,6-dimethoxyphenyl)-6-[(ethyl amino)methyl]pyridine-2,4-diol,
3-{5-[(1,2-benzoxazol-3-yl)methyl]-1,3,4-thiadiazol-2-yl}-5-(2,6-dimethoxyphenyl)-6-(ethoxymethyl)pyridine-2,4-diol,
3-{5-[(5-chloropyridin-2-yl)methyl]-1,3,4-thiadiazol-2-yl}-5-(2,6-dimethoxyphenyl)-6-(ethoxymethyl)pyridine-2,4-diol,
3-{5-[(5-chloropyridin-2-yl)methyl]-1,3,4-thiadiazol-2-yl}-6-cyclopentyl-5-(2, 6-dimethoxyphenyl)pyridine-2,4-diol,
3-{5-[(4-chlorophenyl)methyl]-1,3,4-thiadiazol-2-yl}-5-(2, 6-dimethoxyphenyl)-6-(ethoxymethyl)pyridine-2,4-diol,
N-({5-[5-(2,6-dimethoxyphenyl)-6-(ethoxymethyl)-2,4-dihydroxypyridin-3-yl]-1,3,4-thiadiazol-2-yl}methyl)pyridine-2-carboxamide,
6-butyl-3-{5-[(5-chloro-3-fluoropyridin-2-yl)methyl]-1,3,4-oxadiazol-2-yl}-5-(2,6-dimethoxyphenyl)pyridine-2,4-diol,
3-{5-[(5-chloro-3-fluoropyridin-2-yl)methyl]-1,3,4-oxadiazol-2-yl}-5-(2, 6-dimethoxyphenyl)-6-(ethoxymethyl)pyridine-2,4-diol,
3-{5-[(5-chloropyridin-2-yl)methyl]-1,3,4-oxadiazol-2-yl}-6-cyclopentyl-5-(2,6-dimethoxyphenyl)pyridine-2,4-diol,
3-{5-[(4-chlorophenyl)methyl]-1,3,4-oxadiazol-2-yl}-6-cyclopentyl-5-(2,6-dimethoxyphenyl)pyridine-2,4-diol,
3-{5-[(5-chloropyridin-2-yl)methyl]-1,3,4-oxadiazol-2-yl}-5-(2,6-dimethoxyphenyl)-6-[(2-methoxyethoxy)methyl]pyridine-2,4-diol,
3-{5-[(1,2-benzoxazol-3-yl)methyl]-1,3,4-oxadiazol-2-yl}-5-(2,6-dimethoxyphenyl)-6-[(2-methoxyethoxy)methyl]pyridine-2,4-diol,
5-(2,6-dimethoxyphenyl)-6-(ethoxymethyl)-3-{5-[(phenylamino)methyl]-1,3,4-oxadiazol-2-yl}pyridine-2,4-diol,
3-{5-[(4-chlorophenyl)methyl]-1,3,4-oxadiazol-2-yl}-5-(2, 6-dimethoxyphenyl)-6-[(2-methoxyethoxy)methyl]pyridine-2,4-diol,
N-({5-[6-butyl-5-(2, 5-dimethoxyphenyl)-2,4-dihydroxypyridin-3-yl]-1,3,4-oxadiazol-2-yl}methyl)benzamide,
N-[(5-{6-butyl-2,4-dihydroxy-5-[2-methoxy-5-(propan-2-yl)phenyl]pyridin-3-yl}-1,3,4-oxadiazol-2-yl)methyl]benzamide,
3-{5-[(1,2-benzoxazol-3-yl)methyl]-1,3,4-oxadiazol-2-yl}-6-(ethoxymethyl)-5-(2-methoxyphenyl)pyridine-2,4-diol,
3-{5-[(4-chlorophenyl)methyl]-1,3,4-oxadiazol-2-yl}-6-(ethoxymethyl)-5-(2-methoxyphenyl)pyridine-2,4-diol,
N-({5-[6-butyl-5-(2,3-dimethoxyphenyl)-2,4-dihydroxypyridin-3-yl]-1,3,4-oxadiazol-2-yl}methyl)benzamide,
N-({5-[6-(ethoxymethyl)-2,4-dihydroxy-5-(2-methoxyphenyl)pyridin-3-yl]-1,3,4-oxadiazol-2-yl}methyl)benzamide, 2-{5-[6-butyl-5-(2,6-dimethoxyphenyl)-2,4-dihydroxypyridin-3-yl]-1,3,4-oxadiazol-2-yl}-N-(pyridin-3-yl)acetamide,
2-{5-[5-(2,6-dimethoxyphenyl)-6-(ethoxymethyl)-2,4-dihydroxypyridin-3-yl]-1,3,4-oxadiazol-2-yl}-N-(1,3-thiazol-2-yl)acetamide,
N-[(1,3-benzothiazol-2-yl)methyl]-2-{5-[6-butyl-5-(2,6-dimethoxyphenyl)-2,4-dihydroxypyridin-3-yl]-1,3,4-oxadiazol-2-yl}acetamide,
2-{5-[6-butyl-5-(2,6-dimethoxyphenyl)-2,4-dihydroxypyridin-3-yl]-1,3,4-oxadiazol-2-yl}-N-[(pyridin-3-yl)methyl]acetamide,
2-{5-[6-butyl-5-(2,6-dimethoxyphenyl)-2,4-dihydroxypyridin-3-yl]-1,3,4-oxadiazol-2-yl}-N-[(1,3-oxazol-2-yl)methyl]acetamide,
2-{5-[6-butyl-5-(2,6-dimethoxyphenyl)-2,4-dihydroxypyridin-3-yl]-1,3,4-oxadiazol-2-yl}-N-[2-(4-sulfamoylphenyl)ethyl]acetamide,
2-{5-[6-butyl-5-(2,6-dimethoxyphenyl)-2,4-dihydroxypyridin-3-yl]-1,3,4-oxadiazol-2-yl}-N-[2-(2-chlorophenyl)ethyl]acetamide,
2-{5-[6-butyl-5-(2,6-dimethoxyphenyl)-2,4-dihydroxypyridin-3-yl]-1,3,4-oxadiazol-2-yl}-N-[(3-chlorophenyl)methyl]acetamide,
N-benzyl-2-{5-[6-butyl-5-(2,6-dimethoxyphenyl)-2,4-dihydroxypyridin-3-yl]-1,3,4-oxadiazol-2-yl}-N-methylacetamide,
2-{5-[6-butyl-5-(2,6-dimethoxyphenyl)-2,4-dihydroxypyridin-3-yl]-1,3,4-oxadiazol-2-yl}-N-methyl-N-(2-phenylethyl)acetamide,
2-{5-[6-butyl-5-(2,6-dimethoxyphenyl)-2,4-dihydroxypyridin-3-yl]-1,3,4-oxadiazol-2-yl}-N-(prop-2-yn-1-yl)acetamide,
2-{5-[6-butyl-5-(2,6-dimethoxyphenyl)-2,4-dihydroxypyridin-3-yl]-1,3,4-oxadiazol-2-yl}-N-(3-methyl-1H-pyrazol-5-yl)acetamide,
2-{5-[6-butyl-5-(2,6-dimethoxyphenyl)-2,4-dihydroxypyridin-3-yl]-1,3,4-oxadiazol-2-yl}-N-[(2-methylphenyl)methyl]acetamide,
2-{5-[6-butyl-5-(2,6-dimethoxyphenyl)-2,4-dihydroxypyridin-3-yl]-1,3,4-oxadiazol-2-yl}-N-[(2-chlorophenyl)methyl]acetamide,
2-{5-[6-butyl-5-(2,6-dimethoxyphenyl)-2,4-dihydroxypyridin-3-yl]-1,3,4-oxadiazol-2-yl}-N-[(4-chlorophenyl)methyl]acetamide,
2-{5-[6-butyl-5-(2,6-dimethoxyphenyl)-2,4-dihydroxypyridin-3-yl]-1,3,4-oxadiazol-2-yl}-N-[2-(4-chlorophenyl)ethyl]acetamide,
2-{5-[6-butyl-5-(2,6-dimethoxyphenyl)-2,4-dihydroxypyridin-3-yl]-1,3,4-oxadiazol-2-yl}-N-[(pyridin-4-yl)methyl]acetamide,
2-{5-[6-butyl-5-(2,6-dimethoxyphenyl)-2,4-dihydroxypyridin-3-yl]-1,3,4-oxadiazol-2-yl}-N-[(4-methoxyphenyl)methyl]acetamide,
2-{5-[6-butyl-5-(2,6-dimethoxyphenyl)-2,4-dihydroxypyridin-3-yl]-1,3,4-oxadiazol-2-yl}-N-{[4-(dimethylamino)phenyl]methyl}acetamide,
2-{5-[6-butyl-5-(2,6-dimethoxyphenyl)-2,4-dihydroxypyridin-3-yl]-1,3,4-oxadiazol-2-yl}-N-[(5-methyl-1,3,4-oxadiazol-2-yl)methyl]acetamide, 271
2-{5-[6-butyl-5-(2,6-dimethoxyphenyl)-2,4-dihydroxypyridin-3-yl]-1,3,4-oxadiazol-2-yl}-N-{[3-(propan-2-yl)-1,2-oxazol-5-yl]methyl}acetamide,
2-{5-[6-butyl-5-(2,6-dimethoxyphenyl)-2,4-dihydroxypyridin-3-yl]-1,3,4-oxadiazol-2-yl}-N-[(4-sulfamoylphenyl)methyl]acetamide,
3-{5-[(5-chloropyridin-2-yl)methyl]-1,3,4-oxadiazol-2-yl}-6-(ethoxymethyl)-5-(2-hydroxy-6-methoxyphenyl)pyridine-2,4-diol,
3-{5-[(5-chloropyridin-2-yl)methyl]-1,3,4-oxadiazol-2-yl}-6-(ethoxymethyl)-5-(2-hydroxy-6-methoxyphenyl)pyridine-2,4-diol, and
3-{5-[(5-chloropyridin-2-yl)methyl]-1,3,4-oxadiazol-2-yl}-5-(2,6-dihydroxyphenyl)-6-(ethoxymethyl)pyridine-2,4-diol, or a stereoisomer, a tautomer, a pharmaceutically acceptable salt, or a solvate thereof.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention or a stereoisomer, a tautomer, a pharmaceutically acceptable salt, or a solvate thereof.

In another embodiment, the present invention provides an intermediate for making a compound of the present invention or a stereoisomer, a tautomer, a pharmaceutically acceptable salt, or a solvate thereof.

The present invention provides a pharmaceutical composition further comprising additional therapeutic agent(s). In a preferred embodiment, the present invention provides pharmaceutical composition, wherein the additional therapeutic agent is, for example, angiotensin converting enzyme (ACE) inhibitor, β-adrenergic receptor blocker, angiotensin II receptor blocker, diuretic, aldosterone antagonist and digitalis compound.

In another embodiment, the present invention provides a method for the treatment and/or prophylaxis of multiple diseases or disorders associated with APJ or apelin activity, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

Examples of diseases or disorders associated with the activity of the APJ and apelin that can be prevented, modulated, or treated according to the present invention include, but are not limited to heart failure such as acute decompensated heart failure (ADHF), atrial fibrillation, coronary artery disease, peripheral vascular disease, atherosclerosis, diabetes, metabolic syndrome, hypertension, pulmonary hypertension, cerebrovascular disorders and the sequelae thereof, cardiovascular disorders, angina, ischemia, stroke, myocardial infarction, acute coronary syndrome, reperfusion injury, angioplastic restenosis, vascular complications of diabetes and obesity.

In another embodiment, the present invention provides a method for the treatment and/or prophylaxis of heart failure, coronary artery disease, peripheral vascular disease, atherosclerosis, diabetes, metabolic syndrome, hypertension, pulmonary hypertension, atrial fibrillation, angina, ischemia, stroke, myocardial infarction, acute coronary syndrome, reperfusion injury, angioplastic restenosis, vascular complications of diabetes, obesity, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of heart failure such as ADHF, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of diabetes and obesity, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of hypertension, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of pulmonary hypertension, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of acute coronary syndrome and cardiac ischemia, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment and/or prophylaxis of multiple diseases or disorders associated with APJ and apelin.

In another embodiment, the present invention also provides the use of a compound of the present invention for the manufacture of a medicament for the treatment and/or prophylaxis of multiple diseases or disorders associated with APJ and apelin.

In another embodiment, the present invention provides a method for the treatment and/or prophylaxis of multiple diseases or disorders associated with APJ and apelin, comprising administering to a patient in need thereof a therapeutically effective amount of a first and second therapeutic agent, wherein the first therapeutic agent is a compound of the present invention. Preferably, the second therapeutic agent, for example selected inotropic agent such as (3-adrenergic agonist (for example dobutamine).

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of multiple diseases or disorders associated with APJ and apelin.

Where desired, the compound of the present invention may be used in combination with one or more other types of cardiovascular agents and/or one or more other types of therapeutic agents which may be administered orally in the same dosage form, in a separate oral dosage form or by injection. The other type of cardiovascular agents that may be optionally employed in combination with the APJ agonist of the present invention may be one, two, three or more cardiovascular agents administered orally in the same dosage form, in a separate oral dosage form, or by injection to produce an additional pharmacological benefit.

The compounds of the present invention may be employed in combination with additional therapeutic agent(s) selected from one or more, preferably one to three, of the following therapeutic agents: anti-hypertensive agents, ACE inhibitors, mineralocorticoid receptor antagonists, angiotensin receptor blockers, calcium channel blockers, β-adrenergic receptor blockers, diuretics, vasorelaxation agents such as nitrates, anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, calcium channel blockers, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

In another embodiment, additional therapeutic agent(s) used in combined pharmaceutical compositions or combined methods or combined uses, are selected from one or more, preferably one to three, of the following therapeutic agents in treating heart failure: ACE inhibitors, β-blockers, diuretics, mineralocorticoid receptor antagonists, renin inhibitors, calcium channel blockers, angiotensin II receptor antagonists, nitrates, digitalis compounds, inotropic agents.

The present invention may be embodied in other specific forms without parting from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment.

Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For examples, "$C_1$ to $C_{12}$ alkyl" or "$C_{1-12}$ alkyl" (or alkylene), is intended to include $C_1$, $C_2$, $C_3$, $C_4$, $C_5$, $C_6$, $C_7$, $C_8$, $C_9$, $C_{10}$, $C_{11}$ and $C_{12}$ alkyl groups; "$C_4$ to $C_{18}$ alkyl" or "$C_{4-18}$ alkyl" (or alkylene), is intended to include $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, and $C_{18}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

When the term "hydrocarbon chain" is used, it is intended to include "alkyl", "alkenyl" and "alkynyl", unless otherwise specified.

The term "alkoxy" or "alkyloxy" refers to an —O-alkyl group. For example, "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. For example, "$C_3$ to $C_6$ cycloalkyl" or "$C_{3-6}$ cycloalkyl" is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin).

As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl." A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or bicyclic aromatic hydrocarbons, including, for example, phenyl, and naphthyl. Aryl moieties are well known and described, for example, in Lewis, R. J., ed., *Hawley's Condensed Chemical Dictionary*, 15th Edition, John Wiley & Sons, Inc., New York (2007). "$C_{6-10}$ aryl" refers to phenyl and naphthyl.

The term "benzyl", as used herein, refers to a methyl group on which one of the hydrogen atoms is replaced by a phenyl group.

As used herein, the term "heterocycle", "heterocyclyl", or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate or a positively charged species such as sodium (Na+), potassium (K+), ammonium ($R_nNH_m$+ where n=0-4 and m=0-4) and the like.

When a dotted ring is used within a ring structure, this indicates that the ring structure may be saturated, partially saturated or unsaturated.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. et al., *Protecting Groups in Organic Synthesis,* 4th Edition, Wiley (2007) and *The Peptides: Analysis, Synthesis, Biology,* Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, Jr., L. V., ed., *Remington: The Science and Practice of Pharmacy*, 22nd Edition, Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J., ed., *Prodrugs and Targeted Delivery (Methods and Principles in Medicinal Chemistry)*, Vol. 47, Wiley-VCH (2011).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes.

Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (2nd Edition, reproduced (2006)); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3rd Edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or min, "h" for hour or h, "rt" for room temperature, "RT" for retention time, "atm" for atmosphere, "psi" for pounds per square inch, "conc." for concentrate, "aq" for "aqueous", "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for deR$^a$, "s" for singlet, "d" for doublet, "t" for triplet, "q" for quartet, "m" for multiplet, "br" for broad, "Hz" for hertz, and "α", "β", "R", "S", "E", "Z" and "ee" are stereochemical designations familiar to one skilled in the art.

AcOH or HOAc acetic acid
ACN acetonitrile
Alk alkyl
$BBr_3$ boron tribromide
Bn benzyl
Boc tert-butyloxycarbonyl
BOP reagent benzotriazol-1-yloxytris(dimethylamino)phosphonium hexafluorophosphate
Bu butyl
i-Bu isobutyl
t-Bu tert-butyl
t-BuOH tert-butanol
Cbz carbobenzyloxy
$CDCl_3$ deutero-chloroform
$CD_3OD$ deutero-methanol
CDI 1,1'-carbonyldiimidazole
$CH_2Cl_2$ dichloromethane
$CH_3CN$ acetonitrile
$CHCl_3$ chloroform
$CO_2$ carbon dioxide DCM dichloromethane
DIEA, DIPEA or diisopropylethylamine Hunig's base
DMF dimethyl formamide
DMSO dimethyl sulfoxide
EDC 1-ethyl-3-(3-dimethylaminopropyl)carbodiimide
Et ethyl
$Et_3N$ or TEA triethylamine
$Et_2O$ diethyl ether
EtOAc ethyl acetate
EtOH ethanol
HCl hydrochloric acid
HPLC high-performance liquid chromatography
$K_2CO_3$ potassium carbonate
$K_2HPO_4$ potassium hydrogenphosphate
LCMS liquid chromatography mass spectrometry
LiHMDS lithium bis(trimethylsilyl)amide
LG leaving group
Me methyl
MeOH methanol
$MgSO_4$ magnesium sulfate
MsOH or MSA methylsulfonic acid
NaCl sodium chloride
$Na_2CO_3$ sodium carbonate
$NaHCO_3$ sodium bicarbonate
NaOH sodium hydroxide
$Na_2SO_4$ sodium sulfate
$NH_3$ ammonia
$NH_4Cl$ ammonium chloride
$NH_4OAc$ ammonium acetate
$Pd(OAc)_2$ palladium(II) acetate
$Pd(PPh_3)_4$ tetrakis(triphenylphosphine)palladium(O)
PG protecting group
Ph phenyl
Pr propyl
i-Pr isopropyl
i-PrOH or IPA isopropanol
Rt retention time
$SiO_2$ silica oxide
SFC supercritical fluid chromatography
TEA triethylamine
TFA trifluoroacetic acid
THF tetrahydrofuran
$TiCl_4$ titanium tetrachloride
T3P® 1-propanephosphonic acid cyclic anhydride The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

Synthesis

The compounds of Formula (I) may be prepared by the exemplary processes described in the following schemes and working examples, as well as relevant published literature procedures that are used by one skilled in the art. Exemplary reagents and procedures for these reactions appear hereinafter and in the working examples. Protection and deprotection in the processes below may be carried out by procedures generally known in the art (see, for example, Wuts, P. G. M. et al., *Protecting Groups in Organic Synthesis*, 4th Edition, Wiley (2007)). General methods of organic synthesis and functional group transformations are found in: Trost, B. M. et al., eds., *Comprehensive Organic Synthesis: Selectivity, Strategy & Efficiency in Modern Organic Chemistry*, Pergamon Press, New York, N.Y. (1991); Smith, M. B. et al., *March's Advanced Organic Chemistry: Reactions, Mechanisms, and Structure*. 6th Edition, Wiley & Sons, New York, N.Y. (2007); Katritzky, A. R. et al, eds., *Comprehensive Organic Functional Groups Transformations II*, 2nd Edition, Elsevier Science Inc., Tarrytown, N.Y. (2004); Larock, R. C., *Comprehensive Organic Transformations*, VCH Publishers, Inc., New York, N.Y. (1999), and references therein.

Compounds of Formula (I) can be prepared as described in Scheme 1.

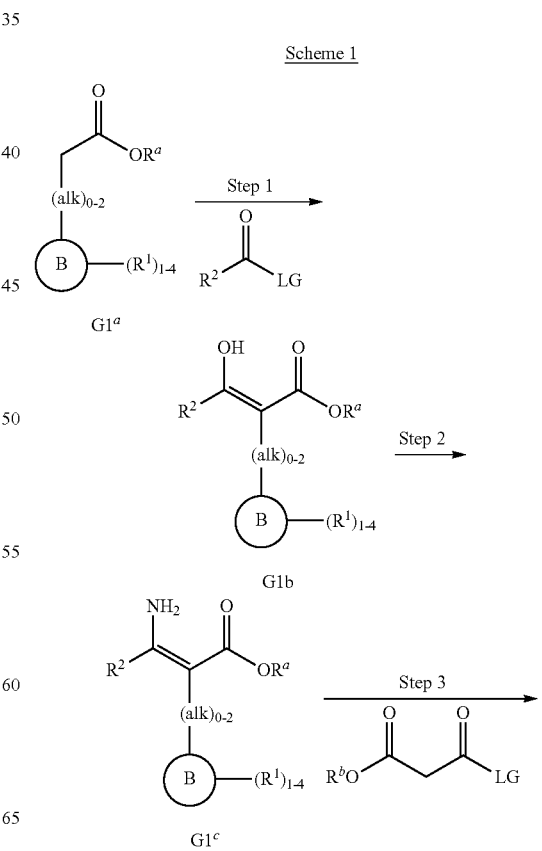

Scheme 1

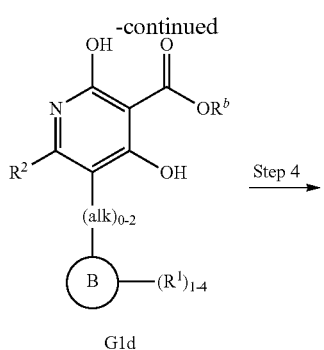

G1d

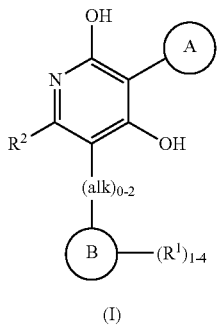

(I)

Step 1 describes the preparation of compounds of Formula G1b by condensing an ester of Formula G1a with an acid $R^2$CO-LG, where LG represents a leaving group (such as halogens and the like). Preferred solvents are ethers (such as tetrahydrofuran, dioxane and the like) and polar aprotic solvents (such as N,N-dimethylformamide). Preferred bases are metal amides (such as lithium bis(trimethylsilyl)amide and lithium diisopropylamide and the like) and metal hydrides (such as sodium hydride and the like).

Step 2 describes the preparation of compounds of Formula G1c by condensation of compounds of Formula G1b with ammonia. Preferred sources of ammonia are ammonia (gas) or salts thereof (such as ammonium acetate, ammonium formate and the like). Preferred solvents are alcohols (such as methanol, ethanol and the like).

Step 3 describes the preparation of pyridine compounds of Formula G1d from compounds of formula G1c by condensation with malonate derivatives $R^b$OCOCH$_2$CO-LG, where LG represents a leaving group (such as halogens or alkoxides such as ethoxide and the like) in the presence of base. The process can be performed in a single step, or stepwise. Preferred solvents for the first step of the two step process are halogenated solvents (such as DCM and the like), ethers (such as tetrahydrofuran, dioxane and the like) and water. Preferred bases for the first step of the two step process are tertiary amines (such as TEA, DIEA and the like) and alkaline metal-carbonates, -bicarbonates, -hydroxides (such as sodium carbonate, sodium bicarbonate, sodium hydroxide and the like). Preferred solvents for the second step and for the single step process are alcohols (such as MeOH and EtOH and the like). Preferred bases for the second step and for the single step process are alkaline metal alkoxides (such as sodium ethoxide and the like).

Step 4 describes the preparation of compounds of Formula (I) by conversion of the ester of compounds of Formula G1d to a heterocycle (A). The conversion of compounds of Formula G1d to compounds of Formula (I) can be performed in one step or in several steps, depending on the heterocycle (A). The ester of Formula G1d can be condensed neat with an N'-hydroxy imidamide to give a 1,2,4-oxadiazole in a single step. Alternatively in a two step process the ester of Formula G1d can by condensed with hydrazine in the presence of alcohol solvents (such as methanol and the like) to form a hydrazide, then the hydrazide condensed with an acid in the presence of a dehydrating reagents (such as T3P®, EDC and the like) and an inert solvent (such as dioxane, EtOAc and the like) to give a 1,3,4-oxadiazole. Alternatively, the hydrazide can be condensed with an imidate in alcohol solvents (such as isopropanol and the like) in the presence of tertiary amines (such as TEA, DIEA and the like) to give a 1,3,4-triazole.

Alternatively compounds of Formula (I) can be prepared as described in Scheme 2.

Scheme 2

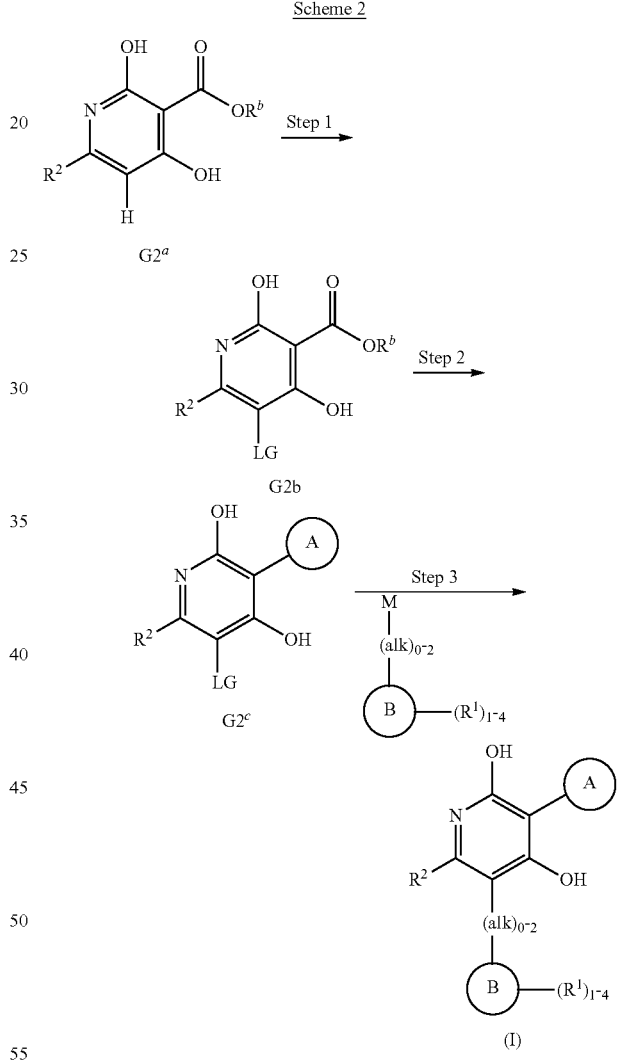

Step 1 describes the preparation of compounds of Formula G2b from a compound of Formula G2a (prepared as described in W2007/197478), where LG represents a leaving group (such as halogens, preferably bromine). Preferred reagents for incorporating the leaving group are sources of bromine (such as elemental bromine and NBS and the like). Preferred solvents are halogenated solvents (such as DCM and the like).

Step 2 describes the preparation of a compound of Formula G2c from a compound of Formula G2b and is analogous to Step 4 in Scheme 1.

Step 3 describes the preparation of compounds of Formula (I) by coupling an organometallic reagent M-(alk)$_{0-2}$-Ⓑ—(R$^1$)$_{1-4}$ with a compound of Formula G2c. The organometallic reagent M-(alk)$_{0-2}$-Ⓑ—(R$^1$)$_{1-4}$ is preferably generated by reaction of a alkylboronic acid or ester B(OR)$_2$-(alk)$_{0-2}$-Ⓑ—(R)$_{1-4}$, R=H or alkyl, with a transition metal catalyst (such as Pd(PPh$_3$)$_4$ and Pd(OAc)$_2$ and the like). Preferred solvents are ethers (such as tetrahydrofuran, dioxane and the like), aprotic solvents (such as toluene and the like) and water. Preferred bases are alkaline metal-carbonates, -bicarbonates (such as sodium carbonate, sodium bicarbonate and the like).

Alternatively compounds of Formula (I) can be prepared as described in Scheme 3.

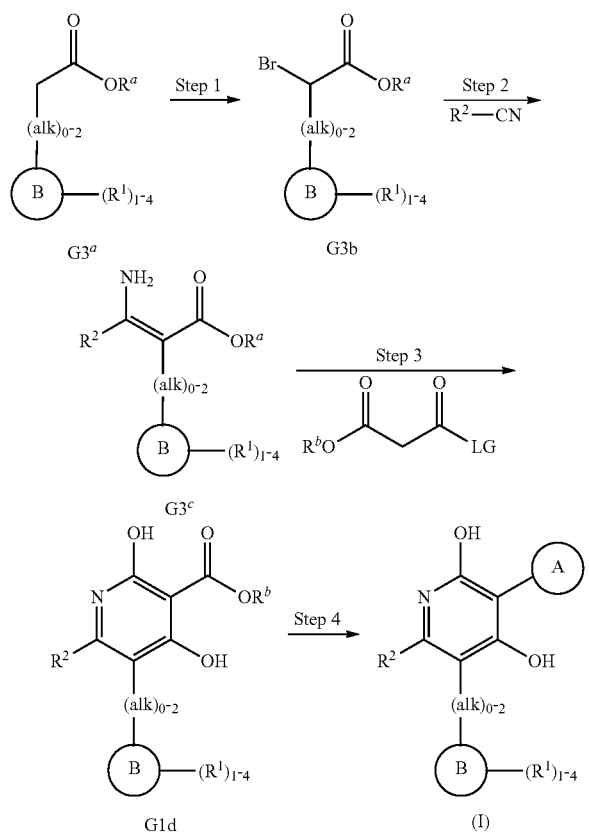

Scheme 3

Step 1 describes the preparation of compounds of Formula G3b by bromination of an ester of Formula G3a. Preferred sources of bromine are elemental bromine and NBS and the like. Preferred solvents are ethers (such as tetrahydrofuran, dioxane and the like). Preferred bases are metal amides (such as lithium bis(trimethylsilyl)amide and lithium diisopropylamide and the like) and metal hydrides (such as sodium hydride and the like).

Step 2 describes the preparation of compounds of Formula G3c from compounds of Formula G3b via condensation with nitrile R$^2$—CN in the presence of a transition metal. The preferred transition metal is zinc, and a co-catalyst (zinc oxide, alkyl sulfonic acids and the like) can be used. Inert solvents such as ethers (such as tetrahydrofuran, dioxane and the like) and aprotic solvents (such as toluene and the like) can be used, preferably the reaction is run under neat conditions.

Step 3 describes the preparation of a compound of Formula G3d from a compound of Formula G2c and is analogous to Step 3 in Scheme 1.

Step 3 describes the preparation of a compound of Formula (I) from a compound of Formula G3d and is analogous to Step 4 in Scheme 1.

IV. Biology

APJ receptor was discovered in 1993 as an orphan G protein-coupled receptor (GPCR) and was subsequently found to recognize apelin peptide as its endogenous ligand. It belongs to class A of GPCRs and has a classical 7-transmembrane domain structure, exhibiting greatest sequence homology to angiotensin AT1 receptor (for review see Pitkin, S. L. et al., *Pharmacol. Rev.*, 62(3):331-342 (2010)). APJ is expressed in wide variety of peripheral tissues and the CNS, and has relatively high expression in placenta, myocardium, vascular endothelial cells, smooth muscle cells as well as cardiac myocytes (Kleinz, J. M. et al., *Pharmacol. Ther.*, 107(2): 198-211(2005)). Apelin peptide was originally identified in bovine stomach extract and remains to date the only known endogenous ligand and agonist of APJ receptor (Tatemoto, K. et al., *Biochem. Biophys. Res. Commun.*, 255:471-476 (1998)). Tissue expression of apelin gene mirrors closely the APJ expression pattern and has been postulated to act in an autocrine or paracrine manner, often exemplified by reference to "apelin-APJ system". Apelin gene encodes 77 amino acid precursor peptide that is cleaved to form mature secreted peptide undergoing further proteolytic cleavage forming shorter C-terminal fragments. Apelin-36, -17 and -13 represent the major active forms with the pyroglutamated form of apelin-13 being the most stable and the most abundant form present in the cardiac tissue (Maguire, J. J. et al., *Hypertension*, 54(3):598-604 (2009)). Apelin has very short half life in circulation, estimated to be less than 5 minutes (Japp, A. G. et al., *Circulation*, 121(16): 1818-1827 (2010)).

Activation of APJ receptor is known to inhibit forskolin-stimulated cyclic AMP (cAMP) levels in pertussis toxin-sensitive manner, indicating coupling to the Gi proteins. The binding affinity of apelin and the EC$_{50}$ values in the cAMP assay are reported to be in the sub-nanomolar range (for review see Pitkin, S. L. et al., *Pharmacol. Rev.*, 62(3):331-342(2010)). In addition to cAMP inhibition, APJ receptor activation also leads to β-arrestin recruitment, receptor internalization and activation of extracellular-regulated kinases (ERKs) (for review see Kleinz, J. M. et al., *Pharmacol. Ther.*, 107(2):198-211 (2005)). Which of these signaling mechanisms contribute to modulation of downstream physiological effects of apelin is not clear at present. APJ receptor has been shown to interact with the AT1 receptor. While apelin does not bind AT1 and angiotensin II does not bind APJ, it has been postulated that certain physiological actions of apelin are mediated, at least in part, via functional antagonism of the angiotensin II and AT1 receptor pathway (Chun, A. J. et al., *J. Clin. Invest.*, 118(10):3343-3354 (2008)).

It is also desirable and preferable to find compounds with advantageous and improved characteristics compared with known HF treatment agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index.

As used herein, the term "patient" encompasses all mammalian species.

As used herein, the term "subject" refers to any human or non-human organism that could potentially benefit from treatment with an APJ agonist. Exemplary subjects include human beings of any age with risk factors for development of heart failure and the sequelae thereof, angina, ischemia, cardiac ischemia, myocardial infarction, reperfusion injury, angioplastic restenosis, hypertension, vascular complications of diabetes, obesity or endotoxemia, stroke, as well as atherosclerosis, coronary artery disease, acute coronary syndrome, and/or dyslipidemias.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to modulate APJ and/or to prevent or treat the disorders listed herein. When applied to a combination, the term refers to combined amounts of the active ingredients that result in the preventive or therapeutic effect, whether administered in combination, serially, or simultaneously.

A. Assay Methods
Intracellular cAMP Accumulation Assay

HEK293 cells stably expressing human APJ receptor were used to assess the activity of compounds. Cultured cells were detached and resuspended in the cAMP Homogeneous Time-Resolved Fluorescence (HTRF) assay buffer (Cisbio cat; #62AM4PEJ). The assay was performed in 384-well assay plates (Perkin-Elmer; cat #6008289) according to assay protocol provided by the manufacturer. Serial dilutions of a compound together with assay buffer containing 0.2 nM IBMX and 2 LM forskolin were added to each well containing 5,000 cells and incubated for 30 minutes at room temperature. Subsequently, cAMP D2 reagent was added in the lysis buffer followed by the EuK antibody (Cisbio; cat #62AM4PEJ) and incubated for 60 min. The fluorescence emission ratio was measured using fluorometer. The intracellular cAMP concentrations (compound-stimulated inhibition of forskolin-mediated cAMP production) were calculated by extrapolation from a standard curve using known cAMP concentrations. The $EC_{50}$ values were obtained by fitting the data to a sigmoidal concentration-response curve with variable slope. The maximal achievable inhibition of forskolin-induced cAMP levels ($Y_{max}$) for each compound was expressed as relative percentage of inhibition attained using pyroglutamated apelin-13 ((Pyr1)apelin-13) peptide, which was set to 100%.

The examples disclosed below were tested in the APJ in vitro assays described above and were found having human APJ cyclic AMP (hcAMP) activity. The $EC_{50}$ value of each compound is presented at the end of the example description.

The compounds of the present invention possess activity as agonists of APJ receptor, and, therefore, may be used in the treatment of diseases associated with APJ activity. Accordingly, the compounds of the present invention can be administered to mammals, preferably humans, for the treatment of a variety of conditions and disorders, including, but not limited to, treating, preventing, or slowing the progression of heart failure, coronary artery disease, peripheral vascular disease, atherosclerosis, diabetes, metabolic syndrome and the sequelae of thereof, hypertension, pulmonary hypertension, cerebrovascular disorders, atrial fibrillation, angina, ischemia, stroke, myocardial infarction, acute coronary syndrome, reperfusion injury, angioplastic restenosis, vascular complications of diabetes and obesity.

The biological activity of the exemplified compounds of this invention determined by the assay described above is shown at the end of each example. The APJ cAMP $EC_{50}$ potency ranges are as follows: A=0.01-10 nM; B=10.01-100 nM; C=100.01-300 nM.

V. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, Jr., L. V. et al., *Remington: The Science and Practice of Pharmacy* (2 Volumes), 22nd Edition, Pharmaceutical Press (2012), The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., agents used in treatment of heart failure or other pharmaceutically active material.

The compounds of the present invention may be employed in combination with other APJ agonists or one or more other suitable therapeutic agents useful in the treatment of the aforementioned disorders including: agents for treating heart failure, anti-hypertensive agents, anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, and agents for treating peripheral arterial disease.

The compounds of the present invention may be employed in combination with additional therapeutic agent(s) selected from one or more, preferably one to three, of the following therapeutic agents in treating heart failure and coronary artery disease: ACE inhibitors, β-blockers, diuretics, mineralocorticoid receptor antagonists, renin inhibitors, calcium channel blockers, angiotensin II receptor antagonists, nitrates, digitalis compounds, inotropic agents and β-receptor agonists, anti-hyperlipidemic agents, plasma HDL-raising agents, anti-hypercholesterolemic agents, cholesterol biosynthesis inhibitors (such as HMG CoA reductase inhibitors), LXR agonist, probucol, raloxifene, nicotinic acid, niacinamide, cholesterol absorption inhibitors, bile acid sequestrants (such as anion exchange resins, or quaternary amines (e.g., cholestyramine or colestipol), low density lipoprotein receptor inducers, clofibrate, fenofibrate, benzofibrate, cipofibrate, gemfibrizol, vitamin $B_6$, vitamin $B_{12}$, anti-oxidant vitamins, anti-diabetes agents, platelet aggregation inhibitors, fibrinogen receptor antagonists, aspirin and fibric acid derivatives.

The compounds of the invention may be used in combination with one or more, preferably one to three, of the following anti-diabetic agents depending on the desired target therapy. Studies indicate that diabetes and hyperlipidemia modulation can be further improved by the addition of a second agent to the therapeutic regimen. Examples of anti-diabetic agents include, but are not limited to, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARPβ and PPARγ; dehydroepiandrosterone (also referred to as DHEA or its conjugated sulphate ester, $DHEA-SO_4$); anti-glucocorticoids; TNFα inhibitors; dipeptidyl peptidase IV (DPP4) inhibitor (such as sitagliptin, saxagliptin), GLP-1 agonists or analogs (such as exenatide), α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the therapeutic agents discussed above for treating heart failure and atherosclerosis.

The compounds of the invention may be used in combination with one or more, preferably one to three, of the following anti-obesity agents selected from phenylpropanolamine, phentermine, diethylpropion, mazindol, fenfluramine, dexfenfluramine, phentiramine, $β_3$-adrenergic receptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients but also to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the APJ receptor and apelin activity. Such compounds may be provided in a commercial kit, for example, for use in pharmaceutical research involving APJ and apelin or anti-heart failure activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving APJ and apelin.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises a first therapeutic agent, comprising a compound of the present invention or a pharmaceutically acceptable salt form thereof; and, (c) a package insert stating that the pharmaceutical composition can be used for the treatment and/or prophylaxis of multiple diseases or disorders associated with APJ and apelin (as defined previously). In another embodiment, the package insert states that the pharmaceutical composition can be used in combination (as defined previously) with a second therapeutic agent for the treatment and/or prophylaxis of multiple diseases or disorders associated with APJ and apelin. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof.

VI. Examples

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

As a person of ordinary skill in the art would be able to understand that a pyridone in a molecule may tautomerize to its keto and enol forms as shown in the following equation, wherein $R^1$, $R^2$, $R^3$ and $R^4$ are as defined above, this disclosure is intended to cover all possible tautomers even when a structure depicts only one of them.

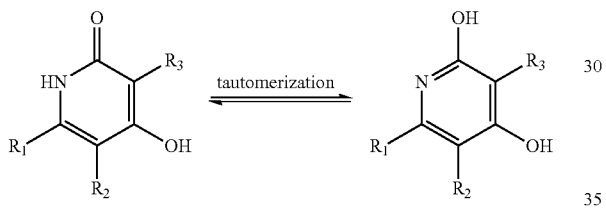

Description of Analytical LCMS Methods:

Method A: Column: Waters Acquity UPLC BEH C18, 2.1×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 minutes, then a 0.75 minute hold at 100% B; Flow: 1.11 mL/min; Detection: UV at 220 nm.

Method B: Column: Waters Acquity UPLC BEH C18, 2.1×50 mm, 1.7 μm particles; Mobile Phase A: 5:95 ACN:water with 0.1% TFA; Mobile Phase B: 95:5 ACN:water with 0.1% TFA; Temperature: 50° C.; Gradient: 0-100% B over 3 minutes, then a 0.75 minute hold at 100% B; Flow: 1.11 mL/min; Detection: UV at 220 nm.

Method C: Column: PHENOMENEX® Luna 3 m C18 (2.0×30 mm); Mobile Phase A: 10:90 MeOH:water with 0.1% TFA; Mobile Phase B: 90:10 MeOH:water with 0.1% TFA; Gradient: 0-100% B over 2 minutes, then a 1 minute hold at 100% B; Flow: 1 mL/min; Detection: UV at 220 nm.

Method D: Column: Waters Acquity UPLC BEH C18, 2.1×50 mm, 1.7 μm particles; Mobile Phase A: water with 0.1% TFA; Mobile Phase B: ACN with 0.1% TFA; Gradient: 2-98% B over 1 minute, then a 0.5 minute hold at 98% B; Flow: 0.8 mL/min; Detection: UV at 220 nm.

Method E: Column: Phenomenex Luna 3u C18(2) 2.0×30 mm; Mobile Phase A: 10:90 MeOH:water with 10 mM NH$_4$OAc; Mobile Phase B: 90:10 MeOH:water with 10 mM NH$_4$OAc; Gradient: 0-100% B over 2 minute, then a 1 minute hold at 100% B; Temperature: 40° C.; Flow: 1.00 mL/min; Detection: UV at 220 nm.

Example 1

3-(5-benzyl-1,3,4-oxadiazol-2-yl)-6-butyl-5-(2,6-dimethoxyphenyl)pyridine-2,4-diol

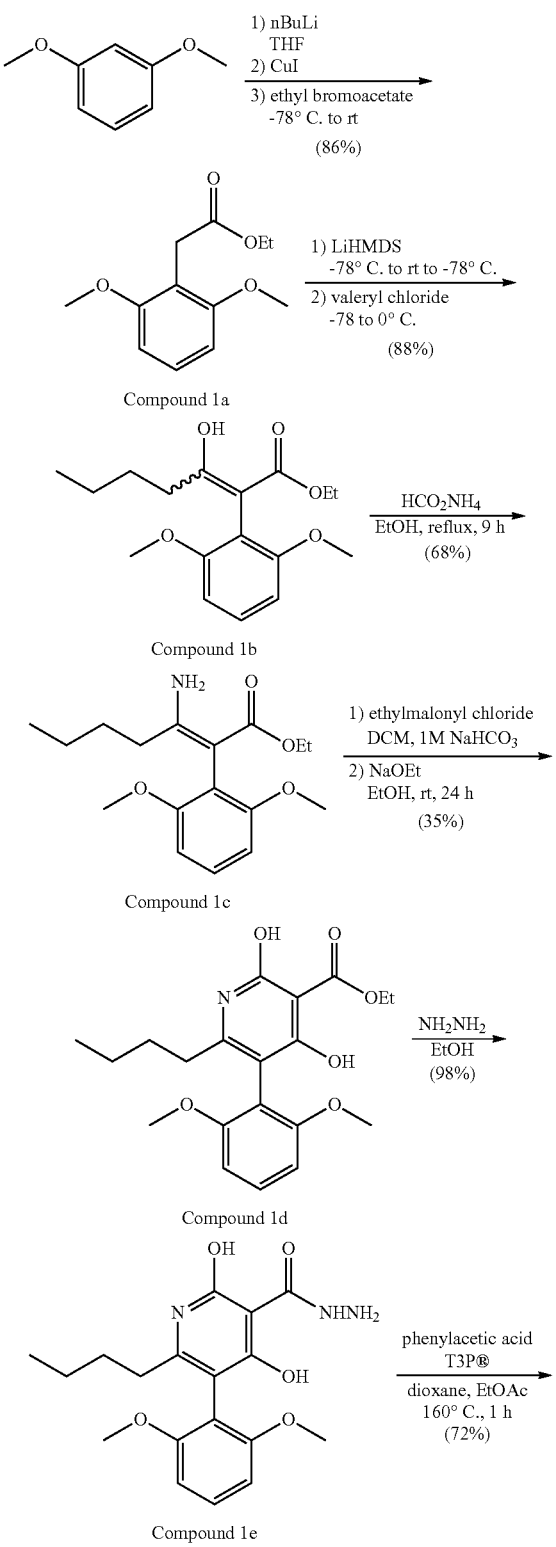

-continued

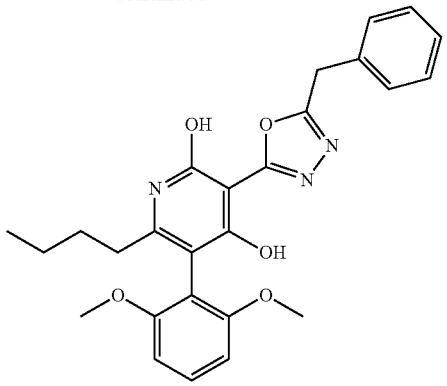

Example 1

Compound 1a. Ethyl 2-(2,6-dimethoxyphenyl)acetate

To a solution of 1,3-dimethoxybenzene (3.3 mL, 25 mmol) in THF (40 mL) was added dropwise 2.5M nBuLi in hexanes (10 mL, 25 mmol) over a 10 min period then the mixture stirred for 2 h. Crushed copper(I) iodide (2.38 g, 12.5 mmol) was added slowly then the mixture stirred for 1 h, turning homogeneous. The mixture was cooled to −78° C. then ethyl bromoacetate (2.8 mL, 25 mmol) was added dropwise over 20 min. The cold bath was removed and the mixture allowed to warm to room temperature. The mixture was quenched by the addition of water then Et$_2$O added and the mixture filtered through celite. The filtrate was diluted with 1.5N K$_2$HPO$_4$ and extracted with Et$_2$O (2×). The extracts were washed with brine, dried (MgSO$_4$) filtered and concentrated under reduced pressure. The residue was purified by silica gel chromatography eluting with 0 to 15% EtOAc/hexanes to give Compound 1a (4.8 g, 86% yield) as a light brown oil which solidified upon standing. MS m/z=225.1 (M+H). $^1$H NMR (500 MHz, CDCl$_3$) δ 7.23 (t, J=8.4 Hz, 1H), 6.58 (d, J=8.3 Hz, 2H), 4.17 (q, J=7.2 Hz, 2H), 3.83 (s, 6H), 3.71 (s, 2H), 1.27 (t, J=7.2 Hz, 3H).

Compound 1b. Ethyl 2-(2,6-dimethoxyphenyl)-3-hydroxyhept-2-enoate

To a solution of Compound 1a (1.50 g, 6.70 mmol) in THF (14 mL) at −78° C. was added dropwise 1.0M LiHMDS in THF (16.7 mL, 16.7 mmol) and the mixture stirred for 10 min then at room temperature for 1 h. The mixture was cooled to −78° C. then valeryl chloride (1.34 mL, 11.0 mmol) was added dropwise and the mixture allowed to warm to 0° C. and stirred for 15 min. The mixture was quenched with satd NH$_4$Cl and extracted with EtOAc (3×). The combined extracts were washed with brine, dried (Na$_2$SO$_4$) filtered and concentrated under reduced pressure. The residue was purified by silica gel chromatography eluting with 0 to 30% EtOAc/hexanes to give an isomeric mixture of Compound 1b (1.81 g, 88% yield) as a clear colorless oil. MS m/z=309.1 (M+H). $^1$H NMR of major isomer (400 MHz, CDCl$_3$) δ 13.22 (s, 1H), 7.26-7.22 (m, 1H), 6.56 (d, J=8.6 Hz, 2H), 4.14 (q, J=7.0 Hz, 2H), 3.75 (s, 5H), 2.05-1.96 (m, 2H), 1.51-1.42 (m, 2H), 1.22-1.17 (m, 2H), 1.14 (t, J=7.2 Hz, 3H), 0.77 (t, J=7.3 Hz, 3H).

Compound 1c. Ethyl 3-amino-2-(2,6-dimethoxyphenyl)hept-2-enoate

To the isomeric mixture of Compound 1b (1.8 g, 5.9 mmol) and ammonium formate (1.9 g, 29 mmol) in absolute ethanol (35 mL) was added molecular sieves then the mixture heated at reflux for 10 h. The mixture was allowed to cool to room temperature then filtered and concentrated under reduced pressure. The residue was dissolved in water and extracted with EtOAc (3×). The combined extracts were dried (Na$_2$SO$_4$) filtered and concentrated under reduced pressure. The residue was purified by silica gel chromatography eluting with 0 to 35% EtOAc/hexanes to give Compound 1c (1.2 g, 68% yield) as a clear colorless oil. MS m/z=308.1 (M+H). $^1$H NMR (400 MHz, CDCl$_3$) δ 7.21 (t, J=8.4 Hz, 1H), 6.55 (d, J=8.4 Hz, 2H), 4.05 (q, J=7.0 Hz, 2H), 3.75 (s, 6H), 1.98-1.88 (m, 2H), 1.43-1.31 (m, 2H), 1.18 (dt, J=15.0, 7.5 Hz, 2H), 1.09 (t, J=7.0 Hz, 3H), 0.73 (t, J=7.4 Hz, 3H).

Compound 1d. Ethyl 6-butyl-5-(2,6-dimethoxyphenyl)-2,4-dihydroxynicotinate

To a solution of Compound 1c (1.23 g, 4.00 mmol) in a mixture of DCM (20 mL) and 1N NaHCO$_3$ (24 mL, 24 mmol) was added dropwise a solution of ethyl malonyl chloride (1.54 mL, 12.0 mmol) in DCM (5 mL) and the mixture vigorously stirred for 10 min. The mixture was diluted with DCM, the layers separated, and aqueous layer extracted with DCM (2×). The combined extracts were washed with satd NH$_4$Cl and brine, dried (Na$_2$SO$_4$) filtered and concentrated under reduced pressure. The residue was dissolved in absolute EtOH (20 mL) then 2.5M sodium ethoxide in ethanol (6.4 mL, 16 mmol) added and the mixture stirred for 24 h, generating a precipitate. The mixture was evaporated to dryness then diluted with satd NH$_4$Cl and extracted with DCM (3×). The combined extracts were washed with brine, dried (Na$_2$SO$_4$), decanted and concentrated under reduced pressure onto celite. The residue was purified by silica gel chromatography eluting with 5 to 75% EtOAc/DCM to give Compound 1d (0.52 g, 35% yield) as a white solid. MS m/z=376.1 (M+H). $^1$H NMR (400 MHz, DMSO-d$_6$) δ 7.33 (t, J=8.4 Hz, 1H), 6.70 (d, J=8.4 Hz, 2H), 4.30 (q, J=6.8 Hz, 2H), 3.68 (s, 6H), 2.09 (t, J=7.2 Hz, 2H), 1.37-1.23 (m, 5H), 1.12-0.99 (m, 2H), 0.65 (t, J=7.4 Hz, 3H).

Compound 1e. 6-Butyl-5-(2,6-dimethoxyphenyl)-2,4-dihydroxynicotinohydrazide

To a suspension of Compound 1d (50 mg, 0.13 mmol) in ethanol (0.75 mL) was added hydrazine (0.084 mL, 2.6 mmol) and the mixture stirred for 0.5 h. The mixture was concentrated under reduced pressure to give Compound 1e (47 mg, 98% yield) as a white solid. MS m/z=362.1 (M+H). $^1$H NMR (400 MHz, DMSO-d$_6$) δ 15.52 (s, 1H), 11.78 (br. s., 1H), 10.89 (t, J=4.4 Hz, 1H), 7.34 (t, J=8.4 Hz, 1H), 6.71 (d, J=8.4 Hz, 2H), 4.72 (d, J=4.8 Hz, 2H), 3.68 (s, 6H), 2.18-2.09 (m, 2H), 1.32 (quin, J=7.5 Hz, 2H), 1.14-1.02 (m, 2H), 0.66 (t, J=7.4 Hz, 3H).

Example 1

3-(5-benzyl-1,3,4-oxadiazol-2-yl)-6-butyl-5-(2,6-dimethoxyphenyl)pyridine-2,4-diol To a solution of Compound 1e (15 mg, 0.042 mmol) in dioxane (0.4 mL) was added phenylacetic acid (6.2 mg, 0.046 mmol) followed by a 50% solution of T3P® in ethyl acetate (0.075 mL, 0.13 mmol) and the mixture heated by microwave irradiation at 160° C. for 1 h. The mixture was concentrated under reduced pressure then purified by prep HPLC to give Example 1 (14 mg, 72% yield). LCMS (Method A) Rt=1.83 min, m/z=462.1 (M+H). $^1$H NMR (500 MHz, DMSO-d$_6$) δ 7.42-7.23 (m, 6H), 6.73 (d, J=8.2 Hz, 2H), 4.36 (s, 2H), 3.68 (s, 6H), 2.15 (t, J=7.3 Hz, 2H), 1.39-1.27 (m, 2H), 1.14-1.02 (m, 2H), 0.70-0.60 (m, 3H). Human APJ cAMP EC$_{50}$ Potency range B.

Example 2 to Example 136 were prepared as described in the general procedure given for Example 1.

Example 137

6-butyl-5-(3-ethylphenyl)-4-hydroxy-3-{5-[(2-methyl-1,3-thiazol-4-yl)methyl]-1,3,4-oxadiazol-2-yl}-1,2-dihydropyridin-2-one

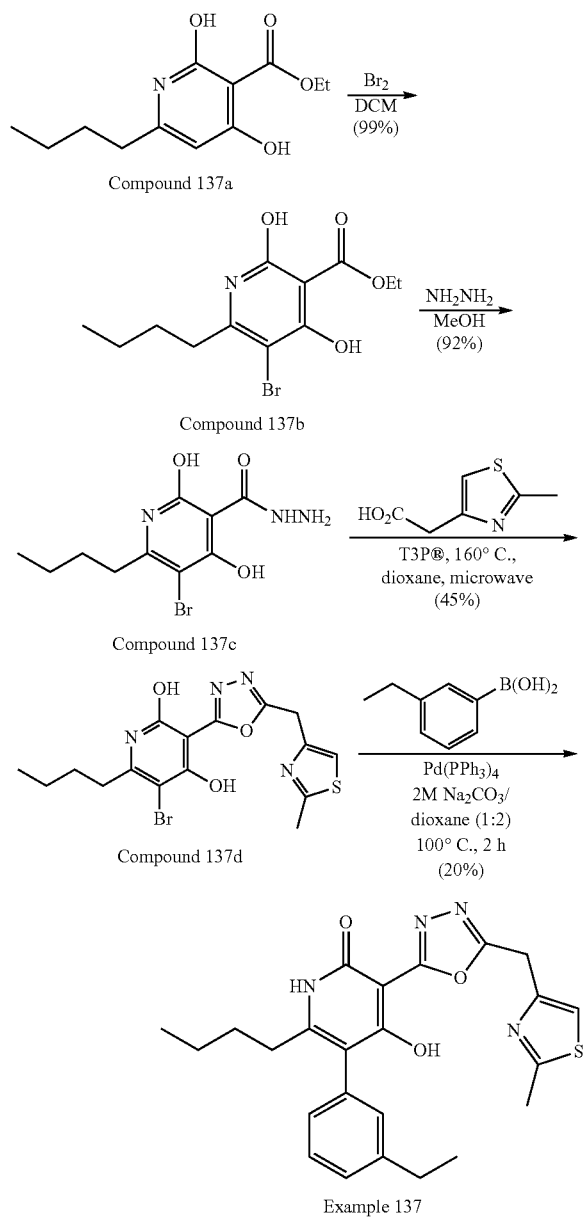

Compound 137b. Ethyl 5-bromo-6-butyl-2,4-dihydroxynicotinate

Bromine (0.55 mL, 11 mmol) was added to Compound 137a (1.7 g, 7.1 mmol; prepared as described in W2007/197478) in DCM (40 mL). After 15 minutes, the reaction mixture was concentrated and purified by silica gel chromatography eluting with 0 to 5% methanol/DCM to give Compound 137b (2.2 g, 99% yield) as a white solid. LCMS (Method D) Rt=0.90 min, m/z=320.0 [M+H]$^+$. $^1$H NMR (500 MHz, CDCl$_3$) δ 14.28 (s, 1H), 12.09-11.75 (m, 1H), 4.45 (q, J=7.0 Hz, 2H), 2.95-2.71 (m, 2H), 1.80-1.64 (m, 2H), 1.52-1.37 (m, 5H), 0.98 (t, J=7.4 Hz, 3H).

Compound 137c. 5-Bromo-6-butyl-2,4-dihydroxynicotinohydrazide

Hydrazine (0.77 mL, 25 mmol) was added to Compound 137b (750 mg, 2.47 mmol) in MeOH (20 mL). After 16 hours, the reaction mixture was concentrated under reduced pressure, suspended in methanol (10 mL), and the solid collected via Buchner filtration to give Compound 137c (690 mg, 92% yield) as a white solid. LCMS (Method D) Rt=0.74 min, m/z=305.9 [M+H]$^+$. $^1$H NMR (500 MHz, DMSO-d$_6$) δ 3.30 (s, 2H), 2.58 (br. s., 2H), 1.53 (d, J=7.4 Hz, 2H), 1.39-1.26 (m, 2H), 0.89 (t, J=7.4 Hz, 3H).

Compound 137d. 5-Bromo-6-butyl-3-(5-((2-methyl-thiazol-4-yl)methyl)-1,3,4-oxadiazol-2-yl)pyridine-2,4-diol Compound 137d (190 mg, 45% yield) was prepared from Compound 137c as described for Example 1. LCMS (Method D) Rt=0.87, m/z=426.9 [M+H]$^+$. $^1$H NMR (500 MHz, DMSO-d$_6$) δ 12.09-11.87 (m, 1H), 7.43 (s, 1H), 4.43 (s, 2H), 2.72-2.64 (m, 2H), 2.62 (s, 3H), 1.62-1.51 (m, 2H), 1.40-1.30 (m, 2H), 0.91 (t, J=7.3 Hz, 3H).

Example 137

6-butyl-5-(3-ethylphenyl)-4-hydroxy-3-{5-[(2-methyl-1,3-thiazol-4-yl)methyl]-1,3,4-oxadiazol-2-yl}-1,2-dihydropyridin-2-one Compound 137d (15 mg, 0.035 mmol), (3-ethylphenyl)boronic acid (7.9 mg, 0.053 mmol) and Pd(PPh$_3$)$_4$(12.2 mg, 10.6 mol) in dioxane (1 mL)/2M Na$_2$CO$_3$ (0.5 mL) were purged with argon and then heated at 100° C. After 2 hours, the reaction mixture was filtered, concentrated, dissolved in DMF/methanol and purified by prep HPLC to give Example 137 (3.2 mg, 20% yield). LCMS (Method A) Rt=1.88 min, m/z=451.0. $^1$H NMR (500 MHz, DMSO-d$_6$) δ 7.42 (s, 1H), 7.38-7.28 (m, 1H), 7.21 (d, J=7.3 Hz, 1H), 7.14-6.99 (m, 2H), 4.43 (s, 2H), 2.72-2.58 (m, 5H), 2.28 (br. s., 2H), 1.50-1.34 (m, 2H), 1.26-1.14 (m, 3H), 1.15-1.01 (m, 2H), 0.67 (t, J=7.3 Hz, 3H). Human APJ cAMP EC$_{50}$ Potency range B.

Example 138 to Example 153 were prepared as described in the general procedure given for Example 137.

Example 154 and Example 155

6-butyl-5-(2,6-dimethoxyphenyl)-3-{5-[(methyl-amino)methyl]-1,3,4-oxadiazol-2-yl}pyridine-2,4-diol and N-({5-[6-butyl-5-(2,6-dimethoxyphenyl)-2,4-dihydroxypyridin-3-yl]-1,3,4-oxadiazol-2-yl}methyl)-N-methyl-2-phenylacetamide

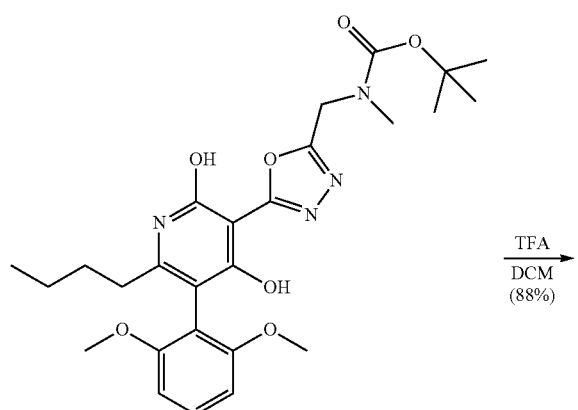

Example 121

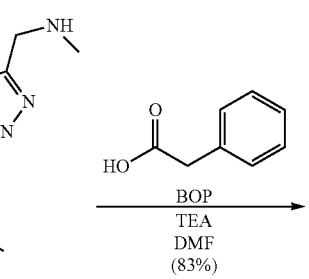

Example 154

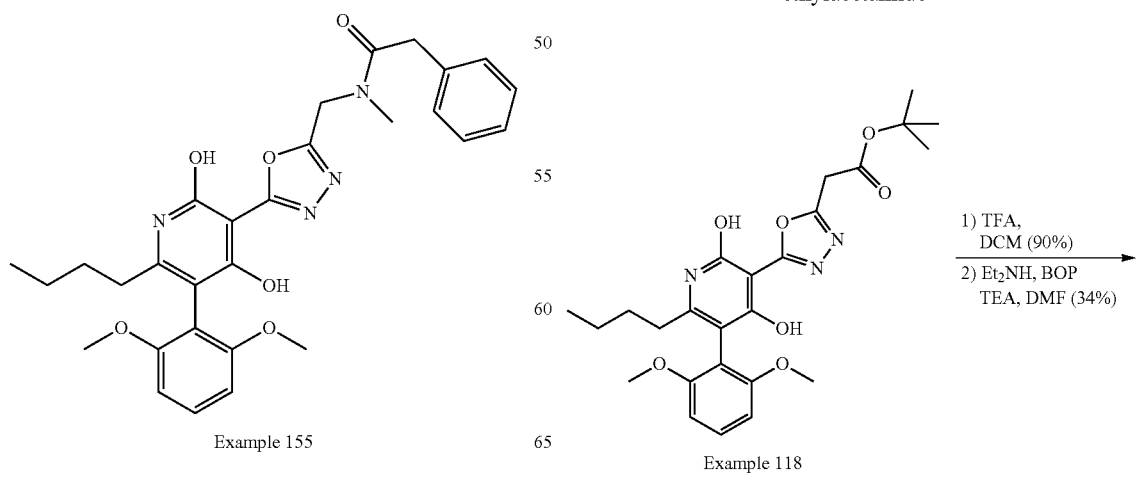

Example 155

Example 154

6-butyl-5-(2,6-dimethoxyphenyl)-3-{5-[(methyl-amino)methyl]-1,3,4-oxadiazol-2-yl}pyridine-2,4-diol To a solution of Example 121 (450 mg, 0.88 mmol) in DCM (3 mL) was added TFA (3 mL) and the mixture was stirred at rt for 30 min. The reaction mixture was concentrated under reduced pressure to give Example 154 (330 mg, 88% yield). LCMS (Method C) Rt=1.59 min, m/z=415.1 (M+H). $^1$H NMR (500 MHz, DMSO-$d_6$) δ 7.37 (t, J=8.4 Hz, 1H), 6.75 (d, J=8.5 Hz, 2H), 4.06 (s, 2H), 3.71 (s, 6H), 2.45-2.36 (m, 3H), 2.17 (t, J=7.4 Hz, 2H), 1.39-1.28 (m, 2H), 1.16-1.04 (m, 2H), 0.68 (t, J=7.2 Hz, 3H). Human APJ cAMP $EC_{50}$ Potency range B.

Example 155

N-({5-[6-butyl-5-(2,6-dimethoxyphenyl)-2,4-dihydroxypyridin-3-yl]-1,3,4-oxadiazol-2-yl}methyl)-N-methyl-2-phenylacetamide To a solution of Example 154 (12 mg, 0.029 mmol) and 2-phenylacetic acid (4.7 mg, 0.035 mmol) in DMF (0.5 mL) was added BOP reagent (15 mg, 0.035 mmol) followed by triethylamine (0.020 mL, 0.15 mmol) and the mixture stirred for 1 h. The reaction mixture was concentrated under reduced pressure then purified by prep HPLC to give Example 155 (13 mg, 83% yield). LCMS (Method C) Rt=2.07 min, m/z=533.2 (M+H). $^1$H NMR (500 MHz, DMSO-$d_6$) δ 7.43-7.16 (m, 6H), 6.80-6.68 (m, 2H), 4.88 (s, 2H), 3.82 (s, 2H), 3.70 (s, 6H), 2.52 (br. s., 3H), 2.20-2.11 (m, 2H), 1.41-1.28 (m, 2H), 1.18-1.02 (m, 2H), 0.67 (t, J=7.3 Hz, 3H). Human APJ cAMP $EC_{50}$ Potency range A.

Example 156 to Example 176 were prepared as described in the general procedure given for Example 155.

Example 177

2-{5-[6-butyl-5-(2,6-dimethoxyphenyl)-2,4-dihydroxypyridin-3-yl]-1,3,4-oxadiazol-2-yl}-N,N-diethylacetamide

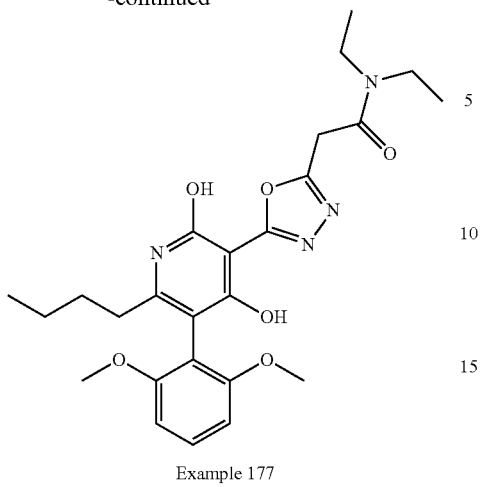

Example 177

Example 177

2-{5-[6-butyl-5-(2,6-dimethoxyphenyl)-2,4-dihydroxypyridin-3-yl]-1,3,4-oxadiazol-2-yl}-N,N-diethylacetamide To a solution of Example 118 (122 mg, 0.250 mmol) in DCM (2 mL) was added TFA (2 mL) and the reaction mixture was stirred at rt for 30 min. The reaction mixture was concentrated under reduced pressure to give the intermediate acid (120 mg, 90% yield). To a portion of the intermediate acid (10 mg, 0.023 mmol) in DMF (0.5 mL) was added diethylamine (0.003 mL, 0.05 mmol) followed by BOP reagent (12 mg, 0.028 mmol) and triethylamine (0.016 mL, 0.12 mmol) and the mixture stirred for 1 h. The mixture was concentrated under reduced pressure then purified by prep HPLC to give Example 177 (4.0 mg, 34% yield). LCMS (Method C) Rt=1.90 min, m/z=485.1 (M+H). $^1$H NMR (500 MHz, DMSO-$d_6$) δ 7.37 (t, J=8.3 Hz, 1H), 6.74 (d, J=8.5 Hz, 2H), 4.27 (s, 2H), 3.70 (s, 6H), 2.56 (s, 6H), 2.17 (t, J=7.7 Hz, 2H), 1.34 (t, J=7.8 Hz, 2H), 1.20 (t, J=7.0 Hz, 2H), 1.12-1.03 (m, 4H), 0.67 (t, J=7.3 Hz, 3H). Human APJ cAMP EC$_{50}$ Potency range A.

Example 178 to Example 201 were prepared as described in the general procedure given for Example 177.

Example 202

3-(3-benzyl-1,2,4-oxadiazol-5-yl)-6-butyl-5-(2,6-dimethoxyphenyl)pyridine-2,4-diol

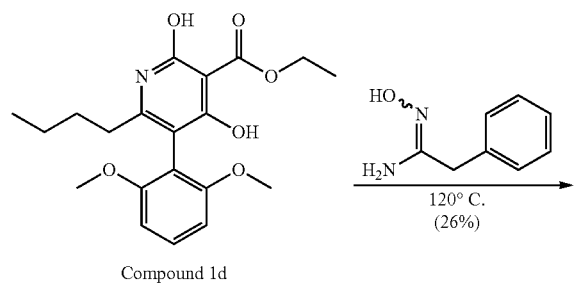

Compound 1d

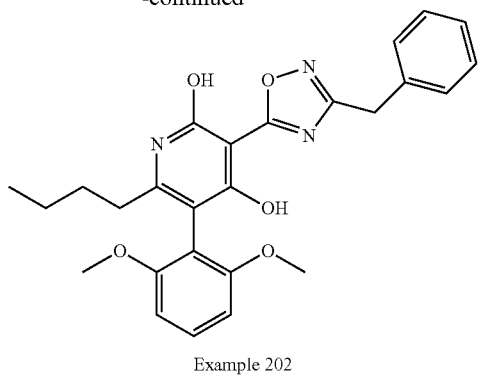

Example 202

Example 202

3-(3-benzyl-1,2,4-oxadiazol-5-yl)-6-butyl-5-(2,6-dimethoxyphenyl)pyridine-2,4-diol A vial containing Compound 1d (25 mg, 0.067 mmol) and N'-hydroxy-2-phenylacetimidamide (50 mg, 0.33 mmol) was sealed then stirred at 120° C. for 3 h. The reaction mixture was purified by prep HPLC to give Example 202 (8.0 mg, 26% yield). LCMS (Method C) Rt=2.17 min, m/z=462.1 (M+H). $^1$H NMR (500 MHz, DMSO-$d_6$) δ 7.48-7.32 (m, 5H), 7.31-7.23 (m, 1H), 6.73 (d, J=8.5 Hz, 2H), 4.15 (s, 2H), 3.68 (s, 6H), 2.17 (t, J=7.7 Hz, 2H), 1.34 (t, J=7.7 Hz, 2H), 1.15-1.02 (m, 2H), 0.67 (t, J=7.3 Hz, 3H). Human APJ cAMP EC$_{50}$ Potency range B.

Example 203 was prepared as described in the general procedure given for Example 202.

Example 204

3-(5-benzyl-4H-1,2,4-triazol-3-yl)-6-butyl-5-(2,6-dimethoxyphenyl)pyridine-2,4-diol

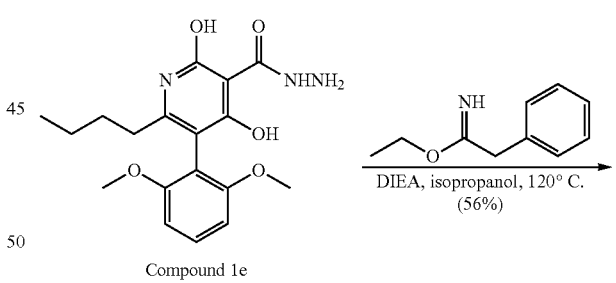

Compound 1e

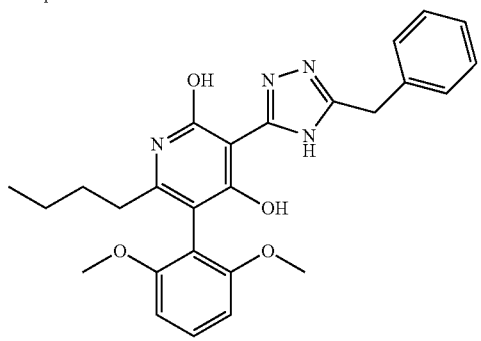

Example 204

Example 204

3-(5-benzyl-4H-1,2,4-triazol-3-yl)-6-butyl-5-(2,6-dimethoxyphenyl)pyridine-2,4-diol To a solution of Compound 1e (6.0 mg, 0.017 mmol) and ethyl 2-phenylacetimidate (2.7 mg, 0.017 mmol) in 2-propanol (0.3 mL) was added DIEA (0.10 mL, 0.57 mmol) and the reaction mixture heated at 120° C. using microwave irradiation for 20 min. The reaction mixture was concentrated under reduced pressure then purified by prep HPLC to give Example 204 (5.3 mg, 56% yield). LCMS (Method C) Rt=2.21 min, m/z=461.2 (M+H). $^1$H NMR (500 MHz, DMSO-$d_6$) 7.34 (t, J=8.4 Hz, 1H), 7.30-7.26 (m, 4H), 7.23-7.17 (m, 1H), 6.71 (d, J=8.6 Hz, 2H), 4.02 (s, 2H), 3.73-3.59 (m, 6H), 2.20-2.07 (m, 2H), 1.33 (dt, J=15.3, 7.5 Hz, 2H), 1.08 (sxt, J=7.4 Hz, 2H), 0.66 (t, J=7.4 Hz, 3H). Human APJ cAMP $EC_{50}$ Potency range C.

Example 205

6-butyl-3-(5-{[5-(4-chlorophenyl)-1,3,4-oxadiazol-2-yl]methyl}-1,3,4-oxadiazol-2-yl)-5-(2,6-dimethoxyphenyl)pyridine-2,4-diol

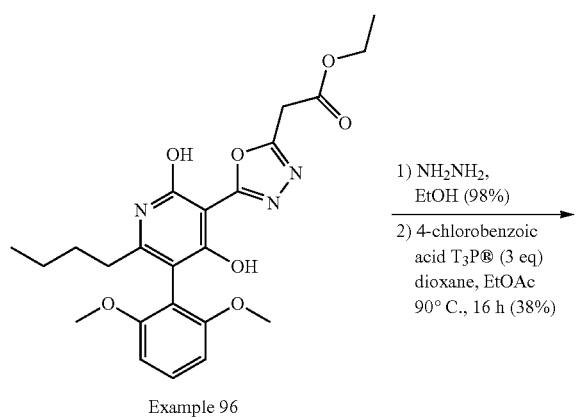

To a solution of Example 96 (500 mg, 1.1 mmol) in ethanol (5 mL) was added hydrazine (0.35 mL, 11 mmol) and the mixture stirred for 1 h. The mixture was concentrated under reduced pressure to give the intermediate hydrazide (480 mg, 98% yield) as a white solid. MS m/z=441.1 (M+H). A portion of the intermediate hydrazide (20 mg, 0.045 mmol) and 4-chlorobenzoic acid (8.5 mg, 0.054 mmol) were dissolved in dioxane (1 mL) then DIEA (0.020 mL, 0.11 mmol) added followed by a 50% solution of T3P® in ethyl acetate (0.067 mL, 0.11 mmol) and the mixture heated at 60° C. for 1 h. To the reaction mixture additional DIEA (0.020 mL, 0.11 mmol) and 50% solution of T3P® in ethyl acetate (0.067 mL, 0.11 mmol) were added and the reaction mixture was heated at 90° C. for 16 h. The reaction mixture was concentrated under reduced pressure then purified by prep HPLC to give Example 205 (9.7 mg, 38% yield). LCMS (Method D) Rt=0.97 min, m/z=564.3 (M+H). $^1$H NMR (500 MHz, DMSO-$d_6$) δ 8.03 (d, J=8.3 Hz, 2H), 7.70 (d, J=8.3 Hz, 2H), 7.35 (t, J=8.5 Hz, 1H), 6.73 (d, J=8.5 Hz, 2H), 4.96 (s, 2H), 3.70 (s, 6H), 2.14 (t, J=7.6 Hz, 2H), 1.41-1.26 (m, 2H), 1.16-1.01 (m, 2H), 0.67 (t, J=7.3 Hz, 3H). Human APJ cAMP $EC_{50}$ Potency range B.

Example 206 to Example 211 were prepared as described in the general procedure given for Example 205.

Example 212

1-({5-[6-(ethoxymethyl)-5-(4-fluoro-2,6-dimethoxyphenyl)-2,4-dihydroxypyridin-3-yl]-1,3,4-oxadiazol-2-yl}methyl)-1,2-dihydropyridin-2-one

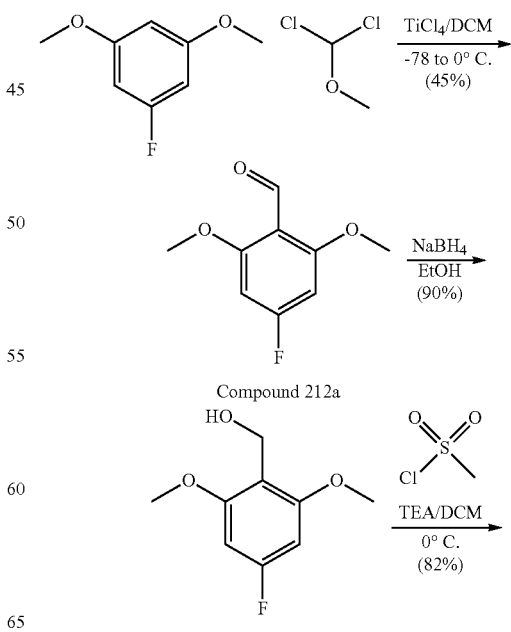

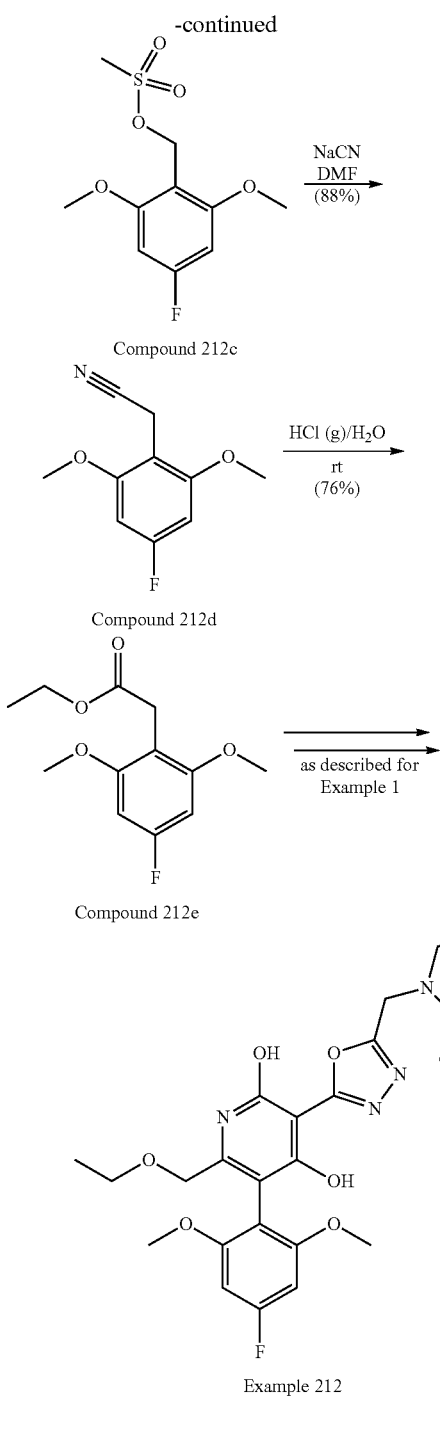

Compound 212c

Compound 212d

Compound 212e

Example 212

Compound 212a.
4-Fluoro-2,6-dimethoxybenzaldehyde

To a stirred solution of 1-fluoro-3,5-dimethoxybenzene (3.00 g, 19.2 mmol) in DCM (45 mL) was slowly added a 1.0 M solution of TiCl$_4$ in DCM (38.4 mL, 38.4 mmol) at 0° C. over 15 min. The reaction mixture was cooled to −78° C. and treated with dichloro(methoxy)methane (2.26 mL, 25.0 mmol) dropwise. The reaction mixture was stirred at −78° C. for 30 min and allowed to warm to 0° C. After 1 hour, the reaction mixture was poured into dilute HCl and extracted with ethyl acetate (2×). The combined organic fractions were dried over Na$_2$SO$_4$, filtered and concentrated under reduced pressure. The residue was purified on silica gel chromatography eluting with 0% to 30% ACN/DCM to afford Compound 212a (1.60 g, 45%) as a white solid. MS m/z=184.9 (M+H). $^1$H NMR (400 MHz, CDCl$_3$) δ 10.42 (s, 1H), 6.34 (s, 1H), 6.31 (s, 1H), 3.91 (s, 6H)

Compound 212b.
(4-Fluoro-2,6-dimethoxyphenyl)methanol

To a suspension of Compound 212a (2.52 g, 13.7 mmol) in ethanol (60 mL) at 0° C. was added sodium borohydride (0.35 g, 9.1 mmol). The ice bath was removed and stirring continued for 20 min. The reaction mixture was cooled to 0° C. then quenched by the addition of sat'd ammonium chloride solution. The resulting suspension was concentrated and redissolved in EtOAc/water mixture. The layers were separated and the organic fraction was washed with brine, dried over Na$_2$SO$_4$, and concentrated under reduced pressure to give Compound 212b (2.3 g, 90%) as a white solid which was used without further purification. LCMS (Method C) Rt=1.38 min. $^1$H NMR (400 MHz, CDCl$_3$) δ 6.33 (s, 1H), 6.31 (s, 1H), 4.74 (m, 2H), 3.85 (s, 6H)

Compound 212c. 4-Fluoro-2,6-dimethoxybenzyl methanesulfonate

To a solution of Compound 212b (2.3 g, 13 mmol) in DCM (80 mL) was added TEA (3.5 mL, 25 mmol). The reaction mixture was cooled to 0° C. and treated with mesyl chloride (7.4 mL, 0.095 mol) in DCM (25 mL). After 30 min, the reaction mixture was diluted with DCM (100 mL) and washed with water (3×50 mL). The organic layer was dried over Na$_2$SO$_4$ and concentrated under reduced pressure to give Compound 212c (2.7 g, 82%) which was used without further purification. LCMS (Method C) Rt=1.64 min. $^1$H NMR (400 MHz, CDCl$_3$) δ 6.23 (s, 1H), 6.20 (s, 1H), 4.64 (s, 2H), 3.78 (s, 6H)

Compound 212d.
2-(4-Fluoro-2,6-dimethoxyphenyl)acetonitrile

To a solution of Compound 212c (2.7 g, 10 mmol) in DMF (40 mL) was added sodium cyanide (1.0 g, 20 mmol) and the reaction mixture was stirred for 30 min. The reaction mixture was diluted with water (800 mL) and extracted with 30% ethyl acetate in hexane (3×200 mL). The combined organic layers were dried over Na$_2$SO$_4$ and concentrated under reduced pressure. The residue was purified by silica gel chromatography eluting with 0 to 5% ethyl acetate in hexane to give Compound 212d (1.8 g, 88%). MS m/z=196.0 (M+H). $^1$H NMR (400 MHz, DMSO-d$_6$) δ 6.67 (s, 1H), 6.64 (s, 1H), 3.85 (s, 6H), 3.65 (s, 2H)

Compound 212e. Ethyl 2-(4-fluoro-2,6-dimethoxyphenyl)acetate

To a solution of Compound 212d (1.75 g, 8.97 mmol) in EtOH (40 mL) was bubbled HCl gas for 2 h. The reaction mixture was concentrated under reduced pressure and the residue was diluted with water (50 mL) and heated at 40° C. overnight. After allowing to cool to rt, the reaction mixture was extracted with ethyl acetate (3×50 mL). The combined organic layers were dried over Na$_2$SO$_4$ and concentrated under reduced pressure to give Compound 212e (1.6 g, 76%). MS m/z=243.1 (M+H). $^1$H NMR (400 MHz, DMSO-d$_6$) δ 6.58 (s, 1H), 6.55 (s, 1H), 4.05 (q, J=7.0 Hz, 2H), 3.76 (s, 6H), 3.49 (s, 2H), 1.17 (t, J=7.2 Hz, 3H)

Example 212

1-({5-[6-(ethoxymethyl)-5-(4-fluoro-2,6-dimethoxyphenyl)-2,4-dihydroxypyridin-3-yl]-1,3,4-oxadiazol-2-yl}methyl)-1,2-dihydropyridin-2-one Example 212 was prepared from Compound 212e as described in the general procedure for Example 1 in 5% yield. LCMS (Method C) Rt=1.66 min, m/z=499.1 (M+H). $^1$H NMR (400 MHz, CDCl$_3$) δ 7.51 (m, 1H), 7.46 (m, 1H), 6.72 (d, J=9.0 Hz, 1H), 6.42 (s, 1H), 6.40 (s, 1H), 6.38-6.33 (m, 1H), 5.49 (s, 2H), 4.19 (s, 2H), 3.75 (s, 6H), 3.57 (m, 2H), 1.28 (t, J=6.9 Hz, 3H). Human APJ cAMP EC$_{50}$ Potency range B.

Example 213 to Example 216 were prepared as described in the general procedure given for Example 212.

Example 217

3-{5-[(4-chlorophenyl)methyl]-1,3,4-oxadiazol-2-yl}-5-(3,5-dimethoxypyridin-4-yl)-6-(ethoxymethyl)pyridine-2,4-diol

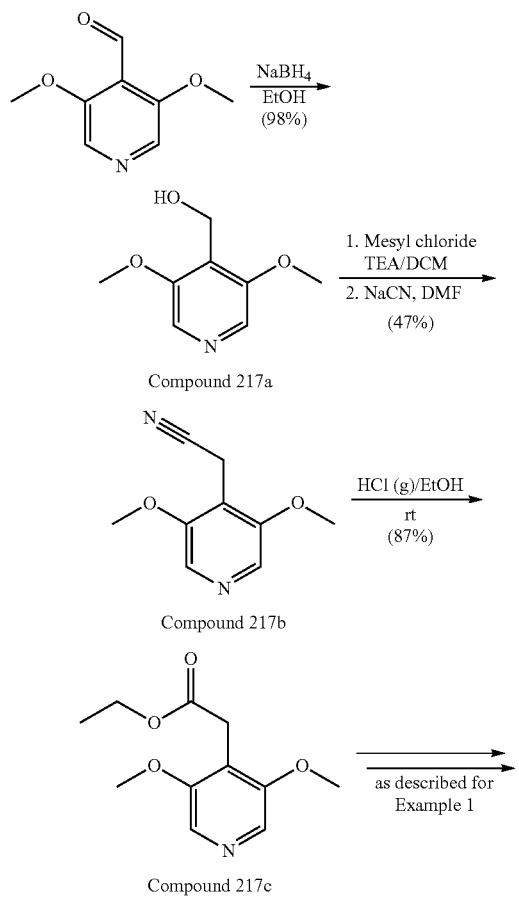

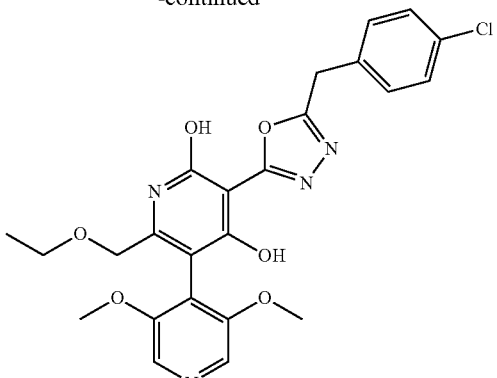

Example 217

Compound 217a.
(3,5-Dimethoxypyridin-4-yl)methanol

To a suspension of 3,5-dimethoxyisonicotinaldehyde (300 mg, 1.80 mmol) in ethanol (12 mL) at 0° C. was added sodium borohydride (45.2 mg, 1.20 mmol). The ice bath was removed and stirring continued for 20 min. The reaction mixture was cooled to 0° C. and quenched by addition of sat'd ammonium chloride. The resulting suspension was concentrated and redissolved in EtOAc/water. The reaction mixture was extracted with EtOAc and the organic extracts washed with brine, dried over MgSO$_4$, and concentrated to give Compound 217a (0.30 g, 98%) as a clear oil. MS m/z=170.0 (M+H). $^1$H NMR (400 MHz, CDCl$_3$) δ 8.04 (s, 2H), 4.77 (s, 2H), 3.95 (s, 6H)

Compound 217b.
2-(3,5-Dimethoxypyridin-4-yl)acetonitrile

To a solution of Compound 217a (400 mg, 2.3 mmol) in DCM (14 mL) and TEA (0.49 mL, 3.6 mmol) at 0° C. was added dropwise a solution of mesyl chloride (7.4 mL, 0.095 mol) in DCM (25 mL). After 0.5 h the mixture was diluted with DCM (100 mL) and washed with water (3×50 mL). The organic layer was dried over Na$_2$SO$_4$ and concentrated under reduced pressure to afford a light brown oil which was dissolved in DMF (10 mL) and treated with sodium cyanide (0.23 g, 4.7 mmol). The reaction mixture was stirred for 0.5 h then diluted with water (80 mL) and extracted with 30% ethyl acetate in hexane (3×200 mL). The combined organic extracts were dried over Na$_2$SO$_4$ and concentrated under reduced pressure. The residue was purified by silica gel chromatography eluting with 0-65% ethyl acetate in hexane to give Compound 217b (200 mg, 47%) as a white solid. MS m/z=179.0 (M+H).

Compound 217c. Ethyl 2-(3,5-dimethoxypyridin-4-yl)acetate

To a solution of Compound 217b (200 mg, 1.12 mmol) in EtOH (8 mL) was bubbled HCl gas for 2 h. The reaction mixture was concentrated under reduced pressure and the residue was diluted with water (15 mL) and heated at 40° C. for 14 h. After allowing to cool to rt, the reaction mixture was extracted with ethyl acetate (3×50 mL). The combined organic layers were dried over magnesium sulfate, filtered and concentrated under reduced pressure. The residue was purified by silica gel chromatography eluting with 0-100% ethyl acetate in hexane to give Compound 217c (220 mg, 87%) as a clear oil. MS m/z=226.0 (M+H). ¹H NMR (400 MHz, CDCl₃) δ 8.02 (br. s., 2H), 4.15 (q, J=7.1 Hz, 2H), 3.91 (s, 6H), 3.67 (s, 2H), 1.24 (t, J=7.0 Hz, 3H)

Example 217

3-{5-[(4-chlorophenyl)methyl]-1,3,4-oxadiazol-2-yl}-5-(3,5-dimethoxypyridin-4-yl)-6-(ethoxymethyl)pyridine-2,4-diol Example 217 was prepared from Compound 217c as described in the general procedure for Example 1 in 1% yield. LCMS (Method C) Rt=1.67 min, m/z=499.0 (M+H). ¹H NMR (400 MHz, CDCl₃) δ 8.16 (s, 2H), 7.33 (m, 4H), 4.30 (s, 2H), 4.12 (s, 2H), 3.89 (s, 6H), 3.53 (m, 2H), 1.25 (t, J=7.0 Hz, 3H). Human APJ cAMP EC$_{50}$ Potency range B.

Example 218

6-butyl-3-{5-[(4-chlorophenyl)methyl]-1,3,4-oxadiazol-2-yl}-5-(3-fluoro-2,6-dimethoxyphenyl)pyridine-2,4-diol (isomer 1) and Example 219. 6-butyl-3-{5-[(4-chlorophenyl)methyl]-1,3,4-oxadiazol-2-yl}-5-(3-fluoro-2,6-dimethoxyphenyl)pyridine-2,4-diol (isomer 2)

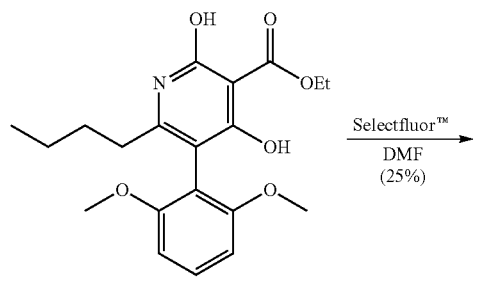

Compound 1d

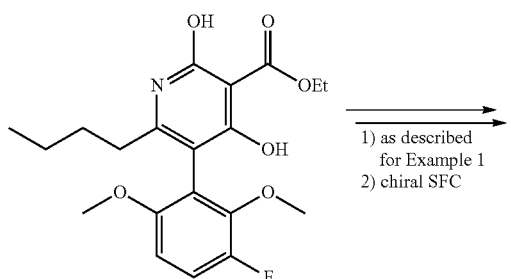

Compound 218a

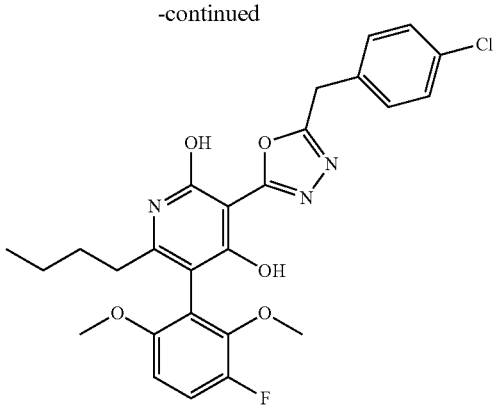

Example 218
(isomer 1)

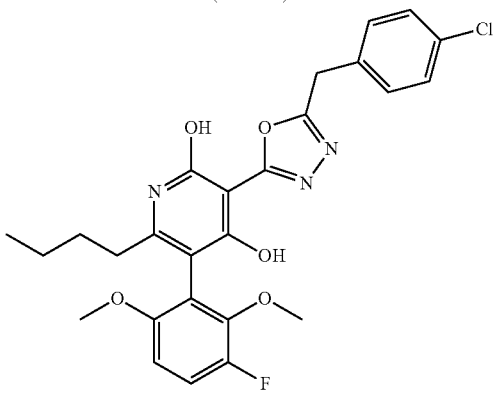

Example 219
(isomer 2)

Compound 218a. Ethyl 6-butyl-5-(3-fluoro-2,6-dimethoxyphenyl)-2,4-dihydroxynicotinate To a solution of Compound 1d (650 mg, 1.73 mmol) in DMF (7.5 mL) at 0° C. was slowly added Selectfluor™ (613 mg, 1.73 mmol). After stirring for a minute at 0° C., the ice bath was removed and stirring continued at rt for 16 h. The reaction mixture was diluted with EtOAc, washed with water (3×), then brine, dried over Na₂SO₄, filtered and concentrated under reduced pressure. The resulting solid was triturated with EtOAc (3×). The triturate was evaporated under reduced pressure and the residue purified by silica gel chromatography eluting with 0-100% ethyl acetate in hexane to give Compound 218a (170 mg, 25%) as a white solid. MS m/z=394.1.0 (M+H). ¹H NMR (400 MHz, CDCl₃) δ 7.10 (dd, J=11.2, 9.2 Hz, 1H), 6.69-6.54 (m, 1H), 4.41 (q, J=7.0 Hz, 2H), 3.82 (m, 3H), 3.72 (s, 3H), 2.35 (t, J=7.8 Hz, 2H), 1.52 (td, J=7.5, 2.5 Hz, 2H), 1.40 (t, J=7.0 Hz, 3H), 0.78 (t, J=7.3 Hz, 3H)

Example 218

6-butyl-3-{5-[(4-chlorophenyl)methyl]-1,3,4-oxadiazol-2-yl}-5-(3-fluoro-2,6-dimethoxyphenyl)pyridine-2,4-diol (isomer 1) and Example 219. 6-butyl-3-{5-[(4-chlorophenyl)methyl]-1,3,4-oxadiazol-2-yl}-5-(3-fluoro-2,6-dimethoxyphenyl)pyridine-2,4-diol (isomer 2)

Example 218 and Example 219 were prepared from Compound 218a as described in the general procedures for Example 1. The atropisomers were separated using chiral SFC after the final step (instrument: Berger Multigram II SFC; column: Chirapak AD-H, 21×250 mm ID, 5 micron;

flow rate: 45 mL/min, 100 bar, 40° C.; mobile phase: 20% isopropanol/80% $CO_2$; wavelength: 220 nm) to give first eluting Example 218 (3 mg, 7%) as a white solid, analytical SFC Rt=4.0 min (instrument: Aurora Analytical SFC; column: Chirapak AD-H, 4.6×250 mm ID, 5 micron; flow rate: 2 mL/min, 150 bar, 35° C.; mobile phase: 25% isopropanol/75% $CO_2$; 220 nm), LCMS (Method C) Rt=2.20 min, m/z=514.0 (M+H), $^1$H NMR (400 MHz, $CDCl_3$) δ 7.24 (m, 4H), 7.06 (m, 1H), 6.54 (m, 1H), 4.20 (s, 2H), 4.01-3.91 (m, 2H), 3.74 (m, 3H), 3.64 (s, 3H), 3.42 (m, 2H), 0.71 (t, J=7.2 Hz, 3H), Human APJ cAMP $EC_{50}$ Potency range B; and the second eluting Example 219 (3 mg, 7%) as a white solid, analytical SFC Rt=5.2 min, LCMS (Method C) Rt=2.20 min, m/z=514.0 (M+H), $^1$H NMR (400 MHz, $CDCl_3$) δ 7.24 (m, 4H), 7.06 (m, 1H), 6.54 (m, 1H), 4.20 (s, 2H), 4.01-3.91 (m, 2H), 3.74 (m, 3H), 3.64 (s, 3H), 3.42 (m, 2H), 0.71 (t, J=7.2 Hz, 3H), Human APJ cAMP $EC_{50}$ Potency range A.

Example 220 to Example 221 were prepared as described in the general procedure given for Example 218 and Example 219.

Example 222 and Example 223. 3-{5-[(4-chlorophenyl)methyl]-1,3,4-oxadiazol-2-yl}-6-(ethoxymethyl)-5-(2-hydroxy-6-methoxyphenyl)pyridine-2,4-diol (Isomer 1) and 3-{5-[(4-chlorophenyl)methyl]-1,3,4-oxadiazol-2-yl}-6-(ethoxymethyl)-5-(2-hydroxy-6-methoxyphenyl)pyridine-2,4-diol (Isomer 2)

To a solution of Example 90 (66 mg, 0.13 mmol) in DCM (2 mL) at −78° C. was added $BBr_3$ (1M in hexanes) (0.13 mL, 0.13 mmol) and the reaction mixture stirred for 15 min. The reaction mixture was cooled to 0° C. and stirred for 15 min. Additional $BBr_3$ (1M in hexanes) (0.07 mL, 0.07 mmol) was added and the reaction mixture stirred for 15 min. The reaction mixture was diluted with water (5 mL), extracted with DCM (3×5 mL) and the combined organic portions dried over $Na_2SO_4$, filtered, then concentrated under reduced pressure. The residue was purified by prep HPLC then the atropisomers separated by chiral SFC (instrument: Berger Multigram II SFC; column: Chirapak AD-H, 21×250 mm ID, 5 micron; flow rate: 45 mL/min, 100 bar, 40° C.; mobile Phase: 35% isopropanol/65% $CO_2$; wavelength: 220 nm) to give Example 222 (11 mg, 16%) as isomer 1, analytical SFC Rt=7.2 min (instrument: Aurora Analytical SFC; column: Chirapak AD-H, 4.6×250 mm ID, 5 micron; flow rate: 2 mL/min, 150 bar, 35° C.; mobile Phase: 35% isopropanol/65% $CO_2$; 220 nm): LCMS (Method D) Rt=0.90 min, m/z=484.1 $[M+H]^+$, $^1$H NMR (500 MHz, $CD_3OD$) δ 7.47-7.31 (m, 4H), 7.22-7.08 (m, 1H), 6.61-6.44 (m, 2H), 4.39-4.25 (m, 2H), 4.18-4.07 (m, 2H), 3.71 (s, 3H), 3.49-3.41 (m, 2H), 1.35-1.28 (m, 3H); Human APJ cAMP $EC_{50}$ Potency range A; and Example 223 (11 mg, 16%) as isomer 2, analytical SFC Rt=12.6 min: LCMS (Method D) Rt=0.90 min, m/z=484.1 $[M+H]^+$. $^1$H NMR (500 MHz, $CD_3OD$) δ 7.47-7.31 (m, 4H), 7.22-7.08 (m, 1H), 6.61-6.44 (m, 2H), 4.39-4.25 (m, 2H), 4.18-4.07 (m, 2H),

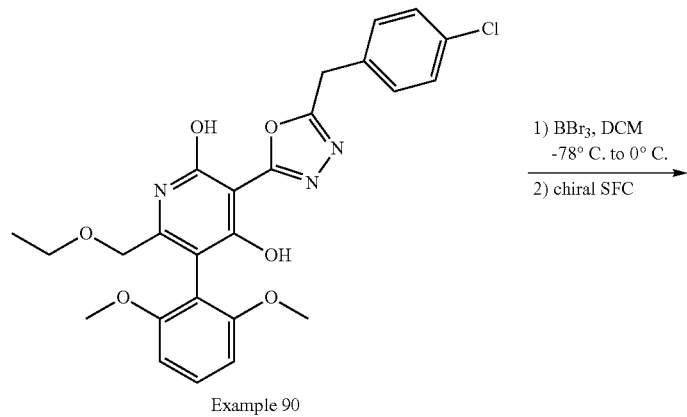

Example 90

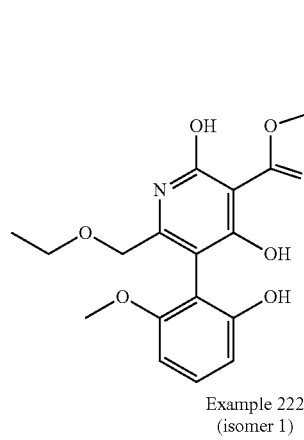

Example 222 (isomer 1)

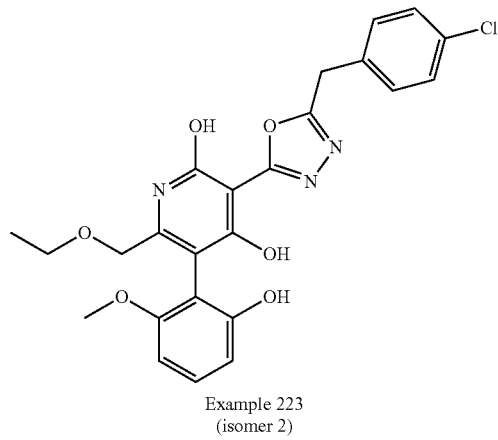

Example 223 (isomer 2)

3.71 (s, 3H), 3.49-3.41 (m, 2H), 1.35-1.28 (m, 3H); Human APJ cAMP EC$_{50}$ Potency range B.

Example 224

3-[5-(1,2-benzoxazol-3-ylmethyl)-1,3,4-oxadiazol-2-yl]-6-butyl-5-(2,6-dimethylphenyl)pyridine-2,4-diol

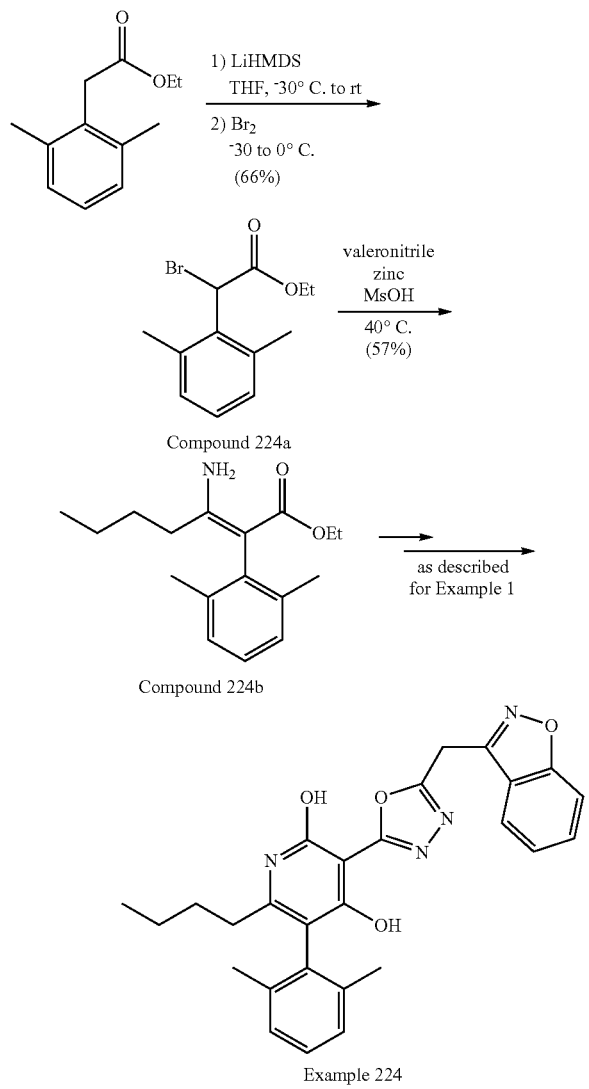

Compound 224a. ethyl 2-bromo-2-(2,6-dimethylphenyl)acetate

To a solution of 1N LiHMDS in THF (4.4 mL, 4.4 mmol) in THF (7 mL) at −30° C. was added dropwise a solution of ethyl 2-(2,6-dimethylphenyl)acetate (800 mg, 4.2 mmol) in THF (7 mL) and the reaction mixture stirred for 15 min. A solution of bromine (0.21 mL, 4.2 mmol) in THF (7 mL) was added dropwise, then the temperature was allowed to warm to −5° C. over a 1 h period. The reaction mixture was quenched by the addition of aqueous sodium thiosulfate then extracted with EtOAc. The organic extract was washed with satd NH$_4$Cl and brine, then dried (MgSO$_4$), filtered and concentrated under reduced pressure. The residue was purified by silica gel chromatography eluting with 1 to 4% EtOAc/hexanes to give Compound 224a (740 mg, 2.7 mmol, 66% yield) as a clear colorless oil which solidified upon standing. MS m/z=271.0 (M+H). $^1$H NMR (400 MHz, CDCl$_3$) δ 7.16-7.09 (m, 1H), 7.06-7.01 (m, 2H), 5.95 (s, 1H), 4.33-4.19 (m, 2H), 2.37 (s, 6H), 1.26 (t, J=7.2 Hz, 3H).

Compound 224b. (Z)-ethyl 3-amino-2-(2,6-dimethylphenyl)hept-2-enoate

To a solution of Compound 224a (130 mg, 0.47 mmol) in valeronitrile (0.50 mL, 4.7 mmol) was added activated zinc (46 mg, 0.71 mmol) followed by methanesulfonic acid (0.61 μl, 9.4 μmol) and the reaction mixture stirred at 40° C. for 1.5 h. The reaction mixture was allowed to cool to room temperature then diluted with EtOAc and filtered. The filtrate was poured into satd NaHCO$_3$ and extracted with EtOAc (3×). The combined extracts were washed with brine, dried (Na$_2$SO$_4$), filtered and concentrated under reduced pressure. The residue was purified by silica gel chromatography eluting with 0 to 15% EtOAc/hexanes to give Compound 224b (74 mg, 0.27 mmol, 57% yield) as a clear oil. MS m/z=276.5 (M+H). $^1$H NMR (400 MHz, CDCl$_3$) δ 7.11-6.99 (m, 3H), 4.06 (q, J=7.0 Hz, 2H), 2.12 (s, 6H), 1.88-1.78 (m, 2H), 1.40-1.28 (m, 2H), 1.23-1.13 (m, 2H), 1.10 (t, J=7.2 Hz, 3H), 0.75 (t, J=7.3 Hz, 3H).

Example 224

3-[5-(1,2-benzoxazol-3-ylmethyl)-1,3,4-oxadiazol-2-yl]-6-butyl-5-(2,6-dimethylphenyl)pyridine-2,4-diol Example 224 was prepared from Compound 224b as described in the general procedure given for Example 1 in 33% yield. LCMS (Method A) Rt=2.12 min, m/z=471.1 (M+H). 1H NMR (500 MHz, DMSO-d6) δ 8.00 (d, J=7.6 Hz, 1H), 7.81 (d, J=8.2 Hz, 1H), 7.72 (t, J=7.2 Hz, 1H), 7.44 (t, J=6.7 Hz, 1H), 7.20 (d, J=7.3 Hz, 1H), 7.17-7.10 (m, 2H), 4.96 (s, 2H), 2.52 (br. s., 5H), 2.15 (br. s., 1H), 1.36 (br. s., 2H), 1.12 (d, J=7.0 Hz, 2H), 0.69 (t, J=6.9 Hz, 3H). Human APJ cAMP EC50 Potency range A.

Example 225 and Example 226 were prepared as described in the general procedure given for Example 224.

Example 227

6-butyl-5-(2,6-dimethoxyphenyl)-3-(5-{[1,2]oxazolo[4,5-b]pyridin-3-ylmethyl}-1,3,4-oxadiazol-2-yl)pyridine-2,4-diol

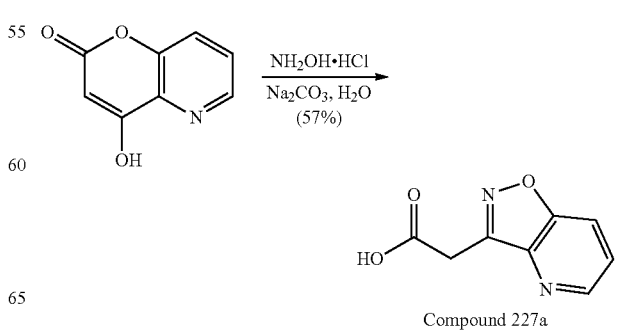

-continued

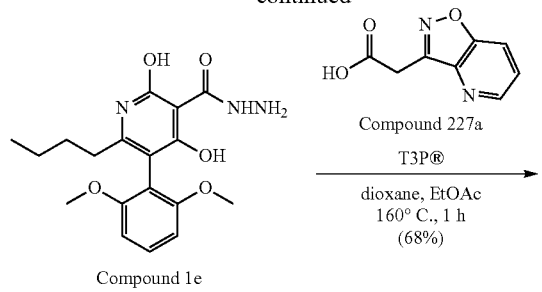

Compound 1e

Compound 227a

T3P®
────────────→
dioxane, EtOAc
160° C., 1 h
(68%)

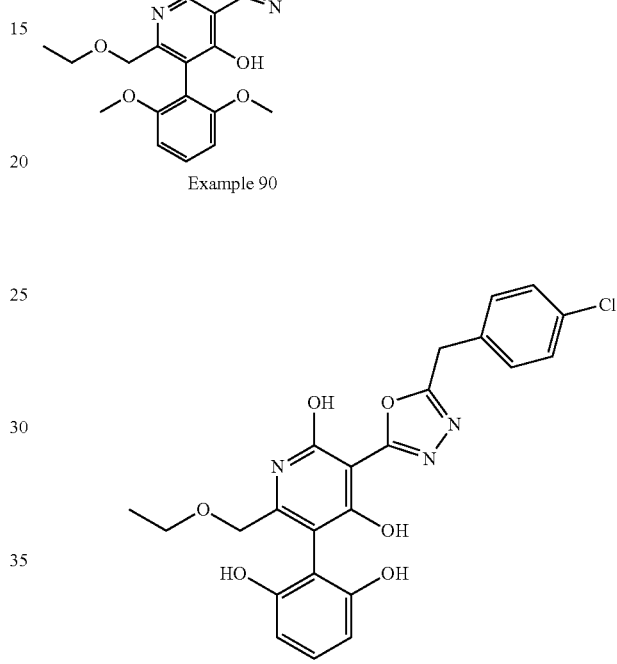

Example 227

Compound 227a.
2-(isoxazolo[4,5-b]pyridin-3-yl)acetic acid

To a flask containing hydroxylamine hydrochloride (280 mg, 4.0 mmol) was added 10% aq sodium carbonate (1.5 mL, 1.5 mmol) and the mixture stirred for 10 min. The solution was added to a flask containing 4-hydroxy-2H-pyrano[3,2-b]pyridin-2-one (130 mg, 0.79 mmol; prepared as described in DE2442666A1, 1975) and the reaction mixture stirred at 50° C. for 16 h. The reaction mixture was cooled to 10° C. then acidified to pH 2 with dilute HCl. The reaction mixture was stirred for 0.5 h then filtered. The filtrate was purified by HPLC to give Compound 227a (80 mg, 0.45 mmol, 57% yield) as a pale yellow solid. MS m/z=179.0 (M+H). $^1$H NMR (500 MHz, DMSO-$d_6$) δ 12.92 (br. s., 1H), 8.80-8.72 (m, 1H), 8.28 (dd, J=8.5, 1.1 Hz, 1H), 7.71 (dd, J=8.5, 4.4 Hz, 1H), 4.13 (s, 2H).

Example 227

6-butyl-5-(2,6-dimethoxyphenyl)-3-(5-{[1,2]oxazolo[4,5-b]pyridin-3-ylmethyl}-1,3,4-oxadiazol-2-yl)pyridine-2,4-diol Example 227 was prepared from Compound 227a and Compound 1e as described in the general procedure given for Example 1 in 68% yield. LCMS (Method A) Rt=1.56 min, m/z=504.2 (M+H). $^1$H NMR (500 MHz, DMSO-$d_6$) δ 8.77 (d, J=4.3 Hz, 1H), 8.34 (d, J=8.5 Hz, 1H), 7.75 (dd, J=8.4, 4.4 Hz, 1H), 7.36 (t, J=8.4 Hz, 1H), 6.73 (d, J=8.5 Hz, 2H), 4.96 (s, 2H), 3.70 (s, 6H), 2.15 (t, J=7.5 Hz, 2H), 1.40-1.27 (m, 2H), 1.15-1.03 (m, 2H), 0.66 (t, J=7.3 Hz, 3H). Human APJ cAMP $EC_{50}$ Potency range A.

Example 228 was prepared as described in the general procedure given for Example 227.

Example 229

3-{5-[(4-chlorophenyl)methyl]-1,3,4-oxadiazol-2-yl}-5-(2,6-dihydroxyphenyl)-6-(ethoxymethyl)pyridine-2,4-diol

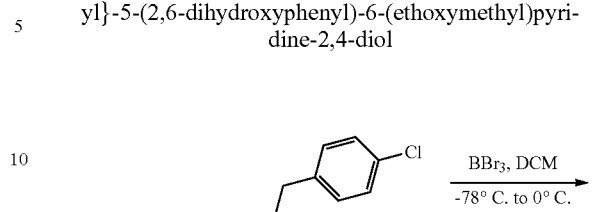

Example 90

BBr$_3$, DCM
────────────→
-78° C. to 0° C.
(23%)

Example 229

Example 229

3-{5-[(4-chlorophenyl)methyl]-1,3,4-oxadiazol-2-yl}-5-(2,6-dihydroxyphenyl)-6-(ethoxymethyl)pyridine-2,4-diol To a solution of Example 90 (86 mg, 0.17 mmol) in DCM (2 mL) at −78° C. was added BBr$_3$ (1.0M in hexanes) (0.17 mL, 0.17 mmol) and the reaction mixture stirred for 15 min. The reaction mixture was then placed in an ice bath and stirred for 15 min. Additional BBr$_3$ (1.0M in hexanes) (0.09 mL, 0.09 mmol) was added and the reaction mixture stirred 15 min then diluted with water (5 mL), extracted with DCM (2×15 mL), dried over Na$_2$SO$_4$, then concentrated under reduced pressure. The residue was purified by prep HPLC to give Example 229 (19 mg, 23% yield) as a white solid. LCMS (Method D) Rt=0.81 min, m/z=470.0 [M+H]$^+$. $^1$H NMR (500 MHz, CD$_3$OD) δ 7.46-7.30 (m, 4H), 7.13-6.97 (m, 1H), 6.50-6.32 (m, 2H), 4.41-4.31 (m, 2H), 4.28-4.22 (m, 2H), 3.51-3.46 (m, 2H), 1.24-1.12 (m, 3H). Human APJ cAP $EC_{50}$ Potency range B

| Ex # | Structure | Name | ¹H NMR | LC/MS Rt (min) Method M + H | hAPJ cAMP EC$_{50}$ Potency range (nM) |
|---|---|---|---|---|---|
| 2 | 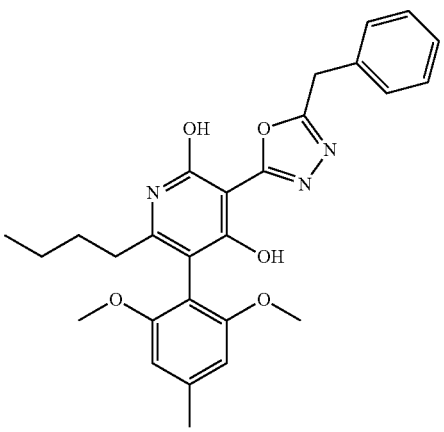 [SMILES: CCCCc1nc(O)c(-c2nnc(Cc3ccccc3)o2)c(O)c1-c1c(OC)cc(C)cc1OC] | 3-(5-benzyl-1,3,4-oxadiazol-2-yl)-6-butyl-5-(2,6-dimethoxy-4-methylphenyl)pyridine-2,4-diol | 1H NMR (500 MHz, DMSO-d6) δ 7.41-7.34 (m, 4H), 7.33-7.27 (m, 1H), 6.55 (s, 2H), 4.37 (s, 2H), 3.66 (s, 6H), 2.36 (s, 3H), 2.14 (t, J = 7.6 Hz, 2H), 1.33 (quin, J = 7.6 Hz, 2H), 1.09 (sxt, J = 7.3 Hz, 2H), 0.68 (t, J = 7.3 Hz, 3H) | 2.00 A 476.3 | C |
| 3 | 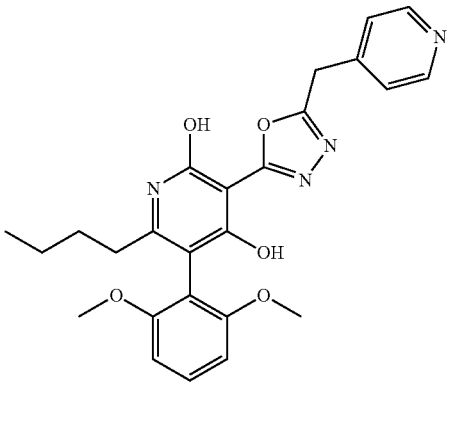 [SMILES: CCCCc1nc(O)c(-c2nnc(Cc3ccncc3)o2)c(O)c1-c1c(OC)cccc1OC] | 6-butyl-5-(2,6-dimethoxyphenyl)-3-[5-(pyridin-4-ylmethyl)-1,3,4-oxadiazol-2-yl]pyridine-2,4-diol | 1H NMR (500 MHz, DMSO-d6) δ 8.56 (d, J = 5.2 Hz, 2H), 7.40 (d, J = 5.3 Hz, 2H), 7.35 (t, J = 8.3 Hz, 1H), 6.72 (s, 2H), 4.44 (s, 2H), 3.68 (s, 6H), 2.13 (t, J = 7.5 Hz, 2H), 1.32 (quin, J = 7.5 Hz, 2H), 1.15-1.01 (m, 2H), 0.65 (t, J = 7.3 Hz, 3H) | 1.37 A 463.2 | B |
| 4 | 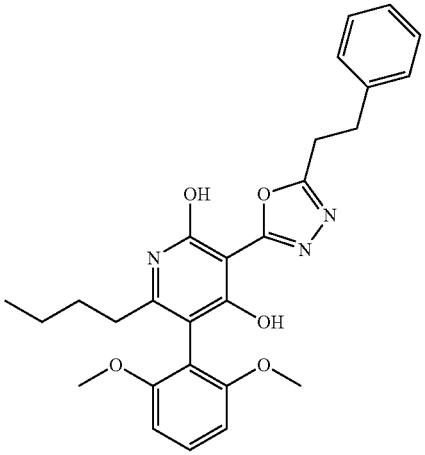 [SMILES: CCCCc1nc(O)c(-c2nnc(CCc3ccccc3)o2)c(O)c1-c1c(OC)cccc1OC] | 6-butyl-5-(2,6-dimethoxyphenyl)-3-[5-(2-phenylethyl)-1,3,4-oxadiazol-2-yl]pyridine-2,4-diol | 1H NMR (500 MHz, DMSO-d6) δ 7.37-7.26 (m, 5H), 7.23-7.16 (m, 1H), 6.70 (d, J = 8.4 Hz, 2H), 3.66 (s, 6H), 3.24-3.18 (m, 2H), 3.13-3.03 (m, 2H), 2.11 (t, J = 7.3 Hz, 2H), 1.40-1.25 (m, 2H), 1.12-1.01 (m, 2H), 0.64 (t, J = 7.3 Hz, 3H) | 1.87 A 476.2 | B |

-continued

| Ex # | Structure | Name | ¹H NMR | LC/MS Rt (min) Method M + H | hAPJ cAMP EC$_{50}$ Potency range (nM) |
|---|---|---|---|---|---|
| 5 | 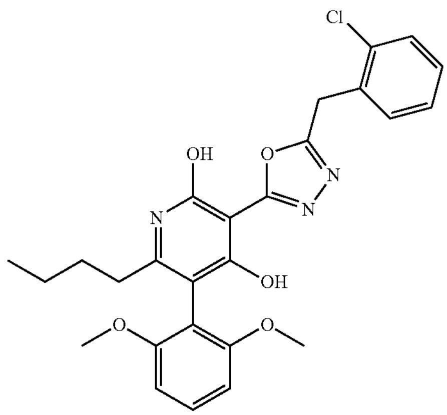 [SMILES: CCCCc1nc(O)c(-c2nnc(Cc3ccccc3Cl)o2)c(O)c1-c1c(OC)cccc1OC] | 6-butyl-3-{5-[(2-chlorophenyl)methyl]-1,3,4-oxadiazol-2-yl}-5-(2,6-dimethoxyphenyl)pyridine-2,4-diol | 1H NMR (500 MHz, DMSO-d6) δ 7.50 (dd, J = 15.7, 4.5 Hz, 2H), 7.42-7.28 (m, 3H), 6.73 (d, J = 8.4 Hz, 2H), 4.47 (s, 2H), 3.75-3.62 (m, 6H), 2.15 (t, J = 7.6 Hz, 2H), 1.35-1.24 (m, 2H), 1.14-1.02 (m, 2H), 0.66 (t, J = 7.3 Hz, 3H) | 1.87 A 496.2 | B |
| 6 | 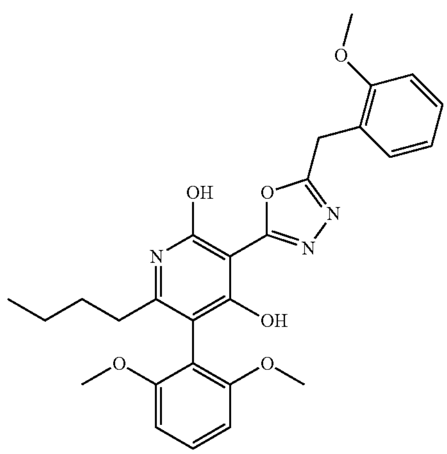 [SMILES: CCCCc1nc(O)c(-c2nnc(Cc3ccccc3OC)o2)c(O)c1-c1c(OC)cccc1OC] | 6-butyl-5-(2,6-dimethoxyphenyl)-3-{5-[(2-methoxyphenyl)methyl]-1,3,4-oxadiazol-2-yl}pyridine-2,4-diol | 1H NMR (500 MHz, DMSO-d6) δ 7.37-7.28 (m, 2H), 7.24 (d, J = 7.1 Hz, 1H), 7.03 (d, J = 8.2 Hz, 1H), 6.94 (t, J = 7.4 Hz, 1H), 6.71 (d, J = 8.4 Hz, 2H), 4.24 (s, 2H), 3.77 (s, 3H), 3.67 (s, 6H), 2.13 (t, J = 7.7 Hz, 2H), 1.36-1.23 (m, 2H), 1.12-1.00 (m, 2H), 0.64 (t, J = 7.3 Hz, 3H) | 1.95 A 492.2 | B |
| 7 | 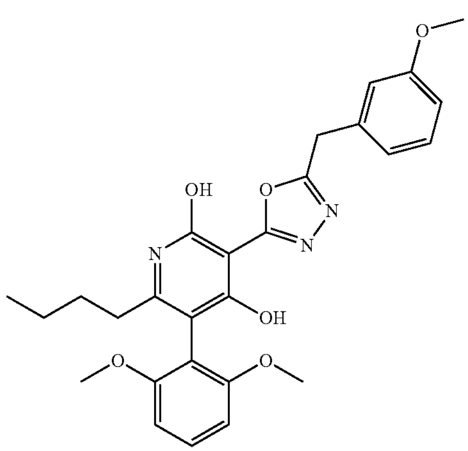 [SMILES: CCCCc1nc(O)c(-c2nnc(Cc3cccc(OC)c3)o2)c(O)c1-c1c(OC)cccc1OC] | 6-butyl-5-(2,6-dimethoxyphenyl)-3-{5-[(3-methoxyphenyl)methyl]-1,3,4-oxadiazol-2-yl}pyridine-2,4-diol | 1H NMR (500 MHz, DMSO-d6) δ 7.34 (t, J = 8.4 Hz, 1H), 7.27 (t, J = 7.9 Hz, 1H), 6.96 (br. s., 1H), 6.88 (dd, J = 16.7, 7.8 Hz, 2H), 6.72 (d, J = 8.3 Hz, 2H), 4.33 (s, 2H), 3.75 (s, 3H), 3.67 (s, 6H), 2.13 (t, J = 7.5 Hz, 2H), 1.37-1.23 (m, 2H), 1.11-0.99 (m, 2H), 0.64 (t, J = 7.3 Hz, 3H) | 1.78 A 492.2 | A |

-continued

| Ex # | Structure | Name | ¹H NMR | LC/MS Rt (min) Method M + H | hAPJ cAMP EC₅₀ Potency range (nM) |
|---|---|---|---|---|---|
| 8 | 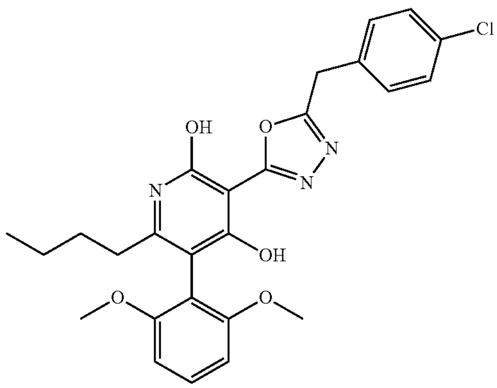 [SMILES: CCCCc1nc(O)c(-c2nnc(Cc3ccc(Cl)cc3)o2)c(O)c1-c1c(OC)cccc1OC] | 6-butyl-3-{5-[(4-chlorophenyl)methyl]-1,3,4-oxadiazol-2-yl}-5-(2,6-dimethoxyphenyl)pyridine-2,4-diol | 1H NMR (400 MHz, CDCl3) δ 10.41 (br. s., 1H), 7.37 (t, J = 8.4 Hz, 1H), 7.30 (s, 4H), 6.65 (d, J = 8.4 Hz, 2H), 4.27 (s, 2H), 3.75 (s, 6H), 2.37-2.29 (m, 2H), 1.49 (dt, J = 15.3, 7.5 Hz, 2H), 1.27-1.15 (m, 2H), 0.76 (t, J = 7.4 Hz, 3H) | 2.19 C 496.1 | A |
| 9 | 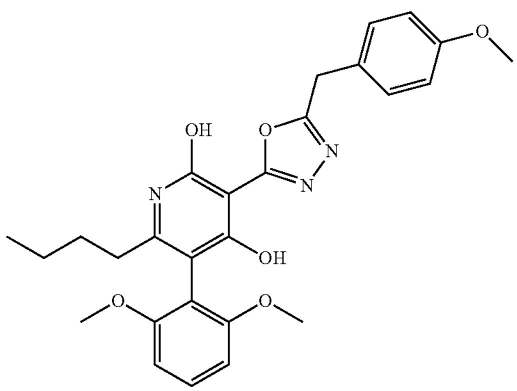 [SMILES: CCCCc1nc(O)c(-c2nnc(Cc3ccc(OC)cc3)o2)c(O)c1-c1c(OC)cccc1OC] | 6-butyl-5-(2,6-dimethoxyphenyl)-3-{5-[(4-methoxyphenyl)methyl]-1,3,4-oxadiazol-2-yl}pyridine-2,4-diol | 1H NMR (500 MHz, DMSO-d6) δ 7.37-7.32 (m, 1H), 7.26 (d, J = 8.5 Hz, 2H), 6.91 (d, J = 8.6 Hz, 2H), 6.71 (d, J = 8.4 Hz, 2H), 4.26 (s, 2H), 3.73 (s, 3H), 3.67 (s, 6H), 2.12 (t, J = 7.6 Hz, 2H), 1.30 (quin, J = 7.5 Hz, 2H), 1.12-0.98 (m, 2H), 0.64 (t, J = 7.3 Hz, 3H) | 1.78 A 492.2 | A |
| 10 | 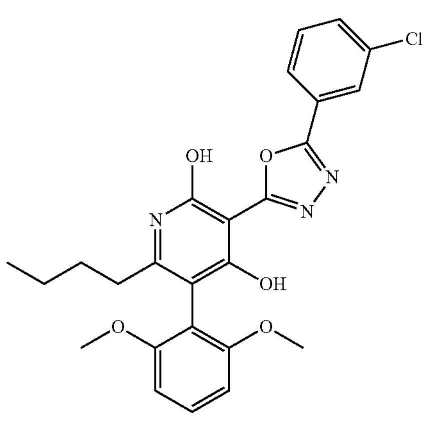 [SMILES: CCCCc1nc(O)c(-c2nnc(-c3cccc(Cl)c3)o2)c(O)c1-c1c(OC)cccc1OC] | 6-butyl-3-[5-(3-chlorophenyl)-1,3,4-oxadiazol-2-yl]-5-(2,6-dimethoxyphenyl)pyridine-2,4-diol | 1H NMR (500 MHz, DMSO-d6) δ 8.02 (br. s., 2H), 7.77-7.60 (m, 2H), 7.34 (br. s., 1H), 6.72 (d, J = 8.2 Hz, 2H), 3.74-3.64 (m, 6H), 2.14 (br. s., 2H), 1.40-1.26 (m, 2H), 1.14-1.04 (m, 2H), 0.66 (t, J = 7.3 Hz, 3H) | 1.96 A 482.1 | B |

-continued

| Ex # | Structure | Name | ¹H NMR | LC/MS Rt (min) Method M + H | hAPJ cAMP EC$_{50}$ Potency range (nM) |
|---|---|---|---|---|---|
| 11 | 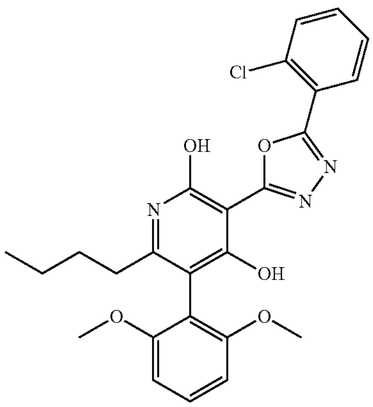 [SMILES: CCCCc1nc(O)c(-c2nnc(-c3ccccc3Cl)o2)c(O)c1-c1c(OC)cccc1OC] | 6-butyl-3-[5-(2-chlorophenyl)-1,3,4-oxadiazol-2-yl]-5-(2,6-dimethoxyphenyl)pyridine-2,4-diol | 1H NMR (500 MHz, DMSO-d6) δ 8.01 (d, J = 7.6 Hz, 1H), 7.79-7.56 (m, 3H), 7.36 (t, J = 8.3 Hz, 1H), 6.74 (d, J = 8.4 Hz, 2H), 3.70 (s, 6H), 2.16 (t, J = 7.6 Hz, 2H), 1.34 (t, J = 7.2 Hz, 2H), 1.13-1.02 (m, 2H), 0.66 (t, J = 7.3 Hz, 3H) | 1.85 A 482.1 | C |
| 12 | 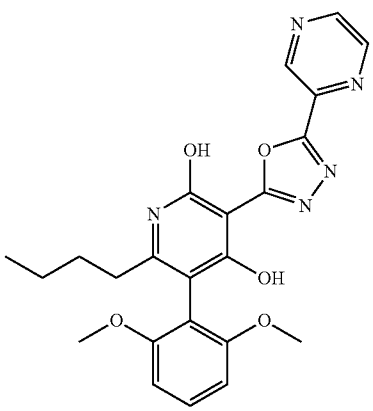 [SMILES: CCCCc1nc(O)c(-c2nnc(-c3cnccn3)o2)c(O)c1-c1c(OC)cccc1OC] | 6-butyl-5-(2,6-dimethoxyphenyl)-3-[5-(pyrazin-2-yl)-1,3,4-oxadiazol-2-yl]pyridine-2,4-diol | 1H NMR (500 MHz, DMSO-d6) δ 9.39 (s, 1H), 8.89 (s, 2H), 7.36 (t, J = 8.4 Hz, 1H), 6.74 (d, J = 8.4 Hz, 2H), 3.70 (s, 6H), 2.16 (t, J = 7.7 Hz, 2H), 1.41-1.27 (m, 2H), 1.14-1.02 (m, 2H), 0.66 (t, J = 7.4 Hz, 3H) | 1.30 A 450.2 | C |
| 13 | 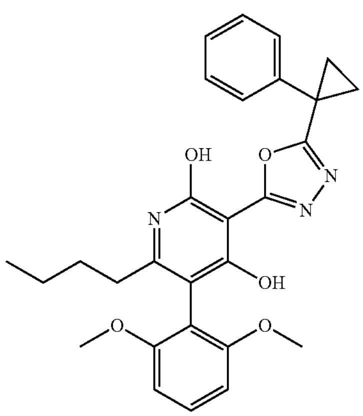 [SMILES: CCCCc1nc(O)c(-c2nnc(C3(c4ccccc4)CC3)o2)c(O)c1-c1c(OC)cccc1OC] | 6-butyl-5-(2,6-dimethoxyphenyl)-3-[5-(1-phenylcyclopropyl)-1,3,4-oxadiazol-2-yl]pyridine-2,4-diol | 1H NMR (500 MHz, DMSO-d6) δ 7.48-7.22 (m, 6H), 6.71 (d, J = 8.4 Hz, 2H), 3.67 (s, 6H), 2.12 (t, J = 7.6 Hz, 2H), 1.70-1.60 (m, 2H), 1.55-1.46 (m, 2H), 1.30 (quin, J = 7.4 Hz, 2H), 1.11-1.00 (m, 2H), 0.64 (t, J = 7.3 Hz, 3H) | 1.92 A 488.2 | B |

| Ex # | Structure | Name | ¹H NMR | LC/MS Rt (min) Method M + H | hAPJ cAMP EC₅₀ Potency range (nM) |
|---|---|---|---|---|---|
| 14 | 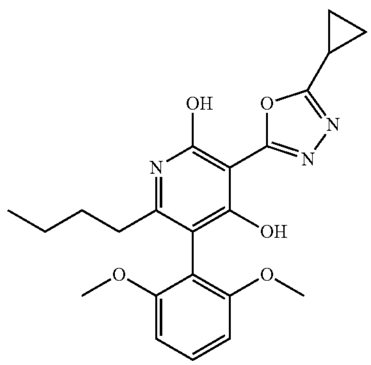 [SMILES: CCCCc1nc(O)c(-c2nnc(C3CC3)o2)c(O)c1-c1c(OC)cccc1OC] | 6-butyl-3-(5-cyclopropyl-1,3,4-oxadiazol-2-yl)-5-(2,6-dimethoxyphenyl)pyridine-2,4-diol | 1H NMR (500 MHz, DMSO-d6) δ 7.34 (t, J = 8.4 Hz, 1H), 6.71 (d, J = 8.4 Hz, 2H), 3.67 (s, 6H), 2.34-2.22 (m, 1H), 2.13 (t, J = 7.7 Hz, 2H), 1.31 (quin, J = 7.4 Hz, 2H), 1.20-1.13 (m, 2H), 1.10-1.00 (m, 4H), 0.64 (t, J = 7.3 Hz, 3H) | 1.65 A 412.2 | C |
| 15 | 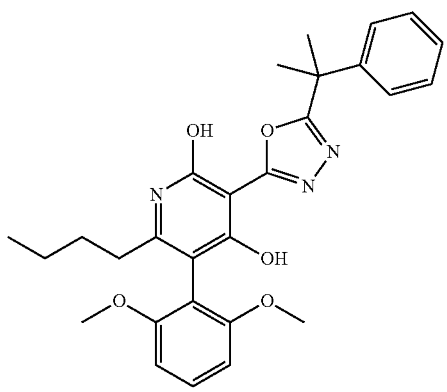 [SMILES: CCCCc1nc(O)c(-c2nnc(C(C)(C)c3ccccc3)o2)c(O)c1-c1c(OC)cccc1OC] | 6-butyl-5-(2,6-dimethoxyphenyl)-3-[5-(2-phenylpropan-2-yl)-1,3,4-oxadiazol-2-yl]pyridine-2,4-diol | 1H NMR (500 MHz, DMSO-d6) δ 7.38-7.32 (m, 3H), 7.31-7.25 (m, 3H), 6.72 (d, J = 8.4 Hz, 2H), 3.67 (s, 6H), 2.12 (t, J = 7.6 Hz, 2H), 1.78 (s, 6H), 1.35-1.24 (m, 2H), 1.12-0.98 (m, 2H), 0.63 (t, J = 7.3 Hz, 3H) | 2.00 A 490.3 | A |
| 17 | 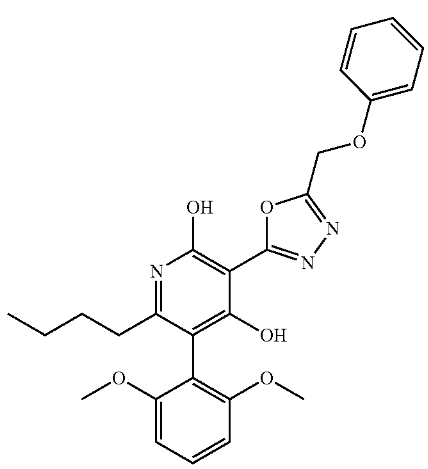 | 6-butyl-5-(2,6-dimethoxyphenyl)-3-[5-(phenoxymethyl)-1,3,4-oxadiazol-2-yl]pyridine-2,4-diol | 1H NMR (500 MHz, DMSO-d6) δ 7.42-7.29 (m, 3H), 7.10 (d, J = 8.0 Hz, 2H), 7.03 (t, J = 7.2 Hz, 1H), 6.73 (d, J = 8.3 Hz, 2H), 5.47 (s, 2H), 3.69 (s, 6H), 2.15 (t, J = 7.5 Hz, 2H), 1.40-1.27 (m, 2H), 1.15-0.99 (m, 2H), 0.65 (t, J = 7.2 Hz, 3H) | 1.75 A 478.2 | B |

-continued

| Ex # | Structure | Name | ¹H NMR | LC/MS Rt (min) Method M + H | hAPJ cAMP EC₅₀ Potency range (nM) |
|---|---|---|---|---|---|
| 18 | 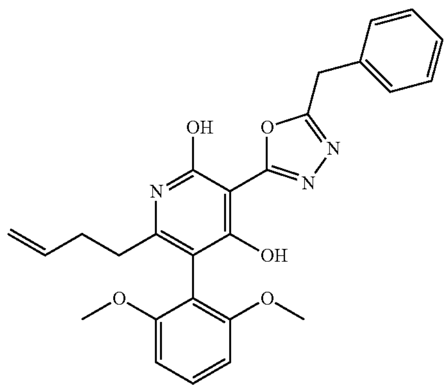 [SMILES: C=CCCc1nc(O)c(-c2nnc(Cc3ccccc3)o2)c(O)c1-c1c(OC)cccc1OC] | 3-(5-benzyl-1,3,4-oxadiazol-2-yl)-6-(but-3-en-1-yl)-5-(2,6-dimethoxyphenyl)pyridine-2,4-diol | 1H NMR (400 MHz, CDCl3) δ 11.10 (br. s., 1H), 7.41-7.25 (m, 6H), 6.66 (d, J = 8.4 Hz, 2H), 5.69 (ddt, J = 17.0, 10.3, 6.6 Hz, 1H), 5.00-4.88 (m, 2H), 4.29 (s, 2H), 3.75 (s, 6H), 2.50-2.41 (m, 2H), 2.28 (q, J = 7.0 Hz, 2H) | 2.05 C 460.1 | B |
| 19 | 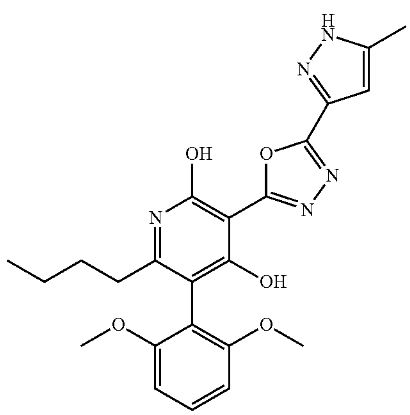 [SMILES: CCCCc1nc(O)c(-c2nnc(-c3cc(C)[nH]n3)o2)c(O)c1-c1c(OC)cccc1OC] | 6-butyl-5-(2,6-dimethoxyphenyl)-3-[5-(5-methyl-1H-pyrazol-3-yl)-1,3,4-oxadiazol-2-yl]pyridine-2,4-diol | 1H NMR (500 MHz, DMSO-d6) δ 7.36 (t, J = 8.2 Hz, 1H), 6.74 (d, J = 8.5 Hz, 2H), 6.67 (br. s., 1H), 3.70 (s, 6H), 2.34 (br. s., 3H), 2.20-2.11 (m, 2H), 1.34 (dd, J = 14.6, 7.3 Hz, 2H), 1.10 (dd, J = 14.6, 7.3 Hz, 2H), 0.67 (t, J = 7.2 Hz, 3H) | 1.76 A 452.3 | C |
| 20 | 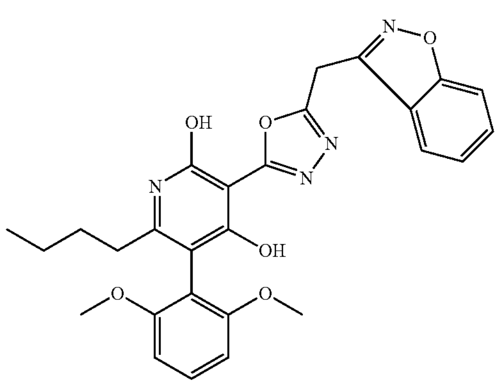 [SMILES: CCCCc1nc(O)c(-c2nnc(Cc3noc4ccccc34)o2)c(O)c1-c1c(OC)cccc1OC] | 3-[5-(1,2-benzoxazol-3-ylmethyl)-1,3,4-oxadiazol-2-yl]-6-butyl-5-(2,6-dimethoxyphenyl)pyridine-2,4-diol | 1H NMR (400 MHz, CDCl3) δ 11.48 (br. s., 1H), 7.86 (d, J = 8.1 Hz, 1H), 7.61-7.53 (m, 2H), 7.41-7.31 (m, 2H), 6.65 (d, J = 8.4 Hz, 2H), 4.71 (s, 2H), 3.74 (s, 6H), 2.42-2.28 (m, 2H), 1.50 (quin, J = 7.6 Hz, 2H), 1.28-1.14 (m, 2H), 0.74 (t, J = 7.3 Hz, 3H) | 2.06 C 503.1 | A |

| Ex # | Structure | Name | $^1$H NMR | LC/MS Rt (min) Method M + H | hAPJ cAMP EC$_{50}$ Potency range (nM) |
|---|---|---|---|---|---|
| 21 | 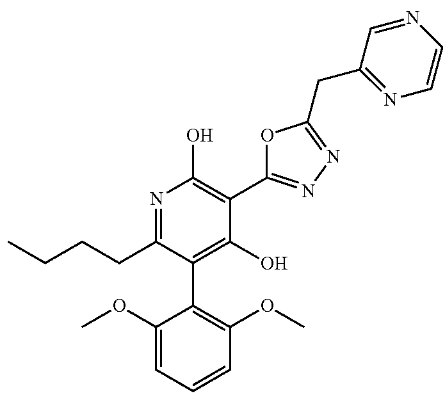 [SMILES: CCCCc1nc(O)c(-c2nnc(Cc3cnccn3)o2)c(O)c1-c1c(OC)cccc1OC] | 6-butyl-5-(2,6-dimethoxyphenyl)-3-[5-(pyrazin-2-ylmethyl)-1,3,4-oxadiazol-2-yl]pyridine-2,4-diol | 1H NMR (500 MHz, DMSO-d6) δ 8.74 (s, 1H), 8.63-8.53 (m, 2H), 7.18 (t, J = 8.2 Hz, 1H), 6.59 (d, J = 8.2 Hz, 2H), 4.44 (s, 2H), 3.62 (s, 6H), 1.91 (d, J = 7.9 Hz, 2H), 1.33-1.25 (m, 2H), 1.12-1.03 (m, 2H), 0.65 (t, J = 7.3 Hz, 3H) | 1.34 A 464.2 | A |
| 22 | 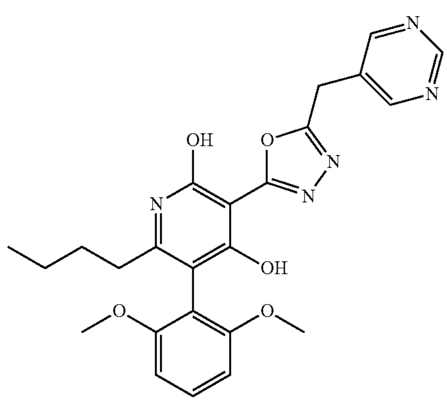 [SMILES: CCCCc1nc(O)c(-c2nnc(Cc3cncnc3)o2)c(O)c1-c1c(OC)cccc1OC] | 6-butyl-5-(2,6-dimethoxyphenyl)-3-[5-(pyrimidin-5-ylmethyl)-1,3,4-oxadiazol-2-yl]pyridine-2,4-diol | 1H NMR (500 MHz, DMSO-d6) δ 9.14 (s, 1H), 8.86 (s, 2H), 7.29 (t, J = 7.8 Hz, 1H), 6.68 (d, J = 8.2 Hz, 2H), 4.42 (br. s., 2H), 3.66 (s, 6H), 2.07 (br. s., 2H), 1.38-1.27 (m, 2H), 1.14-1.02 (m, 2H), 0.66 (t, J = 7.3 Hz, 3H) | 1.57 B 464.3 | B |
| 23 | 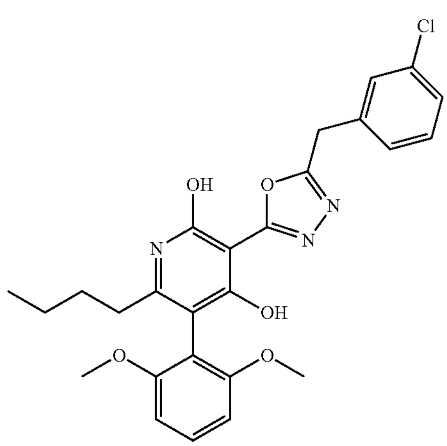 | 6-butyl-3-{5-[(3-chlorophenyl)methyl]-1,3,4-oxadiazol-2-yl}-5-(2,6-dimethoxyphenyl)pyridine-2,4-diol | 1H NMR (500 MHz, DMSO-d6) δ 7.48 (s, 1H), 7.44-7.30 (m, 4H), 6.73 (d, J = 8.4 Hz, 2H), 4.40 (s, 2H), 3.68 (s, 6H), 2.14 (t, J = 7.7 Hz, 2H), 1.32 (quin, J = 7.5 Hz, 2H), 1.08 (sxt, J = 7.3 Hz, 2H), 0.65 (t, J = 7.4 Hz, 3H) | 1.92 A 496.2 | A |

-continued

| Ex # | Structure | Name | ¹H NMR | LC/MS Rt (min) Method M + H | hAPJ cAMP EC₅₀ Potency range (nM) |
|---|---|---|---|---|---|
| 24 | 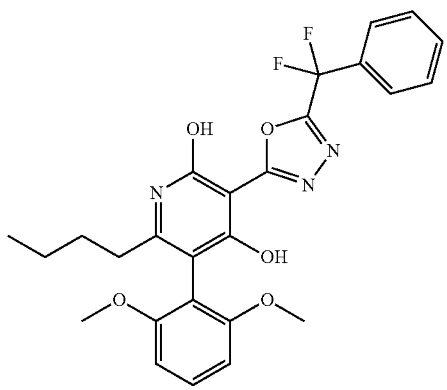 [SMILES: CCCCc1nc(O)c(-c2nnc(C(F)(F)c3ccccc3)o2)c(O)c1-c1c(OC)cccc1OC] | 6-butyl-3-{5-[difluoro(phenyl)methyl]-1,3,4-oxadiazol-2-yl}-5-(2,6-dimethoxyphenyl)pyridine-2,4-diol | 1H NMR (500 MHz, DMSO-d6) δ 7.73 (d, J = 7.6 Hz, 2H), 7.70-7.65 (m, 1H), 7.64-7.58 (m, 2H), 7.35 (t, J = 8.2 Hz, 1H), 6.73 (d, J = 8.2 Hz, 2H), 3.69 (s, 6H), 2.15 (t, J = 7.0 Hz, 2H), 1.33 (quin, J = 7.5 Hz, 2H), 1.09 (sxt, J = 7.3 Hz, 2H), 0.66 (t, J = 7.3 Hz, 3H) | 1.97 A 498.4 | B |
| 25 | 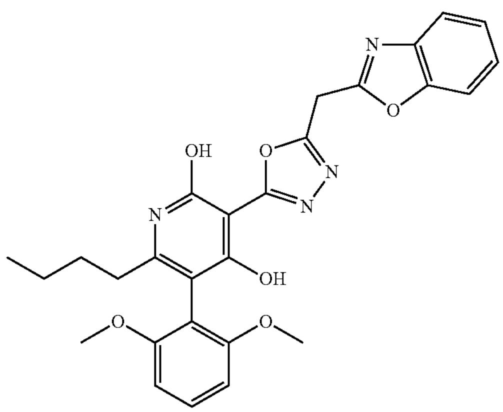 [SMILES: CCCCc1nc(O)c(-c2nnc(Cc3nc4ccccc4o3)o2)c(O)c1-c1c(OC)cccc1OC] | 3-[5-(1,3-benzoxazol-2-ylmethyl)-1,3,4-oxadiazol-2-yl]-6-butyl-5-(2,6-dimethoxyphenyl)pyridine-2,4-diol | 1H NMR (500 MHz, DMSO-d6) δ 7.76 (d, J = 7.3 Hz, 2H), 7.48-7.33 (m, 3H), 6.74 (d, J = 8.5 Hz, 2H), 4.95 (s, 2H), 3.70 (s, 6H), 2.15 (t, J = 7.5 Hz, 2H), 1.38-1.30 (m, 2H), 1.13-1.05 (m, 2H), 0.66 (t, J = 7.2 Hz, 3H) | 1.71 A 503.4 | A |
| 26 | 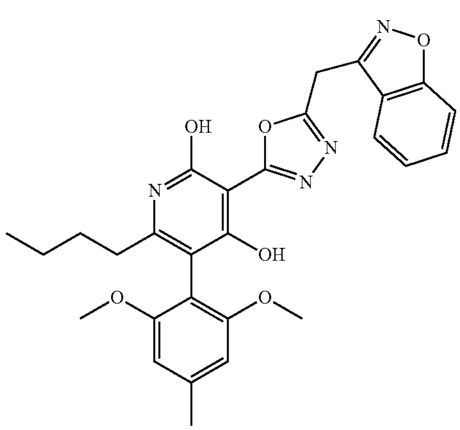 [SMILES: CCCCc1nc(O)c(-c2nnc(Cc3noc4ccccc34)o2)c(O)c1-c1c(OC)cc(C)cc1OC] | 3-[5-(1,2-benzoxazol-3-ylmethyl)-1,3,4-oxadiazol-2-yl]-6-butyl-5-(2,6-dimethoxy-4-methylphenyl)pyridine-2,4-diol | 1H NMR (500 MHz, DMSO-d6) δ 7.96 (d, J = 7.9 Hz, 1H), 7.79 (d, J = 8.5 Hz, 1H), 7.74-7.66 (m, 1H), 7.42 (t, J = 7.3 Hz, 1H), 6.55 (s, 2H), 4.93 (s, 2H), 3.67 (s, 6H), 2.36 (s, 3H), 2.15 (t, J = 7.5 Hz, 2H), 1.38-1.30 (m, 2H), 1.14-1.05 (m, 2H), 0.68 (t, J = 7.2 Hz, 3H) | 1.96 A 517.4 | A |

-continued

| Ex # | Structure | Name | ¹H NMR | LC/MS Rt (min) Method M + H | hAPJ cAMP EC₅₀ Potency range (nM) |
|---|---|---|---|---|---|
| 27 | 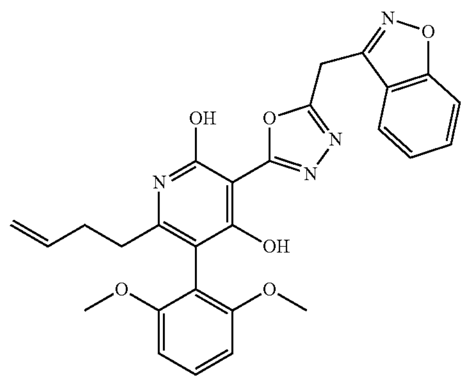 [SMILES: C=CCCc1nc(O)c(-c2nnc(Cc3noc4ccccc34)o2)c(O)c1-c1c(OC)cccc1OC] | 3-[5-(1,2-benzoxazol-3-ylmethyl)-1,3,4-oxadiazol-2-yl]-6-(but-3-en-1-yl)-5-(2,6-dimethoxyphenyl)pyridine-2,4-diol | 1H NMR (500 MHz, DMSO-d6) δ 11.78 (br. s., 1H), 7.97 (d, J = 7.9 Hz, 1H), 7.79 (d, J = 8.2 Hz, 1H), 7.75-7.66 (m, 1H), 7.43 (t, J = 7.2 Hz, 1H), 7.36 (t, J = 8.1 Hz, 1H), 6.73 (d, J = 8.2 Hz, 2H), 5.69-5.57 (m, 1H), 4.93 (br. s., 2H), 4.90-4.81 (m, 2H), 3.35 (br. s., 6H), 2.24 (d, J = 7.0 Hz, 2H), 2.11 (d, J = 6.4 Hz, 2H) | 1.75 A 501.4 | A |
| 28 | 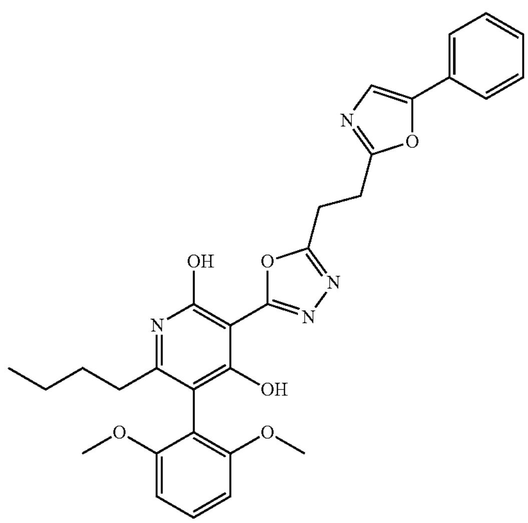 [SMILES: CCCCc1nc(O)c(-c2nnc(CCc3ncc(-c4ccccc4)o3)o2)c(O)c1-c1c(OC)cccc1OC] | 6-butyl-5-(2,6-dimethoxyphenyl)-3-{5-[2-(5-phenyl-1,3-oxazol-2-yl)ethyl]-1,3,4-oxadiazol-2-yl}pyridine-2,4-diol | 1H NMR (500 MHz, DMSO-d6) δ 7.66 (d, J = 7.0 Hz, 2H), 7.56 (br. s., 1H), 7.45 (t, J = 7.0 Hz, 2H), 7.35 (br. s., 2H), 6.73 (d, J = 8.2 Hz, 2H), 3.70 (br. s., 6H), 3.47 (d, J = 6.4 Hz, 2H), 3.37 (br. s., 2H), 2.16 (br. s., 2H), 1.34 (br. s., 2H), 1.10 (d, J = 6.7 Hz, 2H), 0.67 (t, J = 6.6 Hz, 3H) | 1.91 A 543.4 | B |
| 29 | 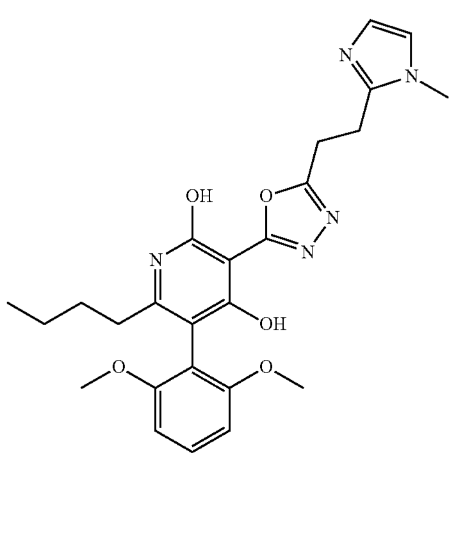 [SMILES: CCCCc1nc(O)c(-c2nnc(CCc3nccn3C)o2)c(O)c1-c1c(OC)cccc1OC] | 6-butyl-5-(2,6-dimethoxyphenyl)-3-{5-[2-(1-methyl-1H-imidazol-2-yl)ethyl]-1,3,4-oxadiazol-2-yl}pyridine-2,4-diol | 1H NMR (500 MHz, DMSO-d6) δ 7.56 (br. s., 1H), 7.50 (br. s., 1H), 7.36 (br. s., 1H), 6.73 (d, J = 7.6 Hz, 2H), 3.83 (br. s., 3H), 3.69 (br. s, 6H), 3.47 (br. s., 4H), 2.15 (br. s., 2H), 1.33 (br. s., 2H), 1.09 (br. s., 2H), 0.66 (br. s., 3H) | 1.34 A 480.4 | A |

-continued

| Ex # | Structure | Name | ¹H NMR | LC/MS Rt (min) Method M + H | hAPJ cAMP EC₅₀ Potency range (nM) |
|---|---|---|---|---|---|
| 30 | 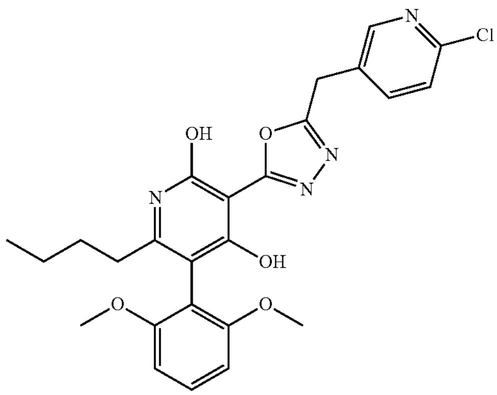 [SMILES: CCCCc1nc(O)c(-c2nnc(Cc3ccc(Cl)nc3)o2)c(O)c1-c1c(OC)cccc1OC] | 6-butyl-3-{5-[(6-chloropyridin-3-yl)methyl]-1,3,4-oxadiazol-2-yl}-5-(2,6-dimethoxyphenyl)pyridine-2,4-diol | 1H NMR (500 MHz, DMSO-d6) δ 8.48 (br. s., 1H), 7.90 (d, J = 7.9 Hz, 1H), 7.55 (d, J = 7.9 Hz, 1H), 7.35 (t, J = 8.1 Hz, 1H), 6.73 (d, J = 8.2 Hz, 2H), 4.46 (br. s., 2H), 3.69 (br. s., 6H), 2.15 (br. s., 2H), 1.33 (br. s., 2H), 1.09 (d, J = 6.7 Hz, 2H), 0.66 (t, J = 6.6 Hz, 3H) | 1.62 A 497.3 | A |
| 31 | 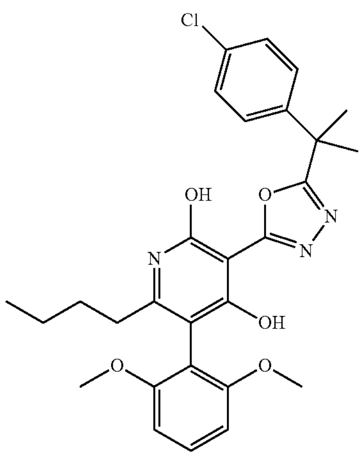 [SMILES: CCCCc1nc(O)c(-c2nnc(C(C)(C)c3ccc(Cl)cc3)o2)c(O)c1-c1c(OC)cccc1OC] | 6-butyl-3-{5-[2-(4-chlorophenyl)propan-2-yl]-1,3,4-oxadiazol-2-yl}-5-(2,6-dimethoxyphenyl)pyridine-2,4-diol | 1H NMR (500 MHz, DMSO-d6) δ 7.42 (d, J = 7.6 Hz, 2H), 7.34 (d, J = 7.6 Hz, 3H), 6.73 (d, J = 7.9 Hz, 2H), 3.69 (br. s., 6H), 2.14 (br. s., 2H), 1.79 (br. s., 6H), 1.32 (br. s., 2H), 1.08 (d, J = 6.4 Hz, 2H), 0.66 (br. s., 3H) | 2.16 A 524.4 | A |
| 32 | 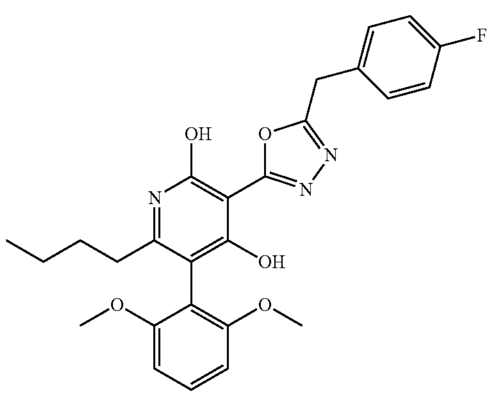 [SMILES: CCCCc1nc(O)c(-c2nnc(Cc3ccc(F)cc3)o2)c(O)c1-c1c(OC)cccc1OC] | 6-butyl-5-(2,6-dimethoxyphenyl)-3-{5-[(4-fluorophenyl)methyl]-1,3,4-oxadiazol-2-yl}pyridine-2,4-diol | 1H NMR (500 MHz, DMSO-d6) δ 7.42 (br. s., 2H), 7.38-7.31 (m, 1H), 7.20 (t, J = 8.1 Hz, 2H), 6.73 (d, J = 7.9 Hz, 2H), 4.38 (br. s., 2H), 3.69 (br. s., 6H), 2.15 (br. s., 2H), 1.33 (br. s., 2H), 1.09 (d, J = 6.7 Hz, 2H), 0.66 (t, J = 6.4 Hz, 3H) | 1.83 A 480.4 | A |

| Ex # | Structure | Name | ¹H NMR | LC/MS Rt (min) Method M + H | hAPJ cAMP EC₅₀ Potency range (nM) |
|---|---|---|---|---|---|
| 33 | 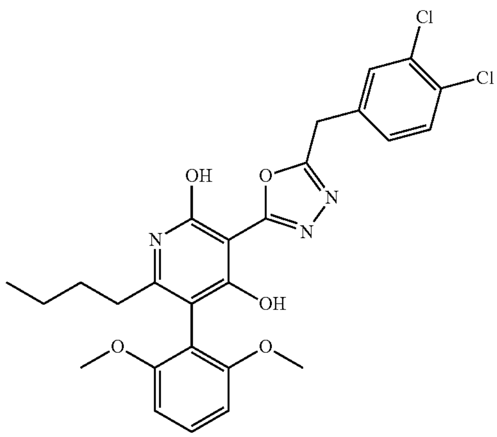 [SMILES: CCCCc1nc(O)c(-c2nnc(Cc3ccc(Cl)c(Cl)c3)o2)c(O)c1-c1c(OC)cccc1OC] | 6-butyl-3-{5-[(3,4-dichlorophenyl)methyl]-1,3,4-oxadiazol-2-yl}-5-(2,6-dimethoxyphenyl)pyridine-2,4-diol | 1H NMR (500 MHz, DMSO-d6) δ 7.64 (br. s., 1H), 7.57 (d, J = 7.9 Hz, 1H), 7.37-7.20 (m, 2H), 6.65 (d, J = 7.9 Hz, 2H), 4.35 (br. s., 2H), 3.62 (br. s., 6H), 2.07 (br. s., 2H), 1.26 (br. s., 2H), 1.01 (d, J = 6.7 Hz, 2H), 0.59 (t, J = 6.7 Hz, 3H) | 2.07 A 530.3 | A |
| 34 | 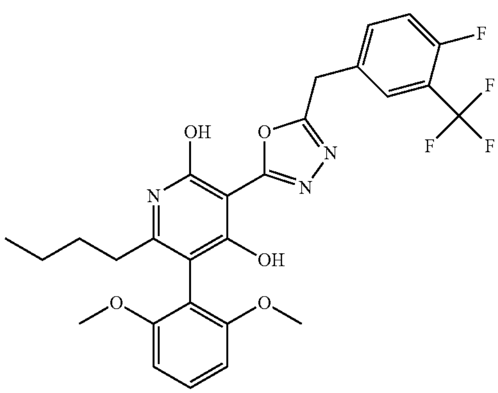 [SMILES: CCCCc1nc(O)c(-c2nnc(Cc3ccc(F)c(C(F)(F)F)c3)o2)c(O)c1-c1c(OC)cccc1OC] | 6-butyl-5-(2,6-dimethoxyphenyl)-3-(5-{[4-fluoro-3-(trifluoromethyl)phenyl]methyl}-1,3,4-oxadiazol-2-yl)pyridine-2,4-diol | 1H NMR (500 MHz, DMSO-d6) δ 7.89 (d, J = 5.2 Hz, 1H), 7.78 (br. s., 1H), 7.53 (t, J = 9.5 Hz, 1H), 7.39-7.29 (m, 1H), 6.72 (d, J = 7.9 Hz, 2H), 4.50 (br. s., 2H), 3.69 (br. s., 6H), 2.14 (br. s., 2H), 1.33 (br. s., 2H), 1.09 (d, J = 7.0 Hz, 2H), 0.73-0.60 (m, 3H) | 2.03 A 548.3 | B |
| 35 | 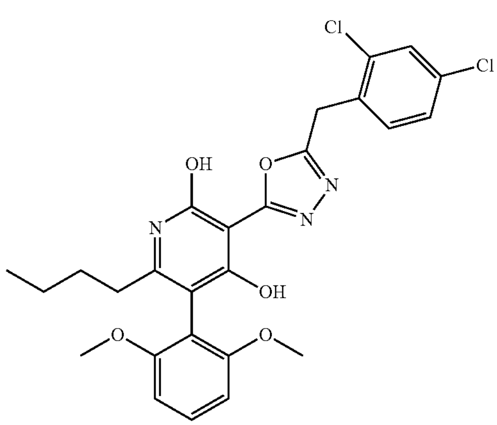 | 6-butyl-3-{5-[(2,4-dichlorophenyl)methyl]-1,3,4-oxadiazol-2-yl}-5-(2,6-dimethoxyphenyl)pyridine-2,4-diol | 1H NMR (500 MHz, DMSO-d6) δ 7.70 (br. s., 1H), 7.58-7.52 (m, 1H), 7.50-7.45 (m, 1H), 7.35 (t, J = 7.5 Hz, 1H), 6.73 (d, J = 7.9 Hz, 2H), 4.47 (br. s., 2H), 3.69 (br. s., 6H), 2.15 (br. s., 2H), 1.33 (br. s., 2H), 1.09 (d, J = 6.7 Hz, 2H), 0.71-0.61 (m, 3H) | 2.07 A 530.3 | A |

-continued

| Ex # | Structure | Name | ¹H NMR | LC/MS Rt (min) Method M + H | hAPJ cAMP EC₅₀ Potency range (nM) |
|---|---|---|---|---|---|
| 36 | 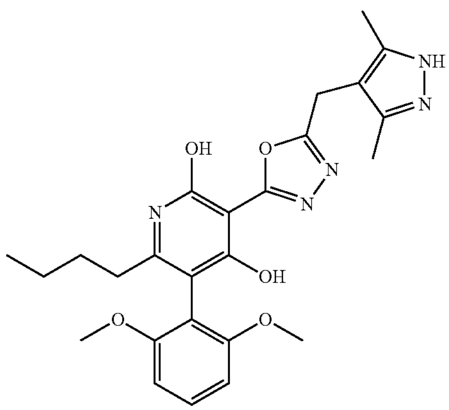 [SMILES: CCCCc1nc(O)c(-c2nnc(Cc3c(C)n[nH]c3C)o2)c(O)c1-c1c(OC)cccc1OC] | 6-butyl-5-(2,6-dimethoxyphenyl)-3-{5-[(3,5-dimethyl-1H-pyrazol-4-yl)methyl]-1,3,4-oxadiazol-2-yl}pyridine-2,4-diol | 1H NMR (500 MHz, DMSO-d6) δ 7.35 (t, J = 7.9 Hz, 1H), 6.73 (d, J = 8.2 Hz, 2H), 4.06 (br. s., 2H), 3.69 (br. s., 6H), 2.20 (br. s., 6H), 2.15 (br. s., 2H), 1.33 (br. s., 2H), 1.09 (d, J = 6.7 Hz, 2H), 0.66 (t, J = 6.3 Hz, 3H) | 1.47 A 480.4 | B |
| 37 | 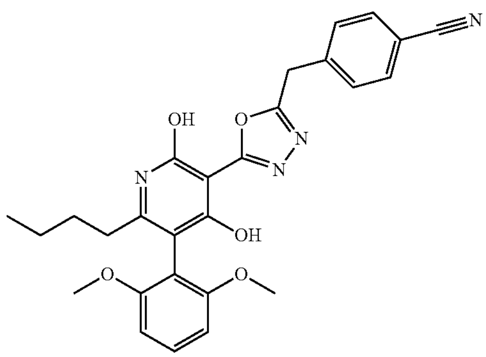 [SMILES: CCCCc1nc(O)c(-c2nnc(Cc3ccc(C#N)cc3)o2)c(O)c1-c1c(OC)cccc1OC] | 4-({5-[6-butyl-5-(2,6-dimethoxyphenyl)-2,4-dihydroxypyridin-3-yl]-1,3,4-oxadiazol-2-yl}methyl)benzonitrile | 1H NMR (500 MHz, DMSO-d6) δ 7.85 (d, J = 7.6 Hz, 2H), 7.59 (d, J = 7.3 Hz, 2H), 7.34 (t, J = 7.3 Hz, 1H), 6.72 (d, J = 7.6 Hz, 2H), 4.51 (br. s., 2H), 3.69 (br. s., 6H), 2.13 (br. s., 2H), 1.33 (br. s., 2H), 1.09 (d, J = 7.0 Hz, 2H), 0.66 (t, J = 6.4 Hz, 3H) | 1.73 A 487.4 | A |
| 38 | 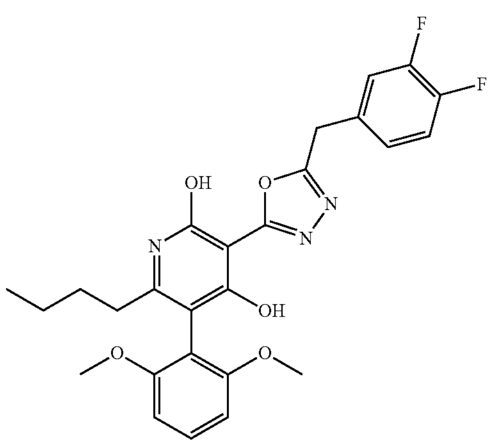 | 6-butyl-3-{5-[(3,4-difluorophenyl)methyl]-1,3,4-oxadiazol-2-yl}-5-(2,6-dimethoxyphenyl)pyridine-2,4-diol | 1H NMR (500 MHz, DMSO-d6) δ 7.47-7.39 (m, 1H), 7.39-7.32 (m, 1H), 7.28 (t, J = 8.1 Hz, 1H), 7.17 (br. s., 1H), 6.66 (d, J = 7.9 Hz, 2H), 4.33 (br. s., 2H), 3.62 (br. s., 6H), 2.07 (br. s., 2H), 1.26 (br. s., 2H), 1.02 (d, J = 7.0 Hz, 2H), 0.59 (t, J = 6.6 Hz, 3H) | 1.86 A 498.4 | A |
| 39 | 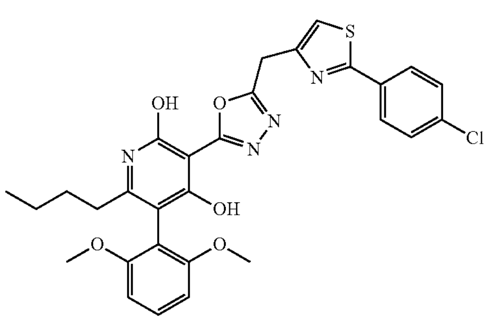 [SMILES: CCCCc1nc(O)c(-c2nnc(Cc3csc(-c4ccc(Cl)cc4)n3)o2)c(O)c1-c1c(OC)cccc1OC] | 6-butyl-3-(5-{[2-(4-chlorophenyl)-1,3-thiazol-4-yl]methyl}-1,3,4-oxadiazol-2-yl)-5-(2,6-dimethoxyphenyl)pyridine-2,4-diol | 1H NMR (500 MHz, DMSO-d6) δ 7.94 (d, J = 7.6 Hz, 2H), 7.72 (br. s., 1H), 7.56 (d, J = 7.9 Hz, 2H), 7.35 (t, J = 7.8 Hz, 1H), 6.73 (d, J = 7.9 Hz, 2H), 4.58 (br. s., 2H), 3.69 (br. s., 6H), 2.15 (br. s., 2H), 1.33 (br. s., 2H), 1.09 (d, J = 6.7 Hz, 2H), 0.66 (t, J = 6.3 Hz, 3H) | 2.12 A 579.3 | B |

| Ex # | Structure | Name | ¹H NMR | LC/MS Rt (min) Method M + H | hAPJ cAMP EC₅₀ Potency range (nM) |
|---|---|---|---|---|---|
| 40 | 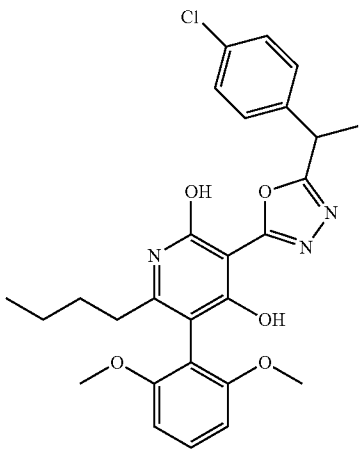 [SMILES: CCCCc1nc(O)c(-c2nnc(C(C)c3ccc(Cl)cc3)o2)c(O)c1-c1c(OC)cccc1OC] | 6-butyl-3-{5-[1-(4-chlorophenyl)ethyl]-1,3,4-oxadiazol-2-yl}-5-(2,6-dimethoxyphenyl)pyridine-2,4-diol | 1H NMR (500 MHz, DMSO-d6) δ 7.48-7.41 (m, 2H), 7.40-7.29 (m, 3H), 6.72 (d, J = 7.9 Hz, 2H), 4.62 (d, J = 6.1 Hz, 1H), 3.69 (br. s., 6H), 2.13 (br. s., 2H), 1.67 (d, J = 6.1 Hz, 3H), 1.32 (br. s., 2H), 1.08 (d, J = 7.0 Hz, 2H), 0.66 (t, J = 6.4 Hz, 3H) | 2.07 A 510.3 | A |
| 41 | 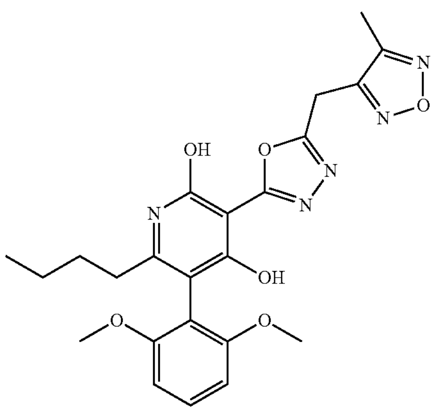 [SMILES: CCCCc1nc(O)c(-c2nnc(Cc3nonc3C)o2)c(O)c1-c1c(OC)cccc1OC] | 6-butyl-5-(2,6-dimethoxyphenyl)-3-{5-[(4-methyl-1,2,5-oxadiazol-3-yl)methyl]-1,3,4-oxadiazol-2-yl}pyridine-2,4-diol | 1H NMR (500 MHz, DMSO-d6) δ 7.35 (br. s., 1H), 6.73 (d, J = 7.3 Hz, 2H), 4.73 (br. s., 2H), 3.69 (br. s., 6H), 2.42 (br. s., 3H), 2.14 (br. s., 2H), 1.34 (br. s., 2H), 1.09 (d, J = 6.1 Hz, 2H), 0.66 (br. s., 3H) | 1.57 A 468.4 | A |
| 42 | 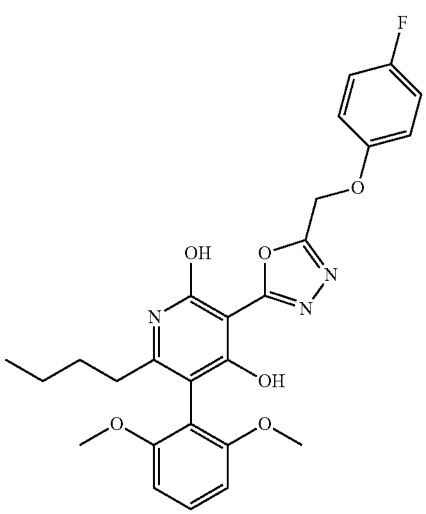 [SMILES: CCCCc1nc(O)c(-c2nnc(COc3ccc(F)cc3)o2)c(O)c1-c1c(OC)cccc1OC] | 6-butyl-5-(2,6-dimethoxyphenyl)-3-[5-(4-fluoro-phenoxymethyl)-1,3,4-oxadiazol-2-yl]pyridine-2,4-diol | 1H NMR (500 MHz, DMSO-d6) δ 7.36 (t, J = 7.8 Hz, 1H), 7.22-7.10 (m, 4H), 6.73 (d, J = 7.9 Hz, 2H), 5.47 (br. s., 2H), 3.70 (br. s., 6H), 2.15 (br. s., 2H), 1.34 (br. s., 2H), 1.09 (d, J = 6.7 Hz, 2H), 0.66 (t, J = 6.6 Hz, 3H) | 1.84 A 496.4 | B |

| Ex # | Structure | Name | ¹H NMR | LC/MS Rt (min) Method M + H | hAPJ cAMP EC₅₀ Potency range (nM) |
|---|---|---|---|---|---|
| 43 | 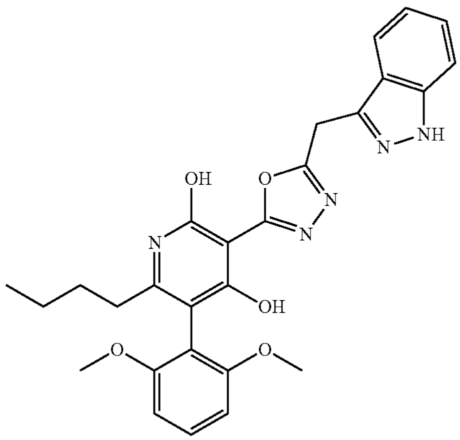 [SMILES: CCCCc1nc(O)c(-c2nnc(Cc3n[nH]c4ccccc34)o2)c(O)c1-c1c(OC)cccc1OC] | 6-butyl-5-(2,6-dimethoxyphenyl)-3-[5-(1H-indazol-3-ylmethyl)-1,3,4-oxadiazol-2-yl]pyridine-2,4-diol | 1H NMR (500 MHz, DMSO-d6) δ 7.80 (d, J = 7.6 Hz, 1H), 7.53 (d, J = 7.9 Hz, 1H), 7.42-7.30 (m, 2H), 7.12 (br. s., 1H), 6.72 (d, J = 7.6 Hz, 2H), 4.71 (br. s., 2H), 3.69 (br. s., 6H), 2.14 (br. s., 2H), 1.32 (br. s., 2H), 1.08 (d, J = 6.7 Hz, 2H), 0.65 (br. s., 3H) | 1.68 A 502.4 | A |
| 44 | 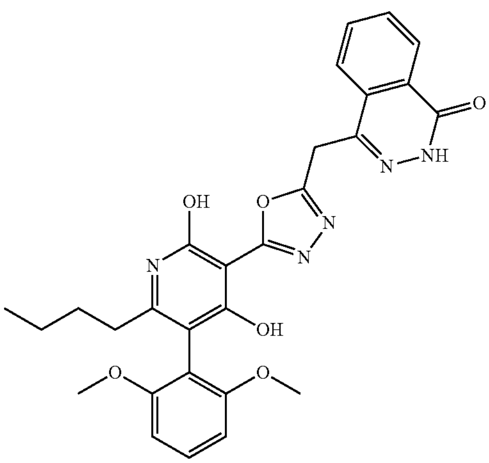 [SMILES: CCCCc1nc(O)c(-c2nnc(Cc3n[nH]c(=O)c4ccccc34)o2)c(O)c1-c1c(OC)cccc1OC] | 4-({5-[6-butyl-5-(2,6-dimethoxyphenyl)-2,4-dihydroxypyridin-3-yl]-1,3,4-oxadiazol-2-yl}methyl)-1,2-dihydrophthalazin-1-one | 1H NMR (500 MHz, DMSO-d6) δ 8.30 (d, J = 7.3 Hz, 1H), 8.06 (d, J = 7.3 Hz, 1H), 7.98 (t, J = 6.9 Hz, 1H), 7.93-7.85 (m, 1H), 7.35 (t, J = 7.6 Hz, 1H), 6.73 (d, J = 7.9 Hz, 2H), 4.78 (br. s., 2H), 3.34 (br. s., 6H), 2.14 (br. s., 2H), 1.33 (br. s., 2H), 1.09 (d, J = 6.7 Hz, 2H), 0.66 (t, J = 6.4 Hz, 3H) | 1.46 A 530.4 | B |
| 45 | 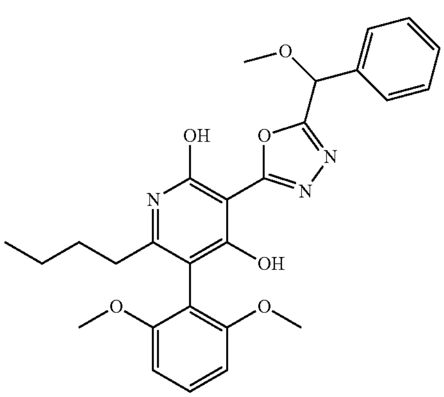 [SMILES: CCCCc1nc(O)c(-c2nnc(C(OC)c3ccccc3)o2)c(O)c1-c1c(OC)cccc1OC] | 6-butyl-5-(2,6-dimethoxyphenyl)-3-{5-[methoxy(phenyl)methyl]-1,3,4-oxadiazol-2-yl}pyridine-2,4-diol | 1H NMR (500 MHz, DMSO-d6) δ 7.51 (d, J = 6.7 Hz, 2H), 7.43 (d, J = 7.3 Hz, 3H), 7.35 (t, J = 7.9 Hz, 1H), 6.72 (d, J = 7.9 Hz, 2H), 5.86 (br. s, 1H), 3.69 (br. s., 6H), 3.41 (br. s., 3H), 2.15 (br. s., 2H), 1.33 (br. s., 2H), 1.09 (d, J = 7.0 Hz, 2H), 0.66 (t, J = 6.6 Hz, 3H) | 1.81 A 492.4 | B |

| Ex # | Structure | Name | ¹H NMR | LC/MS Rt (min) Method M + H | hAPJ cAMP EC$_{50}$ Potency range (nM) |
|---|---|---|---|---|---|
| 46 | 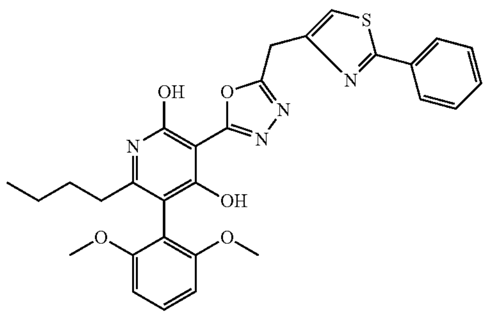 [SMILES: CCCCc1nc(O)c(-c2nnc(Cc3csc(-c4ccccc4)n3)o2)c(O)c1-c1c(OC)cccc1OC] | 6-butyl-5-(2,6-dimethoxyphenyl)-3-{5-[(2-phenyl-1,3-thiazol-4-yl)methyl]-1,3,4-oxadiazol-2-yl}pyridine-2,4-diol | 1H NMR (500 MHz, DMSO-d6) δ 7.93 (d, J = 3.7 Hz, 2H), 7.69 (br. s., 1H), 7.50 (br. s., 3H), 7.36 (t, J = 7.6 Hz, 1H), 6.73 (d, J = 7.9 Hz, 2H), 4.59 (br. s., 2H), 3.69 (br. s., 6H), 2.15 (br. s., 2H), 1.33 (br. s., 2H), 1.09 (d, J = 6.7 Hz, 2H), 0.71-0.60 (m, 3H) | 1.95 A 545.3 | A |
| 47 | 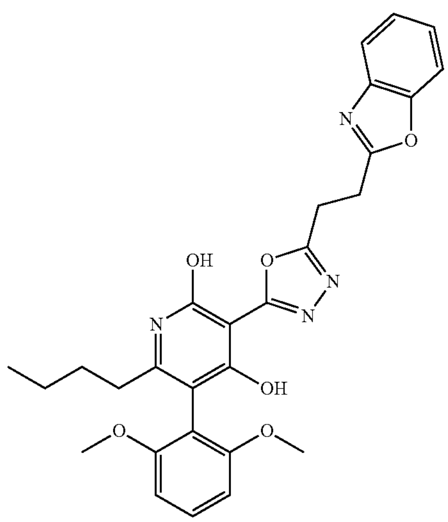 [SMILES: CCCCc1nc(O)c(-c2nnc(CCc3nc4ccccc4o3)o2)c(O)c1-c1c(OC)cccc1OC] | 3-{5-[2-(1,3-benzoxazol-2-yl)ethyl]-1,3,4-oxadiazol-2-yl}-6-butyl-5-(2,6-dimethoxyphenyl)pyridine-2,4-diol | 1H NMR (500 MHz, DMSO-d6) δ 7.69 (d, J = 6.7 Hz, 2H), 7.36 (br. s, 3H), 6.73 (d, J = 7.9 Hz, 2H), 3.69 (br. s., 6H), 3.53 (d, J = 10.7 Hz, 4H), 2.15 (br. s., 2H), 1.34 (br. s., 2H), 1.09 (d, J = 6.7 Hz, 2H), 0.66 (t, J = 6.4 Hz, 3H) | 1.77 A 517.4 | A |
| 48 | 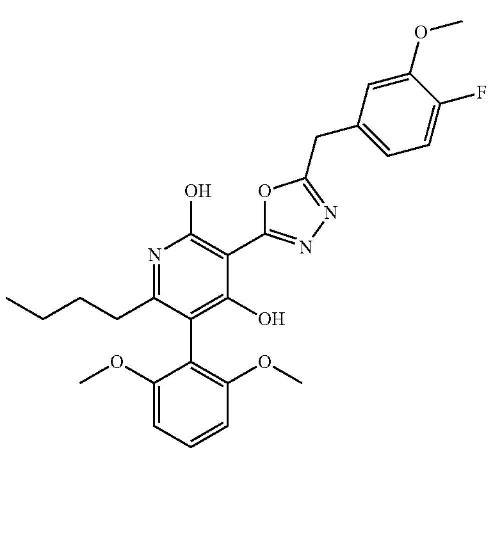 [SMILES: CCCCc1nc(O)c(-c2nnc(Cc3ccc(F)c(OC)c3)o2)c(O)c1-c1c(OC)cccc1OC] | 6-butyl-5-(2,6-dimethoxyphenyl)-3-{5-[(4-fluoro-3-methoxyphenyl)methyl]-1,3,4-oxadiazol-2-yl}pyridine-2,4-diol | 1H NMR (500 MHz, DMSO-d6) δ 7.35 (t, J = 7.8 Hz, 1H), 7.25 (d, J = 7.9 Hz, 1H), 7.19 (t, J = 9.5 Hz, 1H), 6.92 (br. s., 1H), 6.73 (d, J = 7.9 Hz, 2H), 4.36 (br. s., 2H), 3.86 (br. s., 3H), 3.69 (br. s., 6H), 2.15 (br. s., 2H), 1.33 (br. s., 2H), 1.09 (d, J = 6.4 Hz, 2H), 0.66 (br. s., 3H) | 1.84 A 510.4 | A |

-continued

| Ex # | Structure | Name | ¹H NMR | LC/MS Rt (min) Method M + H | hAPJ cAMP EC$_{50}$ Potency range (nM) |
|---|---|---|---|---|---|
| 49 | 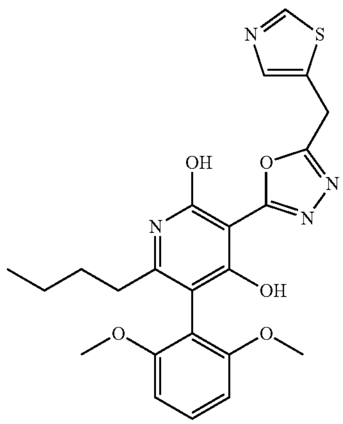 [SMILES: CCCCc1nc(O)c(-c2nnc(Cc3cncs3)o2)c(O)c1-c1c(OC)cccc1OC] | 6-butyl-5-(2,6-dimethoxyphenyl)-3-[5-(1,3-thiazol-5-ylmethyl)-1,3,4-oxadiazol-2-yl]pyridine-2,4-diol | 1H NMR (500 MHz, DMSO-d6) δ 9.08 (br. s., 1H), 7.91 (br. s., 1H), 7.35 (t, J = 7.8 Hz, 1H), 6.73 (d, J = 7.9 Hz, 2H), 4.72 (br. s., 2H), 3.69 (br. s., 6H), 2.14 (br. s., 2H), 1.33 (br. s., 2H), 1.09 (d, J = 6.1 Hz, 2H), 0.66 (br. s., 3H) | 1.44 A 469.3 | C |
| 50 | 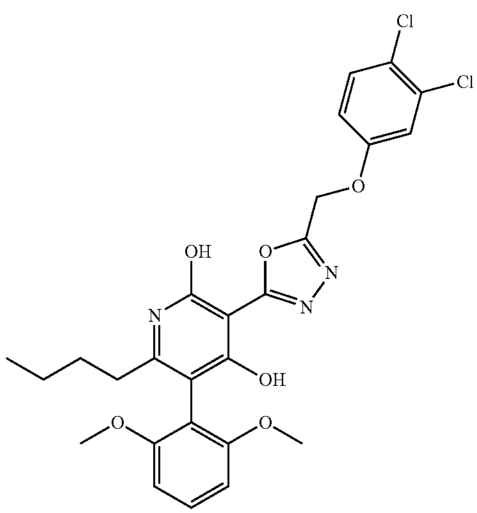 [SMILES: CCCCc1nc(O)c(-c2nnc(COc3ccc(Cl)c(Cl)c3)o2)c(O)c1-c1c(OC)cccc1OC] | 6-butyl-3-[5-(3,4-dichlorophenoxymethyl)-1,3,4-oxadiazol-2-yl]-5-(2,6-dimethoxyphenyl)pyridine-2,4-diol | 1H NMR (500 MHz, DMSO-d6) δ 7.59 (d, J = 8.5 Hz, 1H), 7.48 (br. s., 1H), 7.36 (t, J = 7.5 Hz, 1H), 7.14 (d, J = 8.5 Hz, 1H), 6.73 (d, J = 7.6 Hz, 2H), 5.56 (br. s., 2H), 3.70 (br. s., 6H), 2.15 (br. s., 2H), 1.34 (br. s., 2H), 1.09 (d, J = 6.4 Hz, 2H), 0.66 (br. s., 3H) | 2.08 A 546.3 | B |
| 51 | 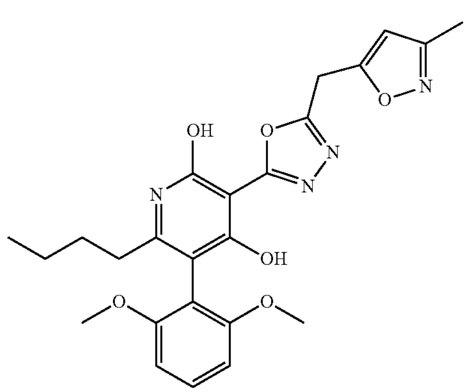 [SMILES: CCCCc1nc(O)c(-c2nnc(Cc3cc(C)no3)o2)c(O)c1-c1c(OC)cccc1OC] | 6-butyl-5-(2,6-dimethoxyphenyl)-3-{5-[(3-methyl-1,2-oxazol-5-yl)methyl]-1,3,4-oxadiazol-2-yl}pyridine-2,4-diol | 1H NMR (500 MHz, DMSO-d6) δ 7.35 (t, J = 7.6 Hz, 1H), 6.73 (d, J = 7.6 Hz, 2H), 6.40 (br. s., 1H), 4.66 (br. s., 2H), 3.70 (br. s., 6H), 2.24 (br. s., 3H), 2.15 (br. s., 2H), 1.34 (br. s., 2H), 1.09 (d, J = 6.4 Hz, 2H), 0.66 (br. s., 3H) | 1.51 A 467.4 | A |

-continued

| Ex # | Structure | Name | ¹H NMR | LC/MS Rt (min) Method M + H | hAPJ cAMP EC₅₀ Potency range (nM) |
|---|---|---|---|---|---|
| 52 | 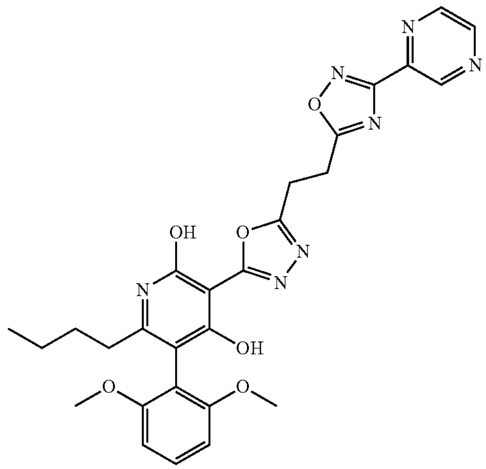 [SMILES: CCCCc1nc(O)c(-c2nnc(CCc3nc(-c4cnccn4)no3)o2)c(O)c1-c1c(OC)cccc1OC] | 6-butyl-5-(2,6-dimethoxyphenyl)-3-(5-{2-[3-(pyrazin-2-yl)-1,2,4-oxadiazol-5-yl]ethyl}-1,3,4-oxadiazol-2-yl)pyridine-2,4-diol | 1H NMR (500 MHz, DMSO-d6) δ 9.26 (br. s., 1H), 8.87 (br. s., 2H), 7.34 (t, J = 7.6 Hz, 1H), 6.72 (d, J = 7.9 Hz, 2H), 3.69 (br. s., 6H), 3.60 (d, J = 14.6 Hz, 4H), 2.14 (br. s., 2H), 1.33 (br. s., 2H), 1.09 (d, J = 6.7 Hz, 2H), 0.70-0.60 (m, 3H) | 1.52 A 546.4 | A |
| 53 | 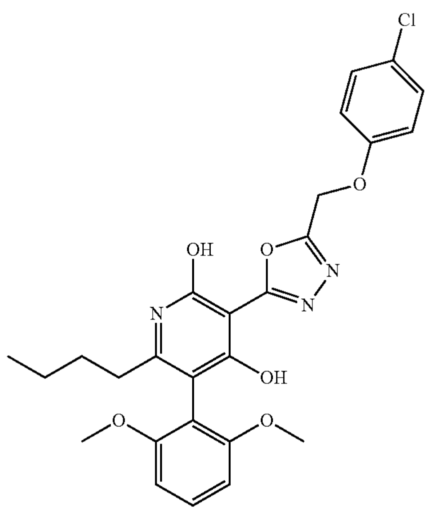 | 6-butyl-3-[5-(4-chlorophenoxy-methyl)-1,3,4-oxadiazol-2-yl]-5-(2,6-dimethoxyphenyl)pyridine-2,4-diol | 1H NMR (500 MHz, DMSO-d6) δ 7.44-7.31 (m, 3H), 7.15 (d, J = 7.6 Hz, 2H), 6.73 (d, J = 7.9 Hz, 2H), 5.50 (br. s., 2H), 3.70 (br. s., 6H), 2.15 (br. s., 2H), 1.34 (br. s., 2H), 1.09 (d, J = 6.7 Hz, 2H), 0.66 (br. s., 3H) | 1.94 A 512.3 | B |
| 54 | 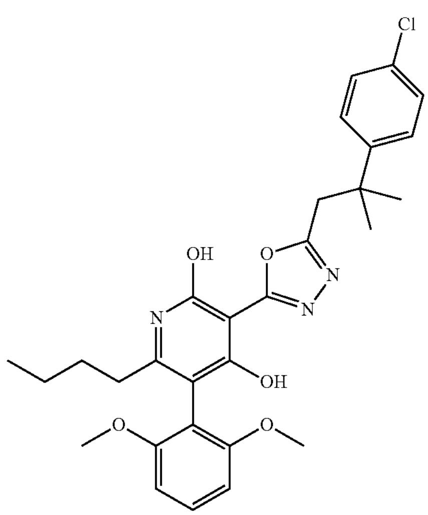 [SMILES: CCCCc1nc(O)c(-c2nnc(CC(C)(C)c3ccc(Cl)cc3)o2)c(O)c1-c1c(OC)cccc1OC] | 6-butyl-3-{5-[2-(4-chlorophenyl)-2-methylpropyl]-1,3,4-oxadiazol-2-yl}-5-(2,6-dimethoxyphenyl)pyridine-2,4-diol | 1H NMR (500 MHz, DMSO-d6) δ 7.45 (br. s., 4H), 7.35 (t, J = 7.6 Hz, 1H), 6.72 (d, J = 7.9 Hz, 2H), 3.68 (br. s., 6H), 3.38-3.21 (m, 2H), 2.14 (br. s., 2H), 1.32 (br. s., 2H), 1.09 (d, J = 6.4 Hz, 2H), 0.98 (br. s., 3H), 0.83 (br. s., 3H), 0.66 (br. s., 3H) | 2.35 A 538.4 | A |

-continued

| Ex # | Structure | Name | ¹H NMR | LC/MS Rt (min) Method M + H | hAPJ cAMP EC₅₀ Potency range (nM) |
|---|---|---|---|---|---|
| 55 | 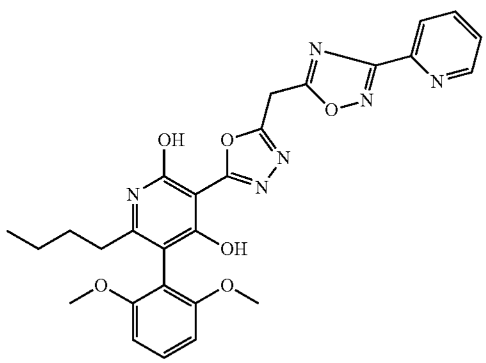 [SMILES: CCCCc1nc(O)c(-c2nnc(Cc3nc(-c4ccccn4)no3)o2)c(O)c1-c1c(OC)cccc1OC] | 6-butyl-5-(2,6-dimethoxyphenyl)-3-(5-{[3-(pyridin-2-yl)-1,2,4-oxadiazol-5-yl]methyl}-1,3,4-oxadiazol-2-yl)pyridine-2,4-diol | 1H NMR (500 MHz, DMSO-d6) δ 8.81-8.75 (m, 1H), 8.13-8.07 (m, 1H), 8.05-7.99 (m, 1H), 7.63 (ddd, J = 7.6, 4.8, 1.4 Hz, 1H), 7.36 (t, J = 8.4 Hz, 1H), 6.74 (d, J = 8.5 Hz, 2H), 5.12 (s, 2H), 3.70 (s, 7H), 2.21-2.11 (m, 2H), 1.39-1.30 (m, 2H), 1.09 (sxt, J = 7.3 Hz, 2H), 0.66 (t, J = 7.3 Hz, 1H) | 0.93 D 531.2 | A |
| 56 | 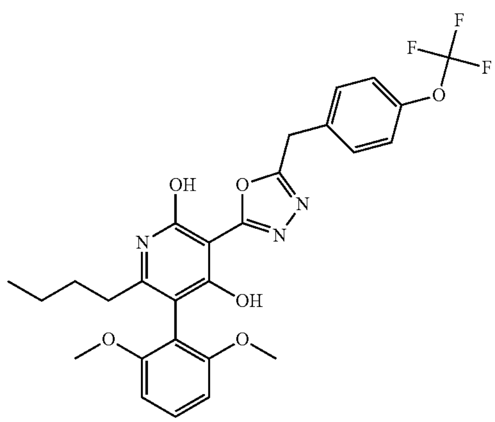 [SMILES: CCCCc1nc(O)c(-c2nnc(Cc3ccc(OC(F)(F)F)cc3)o2)c(O)c1-c1c(OC)cccc1OC] | 6-butyl-5-(2,6-dimethoxyphenyl)-3-(5-{[4-(trifluoromethoxy)phenyl]methyl}-1,3,4-oxadiazol-2-yl)pyridine-2,4-diol | 1H NMR (500 MHz, DMSO-d6) δ 7.44 (d, J = 7.3 Hz, 2H), 7.35-7.23 (m, 3H), 6.65 (d, J = 7.6 Hz, 2H), 4.37 (br. s., 2H), 3.62 (br. s., 6H), 2.07 (br. s., 2H), 1.26 (br. s., 2H), 1.01 (d, J = 6.4 Hz, 2H), 0.59 (br. s., 3H) | 2.09 A 546.4 | A |
| 57 | 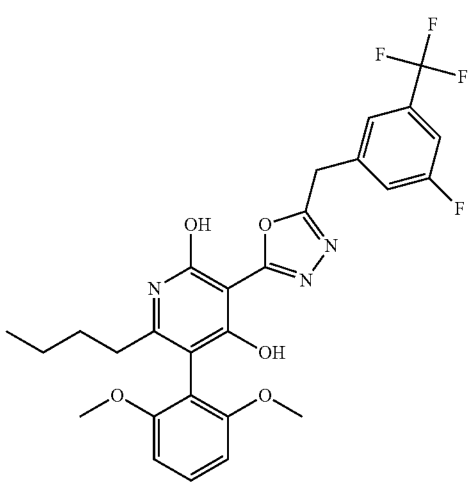 [SMILES: CCCCc1nc(O)c(-c2nnc(Cc3cc(F)cc(C(F)(F)F)c3)o2)c(O)c1-c1c(OC)cccc1OC] | 6-butyl-5-(2,6-dimethoxyphenyl)-3-(5-{[3-fluoro-5-(trifluoromethyl)phenyl]methyl}-1,3,4-oxadiazol-2-yl)pyridine-2,4-diol | 1H NMR (500 MHz, DMSO-d6) δ 7.72 (br. s., 1H), 7.68-7.60 (m, 2H), 7.42-7.27 (m, 1H), 6.73 (d, J = 7.9 Hz, 2H), 4.56 (br. s., 2H), 3.69 (br. s., 6H), 2.15 (br. s., 2H), 1.34 (br. s., 2H), 1.09 (d, J = 6.4 Hz, 2H), 0.66 (br. s., 3H) | 2.07 A 548.3 | B |

-continued

| Ex # | Structure | Name | ¹H NMR | LC/MS Rt (min) Method M + H | hAPJ cAMP EC$_{50}$ Potency range (nM) |
|---|---|---|---|---|---|
| 58 | 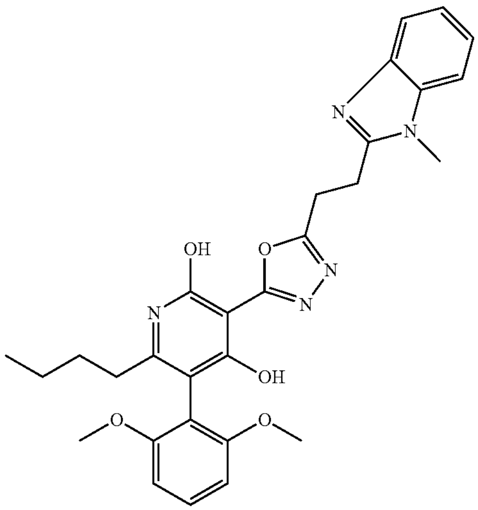 [SMILES: CCCCc1nc(O)c(-c2nnc(CCc3nc4ccccc4n3C)o2)c(O)c1-c1c(OC)cccc1OC] | 6-butyl-5-(2,6-dimethoxyphenyl)-3-{5-[2-(1-methyl-1H-1,3-benzodiazol-2-yl)ethyl]-1,3,4-oxadiazol-2-yl}pyridine-2,4-diol | 1H NMR (500 MHz, DMSO-d6) δ 7.56 (d, J = 7.6 Hz, 1H), 7.52 (d, J = 7.6 Hz, 1H), 7.39-7.32 (m, 1H), 7.25-7.19 (m, 1H), 7.17 (d, J = 7.0 Hz, 1H), 6.73 (d, J = 7.9 Hz, 2H), 3.81 (br. s., 3H), 3.69 (br. s., 6H), 3.55 (br. s., 2H), 3.44 (br. s., 2H), 2.16 (br. s., 2H), 1.34 (br. s., 2H), 1.09 (d, J = 6.7 Hz, 2H), 0.67 (br. s., 3H) | 1.67 A 530.4 | A |
| 59 | 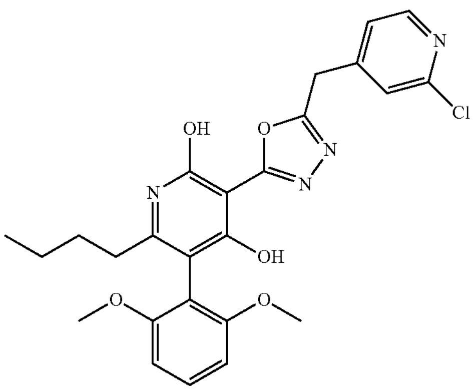 [SMILES: CCCCc1nc(O)c(-c2nnc(Cc3ccnc(Cl)c3)o2)c(O)c1-c1c(OC)cccc1OC] | 6-butyl-3-{5-[(2-chloropyridin-4-yl)methyl]-1,3,4-oxadiazol-2-yl}-5-(2,6-dimethoxyphenyl)pyridine-2,4-diol | 1H NMR (500 MHz, DMSO-d6) δ 8.41 (br. s., 1H), 7.60 (br. s., 1H), 7.45 (br. s., 1H), 7.36 (t, J = 7.8 Hz, 1H), 6.73 (d, J = 7.9 Hz, 2H), 4.51 (br. s., 2H), 3.69 (br. s., 6H), 2.15 (br. s., 2H), 1.34 (br. s., 2H), 1.09 (d, J = 6.4 Hz, 2H), 0.66 (br. s., 3H) | 1.62 A 497.4 | A |
| 60 | 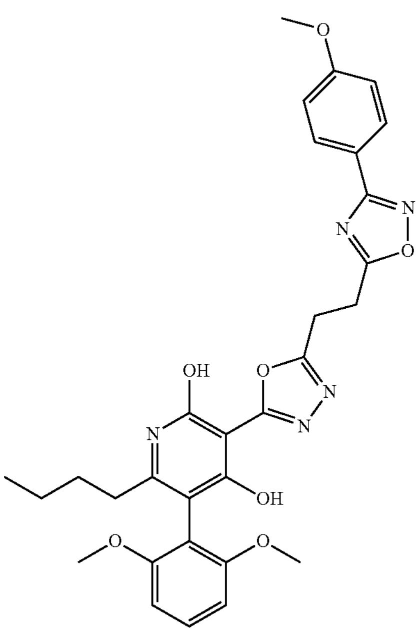 [SMILES: CCCCc1nc(O)c(-c2nnc(CCc3nc(-c4ccc(OC)cc4)no3)o2)c(O)c1-c1c(OC)cccc1OC] | 6-butyl-5-(2,6-dimethoxyphenyl)-3-(5-{2-[3-(4-methoxyphenyl)-1,2,4-oxadiazol-5-yl]ethyl}-1,3,4-oxadiazol-2-yl)pyridine-2,4-diol | 1H NMR (500 MHz, DMSO-d6) δ 7.86 (d, J = 8.2 Hz, 2H), 7.28 (t, J = 7.8 Hz, 1H), 7.03 (d, J = 6.4 Hz, 2H), 6.65 (d, J = 7.9 Hz, 2H), 3.76 (br. s., 3H), 3.62 (br. s., 6H), 3.47 (br. s., 4H), 2.08 (br. s., 2H), 1.27 (br. s., 2H), 1.02 (d, J = 6.4 Hz, 2H), 0.59 (br. s., 3H) | 1.92 A 574.4 | B |

| Ex # | Structure | Name | $^1$H NMR | LC/MS Rt (min) Method M + H | hAPJ cAMP EC$_{50}$ Potency range (nM) |
|---|---|---|---|---|---|
| 61 | 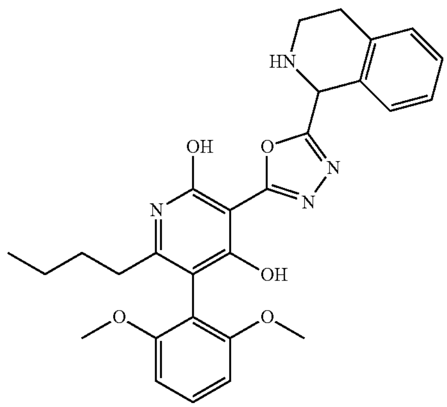 [SMILES: CCCCc1nc(O)c(-c2nnc(C3NCCc4ccccc43)o2)c(O)c1-c1c(OC)cccc1OC] | 6-butyl-5-(2,6-dimethoxyphenyl)-3-[5-(1,2,3,4-tetrahydroisoquinolin-1-yl)-1,3,4-oxadiazol-2-yl]pyridine-2,4-diol | 1H NMR (500 MHz, DMSO-d6) δ 7.36-7.25 (m, 3H), 7.21 (d, J = 12.2 Hz, 2H), 6.66 (d, J = 7.9 Hz, 2H), 6.29 (br. s., 1H), 3.62 (br. s., 6H), 3.49 (br. s., 2H), 3.05 (br. s., 2H), 2.09 (br. s., 2H), 1.26 (br. s., 2H), 1.02 (d, J = 6.1 Hz, 2H), 0.59 (br. s., 3H) | 1.69 A 503.4 | A |
| 62 | 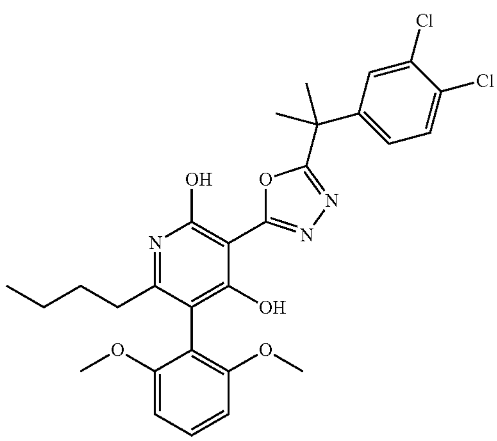 [SMILES: CCCCc1nc(O)c(-c2nnc(C(C)(C)c3ccc(Cl)c(Cl)c3)o2)c(O)c1-c1c(OC)cccc1OC] | 6-butyl-3-{5-[2-(3,4-dichlorophenyl)propan-2-yl]-1,3,4-oxadiazol-2-yl}-5-(2,6-dimethoxyphenyl)pyridine-2,4-diol | 1H NMR (500 MHz, DMSO-d6) δ 7.68-7.58 (m, 2H), 7.35 (t, J = 7.8 Hz, 1H), 7.29 (d, J = 8.5 Hz, 1H), 6.73 (d, J = 7.9 Hz, 2H), 3.69 (br. s., 6H), 2.14 (br. s., 2H), 1.80 (br. s., 6H), 1.32 (br. s., 2H), 1.08 (d, J = 6.7 Hz, 2H), 0.66 (br. s., 3H) | 2.30 A 558.3 | A |
| 63 | 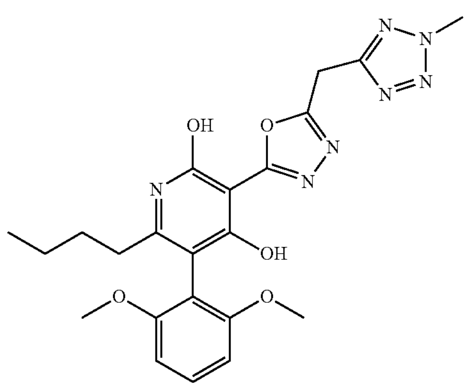 [SMILES: CCCCc1nc(O)c(-c2nnc(Cc3nnn(C)n3)o2)c(O)c1-c1c(OC)cccc1OC] | 6-butyl-5-(2,6-dimethoxyphenyl)-3-{5-[(2-methyl-2H-1,2,3,4-tetrazol-5-yl)methyl]-1,3,4-oxadiazol-2-yl}pyridine-2,4-diol | 1H NMR (500 MHz, DMSO-d6) δ 7.33-7.22 (m, 1H), 6.66 (d, J = 7.9 Hz, 2H), 4.86 (br. s., 2H), 4.05 (br. s., 3H), 3.62 (br. s., 6H), 2.08 (br. s., 2H), 1.27 (br. s., 2H), 1.02 (d, J = 6.4 Hz, 2H), 0.59 (br. s., 3H) | 1.32 A 468.4 | A |

| Ex # | Structure | Name | ¹H NMR | LC/MS Rt (min) Method M + H | hAPJ cAMP EC₅₀ Potency range (nM) |
|---|---|---|---|---|---|
| 64 | 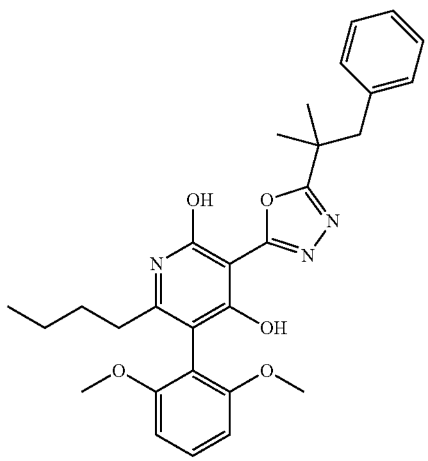 [SMILES: CCCCc1nc(O)c(-c2nnc(C(C)(C)Cc3ccccc3)o2)c(O)c1-c1c(OC)cccc1OC] | 6-butyl-5-(2,6-dimethoxyphenyl)-3-[5-(2-methyl-1-phenylpropan-2-yl)-1,3,4-oxadiazol-2-yl]pyridine-2,4-diol | 1H NMR (500 MHz, DMSO-d6) δ 7.36 (t, J = 7.6 Hz, 1H), 7.28-7.14 (m, 3H), 7.04 (d, J = 5.5 Hz, 2H), 6.74 (d, J = 7.9 Hz, 2H), 3.71 (br. s., 6H), 3.05 (br. s., 2H), 2.17 (br. s., 2H), 1.40 (br. s., 6H), 1.35 (br. s., 2H), 1.11 (d, J = 6.4 Hz, 2H), 0.68 (br. s., 3H) | 2.12 A 504.4 | A |
| 65 | 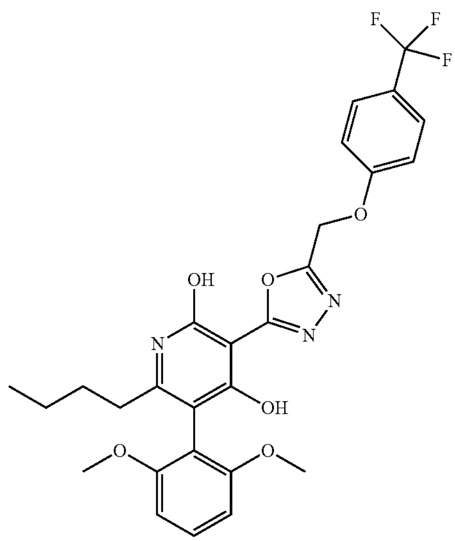 [SMILES: CCCCc1nc(O)c(-c2nnc(COc3ccc(C(F)(F)F)cc3)o2)c(O)c1-c1c(OC)cccc1OC] | 6-butyl-5-(2,6-dimethoxyphenyl)-3-{5-[4-(trifluoromethyl)phenoxymethyl]-1,3,4-oxadiazol-2-yl}pyridine-2,4-diol | 1H NMR (500 MHz, DMSO-d6) δ 7.65 (d, J = 7.9 Hz, 2H), 7.28 (t, J = 8.1 Hz, 1H), 7.24 (d, J = 7.9 Hz, 2H), 6.66 (d, J = 7.6 Hz, 2H), 5.54 (br. s., 2H), 3.62 (br. s., 6H), 2.08 (br. s., 2H), 1.27 (br. s., 2H), 1.02 (d, J = 6.7 Hz, 2H), 0.59 (br. s., 3H) | 2.01 A 546.3 | B |
| 66 | 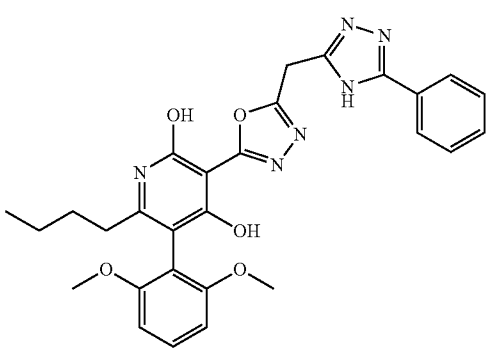 [SMILES: CCCCc1nc(O)c(-c2nnc(Cc3nnc(-c4ccccc4)[nH]3)o2)c(O)c1-c1c(OC)cccc1OC] | 6-butyl-5-(2,6-dimethoxyphenyl)-3-{5-[(5-phenyl-4H-1,2,4-triazol-3-yl)methyl]-1,3,4-oxadiazol-2-yl}pyridine-2,4-diol | 1H NMR (400 MHz, DMSO-d6) δ 7.99 (dd, J = 8.0, 1.4 Hz, 2H), 7.56-7.45 (m, 3H), 7.36 (t, J = 8.4 Hz, 1H), 6.73 (d, J = 8.6 Hz, 2H), 4.57 (br. s., 2H), 3.70 (s, 6H), 2.21-2.08 (m, 2H), 1.33 (t, J = 7.7 Hz, 2H), 1.14-1.03 (m, 2H), 0.66 (t, J = 7.3 Hz, 3H) | 2.00 C 529.2 | A |

| Ex # | Structure | Name | ¹H NMR | LC/MS Rt (min) Method M + H | hAPJ cAMP EC$_{50}$ Potency range (nM) |
|---|---|---|---|---|---|
| 67 | 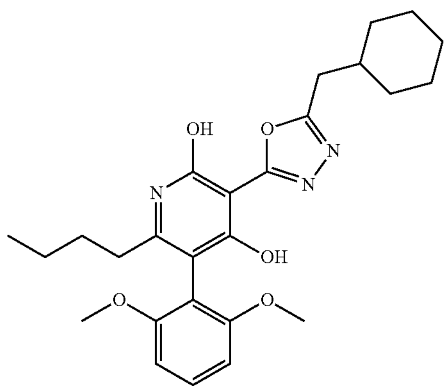 | 6-butyl-3-[5-(cyclohexylmethyl)-1,3,4-oxadiazol-2-yl]-5-(2,6-dimethoxyphenyl)pyridine-2,4-diol | 1H NMR (500 MHz, DMSO-d6) δ 7.35 (t, J = 7.6 Hz, 1H), 6.73 (d, J = 7.9 Hz, 2H), 3.69 (br. s., 6H), 2.83 (d, J = 5.2 Hz, 2H), 2.15 (br. s., 2H), 1.86-1.56 (m, 6H), 1.39-0.99 (m, 9H), 0.67 (br. s., 3H) | 2.11 A 468.5 | A |
| 68 | 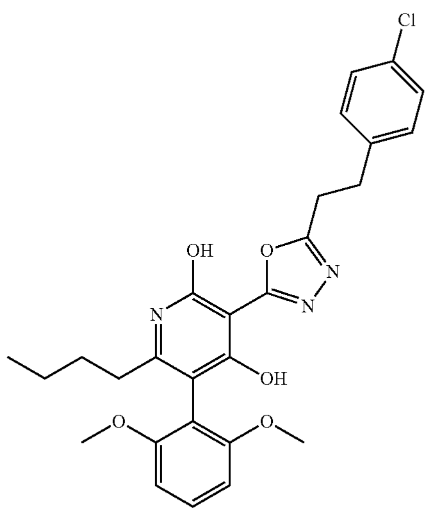 [SMILES: CCCCc1nc(O)c(-c2nnc(CCc3ccc(Cl)cc3)o2)c(O)c1-c1c(OC)cccc1OC] | 6-butyl-3-{5-[2-(4-chlorophenyl)ethyl]-1,3,4-oxadiazol-2-yl}-5-(2,6-dimethoxyphenyl)pyridine-2,4-diol | 1H NMR (500 MHz, DMSO-d6) δ 7.35 (br. s., 5H), 6.73 (d, J = 7.9 Hz, 2H), 3.69 (br. s., 6H), 3.26 (d, J = 5.8 Hz, 2H), 3.10 (br. s., 2H), 2.15 (br. s., 2H), 1.34 (br. s., 2H), 1.09 (d, J = 6.7 Hz, 2H), 0.66 (br. s., 3H) | 2.05 A 510.4 | A |
| 69 | 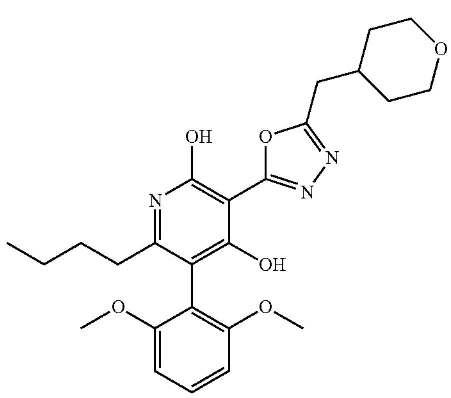 [SMILES: CCCCc1nc(O)c(-c2nnc(CC3CCOCC3)o2)c(O)c1-c1c(OC)cccc1OC] | 6-butyl-5-(2,6-dimethoxyphenyl)-3-[5-(oxan-4-ylmethyl)-1,3,4-oxadiazol-2-yl]pyridine-2,4-diol | 1H NMR (500 MHz, DMSO-d6) δ 7.35 (t, J = 7.2 Hz, 1H), 6.73 (d, J = 7.6 Hz, 2H), 3.85 (d, J = 11.0 Hz, 2H), 3.69 (br. s., 6H), 3.30 (d, J = 11.0 Hz, 2H), 2.90 (br. s., 2H), 2.14 (br. s., 2H), 2.03 (br. s., 1H), 1.65 (d, J = 12.8 Hz, 2H), 1.33 (d, J = 10.1 Hz, 4H), 1.09 (d, J = 6.1 Hz, 2H), 0.67 (br. s., 3H) | 1.56 A 470.4 | B |

| Ex # | Structure | Name | ¹H NMR | LC/MS Rt (min) Method M + H | hAPJ cAMP EC$_{50}$ Potency range (nM) |
|---|---|---|---|---|---|
| 70 | 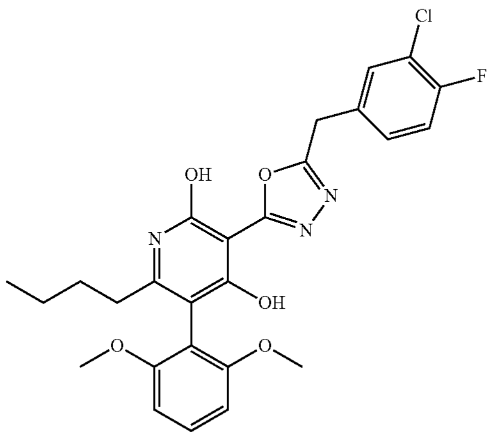 [SMILES: CCCCc1nc(O)c(-c2nnc(Cc3ccc(F)c(Cl)c3)o2)c(O)c1-c1c(OC)cccc1OC] | 6-butyl-3-{5-[(3-chloro-4-fluoro-phenyl)methyl]-1,3,4-oxadiazol-2-yl}-5-(2,6-dimethoxyphenyl)pyridine-2,4-diol | 1H NMR (500 MHz, DMSO-d6) δ 7.67 (br. s., 1H), 7.48-7.39 (m, 2H), 7.35 (t, J = 7.8 Hz, 1H), 6.73 (d, J = 7.6 Hz, 2H), 4.41 (br. s., 2H), 3.69 (br. s., 6H), 2.15 (br. s., 2H), 1.33 (br. s., 2H), 1.09 (d, J = 5.8 Hz, 2H), 0.66 (br. s., 3H) | 1.98 A 514.3 | A |
| 71 | 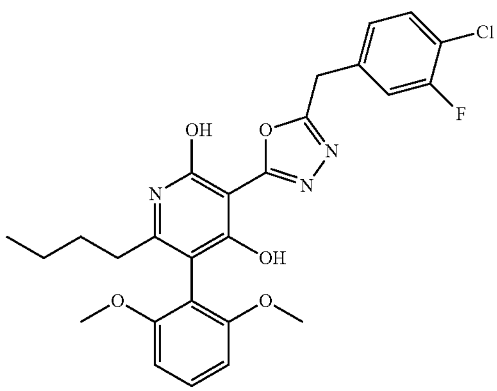 [SMILES: CCCCc1nc(O)c(-c2nnc(Cc3ccc(Cl)c(F)c3)o2)c(O)c1-c1c(OC)cccc1OC] | 6-butyl-3-{5-[(4-chloro-3-fluoro-phenyl)methyl]-1,3,4-oxadiazol-2-yl}-5-(2,6-dimethoxyphenyl)pyridine-2,4-diol | 1H NMR (500 MHz, DMSO-d6) δ 11.72 (br. s., 2H), 7.60 (t, J = 8.1 Hz, 1H), 7.48 (dd, J = 10.5, 1.9 Hz, 1H), 7.35 (t, J = 8.3 Hz, 1H), 7.26 (dd, J = 8.3, 1.7 Hz, 1H), 6.72 (d, J = 8.5 Hz, 2H), 4.43 (s, 2H), 3.69 (s, 6H), 2.14 (t, J = 7.3 Hz, 2H), 1.33 (quin, J = 7.6 Hz, 2H), 1.14-1.03 (m, 2H), 0.66 (t, J = 7.3 Hz, 3H) | 1.08 D 514.1 | A |
| 72 | 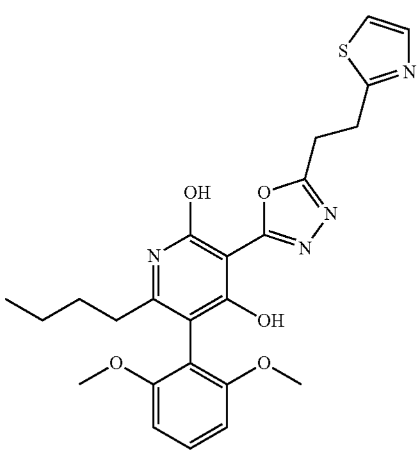 [SMILES: CCCCc1nc(O)c(-c2nnc(CCc3nccs3)o2)c(O)c1-c1c(OC)cccc1OC] | 6-butyl-5-(2,6-dimethoxyphenyl)-3-{5-[2-(1,3-thiazol-2-yl)ethyl]-1,3,4-oxadiazol-2-yl}pyridine-2,4-diol | 1H NMR (500 MHz, DMSO-d6) δ 7.72 (br. s., 1H), 7.61 (br. s., 1H), 7.36 (t, J = 7.5 Hz, 1H), 6.73 (d, J = 7.6 Hz, 2H), 3.70 (br. s., 6H), 3.53 (br. s., 2H), 3.44 (br. s., 2H), 2.16 (br. s., 2H), 1.34 (br. s., 2H), 1.09 (d, J = 5.8 Hz, 2H), 0.67 (br. s., 3H) | 1.58 A 483.4 | A |

-continued

| Ex # | Structure | Name | ¹H NMR | LC/MS Rt (min) Method M + H | hAPJ cAMP EC₅₀ Potency range (nM) |
|---|---|---|---|---|---|
| 73 | 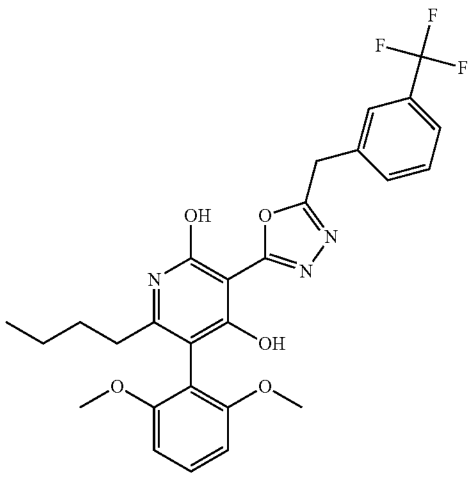 [SMILES: CCCCc1nc(O)c(-c2nnc(Cc3cccc(C(F)(F)F)c3)o2)c(O)c1-c1c(OC)cccc1OC] | 6-butyl-5-(2,6-dimethoxyphenyl)-3-(5-{[3-(trifluoromethyl)phenyl]methyl}-1,3,4-oxadiazol-2-yl)pyridine-2,4-diol | 1H NMR (500 MHz, DMSO-d6) δ 7.82 (br. s., 1H), 7.69 (br. s., 2H), 7.63 (d, J = 6.7 Hz, 1H), 7.35 (t, J = 7.6 Hz, 1H), 6.73 (d, J = 7.9 Hz, 2H), 4.52 (br. s., 2H), 3.69 (br. s., 6H), 2.14 (br. s., 2H), 1.33 (br. s., 2H), 1.09 (d, J = 6.1 Hz, 2H), 0.66 (br. s., 3H) | 2.01 A 530.2 | B |
| 74 | 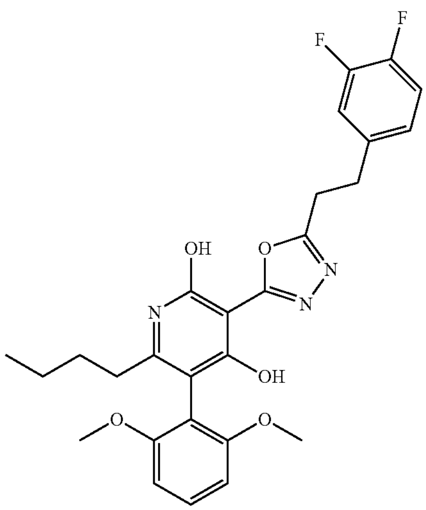 [SMILES: CCCCc1nc(O)c(-c2nnc(CCc3ccc(F)c(F)c3)o2)c(O)c1-c1c(OC)cccc1OC] | 6-butyl-3-{5-[2-(3,4-difluorophenyl)ethyl]-1,3,4-oxadiazol-2-yl}-5-(2,6-dimethoxyphenyl)pyridine-2,4-diol | 1H NMR (500 MHz, DMSO-d6) δ 7.36 (t, J = 9.3 Hz, 1H), 7.32-7.21 (m, 2H), 7.09 (br. s., 1H), 6.67 (d, J = 7.6 Hz, 2H), 3.62 (br. s., 6H), 3.21 (br. s., 2H), 3.04 (br. s., 2H), 2.09 (br. s., 2H), 1.27 (br. s., 2H), 1.02 (d, J = 5.8 Hz, 2H), 0.59 (br. s., 3H) | 1.99 A 512.4 | A |
| 75 | 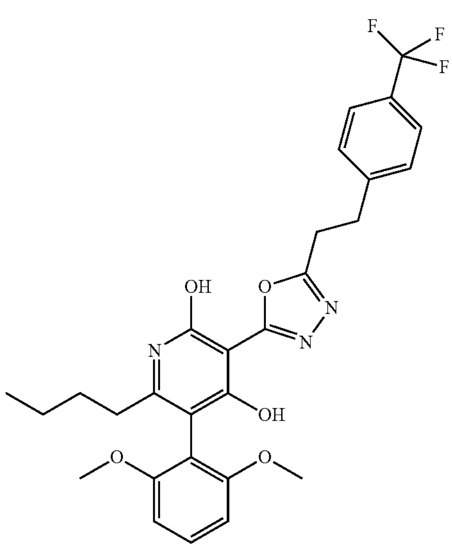 [SMILES: CCCCc1nc(O)c(-c2nnc(CCc3ccc(C(F)(F)F)cc3)o2)c(O)c1-c1c(OC)cccc1OC] | 6-butyl-5-(2,6-dimethoxyphenyl)-3-(5-{2-[4-(trifluoromethyl)phenyl]ethyl}-1,3,4-oxadiazol-2-yl)pyridine-2,4-diol | 1H NMR (500 MHz, DMSO-d6) δ 7.65 (d, J = 6.4 Hz, 2H), 7.54 (d, J = 6.4 Hz, 2H), 7.39-7.30 (m, 1H), 6.73 (d, J = 7.3 Hz, 2H), 3.68 (br. s., 6H), 3.31 (br. s., 2H), 3.20 (br. s., 2H), 2.15 (br. s., 2H), 1.33 (br. s., 2H), 1.08 (d, J = 5.8 Hz, 2H), 0.65 (br. s., 3H) | 2.12 A 544.3 | B |

| Ex # | Structure | Name | ¹H NMR | LC/MS Rt (min) Method M + H | hAPJ cAMP EC₅₀ Potency range (nM) |
|---|---|---|---|---|---|
| 76 | 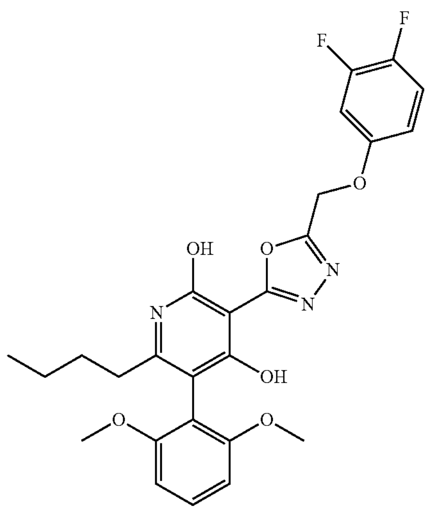 [SMILES: CCCCc1nc(O)c(-c2nnc(COc3ccc(F)c(F)c3)o2)c(O)c1-c1c(OC)cccc1OC] | 6-butyl-3-[5-(3,4-difluorophenoxymethyl)-1,3,4-oxadiazol-2-yl]-5-(2,6-dimethoxyphenyl)pyridine-2,4-diol | 1H NMR (500 MHz, DMSO-d6) δ 7.44-7.32 (m, 1H), 7.28 (br. s., 1H), 6.96 (br. s., 1H), 6.72 (d, J = 7.6 Hz, 2H), 5.48 (br. s., 2H), 3.68 (br. s., 6H), 2.14 (br. s., 2H), 1.33 (br. s., 2H), 1.08 (d, J = 4.9 Hz, 2H), 0.65 (br. s., 3H) | 1.87 A 513.9 | B |
| 77 | 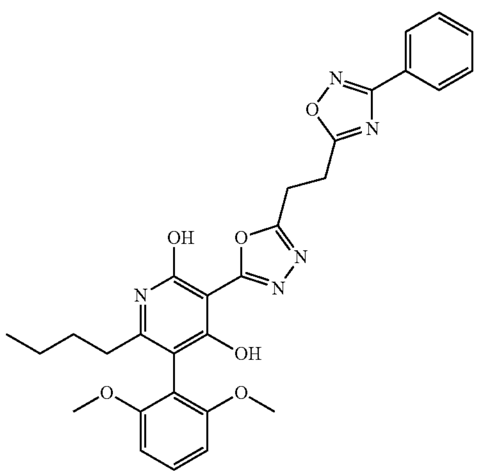 [SMILES: CCCCc1nc(O)c(-c2nnc(CCc3nc(-c4ccccc4)no3)o2)c(O)c1-c1c(OC)cccc1OC] | 6-butyl-5-(2,6-dimethoxyphenyl)-3-{5-[2-(3-phenyl-1,2,4-oxadiazol-5-yl)ethyl]-1,3,4-oxadiazol-2-yl}pyridine-2,4-diol | 1H NMR (500 MHz, DMSO-d6) δ 7.98 (d, J = 4.0 Hz, 1H), 7.56 (d, J = 8.2 Hz, 2H), 7.42-7.28 (m, 1H), 6.72 (d, J = 7.6 Hz, 2H), 3.67 (br. s., 6H), 3.58-3.37 (m, 4H), 2.14 (br. s., 2H), 1.32 (br. s., 2H), 1.08 (d, J = 4.9 Hz, 2H), 0.65 (br. s., 3H) | 1.92 A 544.3 | B |
| 78 | 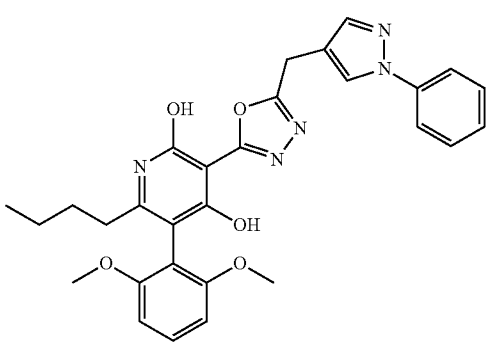 [SMILES: CCCCc1nc(O)c(-c2nnc(Cc3cnn(-c4ccccc4)c3)o2)c(O)c1-c1c(OC)cccc1OC] | 6-butyl-5-(2,6-dimethoxyphenyl)-3-{5-[(1-phenyl-1H-pyrazol-4-yl)methyl]-1,3,4-oxadiazol-2-yl}pyridine-2,4-diol | 1H NMR (500 MHz, DMSO-d6) δ 8.49 (br. s., 1H), 7.84-7.75 (m, 3H), 7.49 (br. s., 2H), 7.41-7.25 (m, 2H), 6.73 (d, J = 7.6 Hz, 2H), 4.30 (br. s., 2H), 3.68 (br. s., 6H), 2.15 (br. s, 2H), 1.32 (br. s., 2H), 1.09 (br. s., 2H), 0.65 (br. s., 3H) | 2.01 B 528.4 | B |

-continued

| Ex # | Structure | Name | ¹H NMR | LC/MS Rt (min) Method M + H | hAPJ cAMP EC₅₀ Potency range (nM) |
|---|---|---|---|---|---|
| 79 | 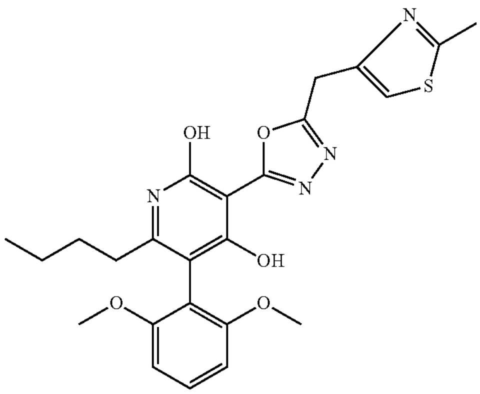 [SMILES: CCCCc1nc(O)c(-c2nnc(Cc3csc(C)n3)o2)c(O)c1-c1c(OC)cccc1OC] | 6-butyl-5-(2,6-dimethoxyphenyl)-3-{5-[(2-methyl-1,3-thiazol-4-yl)methyl]-1,3,4-oxadiazol-2-yl}pyridine-2,4-diol | 1H NMR (500 MHz, DMSO-d6) δ 11.72 (s, 1H), 7.43 (s, 1H), 7.36 (t, J = 8.4 Hz, 1H), 6.73 (d, J = 8.5 Hz, 2H), 4.44 (s, 2H), 3.70 (s, 6H), 2.63 (s, 3H), 2.19-2.11 (m, 2H), 1.33 (dt, J = 15.1, 7.6 Hz, 2H), 1.14-1.05 (m, 2H), 0.66 (t, J = 7.3 Hz, 3H) | 1.90 C 483.1 | A |
| 80 | 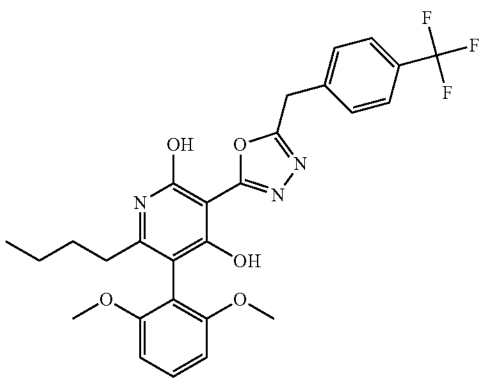 [SMILES: CCCCc1nc(O)c(-c2nnc(Cc3ccc(C(F)(F)F)cc3)o2)c(O)c1-c1c(OC)cccc1OC] | 6-butyl-5-(2,6-dimethoxyphenyl)-3-(5-{[4-(trifluoromethyl)phenyl]methyl}-1,3,4-oxadiazol-2-yl)pyridine-2,4-diol | 1H NMR (500 MHz, DMSO-d6) δ 7.74 (d, J = 6.1 Hz, 2H), 7.61 (br. s., 2H), 7.34 (br. s., 1H), 6.72 (d, J = 7.6 Hz, 2H), 4.48 (br. s., 2H), 3.67 (br. s., 6H), 2.13 (br. s., 2H), 1.31 (br. s., 2H), 1.08 (br. s, 2H), 0.65 (br. s., 3H) | 2.16 B 530.2 | A |
| 81 | 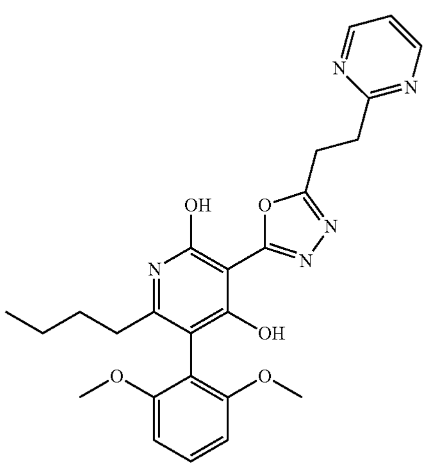 [SMILES: CCCCc1nc(O)c(-c2nnc(CCc3ncccn3)o2)c(O)c1-c1c(OC)cccc1OC] | 6-butyl-5-(2,6-dimethoxyphenyl)-3-{5-[2-(pyrimidin-2-yl)ethyl]-1,3,4-oxadiazol-2-yl}pyridine-2,4-diol | 1H NMR (500 MHz, DMSO-d6) δ 8.73 (br. s., 2H), 7.36 (d, J = 4.0 Hz, 2H), 6.72 (d, J = 7.6 Hz, 2H), 3.68 (br. s., 6H), 3.50 (d, J = 13.7 Hz, 2H), 3.44 (br. s., 2H), 2.15 (br. s., 2H), 1.33 (br. s., 2H), 1.08 (d, J = 5.8 Hz, 2H), 0.65 (br. s., 3H) | 1.43 A 477.9 | A |

-continued

| Ex # | Structure | Name | ¹H NMR | LC/MS Rt (min) Method M + H | hAPJ cAMP EC$_{50}$ Potency range (nM) |
|---|---|---|---|---|---|
| 82 | 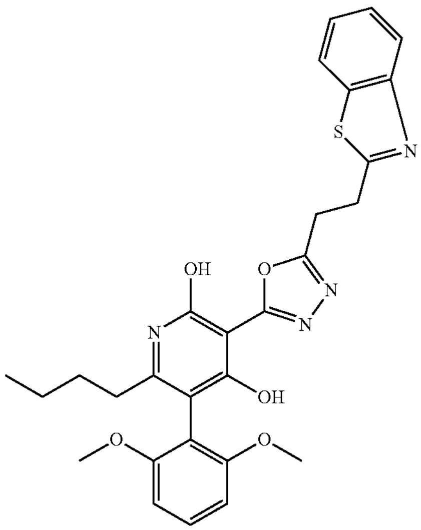 [SMILES: CCCCc1nc(O)c(-c2nnc(CCc3nc4ccccc4s3)o2)c(O)c1-c1c(OC)cccc1OC] | 3-{5-[2-(1,3-benzothiazol-2-yl)ethyl]-1,3,4-oxadiazol-2-yl}-6-butyl-5-(2,6-dimethoxyphenyl)pyridine-2,4-diol | 1H NMR (500 MHz, DMSO-d6) δ 11.75 (s, 1H), 8.07 (dd, J = 8.0, 0.5 Hz, 1H), 7.95 (d, J = 7.4 Hz, 1H), 7.50 (td, J = 7.6, 1.2 Hz, 1H), 7.45-7.39 (m, 1H), 7.35 (t, J = 8.4 Hz, 1H), 6.73 (d, J = 8.5 Hz, 2H), 3.69 (s, 6H), 3.67 (t, J = 6.9 Hz, 2H), 3.56 (t, J = 8.0 Hz, 2H), 2.20-2.11 (m, 2H), 1.39-1.30 (m, 2H), 1.15-1.06 (m, 2H), 0.67 (t, J = 7.4 Hz, 3H) | 2.07 C 533.2 | A |
| 83 | 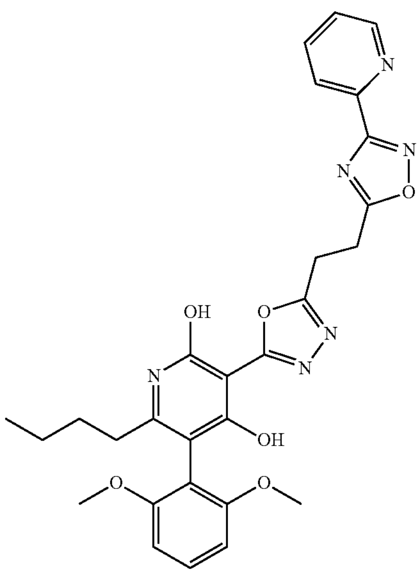 [SMILES: CCCCc1nc(O)c(-c2nnc(CCc3nc(-c4ccccn4)no3)o2)c(O)c1-c1c(OC)cccc1OC] | 6-butyl-5-(2,6-dimethoxyphenyl)-3-(5-{2-[3-(pyridin-2-yl)-1,2,4-oxadiazol-5-yl]ethyl}-1,3,4-oxadiazol-2-yl)pyridine-2,4-diol | 1H NMR (500 MHz, DMSO-d6) δ 8.75 (br. s., 1H), 8.05 (br. s., 1H), 8.01 (br. s., 1H), 7.60 (br. s., 1H), 7.39-7.31 (m, 1H), 6.72 (d, J = 7.9 Hz, 2H), 3.67 (br. s., 6H), 3.58 (br. s., 2H), 3.50 (d, J = 11.0 Hz, 2H), 2.15 (br. s., 2H), 1.32 (br. s., 2H), 1.07 (br. s., 2H), 0.65 (br. s., 3H) | 1.65 A 545.2 | A |
| 84 | 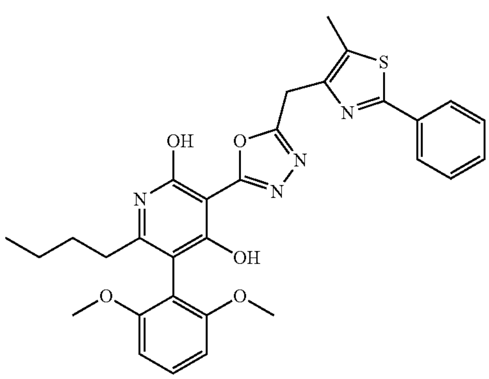 [SMILES: CCCCc1nc(O)c(-c2nnc(Cc3nc(-c4ccccc4)sc3C)o2)c(O)c1-c1c(OC)cccc1OC] | 6-butyl-5-(2,6-dimethoxyphenyl)-3-{5-[(5-methyl-2-phenyl-1,3-thiazol-4-yl)methyl]-1,3,4-oxadiazol-2-yl}pyridine-2,4-diol | 1H NMR (500 MHz, DMSO-d6) δ 7.83 (br. s., 2H), 7.46 (br. s., 3H), 7.39-7.29 (m, 1H), 6.72 (d, J = 7.9 Hz, 2H), 4.47 (br. s., 2H), 3.67 (br. s., 6H), 2.55 (br. s., 3H), 2.14 (br. s., 2H), 1.32 (br. s., 2H), 1.07 (br. s., 2H), 0.64 (br. s, 3H) | 2.19 B 559.2 | A |

| Ex # | Structure | Name | ¹H NMR | LC/MS Rt (min) Method M + H | hAPJ cAMP EC₅₀ Potency range (nM) |
|---|---|---|---|---|---|
| 85 | 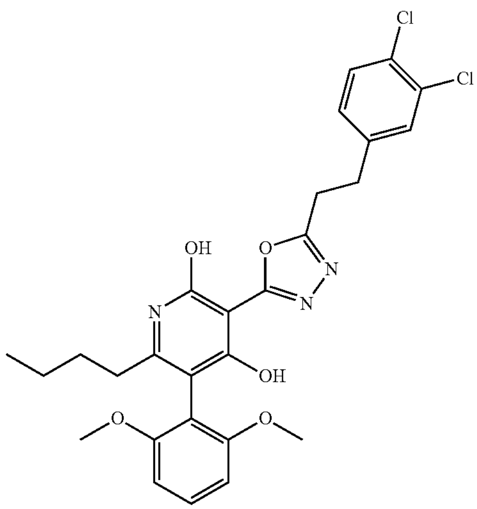 | 6-butyl-3-{5-[2-(3,4-dichloro-phenyl)ethyl]-1,3,4-oxadiazol-2-yl}-5-(2,6-dimethoxyphenyl)pyridine-2,4-diol | 1H NMR (500 MHz, DMSO-d6) δ 7.58 (br. s., 1H), 7.48 (d, J = 7.6 Hz, 1H), 7.33-7.22 (m, 2H), 6.66 (d, J = 7.9 Hz, 2H), 3.62 (br. s., 6H), 3.23 (br. s., 2H), 3.05 (br. s., 2H), 2.08 (br. s., 2H), 1.27 (br. s., 2H), 1.02 (br. s., 2H), 0.59 (br. s., 3H) | 2.16 A 544.3 | B |
| 86 | 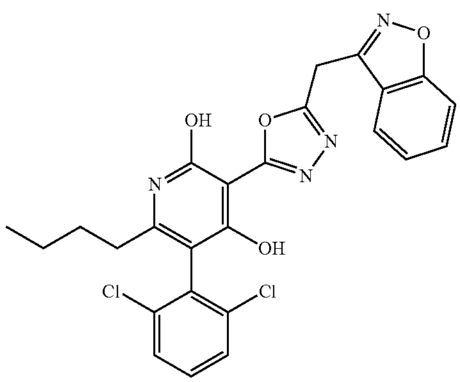 [SMILES: CCCCc1nc(O)c(-c2nnc(Cc3noc4ccccc34)o2)c(O)c1-c1c(Cl)cccc1Cl] | 3-[5-(1,2-benzoxazol-3-ylmethyl)-1,3,4-oxadiazol-2-yl]-6-butyl-5-(2,6-dichlorophenyl)pyridine-2,4-diol | 1H NMR (400 MHz, CDCl3) δ 12.26 (br. s., 1H), 7.81 (d, J = 7.9 Hz, 1H), 7.61-7.54 (m, 2H), 7.50-7.43 (m, 2H), 7.37-7.30 (m, 2H), 4.70 (s, 2H), 2.46-2.32 (m, 2H), 1.59 (quin, J = 7.6 Hz, 2H), 1.34-1.20 (m, 2H), 0.77 (t, J = 7.3 Hz, 3H) | 2.18 C 511.0 | A |
| 87 | 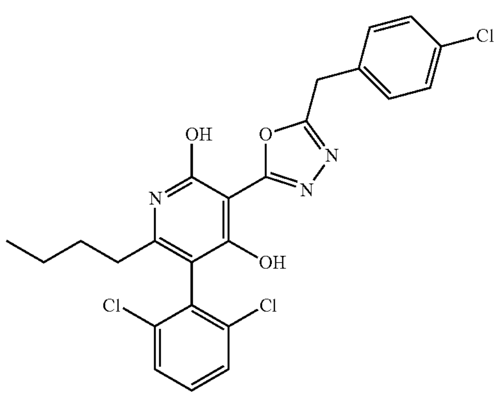 [SMILES: CCCCc1nc(O)c(-c2nnc(Cc3ccc(Cl)cc3)o2)c(O)c1-c1c(Cl)cccc1Cl] | 6-butyl-3-{5-[(4-chlorophenyl)methyl]-1,3,4-oxadiazol-2-yl}-5-(2,6-dichloro-phenyl)pyridine-2,4-diol | 1H NMR (400 MHz, CDCl3) δ 11.94 (br. s., 1H), 7.50-7.44 (m, 2H), 7.37-7.27 (m, 5H), 4.26 (s, 2H), 2.43-2.34 (m, 2H), 1.62-1.52 (m, 2H), 1.32-1.20 (m, 2H), 0.79 (t, J = 7.3 Hz, 3H) | 2.29 C 506.0 | B |

| Ex # | Structure | Name | ¹H NMR | LC/MS Rt (min) Method M + H | hAPJ cAMP EC₅₀ Potency range (nM) |
|---|---|---|---|---|---|
| 88 | 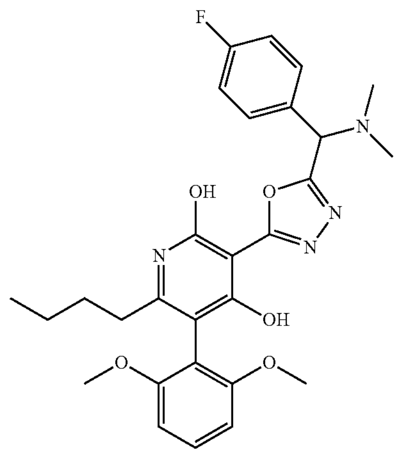 [SMILES: CCCCc1nc(O)c(-c2nnc(C(c3ccc(F)cc3)N(C)C)o2)c(O)c1-c1c(OC)cccc1OC] | 6-butyl-5-(2,6-dimethoxyphenyl)-3-{5-[(dimethylamino)(4-fluorophenyl)methyl]-1,3,4-oxadiazol-2-yl}pyridine-2,4-diol | 1H NMR (500 MHz, DMSO-d6) δ 7.60-7.50 (m, 2H), 7.35 (t, J = 8.2 Hz, 1H), 7.28-7.18 (m, 2H), 6.73 (d, J = 8.2 Hz, 2H), 5.14 (br. s., 1H), 3.68 (br. s., 6H), 2.23 (br. s., 6H), 2.15 (t, J = 7.5 Hz, 2H), 1.39-1.28 (m, 2H), 1.15-1.03 (m, 2H), 0.66 (t, J = 7.2 Hz, 3H) | 1.92 A 523.4 | A |
| 89 | 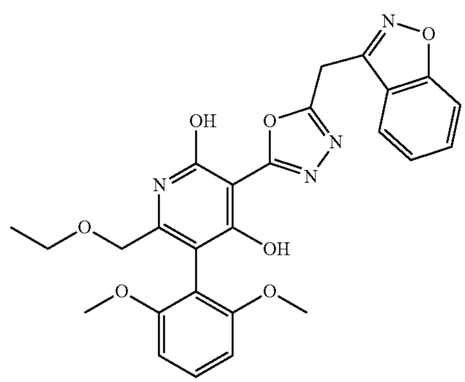 [SMILES: CCOCc1nc(O)c(-c2nnc(Cc3noc4ccccc34)o2)c(O)c1-c1c(OC)cccc1OC] | 3-[5-(1,2-benzoxazol-3-ylmethyl)-1,3,4-oxadiazol-2-yl]-5-(2,6-dimethoxyphenyl)-6-(ethoxymethyl)pyridine-2,4-diol | 1H NMR (500 MHz, DMSO-d6) δ 7.96 (d, J = 7.9 Hz, 1H), 7.79 (d, J = 8.2 Hz, 1H), 7.71 (t, J = 7.6 Hz, 1H), 7.43 (t, J = 7.5 Hz, 1H), 7.37 (t, J = 8.4 Hz, 1H), 6.73 (d, J = 8.2 Hz, 2H), 4.92 (s, 2H), 3.96 (s, 2H), 3.69 (s, 6H), 3.27 (q, J = 6.8 Hz, 2H), 0.99 (t, J = 7.0 Hz, 3H) | 1.41 A 505.3 | A |
| 90 | 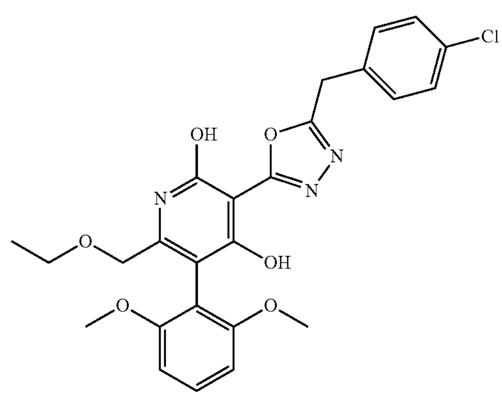 | 3-{5-[(4-chlorophenyl)methyl]-1,3,4-oxadiazol-2-yl}-5-(2,6-dimethoxyphenyl)-6-(ethoxymethyl)pyridine-2,4-diol | 1H NMR (500 MHz, DMSO-d6) δ 7.53-7.29 (m, 5H), 6.74 (d, J = 8.5 Hz, 2H), 4.40 (s, 2H), 3.96 (s, 2H), 3.69 (s, 6H), 3.27 (d, J = 7.0 Hz, 2H), 1.00 (t, J = 7.0 Hz, 3H) | 1.63 A 498.6 | A |

| Ex # | Structure | Name | ¹H NMR | LC/MS Rt (min) Method M + H | hAPJ cAMP EC₅₀ Potency range (nM) |
|---|---|---|---|---|---|
| 91 | 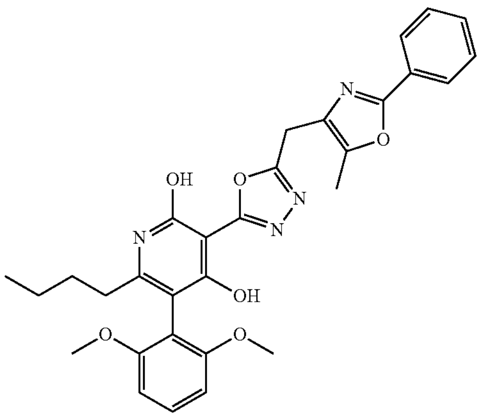 [SMILES: CCCCc1nc(O)c(-c2nnc(Cc3nc(-c4ccccc4)oc3C)o2)c(O)c1-c1c(OC)cccc1OC] | 6-butyl-5-(2,6-dimethoxyphenyl)-3-{5-[(5-methyl-2-phenyl-1,3-oxazol-4-yl)methyl]-1,3,4-oxadiazol-2-yl}pyridine-2,4-diol | 1H NMR (500 MHz, DMSO-d6) δ 7.92 (dd, J = 7.3, 2.3 Hz, 2H), 7.55-7.48 (m, 3H), 7.36 (t, J = 8.4 Hz, 1H), 6.73 (d, J = 8.5 Hz, 2H), 4.32 (s, 2H), 3.69 (s, 6H), 2.45 (s, 3H), 2.20-2.12 (m, 2H), 1.39-1.29 (m, 2H), 1.14-1.04 (m, 2H), 0.66 (t, J = 7.4 Hz, 3H) | 1.97 A 543.4 | A |
| 92 | 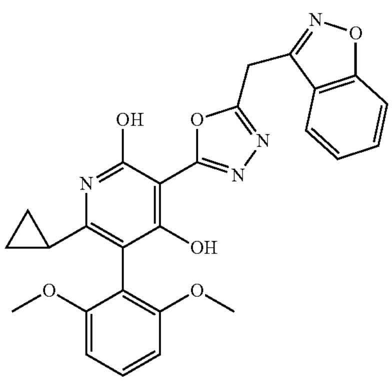 [SMILES: COc1cccc(OC)c1-c1c(C2CC2)nc(O)c(-c2nnc(Cc3noc4ccccc34)o2)c1O] | 3-[5-(1,2-benzoxazol-3-ylmethyl)-1,3,4-oxadiazol-2-yl]-6-cyclopropyl-5-(2,6-dimethoxyphenyl)pyridine-2,4-diol | 1H NMR (500 MHz, DMSO-d6) δ 7.98 (d, J = 7.9 Hz, 1H), 7.79 (d, J = 8.2 Hz, 1H), 7.70 (t, J = 7.8 Hz, 1H), 7.43 (t, J = 7.5 Hz, 1H), 7.35 (t, J = 8.2 Hz, 1H), 6.74 (d, J = 8.5 Hz, 2H), 4.92 (s, 2H), 3.71 (s, 6H), 1.48 (br. s., 1H), 0.98 (d, J = 4.9 Hz, 2H), 0.77 (d, J = 6.7 Hz, 2H) | 1.60 A 486.9 | B |
| 93 | 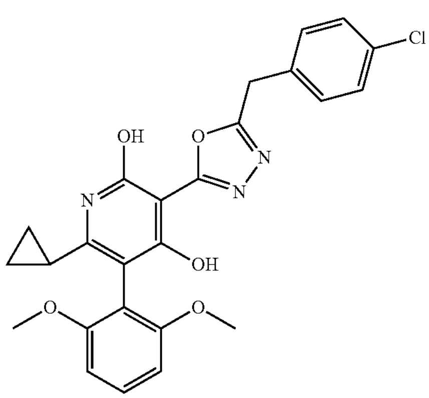 [SMILES: COc1cccc(OC)c1-c1c(C2CC2)nc(O)c(-c2nnc(Cc3ccc(Cl)cc3)o2)c1O] | 3-{5-[(4-chlorophenyl)methyl]-1,3,4-oxadiazol-2-yl}-6-cyclopropyl-5-(2,6-dimethoxyphenyl)pyridine-2,4-diol | 1H NMR (500 MHz, DMSO-d6) δ 7.51-7.29 (m, 5H), 6.74 (d, J = 8.5 Hz, 2H), 4.39 (s, 2H), 3.71 (s, 6H), 1.47 (br. s., 1H), 0.97 (d, J = 4.3 Hz, 2H), 0.76 (d, J = 6.4 Hz, 2H) | 1.74 A 480.0 | B |

-continued

| Ex # | Structure | Name | ¹H NMR | LC/MS Rt (min) Method M + H | hAPJ cAMP EC₅₀ Potency range (nM) |
|---|---|---|---|---|---|
| 94 | 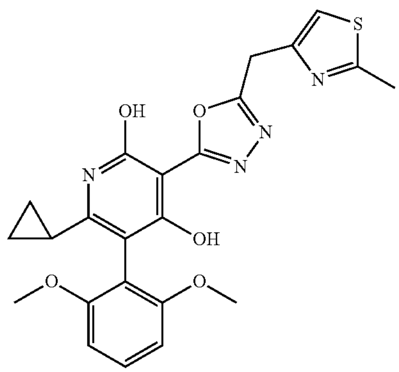 [SMILES: COc1cccc(OC)c1-c1c(C2CC2)nc(O)c(-c2nnc(Cc3csc(C)n3)o2)c1O] | 6-cyclopropyl-5-(2,6-dimethoxyphenyl)-3-{5-[(2-methyl-1,3-thiazol-4-yl)methyl]-1,3,4-oxadiazol-2-yl}pyridine-2,4-diol | 1H NMR (500 MHz, DMSO-d6) δ 7.43 (s, 1H), 7.36 (t, J = 8.2 Hz, 2H), 6.74 (d, J = 8.2 Hz, 2H), 4.44 (s, 2H), 3.76-3.65 (m, 6H), 2.63 (s, 3H), 1.47 (d, J = 5.5 Hz, 1H), 0.97 (d, J = 4.6 Hz, 2H), 0.76 (d, J = 7.0 Hz, 2H) | 1.40 A 467.2 | B |
| 95 | 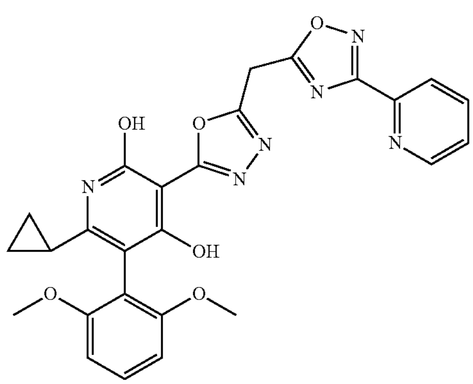 [SMILES: COc1cccc(OC)c1-c1c(C2CC2)nc(O)c(-c2nnc(Cc3nc(-c4ccccn4)no3)o2)c1O] | 6-cyclopropyl-5-(2,6-dimethoxyphenyl)-3-(5-{[3-(pyridin-2-yl)-1,2,4-oxadiazol-5-yl]methyl}-1,3,4-oxadiazol-2-yl)pyridine-2,4-diol | 1H NMR (500 MHz, DMSO-d6) δ 8.77 (d, J = 4.6 Hz, 1H), 8.08 (d, J = 7.6 Hz, 1H), 8.03 (t, J = 7.6 Hz, 1H), 7.70-7.49 (m, 1H), 7.36 (t, J = 8.4 Hz, 1H), 6.75 (d, J = 8.5 Hz, 2H), 5.10 (s, 2H), 3.71 (s, 6H), 1.47 (d, J = 5.5 Hz, 1H), 0.97 (d, J = 4.3 Hz, 2H), 0.77 (d, J = 6.7 Hz, 2H) | 1.37 A 515.0 | A |
| 96 | 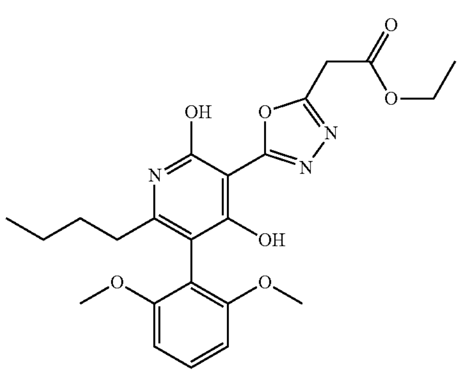 [SMILES: CCCCc1nc(O)c(-c2nnc(CC(=O)OCC)o2)c(O)c1-c1c(OC)cccc1OC] | ethyl 2-{5-[6-butyl-5-(2,6-dimethoxyphenyl)-2,4-dihydroxypyridin-3-yl]-1,3,4-oxadiazol-2-yl}acetate | 1H NMR (500 MHz, DMSO-d6) δ 7.37 (t, J = 8.4 Hz, 1H), 6.74 (d, J = 8.2 Hz, 2H), 4.27 (s, 2H), 4.18 (q, J = 7.0 Hz, 2H), 3.70 (s, 6H), 2.16 (t, J = 7.6 Hz, 2H), 1.39-1.29 (m, 2H), 1.23 (t, J = 6.9 Hz, 3H), 1.17-1.01 (m, 2H), 0.66 (t, J = 7.3 Hz, 3H) | 1.63 A 458.3 | B |

-continued

| Ex # | Structure | Name | ¹H NMR | LC/MS Rt (min) Method M + H | hAPJ cAMP EC$_{50}$ Potency range (nM) |
|---|---|---|---|---|---|
| 98 | 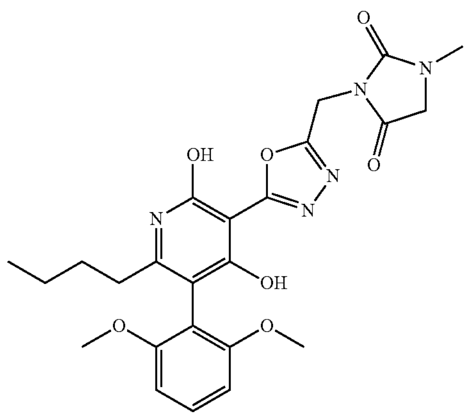 [SMILES: CCCCc1nc(O)c(-c2nnc(CN3C(=O)CN(C)C3=O)o2)c(O)c1-c1c(OC)cccc1OC] | 3-({5-[6-butyl-5-(2,6-dimethoxyphenyl)-2,4-dihydroxypyridin-3-yl]-1,3,4-oxadiazol-2-yl}methyl)-1-methyl-imidazolidine-2,4-dione | 1H NMR (500 MHz, DMSO-d6) δ 7.34 (t, J = 8.2 Hz, 1H), 6.71 (d, J = 8.3 Hz, 2H), 4.89 (s, 2H), 4.10 (s, 2H), 3.68 (s, 6H), 2.89 (s, 3H), 2.12 (t, J = 7.2 Hz, 2H), 1.40-1.24 (m, 2H), 1.14-0.99 (m, 2H), 0.65 (t, J = 7.3 Hz, 3H) | 1.18 A 498.1 | A |
| 99 | 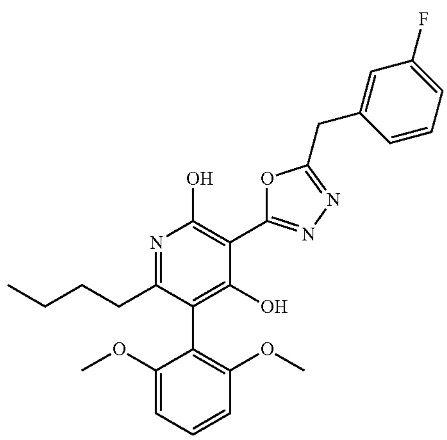 [SMILES: CCCCc1nc(O)c(-c2nnc(Cc3cccc(F)c3)o2)c(O)c1-c1c(OC)cccc1OC] | 6-butyl-5-(2,6-dimethoxyphenyl)-3-{5-[(3-fluorophenyl)methyl]-1,3,4-oxadiazol-2-yl}pyridine-2,4-diol | 1H NMR (500 MHz, DMSO-d6) δ 7.41 (q, J = 7.3 Hz, 1H), 7.35 (t, J = 8.4 Hz, 1H), 7.26-7.17 (m, 2H), 7.13 (t, J = 7.7 Hz, 1H), 6.72 (d, J = 8.4 Hz, 2H), 4.38 (s, 2H), 3.66 (s, 6H), 2.13 (t, J = 7.6 Hz, 2H), 1.36-1.24 (m, 2H), 1.12-1.00 (m, 2H), 0.63 (t, J = 7.3 Hz, 3H) | 1.76 A 480.3 | A |
| 100 | 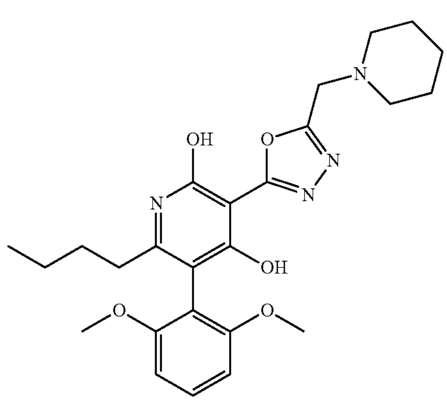 [SMILES: CCCCc1nc(O)c(-c2nnc(CN3CCCCC3)o2)c(O)c1-c1c(OC)cccc1OC] | 6-butyl-5-(2,6-dimethoxyphenyl)-3-[5-(piperidin-1-ylmethyl)-1,3,4-oxadiazol-2-yl]pyridine-2,4-diol | 1H NMR (500 MHz, DMSO-d6) δ 7.36 (t, J = 8.3 Hz, 1H), 6.73 (d, J = 8.4 Hz, 2H), 3.74 (br. s., 6H), 3.67 (br. s., 2H), 2.44 (br. s., 4H), 2.15 (br. s., 2H), 1.50 (br. s., 4H), 1.40-1.24 (m, 4H), 1.07 (d, J = 7.0 Hz, 2H), 0.64 (t, J = 7.2 Hz, 3H) | 1.57 A 469.1 | B |

-continued

| Ex # | Structure | Name | ¹H NMR | LC/MS Rt (min) Method M + H | hAPJ cAMP EC₅₀ Potency range (nM) |
|---|---|---|---|---|---|
| 101 | 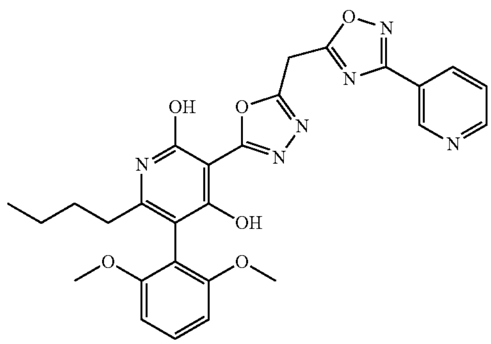 [SMILES: CCCCc1nc(O)c(-c2nnc(Cc3nc(-c4cccnc4)no3)o2)c(O)c1-c1c(OC)cccc1OC] | 6-butyl-5-(2,6-dimethoxyphenyl)-3-(5-{[3-(pyridin-3-yl)-1,2,4-oxadiazol-5-yl]methyl}-1,3,4-oxadiazol-2-yl)pyridine-2,4-diol | 1H NMR (500 MHz, DMSO-d6) δ 9.17 (s, 1H), 8.80 (d, J = 4.6 Hz, 1H), 8.38 (d, J = 7.9 Hz, 1H), 7.63 (dd, J = 7.8, 5.0 Hz, 1H), 7.37 (t, J = 8.4 Hz, 1H), 6.74 (d, J = 8.5 Hz, 2H), 5.11 (s, 2H), 3.70 (s, 6H), 2.16 (t, J = 7.5 Hz, 1H), 1.41-1.30 (m, 1H), 1.14-1.03 (m, 1H), 0.66 (t, J = 7.3 Hz, 1H) | 1.87 C 531.1 | A |
| 102 | 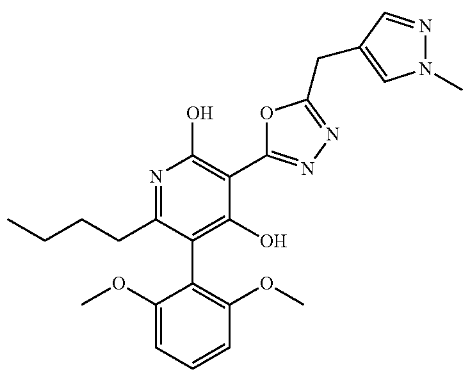 [SMILES: CCCCc1nc(O)c(-c2nnc(Cc3cnn(C)c3)o2)c(O)c1-c1c(OC)cccc1OC] | 6-butyl-5-(2,6-dimethoxyphenyl)-3-{5-[(1-methyl-1H-pyrazol-4-yl)methyl]-1,3,4-oxadiazol-2-yl}pyridine-2,4-diol | 1H NMR (500 MHz, DMSO-d6) δ 7.68 (s, 1H), 7.42 (s, 1H), 7.36 (t, J = 8.3 Hz, 1H), 6.73 (d, J = 8.3 Hz, 2H), 4.17 (s, 2H), 3.80 (s, 3H), 3.69 (s, 6H), 2.14 (t, J = 7.6 Hz, 2H), 1.40-1.27 (m, 2H), 1.14-1.00 (m, 2H), 0.66 (t, J = 7.3 Hz, 3H) | 1.34 A 466.1 | C |
| 103 | 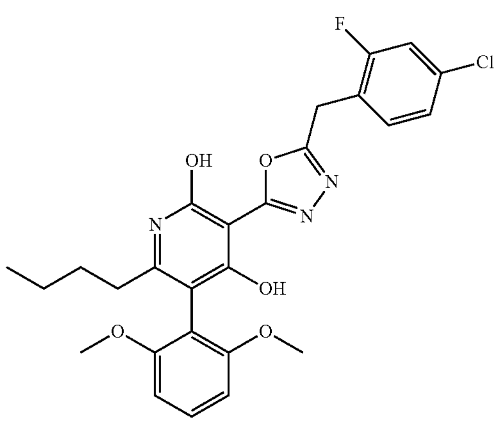 [SMILES: CCCCc1nc(O)c(-c2nnc(Cc3ccc(Cl)cc3F)o2)c(O)c1-c1c(OC)cccc1OC] | 6-butyl-3-{5-[(4-chloro-2-fluorophenyl)methyl]-1,3,4-oxadiazol-2-yl}-5-(2,6-dimethoxyphenyl)pyridine-2,4-diol | 1H NMR (500 MHz, DMSO-d6) δ 7.58-7.43 (m, 2H), 7.39-7.23 (m, 2H), 6.72 (d, J = 8.4 Hz, 2H), 4.38 (s, 2H), 3.67 (s, 6H), 2.13 (t, J = 7.5 Hz, 2H), 1.39-1.25 (m, 2H), 1.16-0.97 (m, 2H), 0.64 (t, J = 7.3 Hz, 3H) | 1.90 A 514.1 | A |
| 104 | 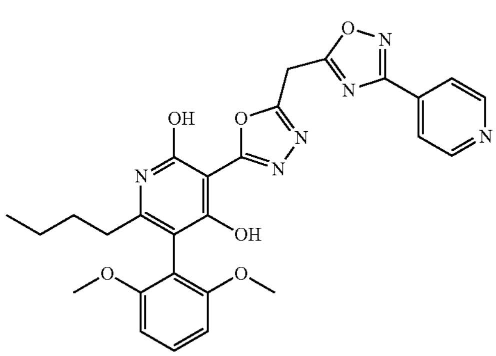 [SMILES: CCCCc1nc(O)c(-c2nnc(Cc3nc(-c4ccncc4)no3)o2)c(O)c1-c1c(OC)cccc1OC] | 6-butyl-5-(2,6-dimethoxyphenyl)-3-(5-{[3-(pyridin-4-yl)-1,2,4-oxadiazol-5-yl]methyl}-1,3,4-oxadiazol-2-yl)pyridine-2,4-diol | 1H NMR (500 MHz, DMSO-d6) δ 8.81 (d, J = 4.6 Hz, 2H), 7.95 (d, J = 5.2 Hz, 2H), 7.36 (t, J = 8.2 Hz, 1H), 6.74 (d, J = 8.2 Hz, 2H), 5.11 (s, 2H), 3.70 (s, 6H), 2.16 (t, J = 7.6 Hz, 2H), 1.40-1.30 (m, 2H), 1.15-1.04 (m, 2H), 0.66 (t, J = 7.2 Hz, 3H) | 1.81 C 531.1 | A |

-continued

| Ex # | Structure | Name | ¹H NMR | LC/MS Rt (min) Method M + H | hAPJ cAMP EC₅₀ Potency range (nM) |
|---|---|---|---|---|---|
| 105 | 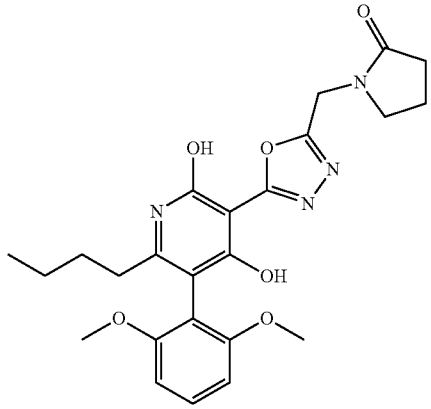 [SMILES: CCCCc1nc(O)c(-c2nnc(CN3CCCC3=O)o2)c(O)c1-c1c(OC)cccc1OC] | 1-({5-[6-butyl-5-(2,6-dimethoxyphenyl)-2,4-dihydroxypyridin-3-yl]-1,3,4-oxadiazol-2-yl}methyl)pyrrolidin-2-one | 1H NMR (500 MHz, DMSO-d6) δ 11.73 (br. s., 1H), 11.62 (br. s., 1H), 7.36 (t, J = 8.4 Hz, 1H), 6.73 (d, J = 8.5 Hz, 2H), 4.75 (s, 2H), 3.70 (s, 6H), 3.47 (t, J = 7.0 Hz, 2H), 2.30 (t, J = 8.1 Hz, 2H), 2.15 (t, J = 7.7 Hz, 2H), 2.06-1.90 (m, 2H), 1.34 (dt, J = 15.1, 7.5 Hz, 2H), 1.16-1.01 (m, 2H), 0.66 (t, J = 7.3 Hz, 3H) | 1.80 C 469.0 | A |
| 106 | 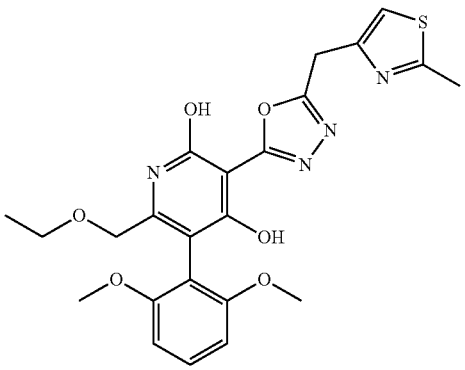 [SMILES: CCOCc1nc(O)c(-c2nnc(Cc3csc(C)n3)o2)c(O)c1-c1c(OC)cccc1OC] | 5-(2,6-dimethoxyphenyl)-6-(ethoxymethyl)-3-{5-[(2-methyl-1,3-thiazol-4-yl)methyl]-1,3,4-oxadiazol-2-yl}pyridine-2,4-diol | 1H NMR (500 MHz, DMSO-d6) δ 7.44 (s, 1H), 7.37 (t, J = 8.4 Hz, 1H), 6.74 (d, J = 8.5 Hz, 2H), 4.44 (s, 2H), 3.95 (s, 2H), 3.70 (s, 6H), 3.28 (q, J = 7.0 Hz, 2H), 2.64 (s, 3H), 1.00 (t, J = 7.0 Hz, 3H) | 1.25 A 485.2 | A |
| 107 | 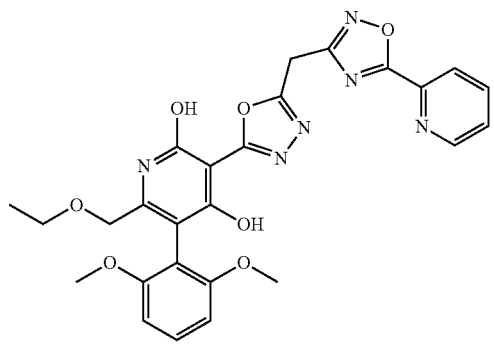 [SMILES: CCOCc1nc(O)c(-c2nnc(Cc3noc(-c4ccccn4)n3)o2)c(O)c1-c1c(OC)cccc1OC] | 5-(2,6-dimethoxyphenyl)-6-(ethoxymethyl)-3-(5-{[5-(pyridin-2-yl)-1,2,4-oxadiazol-3-yl]methyl}-1,3,4-oxadiazol-2-yl)pyridine-2,4-diol | 1H NMR (500 MHz, DMSO-d6) δ 8.78 (d, J = 4.3 Hz, 1H), 8.09 (d, J = 7.3 Hz, 1H), 8.04 (t, J = 7.6 Hz, 1H), 7.69-7.57 (m, 1H), 7.38 (t, J = 8.2 Hz, 1H), 6.74 (d, J = 8.5 Hz, 2H), 5.12 (s, 2H), 3.97 (s, 2H), 3.71 (s, 6H), 3.28 (q, J = 7.0 Hz, 2H), 1.00 (t, J = 6.9 Hz, 3H) | 1.21 A 533.0 | A |
| 108 | 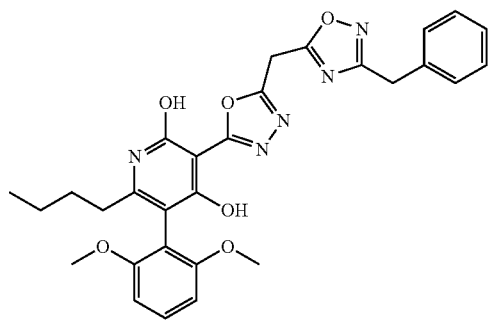 [SMILES: CCCCc1nc(O)c(-c2nnc(Cc3nc(Cc4ccccc4)no3)o2)c(O)c1-c1c(OC)cccc1OC] | 3-{5-[(3-benzyl-1,2,4-oxadiazol-5-yl)methyl]-1,3,4-oxadiazol-2-yl}-6-butyl-5-(2,6-dimethoxyphenyl)pyridine-2,4-diol | 1H NMR (500 MHz, DMSO-d6) δ 7.38-7.21 (m, 6H), 6.74 (d, J = 8.5 Hz, 2H), 4.95 (s, 2H), 4.12 (s, 2H), 3.70 (s, 6H), 2.16 (t, J = 7.6 Hz, 2H), 1.34 (quin, J = 7.4 Hz, 2H), 1.15-1.03 (m, 2H), 0.66 (t, J = 7.3 Hz, 3H) | 2.12 C 544.1 | A |

-continued

| Ex # | Structure | Name | ¹H NMR | LC/MS Rt (min) Method M + H | hAPJ cAMP EC₅₀ Potency range (nM) |
|---|---|---|---|---|---|
| 109 | 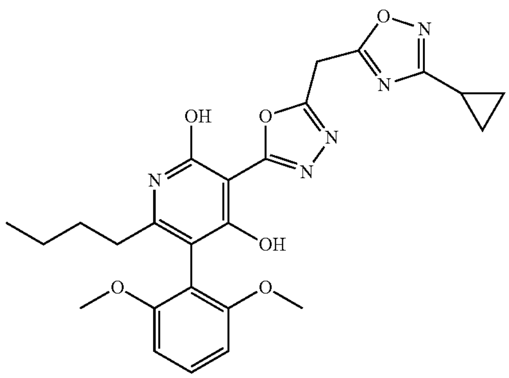 [SMILES: CCCCc1nc(O)c(-c2nnc(Cc3nc(C4CC4)no3)o2)c(O)c1-c1c(OC)cccc1OC] | 6-butyl-3-{5-[(3-cyclopropyl-1,2,4-oxadiazol-5-yl)methyl]-1,3,4-oxadiazol-2-yl}-5-(2,6-dimethoxyphenyl)pyridine-2,4-diol | 1H NMR (500 MHz, DMSO-d6) δ 7.36 (t, J = 8.3 Hz, 1H), 6.74 (d, J = 8.5 Hz, 3H), 4.91 (s, 2H), 3.70 (s, 6H), 2.20-2.10 (m, 2H), 1.38-1.29 (m, 2H), 1.15-1.03 (m, 4H), 0.94-0.85 (m, 2H), 0.67 (t, J = 7.2 Hz, 3H). Methine peak obscured by solvent | 2.00 C 494.0 | A |
| 110 | 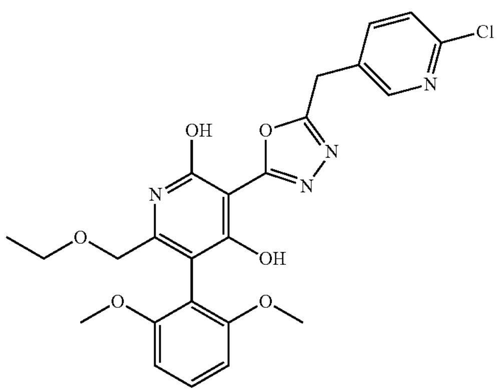 [SMILES: CCOCc1nc(O)c(-c2nnc(Cc3ccc(Cl)nc3)o2)c(O)c1-c1c(OC)cccc1OC] | 3-{5-[(6-chloropyridin-3-yl)methyl]-1,3,4-oxadiazol-2-yl}-5-(2,6-dimethoxyphenyl)-6-(ethoxymethyl)pyridine-2,4-diol | 1H NMR (500 MHz, DMSO-d6) δ 8.49 (s, 1H), 7.92 (d, J = 7.6 Hz, 1H), 7.56 (d, J = 8.2 Hz, 1H), 7.37 (t, J = 8.2 Hz, 1H), 6.74 (d, J = 8.5 Hz, 2H), 4.48 (s, 2H), 3.97 (s, 2H), 3.70 (s, 6H), 3.41-3.20 (m, 2H), 1.00 (t, J = 6.9 Hz, 3H) | 1.41 A 499.1 | A |
| 111 | 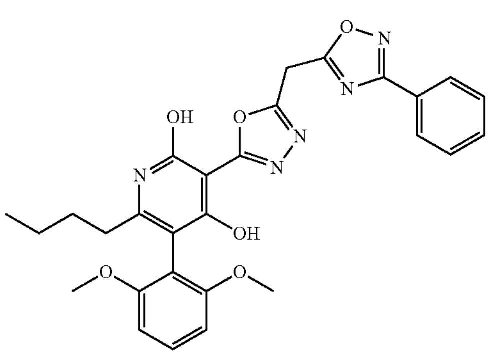 [SMILES: CCCCc1nc(O)c(-c2nnc(Cc3nc(-c4ccccc4)no3)o2)c(O)c1-c1c(OC)cccc1OC] | 6-butyl-5-(2,6-dimethoxyphenyl)-3-{5-[(3-phenyl-1,2,4-oxadiazol-5-yl)methyl]-1,3,4-oxadiazol-2-yl}pyridine-2,4-diol | 1H NMR (500 MHz, DMSO-d6) δ 8.03 (d, J = 8.0 Hz, 2H), 7.65-7.53 (m, 3H), 7.37 (t, J = 8.1 Hz, 1H), 6.74 (d, J = 8.3 Hz, 2H), 5.09 (s, 2H), 3.70 (s, 6H), 2.16 (t, J = 7.7 Hz, 2H), 1.34 (quin, J = 7.2 Hz, 2H), 1.13-1.03 (m, 2H), 0.67 (t, J = 7.2 Hz, 3H) | 2.14 C 530.1 | A |

| Ex # | Structure | Name | ¹H NMR | LC/MS Rt (min) Method M + H | hAPJ cAMP EC₅₀ Potency range (nM) |
|---|---|---|---|---|---|
| 112 | 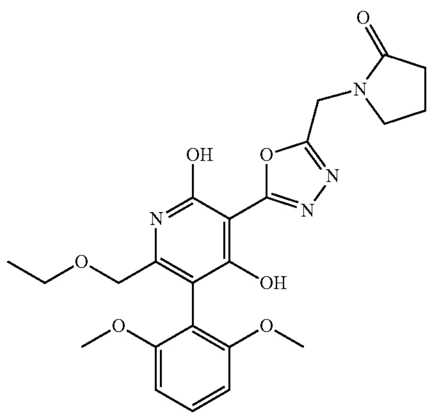 [SMILES: CCOCc1nc(O)c(-c2nnc(CN3CCCC3=O)o2)c(O)c1-c1c(OC)cccc1OC] | 1-({5-[5-(2,6-dimethoxyphenyl)-6-(ethoxymethyl)-2,4-dihydroxypyridin-3-yl]-1,3,4-oxadiazol-2-yl}methyl)pyrrolidin-2-one | 1H NMR (500 MHz, CDCl3) δ 7.38 (t, J = 8.4 Hz, 1H), 6.65 (d, J = 8.5 Hz, 2H), 4.84 (s, 2H), 4.15 (s, 2H), 3.76 (s, 6H), 3.61 (t, J = 7.2 Hz, 2H), 3.53 (q, J = 7.2 Hz, 2H), 2.47 (t, J = 8.1 Hz, 2H), 2.13 (quin, J = 7.6 Hz, 2H), 1.24 (t, J = 7.0 Hz, 3H) | 1.64 C 471.1 | A |
| 113 | 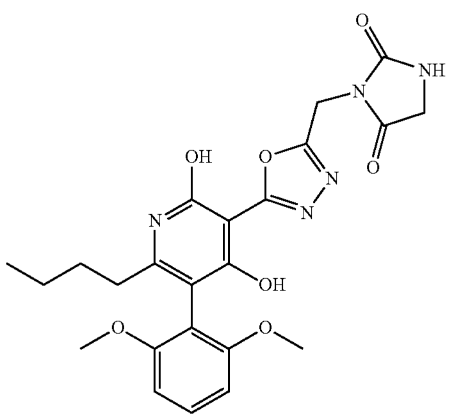 [SMILES: CCCCc1nc(O)c(-c2nnc(CN3C(=O)CNC3=O)o2)c(O)c1-c1c(OC)cccc1OC] | 3-({5-[6-butyl-5-(2,6-dimethoxyphenyl)-2,4-dihydroxypyridin-3-yl]-1,3,4-oxadiazol-2-yl}methyl)imidazolidine-2,4-dione | 1H NMR (500 MHz, DMSO-d6) δ 7.36 (t, J = 8.4 Hz, 1H), 6.74 (d, J = 8.2 Hz, 2H), 4.83 (s, 2H), 4.07 (s, 2H), 3.70 (s, 6H), 2.16 (t, J = 7.6 Hz, 2H), 1.41-1.29 (m, 2H), 1.14-1.02 (m, 2H), 0.67 (t, J = 7.3 Hz, 3H) | 1.30 A 484.1 | B |
| 114 | 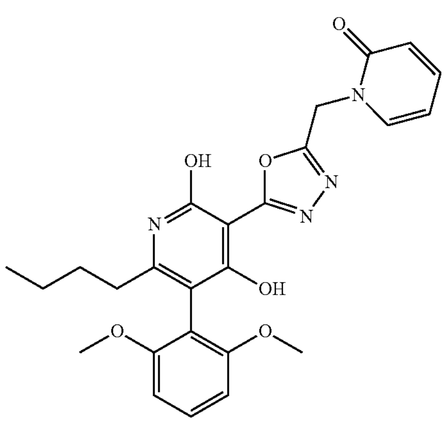 [SMILES: CCCCc1nc(O)c(-c2nnc(Cn3ccccc3=O)o2)c(O)c1-c1c(OC)cccc1OC] | 1-({5-[6-butyl-5-(2,6-dimethoxyphenyl)-2,4-dihydroxypyridin-3-yl]-1,3,4-oxadiazol-2-yl}methyl)-1,2-dihydropyridin-2-one | 1H NMR (500 MHz, DMSO-d6) δ 7.89-7.80 (m, 1H), 7.52 (ddd, J = 9.0, 6.9, 1.8 Hz, 1H), 7.36 (t, J = 8.4 Hz, 1H), 6.73 (d, J = 8.5 Hz, 2H), 6.46 (d, J = 9.2 Hz, 1H), 6.35 (t, J = 6.1 Hz, 1H), 5.47 (s, 2H), 3.70 (s, 6H), 2.16 (t, J = 7.8 Hz, 2H), 1.34 (quin, J = 7.5 Hz, 2H), 1.10 (sxt, J = 7.3 Hz, 2H), 0.67 (t, J = 7.3 Hz, 3H) | 1.36 A 479.1 | A |

-continued

| Ex # | Structure | Name | ¹H NMR | LC/MS Rt (min) Method M + H | hAPJ cAMP EC₅₀ Potency range (nM) |
|---|---|---|---|---|---|
| 115 | 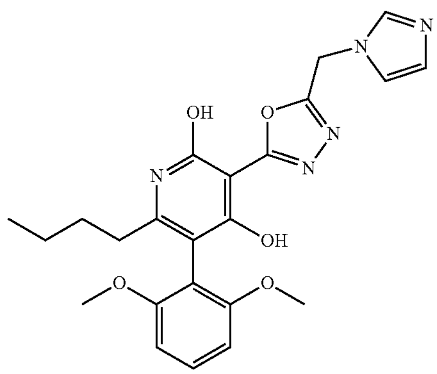 [SMILES: CCCCc1nc(O)c(-c2nnc(Cn3ccnc3)o2)c(O)c1-c1c(OC)cccc1OC] | 6-butyl-5-(2,6-dimethoxyphenyl)-3-[5-(1H-imidazol-1-ylmethyl)-1,3,4-oxadiazol-2-yl]pyridine-2,4-diol | 1H NMR (500 MHz, DMSO-d6) δ 7.89 (s, 1H), 7.36 (t, J = 8.4 Hz, 1H), 7.32 (s, 1H), 7.01 (s, 1H), 6.74 (d, J = 8.5 Hz, 2H), 5.73 (s, 2H), 3.70 (s, 6H), 2.16 (t, J = 7.6 Hz, 2H), 1.34 (quin, J = 7.5 Hz, 2H), 1.15-1.05 (m, 2H), 0.67 (t, J = 7.3 Hz, 3H) | 1.33 A 452.2 | B |
| 116 | 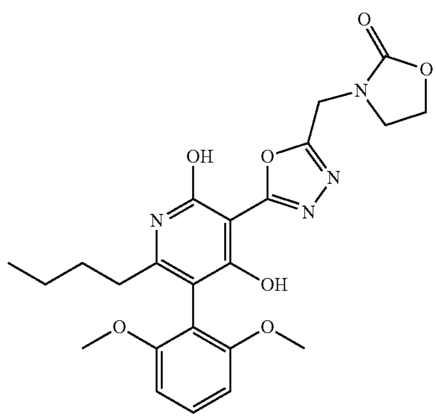 [SMILES: CCCCc1nc(O)c(-c2nnc(CN3CCOC3=O)o2)c(O)c1-c1c(OC)cccc1OC] | 3-({5-[6-butyl-5-(2,6-dimethoxyphenyl)-2,4-dihydroxypyridin-3-yl]-1,3,4-oxadiazol-2-yl}methyl)-1,3-oxazolidin-2-one | 1H NMR (500 MHz, DMSO-d6) δ 7.36 (t, J = 8.4 Hz, 1H), 6.74 (d, J = 8.2 Hz, 2H), 4.76 (s, 2H), 4.36 (t, J = 7.9 Hz, 2H), 3.73-3.66 (m, 8H), 2.15 (t, J = 7.6 Hz, 2H), 1.40-1.29 (m, 2H), 1.15-1.06 (m, 2H), 0.67 (t, J = 7.2 Hz, 3H) | 1.39 A 471.3 | A |
| 117 | 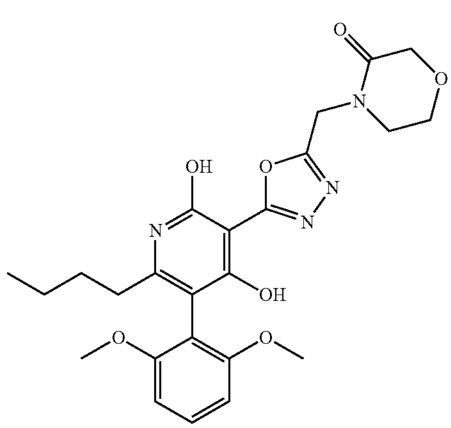 [SMILES: CCCCc1nc(O)c(-c2nnc(CN3CCOCC3=O)o2)c(O)c1-c1c(OC)cccc1OC] | 4-({5-[6-butyl-5-(2,6-dimethoxyphenyl)-2,4-dihydroxypyridin-3-yl]-1,3,4-oxadiazol-2-yl}methyl)morpholin-3-one | 1H NMR (500 MHz, DMSO-d6) δ 7.36 (t, J = 8.4 Hz, 1H), 6.74 (d, J = 8.2 Hz, 2H), 4.92 (s, 2H), 4.14 (s, 2H), 3.90 (t, J = 4.9 Hz, 2H), 3.70 (s, 6H), 3.54 (t, J = 4.9 Hz, 2H), 2.16 (t, J = 7.5 Hz, 2H), 1.40-1.28 (m, 2H), 1.16-1.04 (m, 2H), 0.67 (t, J = 7.3 Hz, 3H) | 1.37 A 485.4 | A |

-continued

| Ex # | Structure | Name | ¹H NMR | LC/MS Rt (min) Method M + H | hAPJ cAMP EC₅₀ Potency range (nM) |
|---|---|---|---|---|---|
| 118 | 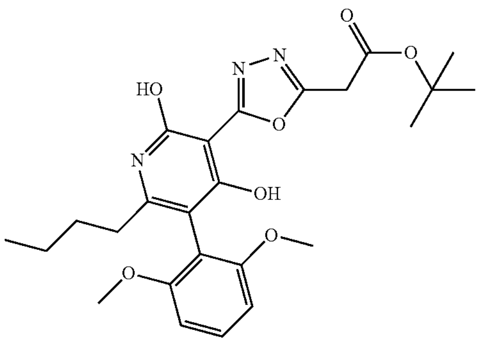 [SMILES: CCCCc1nc(O)c(-c2nnc(CC(=O)OC(C)(C)C)o2)c(O)c1-c1c(OC)cccc1OC] | tert-butyl 2-{5-[6-butyl-5-(2,6-dimethoxyphenyl)-2,4-dihydroxypyridin-3-yl]-1,3,4-oxadiazol-2-yl}acetate | 1H NMR (500 MHz, DMSO-d6) δ 7.37 (t, J = 8.3 Hz, 1H), 6.74 (d, J = 8.5 Hz, 2H), 4.16 (s, 2H), 3.70 (s, 6H), 2.16 (t, J = 7.6 Hz, 2H), 1.45 (s, 9H), 1.37-1.27 (m, 2H), 1.15-1.02 (m, 2H), 0.67 (t, J = 7.3 Hz, 3H) | 2.07 C 486.2 | A |
| 119 | 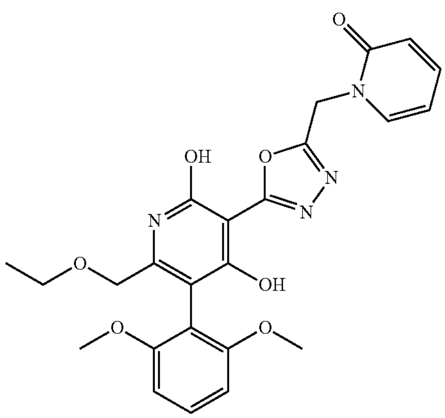 [SMILES: CCOCc1nc(O)c(-c2nnc(Cn3ccccc3=O)o2)c(O)c1-c1c(OC)cccc1OC] | 1-({5-[5-(2,6-dimethoxyphenyl)-6-(ethoxymethyl)-2,4-dihydroxypyridin-3-yl]-1,3,4-oxadiazol-2-yl}methyl)-1,2-dihydropyridin-2-one | 1H NMR (500 MHz, DMSO-d6) δ 7.85 (d, J = 6.7 Hz, 1H), 7.52 (t, J = 7.8 Hz, 1H), 7.36 (t, J = 8.2 Hz, 1H), 6.73 (d, J = 8.5 Hz, 2H), 6.47 (d, J = 9.2 Hz, 1H), 6.35 (t, J = 6.6 Hz, 1H), 5.47 (s, 2H), 3.96 (s, 2H), 3.70 (s, 6H), 3.29 (q, J = 6.7 Hz, 2H), 1.01 (t, J = 6.9 Hz, 3H) | 1.61 A 481.1 | A |
| 120 | 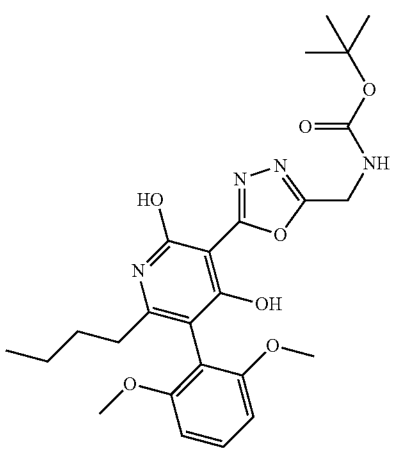 [SMILES: CCCCc1nc(O)c(-c2nnc(CNC(=O)OC(C)(C)C)o2)c(O)c1-c1c(OC)cccc1OC] | tert-butyl N-({5-[6-butyl-5-(2,6-dimethoxyphenyl)-2,4-dihydroxypyridin-3-yl]-1,3,4-oxadiazol-2-yl}methyl)carbamate | 1H NMR (500 MHz, CDCl3) δ 7.39 (t, J = 8.4 Hz, 1H), 6.68 (d, J = 8.5 Hz, 2H), 4.69 (d, J = 5.8 Hz, 2H), 3.78 (s, 6H), 2.34 (t, J = 7.7 Hz, 2H), 1.53-1.45 (m, 9H), 1.37-1.18 (m, 4H), 0.82 (t, J = 7.4 Hz, 3H). | 2.03 C 501.1 | B |
| 121 | 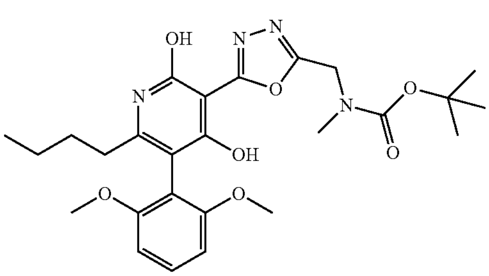 [SMILES: CCCCc1nc(O)c(-c2nnc(CN(C)C(=O)OC(C)(C)C)o2)c(O)c1-c1c(OC)cccc1OC] | tert-butyl N-({5-[6-butyl-5-(2,6-dimethoxyphenyl)-2,4-dihydroxypyridin-3-yl]-1,3,4-oxadiazol-2-yl}methyl)-N-methylcarbamate | 1H NMR (500 MHz, CDCl3) δ 7.39 (t, J = 8.3 Hz, 1H), 6.68 (d, J = 8.5 Hz, 2H), 4.84-4.64 (m, 2H), 3.78 (s, 6H), 3.06 (br. s., 3H), 2.35 (t, J = 7.7 Hz, 2H), 1.55-1.41 (m, 11H), 1.33-1.19 (m, 2H), 0.81 (t, J = 7.4 Hz, 3H) | 2.09 C 515.2 | B |

-continued

| Ex # | Structure | Name | ¹H NMR | LC/MS Rt (min) Method M + H | hAPJ cAMP EC₅₀ Potency range (nM) |
|---|---|---|---|---|---|
| 122 | 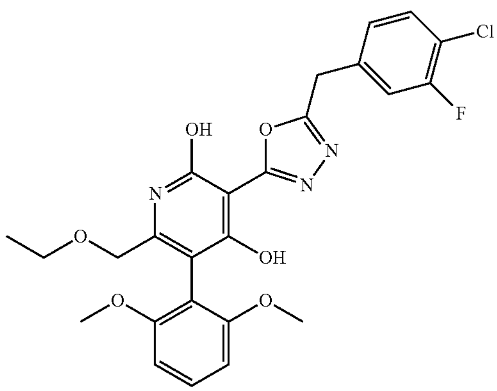 [SMILES: CCOCc1nc(O)c(-c2nnc(Cc3ccc(Cl)c(F)c3)o2)c(O)c1-c1c(OC)cccc1OC] | 3-{5-[(4-chloro-3-fluorophenyl)methyl]-1,3,4-oxadiazol-2-yl}-5-(2,6-dimethoxyphenyl)-6-(ethoxymethyl)pyridine-2,4-diol | 1H NMR (500 MHz, DMSO-d6) δ 7.59 (t, J = 8.1 Hz, 1H), 7.47 (d, J = 10.4 Hz, 1H), 7.35 (t, J = 8.4 Hz, 1H), 7.26 (d, J = 8.2 Hz, 1H), 6.72 (d, J = 8.2 Hz, 2H), 4.43 (s, 2H), 3.95 (s, 2H), 3.68 (s, 6H), 3.26 (q, J = 6.9 Hz, 2H), 0.98 (t, J = 6.9 Hz, 3H) | 1.71 A 516.3 | A |
| 123 | 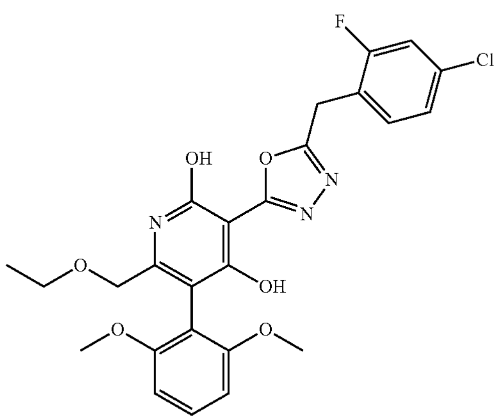 [SMILES: CCOCc1nc(O)c(-c2nnc(Cc3ccc(Cl)cc3F)o2)c(O)c1-c1c(OC)cccc1OC] | 3-{5-[(4-chloro-2-fluorophenyl)methyl]-1,3,4-oxadiazol-2-yl}-5-(2,6-dimethoxyphenyl)-6-(ethoxymethyl)pyridine-2,4-diol | 1H NMR (500 MHz, DMSO-d6) δ 11.76 (br. s., 1H), 11.44 (br. s., 1H), 7.57-7.45 (m, 2H), 7.39-7.26 (m, 2H), 6.79-6.67 (m, 2H), 4.41 (s, 2H), 3.94 (s, 2H), 3.68 (s, 6H), 3.29-3.21 (m, 2H), 0.98 (t, J = 6.9 Hz, 3H) | 1.70 A 516.0 | A |
| 124 | 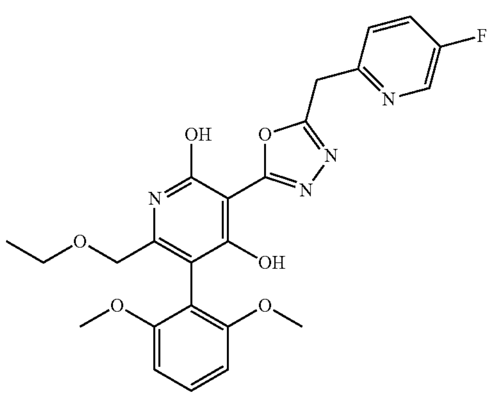 [SMILES: CCOCc1nc(O)c(-c2nnc(Cc3ccc(F)cn3)o2)c(O)c1-c1c(OC)cccc1OC] | 5-(2,6-dimethoxyphenyl)-6-(ethoxymethyl)-3-{5-[(5-fluoropyridin-2-yl)methyl]-1,3,4-oxadiazol-2-yl}pyridine-2,4-diol | 1H NMR (500 MHz, DMSO-d6) δ 11.92 (br. s., 1H), 11.45 (br. s., 1H), 8.51 (d, J = 3.0 Hz, 1H), 7.78 (td, J = 8.7, 3.0 Hz, 1H), 7.59 (dd, J = 8.5, 4.4 Hz, 1H), 7.37 (t, J = 8.4 Hz, 1H), 6.73 (d, J = 8.5 Hz, 2H), 4.58 (s, 2H), 3.95 (s, 2H), 3.27 (q, J = 6.9 Hz, 2H), 0.99 (t, J = 6.9 Hz, 3H) | 0.84 D 483.1 | A |

-continued

| Ex # | Structure | Name | ¹H NMR | LC/MS Rt (min) Method M + H | hAPJ cAMP EC$_{50}$ Potency range (nM) |
|---|---|---|---|---|---|
| 125 | 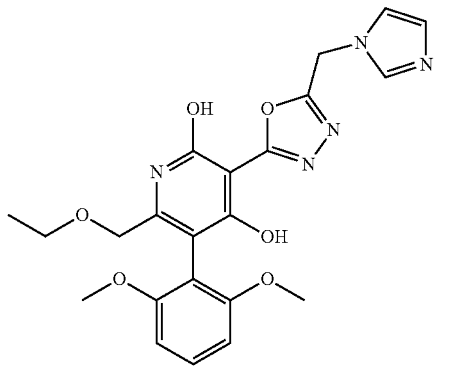 [SMILES: CCOCc1nc(O)c(-c2nnc(Cn3ccnc3)o2)c(O)c1-c1c(OC)cccc1OC] | 5-(2,6-dimethoxyphenyl)-6-(ethoxymethyl)-3-[5-(1H-imidazol-1-ylmethyl)-1,3,4-oxadiazol-2-yl]pyridine-2,4-diol | 1H NMR (500 MHz, DMSO-d6) δ 7.86 (br. s., 1H), 7.38 (s, 1H), 7.31 (br. s., 1H), 7.00 (br. s., 1H), 6.74 (d, J = 8.2 Hz, 2H), 5.73 (s, 2H), 3.97 (s, 2H), 3.36 (br. s., 4H), 3.30 (br. s., 2H), 3.29-3.11 (m, 2H), 1.00 (t, J = 6.9 Hz, 3H) | 1.12 A 454.3 | B |
| 126 | 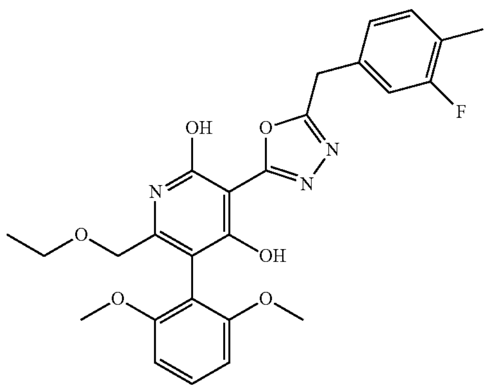 [SMILES: CCOCc1nc(O)c(-c2nnc(Cc3ccc(C)c(F)c3)o2)c(O)c1-c1c(OC)cccc1OC] | 5-(2,6-dimethoxyphenyl)-6-(ethoxymethyl)-3-{5-[(3-fluoro-4-methylphenyl)methyl]-1,3,4-oxadiazol-2-yl}pyridine-2,4-diol | 1H NMR (500 MHz, DMSO-d6) δ 7.42-7.02 (m, 4H), 6.68 (d, J = 8.5 Hz, 2H), 4.32 (s, 2H), 3.91 (s, 2H), 3.39 (br. s., 6H), 3.22 (q, J = 7.0 Hz, 2H), 2.18 (s, 3H), 0.94 (t, J = 6.7 Hz, 3H) | 1.78 A 496.2 | A |
| 127 | 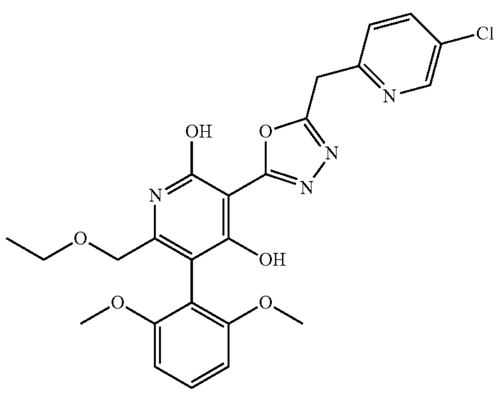 [SMILES: CCOCc1nc(O)c(-c2nnc(Cc3ccc(Cl)cn3)o2)c(O)c1-c1c(OC)cccc1OC] | 3-{5-[(5-chloropyridin-2-yl)methyl]-1,3,4-oxadiazol-2-yl}-5-(2,6-dimethoxyphenyl)-6-(ethoxymethyl)pyridine-2,4-diol | 1H NMR (500 MHz, DMSO-d6) δ 8.58 (s, 1H), 7.99 (d, J = 8.5 Hz, 1H), 7.57 (d, J = 8.2 Hz, 1H), 7.38 (t, J = 8.4 Hz, 1H), 6.74 (d, J = 8.2 Hz, 2H), 4.60 (s, 2H), 3.96 (s, 2H), 3.71 (s, 6H), 3.37-3.14 (m, 2H), 1.00 (t, J = 6.9 Hz, 3H) | 1.46 A 499.0 | A |
| 128 | 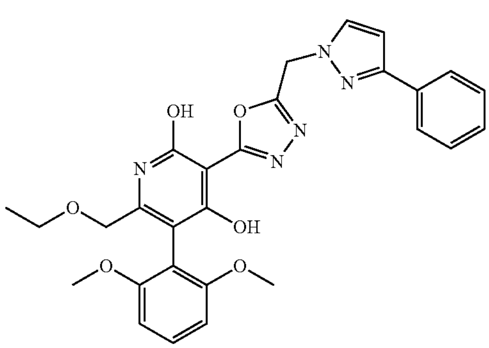 [SMILES: CCOCc1nc(O)c(-c2nnc(Cn3ccc(-c4ccccc4)n3)o2)c(O)c1-c1c(OC)cccc1OC] | 5-(2,6-dimethoxyphenyl)-6-(ethoxymethyl)-3-{5-[(3-phenyl-1H-pyrazol-1-yl)methyl]-1,3,4-oxadiazol-2-yl}pyridine-2,4-diol | 1H NMR (500 MHz, DMSO-d6) δ 8.01 (br. s., 1H), 7.87-7.70 (m, J = 7.3 Hz, 2H), 7.45-7.25 (m, 4H), 6.84 (br. s., 1H), 6.78-6.63 (m, J = 7.9 Hz, 2H), 5.85 (br. s., 2H), 3.95 (s, 2H), 3.69 (s, 6H), 3.38-3.14 (m, 1H), 2.56 (s, 1H), 0.99 (t, J = 6.7 Hz, 3H) | 1.62 A 530.3 | A |

-continued

| Ex # | Structure | Name | ¹H NMR | LC/MS Rt (min) Method M + H | hAPJ cAMP EC₅₀ Potency range (nM) |
|---|---|---|---|---|---|
| 129 | 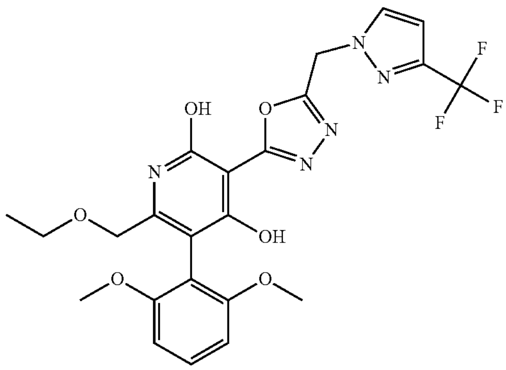 [SMILES: CCOCc1nc(O)c(-c2nnc(Cn3ccc(C(F)(F)F)n3)o2)c(O)c1-c1c(OC)cccc1OC] | 5-(2,6-dimethoxyphenyl)-6-(ethoxymethyl)-3-(5-{[3-(trifluoromethyl)-1H-pyrazol-1-yl]methyl}-1,3,4-oxadiazol-2-yl)pyridine-2,4-diol | 1H NMR (500 MHz, DMSO-d6) δ 8.20 (br. s., 1H), 7.36 (br. s., 1H), 6.86 (br. s., 1H), 6.73 (d, J = 8.2 Hz, 2H), 5.96 (s, 2H), 3.95 (s, 2H), 3.45-3.21 (m, 8H), 1.00 (t, J = 6.7 Hz, 3H) | 1.54 A 522.2 | B |
| 130 | 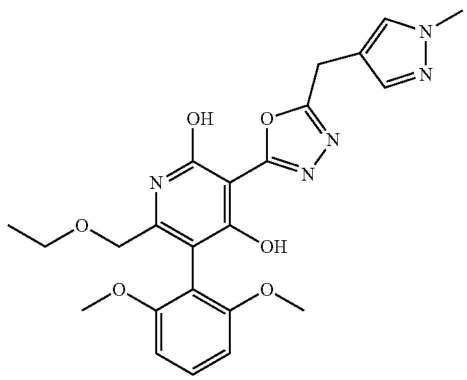 [SMILES: CCOCc1nc(O)c(-c2nnc(Cc3cnn(C)c3)o2)c(O)c1-c1c(OC)cccc1OC] | 5-(2,6-dimethoxyphenyl)-6-(ethoxymethyl)-3-{5-[(1-methyl-1H-pyrazol-4-yl)methyl]-1,3,4-oxadiazol-2-yl}pyridine-2,4-diol | 1H NMR (500 MHz, DMSO-d6) δ 7.69 (s, 1H), 7.42 (s, 1H), 7.35 (t, J = 7.8 Hz, 1H), 6.72 (d, J = 8.2 Hz, 2H), 4.17 (br. s., 2H), 3.94 (s, 2H), 3.82 (s, 3H), 3.69 (s, 6H), 3.28 (d, J = 7.0 Hz, 2H), 1.01 (t, J = 6.7 Hz, 3H) | 1.30 A 468.3 | B |
| 131 | 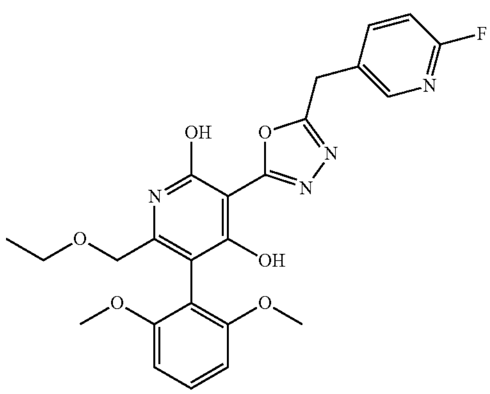 [SMILES: CCOCc1nc(O)c(-c2nnc(Cc3ccc(F)nc3)o2)c(O)c1-c1c(OC)cccc1OC] | 5-(2,6-dimethoxyphenyl)-6-(ethoxymethyl)-3-{5-[(6-fluoropyridin-3-yl)methyl]-1,3,4-oxadiazol-2-yl}pyridine-2,4-diol | 1H NMR (500 MHz, DMSO-d6) δ 8.31 (br. s., 1H), 8.04 (t, J = 7.9 Hz, 1H), 7.37 (t, J = 8.2 Hz, 1H), 7.23 (d, J = 8.2 Hz, 1H), 6.74 (d, J = 8.2 Hz, 2H), 4.47 (s, 2H), 3.96 (s, 2H), 3.36 (br. s., 3H), 3.28 (q, J = 6.7 Hz, 3H), 1.00 (t, J = 6.7 Hz, 3H) | 1.32 A 483.2 | A |
| 132 | 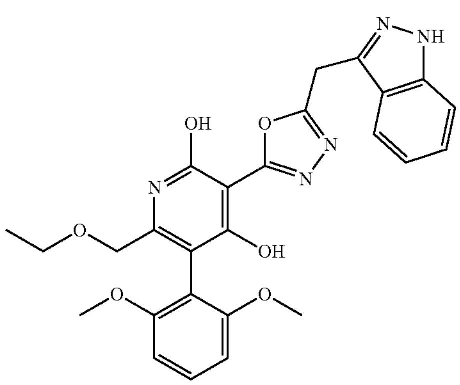 [SMILES: CCOCc1nc(O)c(-c2nnc(Cc3n[nH]c4ccccc34)o2)c(O)c1-c1c(OC)cccc1OC] | 5-(2,6-dimethoxyphenyl)-6-(ethoxymethyl)-3-[5-(1H-indazol-3-ylmethyl)-1,3,4-oxadiazol-2-yl]pyridine-2,4-diol | 1H NMR (500 MHz, DMSO-d6) δ 7.75 (d, J = 7.9 Hz, 1H), 7.47 (d, J = 8.2 Hz, 1H), 7.40-7.24 (m, 2H), 7.07 (t, J = 7.0 Hz, 1H), 6.66 (d, J = 7.9 Hz, 2H), 4.63 (br. s., 2H), 3.87 (br. s., 2H), 3.63 (s, 6H), 3.21 (d, J = 6.7 Hz, 2H), 0.94 (t, J = 6.7 Hz, 3H) | 1.50 A 504.3 | A |

-continued

| Ex # | Structure | Name | ¹H NMR | LC/MS Rt (min) Method M + H | hAPJ cAMP EC₅₀ Potency range (nM) |
|---|---|---|---|---|---|
| 133 | 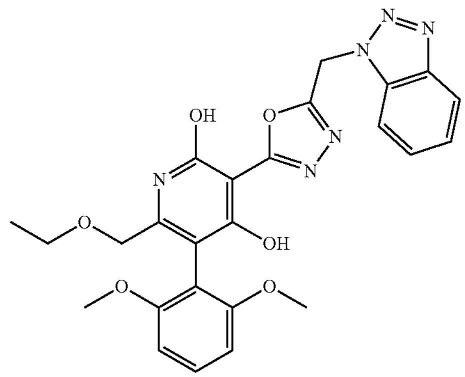 [SMILES: CCOCc1nc(O)c(-c2nnc(Cn3nnc4ccccc43)o2)c(O)c1-c1c(OC)cccc1OC] | 3-[5-(1H-1,2,3-benzotriazol-1-ylmethyl)-1,3,4-oxadiazol-2-yl]-5-(2,6-dimethoxyphenyl)-6-(ethoxymethyl)pyridine-2,4-diol | 1H NMR (500 MHz, DMSO-d6) δ 8.11 (d, J = 8.2 Hz, 1H), 7.95 (d, J = 8.2 Hz, 1H), 7.61 (t, J = 7.6 Hz, 1H), 7.46 (t, J = 7.5 Hz, 1H), 7.34 (t, J = 8.2 Hz, 1H), 6.71 (d, J = 8.2 Hz, 2H), 6.50 (s, 2H), 3.93 (s, 2H), 3.67 (s, 6H), 3.25 (q, J = 6.5 Hz, 2H), 0.98 (t, J = 6.9 Hz, 3H) | 1.32 A 505.2 | A |
| 134 | 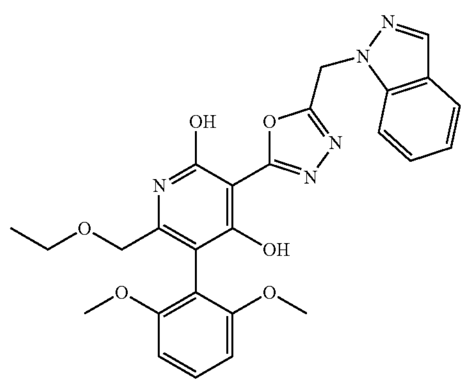 [SMILES: CCOCc1nc(O)c(-c2nnc(Cn3ncc4ccccc43)o2)c(O)c1-c1c(OC)cccc1OC] | 5-(2,6-dimethoxyphenyl)-6-(ethoxymethyl)-3-[5-(1H-indazol-1-ylmethyl)-1,3,4-oxadiazol-2-yl]pyridine-2,4-diol | 1H NMR (500 MHz, DMSO-d6) δ 8.17 (s, 1H), 7.80 (t, J = 8.7 Hz, 2H), 7.45 (t, J = 7.5 Hz, 1H), 7.34 (t, J = 8.1 Hz, 1H), 7.20 (t, J = 7.3 Hz, 1H), 6.71 (d, J = 7.9 Hz, 2H), 6.10 (s, 2H), 3.93 (s, 2H), 3.67 (s, 6H), 3.25 (q, J = 6.3 Hz, 2H), 0.97 (t, J = 6.6 Hz, 3H) | 1.43 A 504.0 | A |
| 135 | 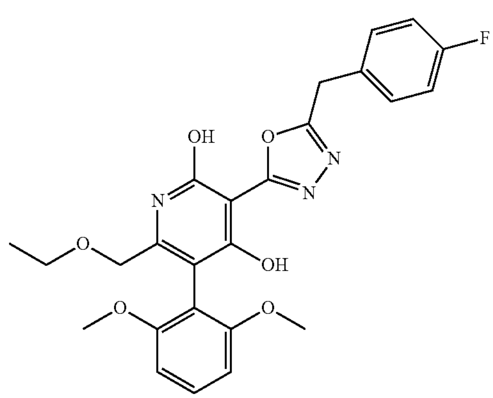 [SMILES: CCOCc1nc(O)c(-c2nnc(Cc3ccc(F)cc3)o2)c(O)c1-c1c(OC)cccc1OC] | 5-(2,6-dimethoxyphenyl)-6-(ethoxymethyl)-3-{5-[(4-fluorophenyl)methyl]-1,3,4-oxadiazol-2-yl}pyridine-2,4-diol | 1H NMR (500 MHz, DMSO-d6) δ 7.52-7.30 (m, 3H), 7.19 (t, J = 8.2 Hz, 2H), 6.71 (d, J = 8.2 Hz, 2H), 4.36 (s, 2H), 3.93 (s, 2H), 3.68 (s, 6H), 3.26 (q, J = 6.6 Hz, 2H), 0.98 (t, J = 6.6 Hz, 3H) | 1.78 A 482.0 | A |

-continued

| Ex # | Structure | Name | ¹H NMR | LC/MS Rt (min) Method M + H | hAPJ cAMP EC₅₀ Potency range (nM) |
|---|---|---|---|---|---|
| 136 | 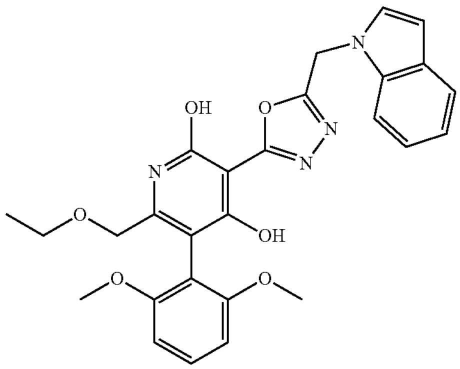 [SMILES: CCOCc1nc(O)c(-c2nnc(Cn3ccc4ccccc43)o2)c(O)c1-c1c(OC)cccc1OC] | 5-(2,6-dimethoxyphenyl)-6-(ethoxymethyl)-3-[5-(1H-indol-1-ylmethyl)-1,3,4-oxadiazol-2-yl]pyridine-2,4-diol | 1H NMR (500 MHz, DMSO-d6) δ 7.65-6.94 (m, 6H), 6.67 (d, J = 8.5 Hz, 2H), 6.49 (d, J = 3.1 Hz, 1H), 5.96-5.73 (m, 2H), 3.89 (s, 2H), 3.68-3.58 (s, 6H), 3.21 (q, J = 6.8 Hz, 2H), 0.94 (t, J = 6.9 Hz, 3H) | 1.75 A 503.3 | B |
| 138 | 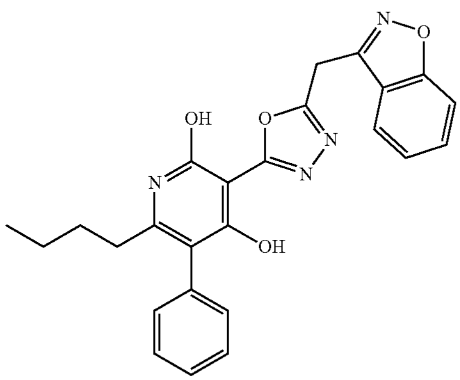 [SMILES: CCCCc1nc(O)c(-c2nnc(Cc3noc4ccccc34)o2)c(O)c1-c1ccccc1] | 3-[5-(1,2-benzoxazol-3-ylmethyl)-1,3,4-oxadiazol-2-yl]-6-butyl-5-phenyl-pyridine-2,4-diol | 1H NMR (500 MHz, DMSO-d6) δ 7.96 (d, J = 7.9 Hz, 1H), 7.80 (d, J = 8.5 Hz, 1H), 7.71 (t, J = 7.6 Hz, 1H), 7.48-7.34 (m, 4H), 7.27 (d, J = 7.0 Hz, 2H), 4.93 (s, 2H), 2.37-2.26 (m, 2H), 1.41 (quin, J = 7.5 Hz, 2H), 1.11 (sxt, J = 7.3 Hz, 2H), 0.68 (t, J = 7.3 Hz, 3H) | 2.17 C 443.1 | B |
| 139 | 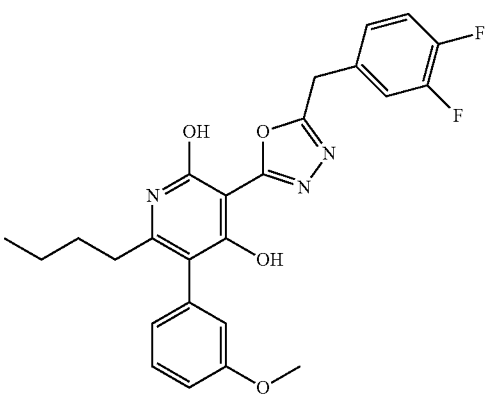 [SMILES: CCCCc1nc(O)c(-c2nnc(Cc3ccc(F)c(F)c3)o2)c(O)c1-c1cccc(OC)c1] | 6-butyl-3-{5-[(3,4-difluorophenyl)methyl]-1,3,4-oxadiazol-2-yl}-5-(3-methoxyphenyl)pyridine-2,4-diol | 1H NMR (500 MHz, DMSO-d6) δ 7.55-6.72 (m, 9H), 4.45-4.30 (m, 2H), 4.35 (s, 2H), 3.71 (s, 3H), 3.59-3.58 (m, 1H), 2.26 (t, J = 7.6 Hz, 2H), 2.35-2.18 (m, 2H), 1.44-1.32 (m, 2H), 1.49-1.31 (m, 2H), 1.13-0.99 (m, 2H), 1.12-0.99 (m, 2H), 0.74-0.56 (m, 3H), 0.65 (t, J = 7.3 Hz, 3H) | 1.83 A 468.1 | B |

| Ex # | Structure | Name | ¹H NMR | LC/MS Rt (min) Method M + H | hAPJ cAMP EC₅₀ Potency range (nM) |
|---|---|---|---|---|---|
| 140 | 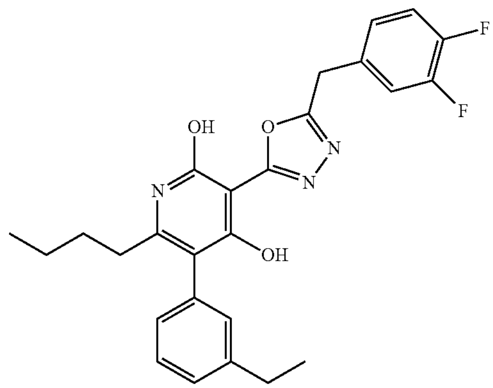 [SMILES: CCCCc1nc(O)c(-c2nnc(Cc3ccc(F)c(F)c3)o2)c(O)c1-c1cccc(CC)c1] | 6-butyl-3-{5-[(3,4-difluorophenyl)methyl]-1,3,4-oxadiazol-2-yl}-5-(3-ethylphenyl)pyridine-2,4-diol | 1H NMR (500 MHz, DMSO-d6) δ 7.59-6.92 (m, 7H), 4.39 (s, 2H), 2.62 (q, J = 7.3 Hz, 2H), 2.28 (br. s., 2H), 1.58-1.33 (m, 2H), 1.18 (t, J = 7.5 Hz, 3H), 1.14-0.92 (m, 2H), 0.67 (t, J = 7.2 Hz, 3H) | 2.11 A 466.0 | B |
| 141 | 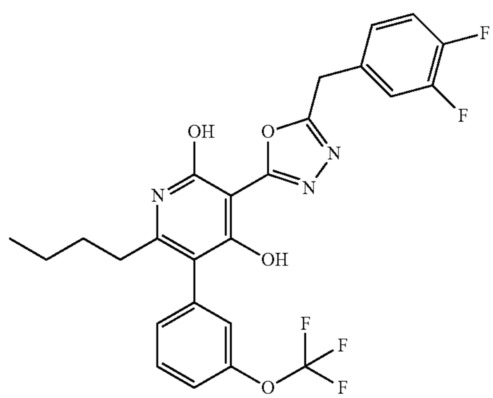 [SMILES: CCCCc1nc(O)c(-c2nnc(Cc3ccc(F)c(F)c3)o2)c(O)c1-c1cccc(OC(F)(F)F)c1] | 6-butyl-3-{5-[(3,4-difluorophenyl)methyl]-1,3,4-oxadiazol-2-yl}-5-[3-(trifluoromethoxy)phenyl]pyridine-2,4-diol | 1H NMR (500 MHz, DMSO-d6) δ 7.72-7.16 (m, 7H), 4.39 (s, 2H), 2.39-2.21 (m, 2H), 1.52-1.31 (m, 2H), 1.19-1.00 (m, 2H), 0.66 (t, J = 7.3 Hz, 3H) | 1.13 D 522.2 | B |
| 142 | 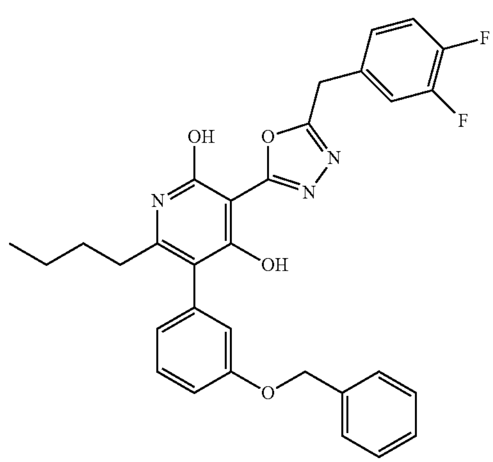 [SMILES: CCCCc1nc(O)c(-c2nnc(Cc3ccc(F)c(F)c3)o2)c(O)c1-c1cccc(OCc2ccccc2)c1] | 5-[3-(benzyloxy)phenyl]-6-butyl-3-{5-[(3,4-difluorophenyl)methyl]-1,3,4-oxadiazol-2-yl}pyridine-2,4-diol | 1H NMR (500 MHz, DMSO-d6) δ 7.61-6.77 (m, 12H), 5.11 (s, 2H), 4.40 (s, 2H), 2.27 (t, J = 7.6 Hz, 2H), 1.50-1.33 (m, 2H), 1.17-1.00 (m, 2H), 0.67 (t, J = 7.3 Hz, 3H) | 2.29 A 544.0 | B |

| Ex # | Structure | Name | ¹H NMR | LC/MS Rt (min) Method M + H | hAPJ cAMP EC₅₀ Potency range (nM) |
|---|---|---|---|---|---|
| 143 | 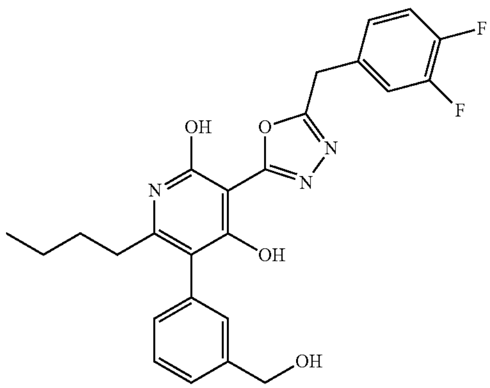 [SMILES: CCCCc1nc(O)c(-c2nnc(Cc3ccc(F)c(F)c3)o2)c(O)c1-c1cccc(CO)c1] | 6-butyl-3-{5-[(3,4-difluorophenyl) methyl]-1,3,4-oxadiazol-2-yl}-5-[3-(hydroxymethyl) phenyl]pyridine-2,4-diol | 1H NMR (500 MHz, DMSO-d6) δ 7.55-7.07 (m, 7H), 4.52 (d, J = 5.5 Hz, 2H), 4.40 (s, 2H), 2.29 (t, J = 7.6 Hz, 2H), 1.50-1.35 (m, 2H), 1.18-1.02 (m, 2H), 0.69 (t, J = 7.3 Hz, 3H) | 1.53 A 468.0 | A |
| 144 | 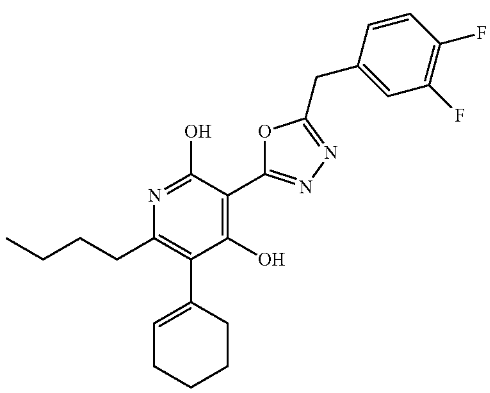 [SMILES: CCCCc1nc(O)c(-c2nnc(Cc3ccc(F)c(F)c3)o2)c(O)c1C1=CCCCC1] | 6-butyl-5-(cyclohex-1-en-1-yl)-3-{5-[(3,4-difluorophenyl) methyl]-1,3,4-oxadiazol-2-yl}pyridine-2,4-diol | 1H NMR (500 MHz, DMSO-d6) δ 7.45 (td, J = 19.0, 9.0 Hz, 2H), 7.23 (br. s., 1H), 5.58 (br. s., 1H), 4.39 (s, 2H), 2.46-2.17 (m, 3H), 2.10 (br. s., 2H), 1.86 (br. s., 1H), 1.75-1.43 (m, 6H), 1.39-1.19 (m, 2H), 0.87 (t, J = 7.3 Hz, 3H) | 2.36 A 442.0 | B |
| 145 | 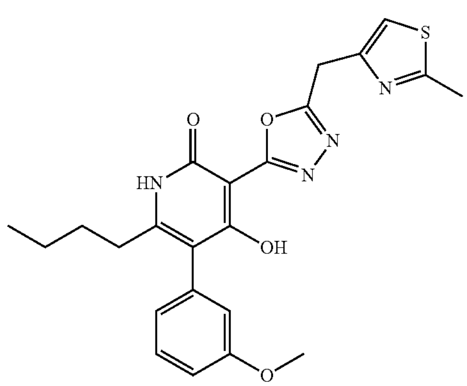 [SMILES: CCCCc1[nH]c(=O)c(-c2nnc(Cc3csc(C)n3)o2)c(O)c1-c1cccc(OC)c1] | 6-butyl-3-{5-[(3,4-difluorophenyl) methyl]-1,3,4-oxadiazol-2-yl}-5-[3-(propan-2-yl)phenyl]pyridine-2,4-diol | 1H NMR (500 MHz, DMSO-d6) δ 7.51-6.98 (m, 7H), 4.37 (s, 2H), 2.89 (dt, J = 13.7, 6.9 Hz, 1H), 2.26 (br. s., 2H), 1.39 (quin, J = 7.5 Hz, 2H), 1.18 (d, J = 7.0 Hz, 6H), 1.13-0.97 (m, 2H), 0.64 (t, J = 7.3 Hz, 3H) | 2.42 A 480.1 | B |

| Ex # | Structure | Name | ¹H NMR | LC/MS Rt (min) Method M + H | hAPJ cAMP EC₅₀ Potency range (nM) |
|---|---|---|---|---|---|
| 146 | 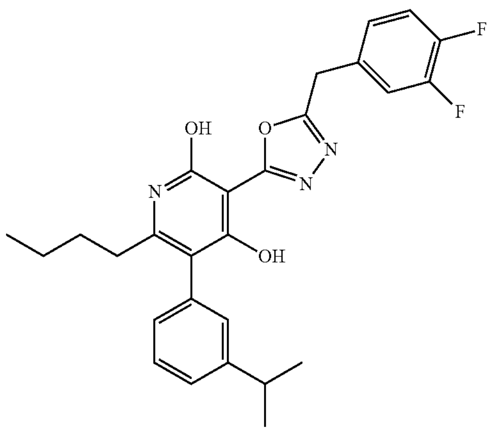 [SMILES: CCCCc1nc(O)c(-c2nnc(Cc3ccc(F)c(F)c3)o2)c(O)c1-c1cccc(C(C)C)c1] | 6-butyl-3-{5-[(3,4-difluorophenyl)methyl]-1,3,4-oxadiazol-2-yl}-5-[3-(methoxymethyl)phenyl]pyridine-2,4-diol | 1H NMR (500 MHz, DMSO-d6) δ 7.55-7.10 (m, 7H), 4.43 (s, 2H), 4.38 (s, 2H), 2.54 (s, 3H), 2.27 (t, J = 7.6 Hz, 2H), 1.48-1.34 (m, 2H), 1.17-1.02 (m, 2H), 0.68 (t, J = 7.3 Hz, 3H) | 1.95 A 482.1 | B |
| 147 | 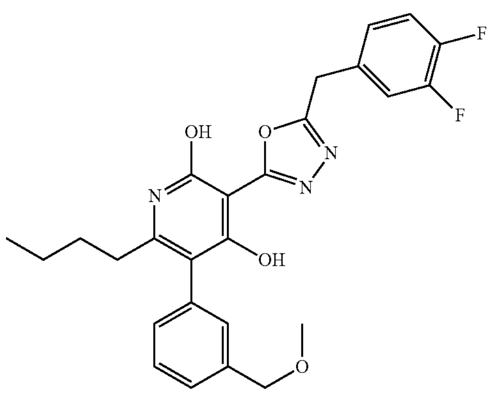 [SMILES: CCCCc1nc(O)c(-c2nnc(Cc3ccc(F)c(F)c3)o2)c(O)c1-c1cccc(COC)c1] | 3-(2-butyl-5-{5-[(3,4-difluorophenyl)methyl]-1,3,4-oxadiazol-2-yl}-4,6-dihydroxypyridin-3-yl)-N-(propan-2-yl)benzamide | 1H NMR (500 MHz, DMSO-d6) δ 8.29-7.17 (m, 8H), 4.31 (s, 2H), 4.15-4.00 (m, 1H), 2.20 (t, J = 7.5 Hz, 2H), 1.51-1.34 (m, 2H), 1.21-1.02 (m, 8H), 0.68 (t, J = 7.3 Hz, 3H) | 1.54 A 522.9 | B |
| 148 | 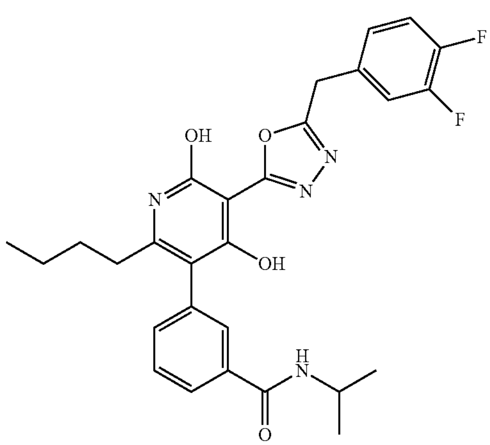 [SMILES: CCCCc1nc(O)c(-c2nnc(Cc3ccc(F)c(F)c3)o2)c(O)c1-c1cccc(C(=O)NC(C)C)c1] | 6-butyl-4-hydroxy-3-{5-[(2-methyl-1,3-thiazol-4-yl)methyl]-1,3,4-oxadiazol-2-yl}-5-[3-(propan-2-yl)phenyl]-1,2-dihydropyridin-2-one | 1H NMR (500 MHz, DMSO-d6)d 7.65-7.18 (m, 3H), 7.17-6.98 (m, 2H), 4.44 (s, 2H), 3.07-2.83 (m, 1H), 2.62 (s, 3H), 2.27 (br. s., 2H), 1.50-1.35 (m, 2H), 1.21 (d, J = 6.7 Hz, 6H), 1.16-1.03 (m, 2H), 0.67 (t, J = 6.9 Hz, 3H) | 2.09 A 465.3 | A |

| Ex # | Structure | Name | ¹H NMR | LC/MS Rt (min) Method M + H | hAPJ cAMP EC₅₀ Potency range (nM) |
|---|---|---|---|---|---|
| 149 | 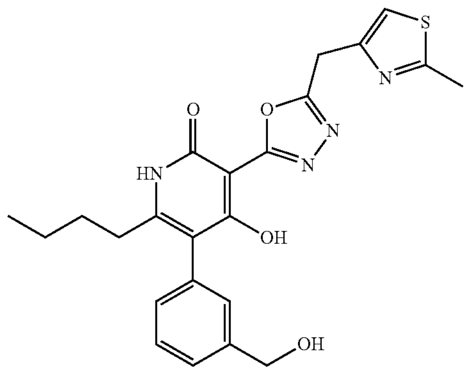 [SMILES: CCCCc1[nH]c(=O)c(-c2nnc(Cc3csc(C)n3)o2)c(O)c1-c1cccc(CO)c1] | 3-(2-butyl-4-hydroxy-5-{5-[(2-methyl-1,3-thiazol-4-yl)methyl]-1,3,4-oxadiazol-2-yl}-6-oxo-1,6-dihydropyridin-3-yl)-N-(propan-2-yl)benzamide | 1H NMR (500 MHz, DMSO-d6) δ 8.22 (d, J = 7.6 Hz, 1H), 7.92-7.65 (m, 2H), 7.55-7.28 (m, 3H), 4.41 (s, 2H), 4.20-4.04 (m, 1H), 2.62 (s, 3H), 2.25 (d, J = 7.0 Hz, 2H), 1.51-1.32 (m, 2H), 1.21-1.00 (m, 8H), 0.67 (t, J = 7.2 Hz, 3H) | 1.32 A 508.0 | A |
| 150 | 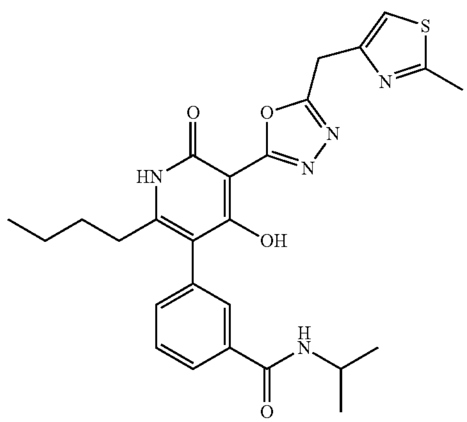 [SMILES: CCCCc1[nH]c(=O)c(-c2nnc(Cc3csc(C)n3)o2)c(O)c1-c1cccc(C(=O)NC(C)C)c1] | 6-butyl-5-(3-cyclopropylphenyl)-4-hydroxy-3-{5-[(2-methyl-1,3-thiazol-4-yl)methyl]-1,3,4-oxadiazol-2-yl}-1,2-dihydropyridin-2-one | 1H NMR (500 MHz, DMSO-d6) δ 7.42 (s, 1H), 7.29 (t, J = 7.5 Hz, 1H), 7.10-6.86 (m, 3H), 4.44 (s, 2H), 2.62 (s, 3H), 2.28 (t, J = 7.3 Hz, 2H), 1.93 (br. s., 1H), 1.49-1.35 (m, 2H), 1.17-1.03 (m, 2H), 0.95 (d, J = 7.9 Hz, 2H), 0.68 (t, J = 7.2 Hz, 5H) | 1.99 A 463.3 | A |
| 151 | 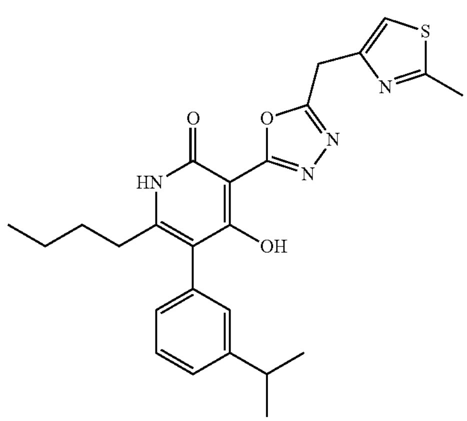 [SMILES: CCCCc1[nH]c(=O)c(-c2nnc(Cc3csc(C)n3)o2)c(O)c1-c1cccc(C(C)C)c1] | 6-butyl-4-hydroxy-5-(3-methoxyphenyl)-3-{5-[(2-methyl-1,3-thiazol-4-yl)methyl]-1,3,4-oxadiazol-2-yl}-1,2-dihydropyridin-2-one | 1H NMR (500 MHz, DMSO-d6) δ 7.47-7.25 (m, 2H), 6.93 (d, J = 8.5 Hz, 1H), 6.86-6.67 (m, 2H), 4.40 (s, 2H), 3.74 (s, 3H), 2.60 (s, 3H), 2.29 (t, J = 7.6 Hz, 2H), 1.40 (quin, J = 7.5 Hz, 2H), 1.16-1.00 (m, 2H), 0.67 (t, J = 7.3 Hz, 3H) | 1.64 A 453.1 | A |

-continued

| Ex # | Structure | Name | ¹H NMR | LC/MS Rt (min) Method M + H | hAPJ cAMP EC$_{50}$ Potency range (nM) |
|---|---|---|---|---|---|
| 152 | 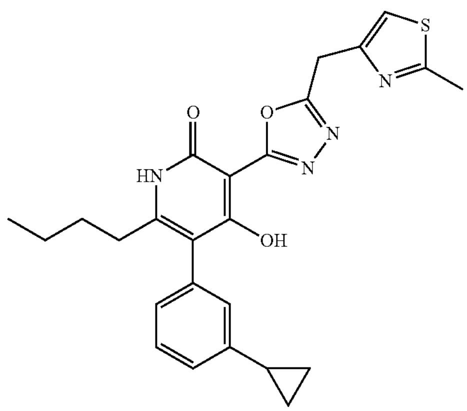 [SMILES: CCCCc1[nH]c(=O)c(-c2nnc(Cc3csc(C)n3)o2)c(O)c1-c1cccc(C2CC2)c1] | 6-butyl-4-hydroxy-5-[3-(hydroxymethyl)phenyl]-3-{5-[(2-methyl-1,3-thiazol-4-yl)methyl]-1,3,4-oxadiazol-2-yl}-1,2-dihydropyridin-2-one | 1H NMR (500 MHz, DMSO-d6) δ 7.50-7.26 (m, 3H), 7.23-6.94 (m, 2H), 4.52 (br. s., 2H), 4.44 (s, 2H), 2.62 (s, 3H), 2.29 (t, J = 7.3 Hz, 2H), 1.62-1.30 (m, 2H), 1.18-1.01 (m, 2H), 0.69 (t, J = 7.2 Hz, 3H) | 1.24 A 453.0 | B |
| 153 | 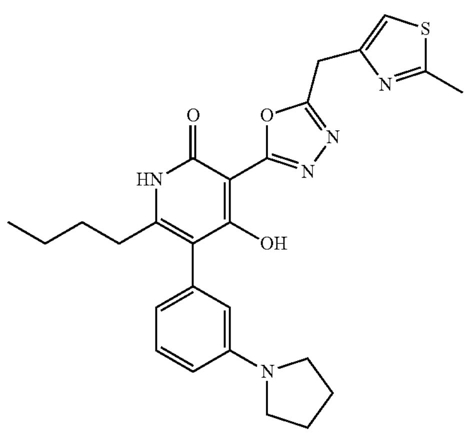 [SMILES: CCCCc1[nH]c(=O)c(-c2nnc(Cc3csc(C)n3)o2)c(O)c1-c1cccc(N2CCCC2)c1] | 6-butyl-4-hydroxy-3-{5-[(2-methyl-1,3-thiazol-4-yl)methyl]-1,3,4-oxadiazol-2-yl}-5-[3-(pyrrolidin-1-yl)phenyl]-1,2-dihydropyridin-2-one | 1H NMR (500 MHz, DMSO-d6) δ 7.42 (s, 1H), 7.19 (t, J = 7.8 Hz, 1H), 6.68-6.19 (m, 3H), 4.43 (s, 2H), 3.20 (br. s, 4H), 2.62 (s, 3H), 2.31 (d, J = 7.0 Hz, 2H), 1.94 (br. s., 4H), 1.44 (d, J = 6.7 Hz, 2H), 1.19-1.03 (m, 2H), 0.71 (t, J = 7.3 Hz, 3H) | 2.11 A 492.3 | B |
| 156 | 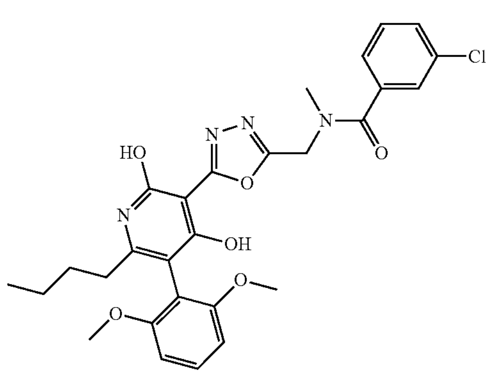 [SMILES: CCCCc1nc(O)c(-c2nnc(CN(C)C(=O)c3cccc(Cl)c3)o2)c(O)c1-c1c(OC)cccc1OC] | N-({5-[6-butyl-5-(2,6-dimethoxyphenyl)-2,4-dihydroxypyridin-3-yl]-1,3,4-oxadiazol-2-yl}methyl)-3-chloro-N-methylbenzamide | 1H NMR (500 MHz, DMSO-d6) δ 7.64-7.47 (m, 4H), 7.35 (t, J = 8.4 Hz, 1H), 6.73 (d, J = 8.3 Hz, 2H), 5.02 (br. s., 2H), 3.70 (s, 6H), 3.05 (br. s., 3H), 2.14 (t, J = 7.4 Hz, 2H), 1.40-1.27 (m, 2H), 1.14-1.02 (m, 2H), 0.67 (t, J = 7.2 Hz, 3H) | 0.96 D 553.3 | A |

-continued

| Ex # | Structure | Name | ¹H NMR | LC/MS Rt (min) Method M + H | hAPJ cAMP EC₅₀ Potency range (nM) |
|---|---|---|---|---|---|
| 157 | 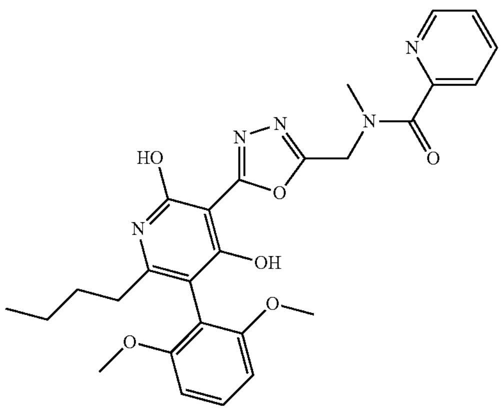 [SMILES: CCCCc1nc(O)c(-c2nnc(CN(C)C(=O)c3ccccn3)o2)c(O)c1-c1c(OC)cccc1OC] | N-({5-[6-butyl-5-(2,6-dimethoxyphenyl)-2,4-dihydroxypyridin-3-yl]-1,3,4-oxadiazol-2-yl}methyl)-N-methylpyridine-2-carboxamide | 1H NMR (500 MHz, DMSO-d6) δ 8.66-8.54 (m, 1H), 7.95 (dt, J = 15.1, 7.5 Hz, 1H), 7.82-7.62 (m, 1H), 7.53 (dd, J = 13.3, 7.0 Hz, 1H), 7.36 (t, J = 8.4 Hz, 1H), 6.74 (d, J = 8.5 Hz, 2H), 5.07 (d, J = 15.1 Hz, 2H), 3.70 (d, J = 4.7 Hz, 6H), 3.14 (d, J = 9.6 Hz, 3H), 2.16 (br. s., 2H), 1.34 (d, J = 8.0 Hz, 2H), 1.10 (br. s, 2H), 0.67 (t, J = 6.9 Hz, 3H) | 0.84 D 520.4 | A |
| 158 | 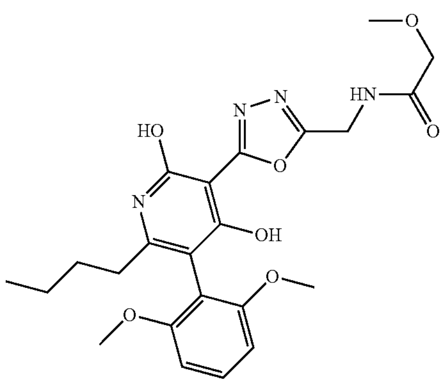 [SMILES: CCCCc1nc(O)c(-c2nnc(CNC(=O)COC)o2)c(O)c1-c1c(OC)cccc1OC] | N-({5-[6-butyl-5-(2,6-dimethoxyphenyl)-2,4-dihydroxypyridin-3-yl]-1,3,4-oxadiazol-2-yl}methyl)-2-methoxyacetamide | 1H NMR (500 MHz, DMSO-d6) δ 8.64 (t, J = 5.8 Hz, 1H), 7.36 (t, J = 8.3 Hz, 1H), 6.74 (d, J = 8.3 Hz, 2H), 4.61 (d, J = 5.8 Hz, 2H), 3.91 (s, 2H), 3.70 (s, 6H), 2.57-2.47 (m, 3H), 2.15 (t, J = 7.6 Hz, 2H), 1.41-1.27 (m, 2H), 1.15-1.03 (m, 2H), 0.67 (t, J = 7.4 Hz, 3H) | 0.81 D 473.4 | A |
| 159 | 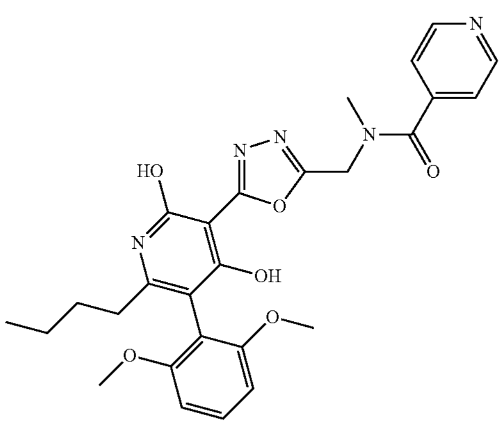 [SMILES: CCCCc1nc(O)c(-c2nnc(CN(C)C(=O)c3ccncc3)o2)c(O)c1-c1c(OC)cccc1OC] | N-({5-[6-butyl-5-(2,6-dimethoxyphenyl)-2,4-dihydroxypyridin-3-yl]-1,3,4-oxadiazol-2-yl}methyl)-N-methylpyridine-4-carboxamide | 1H NMR (500 MHz, DMSO-d6) δ 8.78-8.62 (m, 2H), 7.62 (br. s., 1H), 7.49 (br. s., 1H), 7.31 (br. s., 1H), 6.70 (d, J = 8.3 Hz, 2H), 5.00 (br. s., 1H), 4.67 (br. s., 1H), 3.68 (s, 6H), 3.03 (d, J = 10.5 Hz, 3H), 2.09 (br. s., 2H), 1.38-1.25 (m, 2H), 1.13-1.00 (m, 2H), 0.67 (t, J = 7.3 Hz, 3H) | 0.76 D 520.4 | A |

-continued

| Ex # | Structure | Name | $^1$H NMR | LC/MS Rt (min) Method M + H | hAPJ cAMP EC$_{50}$ Potency range (nM) |
|---|---|---|---|---|---|
| 160 | 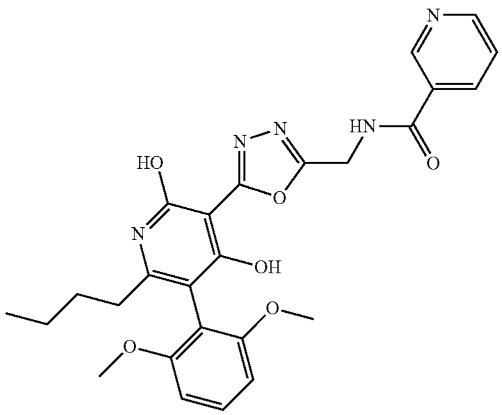 [SMILES: CCCCc1nc(O)c(-c2nnc(CNC(=O)c3cccnc3)o2)c(O)c1-c1c(OC)cccc1OC] | N-({5-[6-butyl-5-(2,6-dimethoxyphenyl)-2,4-dihydroxypyridin-3-yl]-1,3,4-oxadiazol-2-yl}methyl)pyridine-3-carboxamide | 1H NMR (500 MHz, DMSO-d6) δ 9.66-9.50 (m, 1H), 9.07 (s, 1H), 8.76 (d, J = 4.4 Hz, 1H), 8.26 (d, J = 7.4 Hz, 1H), 7.63-7.48 (m, 1H), 7.35 (t, J = 8.3 Hz, 1H), 6.73 (d, J = 8.0 Hz, 2H), 4.82 (d, J = 5.5 Hz, 2H), 3.70 (s, 6H), 2.15 (t, J = 7.7 Hz, 2H), 1.40-1.27 (m, 2H), 1.14-1.02 (m, 2H), 0.66 (t, J = 7.3 Hz, 3H) | 0.76 D 506.4 | A |
| 161 | 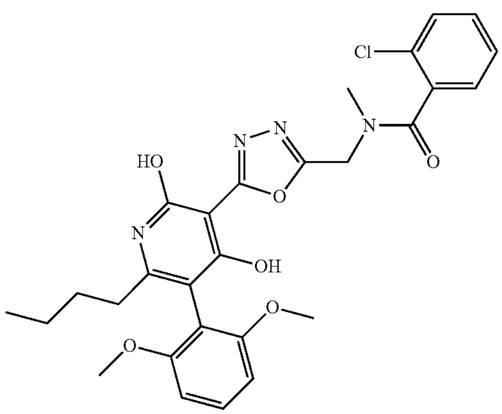 [SMILES: CCCCc1nc(O)c(-c2nnc(CN(C)C(=O)c3ccccc3Cl)o2)c(O)c1-c1c(OC)cccc1OC] | N-({5-[6-butyl-5-(2,6-dimethoxyphenyl)-2,4-dihydroxypyridin-3-yl]-1,3,4-oxadiazol-2-yl}methyl)-2-chloro-N-methylbenzamide | 1H NMR (500 MHz, DMSO-d6) δ 7.73-7.31 (m, 5H), 6.75 (d, J = 8.3 Hz, 2H), 5.08 (br. s., 2H), 3.74-3.63 (m, 6H), 3.05 (br. s., 3H 2.93 (s, 2H), 2.17 (t, J = 7.4 Hz, 2H), 1.35 (d, J = 6.9 Hz, 2H), 1.15-1.03 (m, 2H), 0.67 (t, J = 7.3 Hz, 3H) | 0.94 D 553.3 | A |
| 162 | 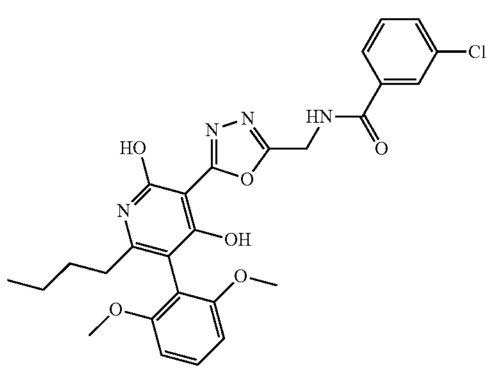 [SMILES: CCCCc1nc(O)c(-c2nnc(CNC(=O)c3cccc(Cl)c3)o2)c(O)c1-c1c(OC)cccc1OC] | N-({5-[6-butyl-5-(2,6-dimethoxyphenyl)-2,4-dihydroxypyridin-3-yl]-1,3,4-oxadiazol-2-yl}methyl)-3-chlorobenzamide | 1H NMR (400 MHz, DMSO-d6) δ 7.94 (t, J = 1.8 Hz, 1H), 7.86 (d, J = 7.7 Hz, 1H), 7.70-7.64 (m, 1H), 7.60-7.47 (m, 1H), 7.34 (t, J = 8.4 Hz, 1H), 6.72 (d, J = 8.6 Hz, 2H), 4.78 (d, J = 5.5 Hz, 2H), 3.69 (s, 6H), 2.14 (t, J = 7.5 Hz, 2H), 1.35-1.27 (m, 2H), 1.13-1.02 (m, 2H), 0.65 (t, J = 7.4 Hz, 3H) | 2.10 C 539.1 | A |

| Ex # | Structure | Name | ¹H NMR | LC/MS Rt (min) Method M + H | hAPJ cAMP EC₅₀ Potency range (nM) |
|---|---|---|---|---|---|
| 163 | 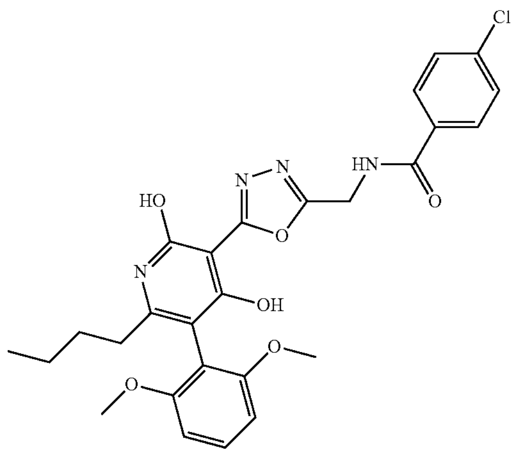 [SMILES: CCCCc1nc(O)c(-c2nnc(CNC(=O)c3ccc(Cl)cc3)o2)c(O)c1-c1c(OC)cccc1OC] | N-({5-[6-butyl-5-(2,6-dimethoxyphenyl)-2,4-dihydroxypyridin-3-yl]-1,3,4-oxadiazol-2-yl}methyl)-4-chlorobenzamide | 1H NMR (500 MHz, DMSO-d6) δ 7.93 (d, J = 7.7 Hz, 2H), 7.59 (d, J = 8.0 Hz, 2H), 7.36 (t, J = 8.4 Hz, 1H), 6.73 (d, J = 8.3 Hz, 2H), 4.79 (d, J = 5.0 Hz, 2H), 3.70 (s, 6H), 2.15 (t, J = 7.6 Hz, 2H), 1.40-1.26 (m, 2H), 1.13-1.03 (m, 2H), 0.67 (t, J = 7.2 Hz, 3H) | 0.94 D 539.3 | A |
| 164 | 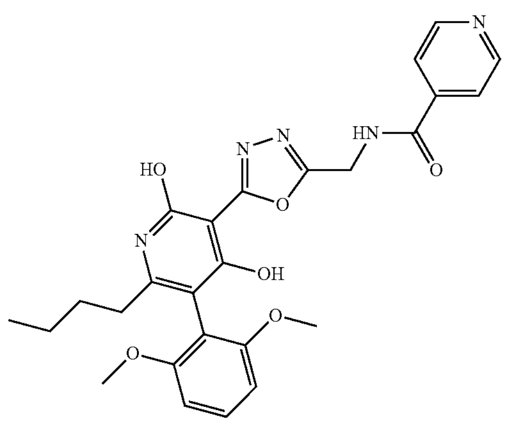 [SMILES: CCCCc1nc(O)c(-c2nnc(CNC(=O)c3ccncc3)o2)c(O)c1-c1c(OC)cccc1OC] | N-({5-[6-butyl-5-(2,6-dimethoxyphenyl)-2,4-dihydroxypyridin-3-yl]-1,3,4-oxadiazol-2-yl}methyl)pyridine-4-carboxamide | 1H NMR (500 MHz, DMSO-d6) δ 8.77 (d, J = 5.0 Hz, 2H), 7.81 (d, J = 5.0 Hz, 2H), 7.36 (t, J = 8.4 Hz, 1H), 6.74 (d, J = 8.3 Hz, 2H), 4.82 (d, J = 5.5 Hz, 2H), 3.70 (s, 6H), 2.16 (t, J = 7.6 Hz, 2H), 1.39-1.28 (m, 2H), 1.13-1.04 (m, 2H), 0.66 (t, J = 7.3 Hz, 3H) | 0.75 D 506.4 | A |
| 165 | 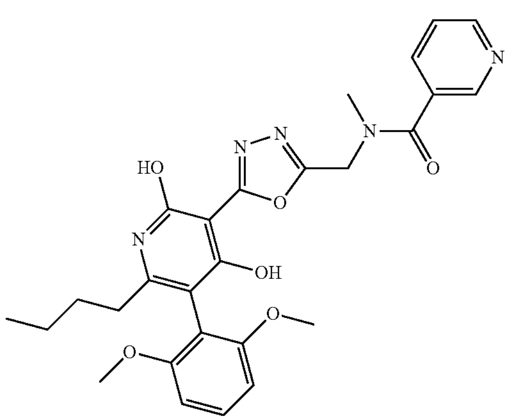 [SMILES: CCCCc1nc(O)c(-c2nnc(CN(C)C(=O)c3cccnc3)o2)c(O)c1-c1c(OC)cccc1OC] | N-({5-[6-butyl-5-(2,6-dimethoxyphenyl)-2,4-dihydroxypyridin-3-yl]-1,3,4-oxadiazol-2-yl}methyl)-N-methylpyridine-3-carboxamide | 1H NMR (500 MHz, DMSO-d6) δ 8.70 (d, J = 15.4 Hz, 2H), 8.14-7.88 (m, 1H), 7.51 (br, s., 1H), 7.30 (br. s., 1H), 6.69 (d, J = 8.5 Hz, 2H), 5.00 (br. s., 2H), 3.68 (s, 6H), (d, J = 10.5 Hz, 3H), 2.09 (br. s., 2H), 1.44-1.27 (m, 2H), 1.15-0.98 (m, 2H), 0.67 (t, J = 7.3 Hz, 3H) | 0.77 D 520.4 | A |

-continued

| Ex # | Structure | Name | ¹H NMR | LC/MS Rt (min) Method M + H | hAPJ cAMP EC₅₀ Potency range (nM) |
|---|---|---|---|---|---|
| 166 | 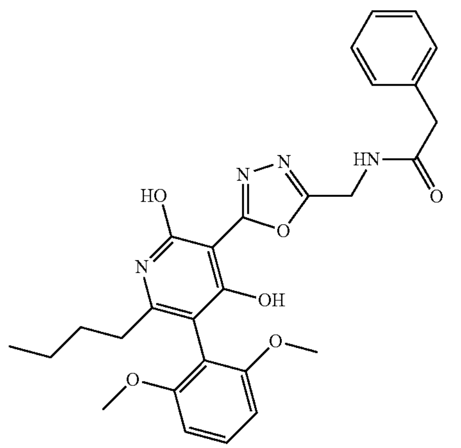 [SMILES: CCCCc1nc(O)c(-c2nnc(CNC(=O)Cc3ccccc3)o2)c(O)c1-c1c(OC)cccc1OC] | N-({5-[6-butyl-5-(2,6-dimethoxyphenyl)-2,4-dihydroxypyridin-3-yl]-1,3,4-oxadiazol-2-yl}methyl)-2-phenylacetamide | 1H NMR (500 MHz, DMSO-d6) δ 7.37- 7.29 (m, 5H), 7,23 (d, J = 3.9 Hz, 1H), 6.72 (d, J = 8.5 Hz, 2H), 4.59 (d, J = 5.5 Hz, 2H), 3.69 (s, 6H), 3.53 (s, 2H), 2.14 (t, J = 7.6 Hz, 2H), 1.34 (t, J = 7.4 Hz, 2H), 1.16-1.04 (m, 2H), 0.67 (t, J = 7.3 Hz, 3H) | 0.91 D 519.4 | A |
| 167 | 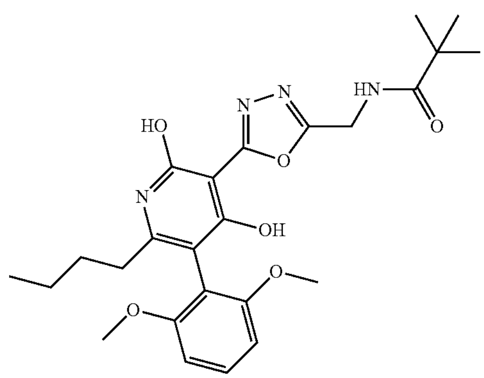 [SMILES: CCCCc1nc(O)c(-c2nnc(CNC(=O)C(C)(C)C)o2)c(O)c1-c1c(OC)cccc1OC] | N-({5-[6-butyl-5-(2,6-dimethoxyphenyl)-2,4-dihydroxy-pyridin-3-yl]-1,3,4-oxadiazol-2-yl}methyl)-2,2-dimethyl-propanamide | 1H NMR (500 MHz, DMSO-d6) δ 7.35 (t, J = 8.5 Hz, 1H), 6.73 (d, J = 8.3 Hz, 2H), 4.53 (d, J = 5.5 Hz, 2H), 3.70 (s, 6H), 2.13 (t, J = 7.7 Hz, 2H), 1.38-1.26 (m, 2H), 1.18-1.01 (m, 11H), 0.67 (t, J = 7.3 Hz, 3H) | 0.88 D 485.5 | A |
| 168 | 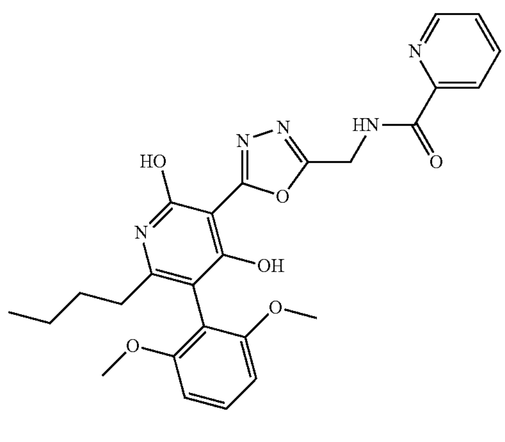 [SMILES: CCCCc1nc(O)c(-c2nnc(CNC(=O)c3ccccn3)o2)c(O)c1-c1c(OC)cccc1OC] | N-({5-[6-butyl-5-(2,6-dimethoxyphenyl)-2,4-dihydroxypyridin-3-yl]-1,3,4-oxadiazol-2-yl}methyl)pyridine-2-carboxamide | 1H NMR (500 MHz, DMSO-d6) δ 9.54 (t, J = 5.8 Hz, 1H), 8.71 (d, J = 4.4 Hz, 1H), 8.12-7.98 (m, 2H), 7.67 (d, J = 4.7 Hz, 1H), 7.36 (t, J = 8.5 Hz, 1H), 6.74 (d, J = 8.3 Hz, 2H), 4.82 (d, J = 5.8 Hz, 2H), 3.70 (s, 6H), 2.24-2.06 (m, 2H), 1.41-1.30 (m, 2H), 1.13-1.02 (m, 2H), 0.67 (t, J = 7.3 Hz, 3H) | 0.86 D 506.4 | A |

| Ex # | Structure | Name | ¹H NMR | LC/MS Rt (min) Method M + H | hAPJ cAMP EC₅₀ Potency range (nM) |
|---|---|---|---|---|---|
| 169 | 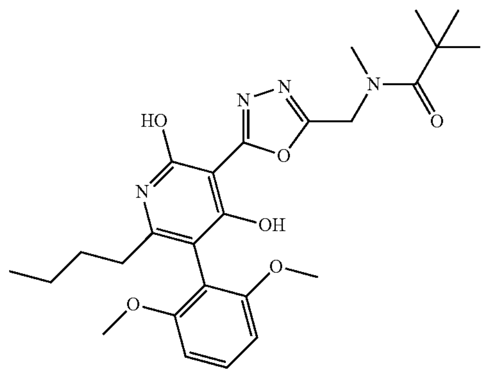 [SMILES: CCCCc1nc(O)c(-c2nnc(CN(C)C(=O)C(C)(C)C)o2)c(O)c1-c1c(OC)cccc1OC] | N-({5-[6-butyl-5-(2,6-dimethoxyphenyl)-2,4-dihydroxypyridin-3-yl]-1,3,4-oxadiazol-2-yl}methyl)-N,2,2-trimethylpropanamide | 1H NMR (500 MHz, DMSO-d6) δ 7.34-7.25 (m, 1H), 6.68 (d, J = 8.3 Hz, 2H), 4.79 (br. s., 2H), 3.67 (s, 6H), 2.56 (s, 3H), 2.06 (br. s, 2H), 1.36-1.29 (m, 2H), 1.25 (s, 9H), 1.14-1.02 (m, 2H), 0.66 (t, J = 7.4 Hz, 3H) | 2.03 C 499.2 | A |
| 170 | 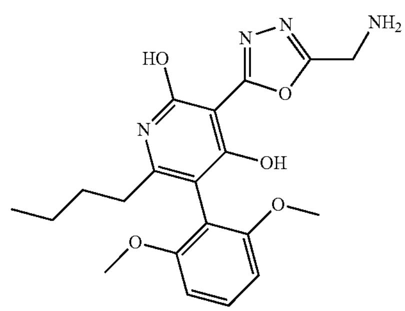 [SMILES: CCCCc1nc(O)c(-c2nnc(CN)o2)c(O)c1-c1c(OC)cccc1OC] | 3-[5-(aminomethyl)-1,3,4-oxadiazol-2-yl]-6-butyl-5-(2,6-dimethoxyphenyl)pyridine-2,4-diol | 1H NMR (500 MHz, DMSO-d6) δ 7.36 (t, J = 8.5 Hz, 1H), 6.74 (d, J = 8.0 Hz, 2H), 3.99 (s, 2H), 3.70 (s, 6H), 2.15 (t, J = 7.6 Hz, 2H), 1.41-1.29 (m, 2H), 1.14-1.01 (m, 2H), 0.67 (t, J = 7.0 Hz, 3H) | 1.60 C 401.1 | B |
| 171 | 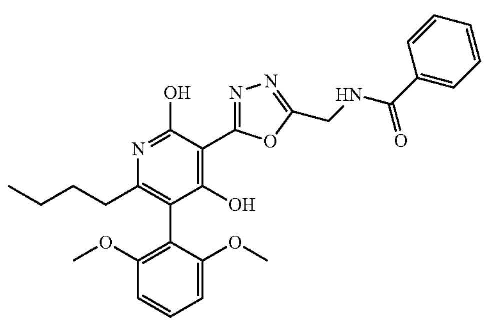 [SMILES: CCCCc1nc(O)c(-c2nnc(CNC(=O)c3ccccc3)o2)c(O)c1-c1c(OC)cccc1OC] | N-({5-[6-butyl-5-(2,6-dimethoxyphenyl)-2,4-dihydroxypyridin-3-yl]-1,3,4-oxadiazol-2-yl}methyl)benzamide | 1H NMR (500 MHz, DMSO-d6) δ 7.91 (d, J = 7.4 Hz, 2H), 7.61-7.56 (m, 1H), 7.54-7.46 (m, 2H), 7.36 (t, J = 8.4 Hz, 1H), 6.73 (d, J = 8.5 Hz, 2H), 4.78 (d, J = 5.2 Hz, 2H), 3.69 (s, 6H), 2.15 (t, J = 7.4 Hz, 2H), 1.38-1.27 (m, 2H), 1.13-1.03 (m, 2H), 0.66 (t, J = 7.0 Hz, 3H) | 1.99 C 505.1 | A |
| 172 | 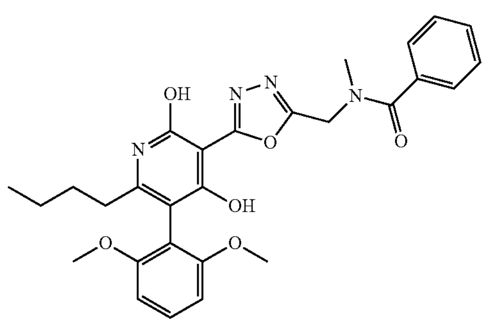 [SMILES: CCCCc1nc(O)c(-c2nnc(CN(C)C(=O)c3ccccc3)o2)c(O)c1-c1c(OC)cccc1OC] | N-({5-[6-butyl-5-(2,6-dimethoxyphenyl)-2,4-dihydroxypyridin-3-yl]-1,3,4-oxadiazol-2-yl}methyl)-N-methylbenzamide | 1H NMR (500 MHz, DMSO-d6) δ 7.50 (br. s., 5H), 7.37 (t, J = 8.4 Hz, 1H), 6.75 (d, J = 8.3 Hz, 2H), 5.03 (br. s., 2H), 3.71 (s, 6H), 3.06 (br. s., 3H), 2.17 (t, J = 7.6 Hz, 2H), 1.40-1.31 (m, 2H), 1.15-1.05 (m, 2H), 0.68 (t, J = 7.3 Hz, 3H) | 1.99 C 519.2 | A |

-continued

| Ex # | Structure | Name | ¹H NMR | LC/MS Rt (min) Method M + H | hAPJ cAMP EC₅₀ Potency range (nM) |
|---|---|---|---|---|---|
| 173 | 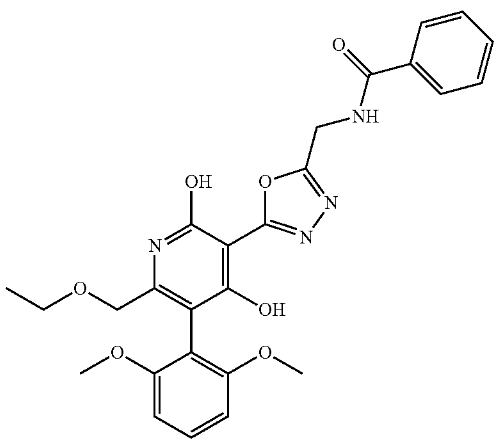 [SMILES: CCOCc1nc(O)c(-c2nnc(CNC(=O)c3ccccc3)o2)c(O)c1-c1c(OC)cccc1OC] | N-({5-[5-(2,6-dimethoxyphenyl)-6-(ethoxymethyl)-2,4-dihydroxypyridin-3-yl]-1,3,4-oxadiazol-2-yl}methyl)benzamide | 1H NMR (500 MHz, DMSO-d6) δ 7.90 (d, J = 8.0 Hz, 2H), 7.65-7.48 (m, 3H), 7.40-7.29 (m, 1H), 6.72 (d, J = 8.3 Hz, 2H), 4.78 (d, J = 4.7 Hz, 2H), 3.94 (s, 2H), 3.68 (s, 6H), 0.98 (t, J = 7.0 Hz, 3H) methylene obscured by water peak. | 1.86 C 507.1 | A |
| 174 | 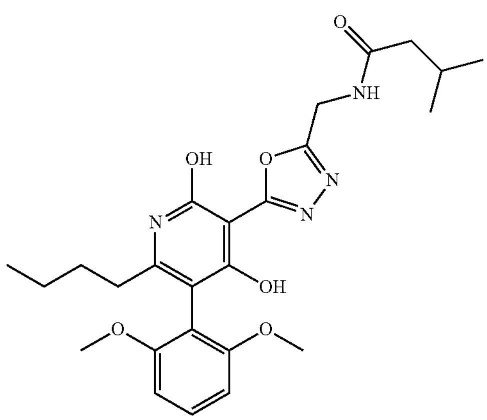 [SMILES: CCCCc1nc(O)c(-c2nnc(CNC(=O)CC(C)C)o2)c(O)c1-c1c(OC)cccc1OC] | N-({5-[6-butyl-5-(2,6-dimethoxyphenyl)-2,4-dihydroxypyridin-3-yl]-1,3,4-oxadiazol-2-yl}methyl)-3-methylbutanamide | 1H NMR (500 MHz, DMSO-d6) δ 7.33 (t, J = 8.4 Hz, 1H), 6.71 (d, J = 8.3 Hz, 2H), 4.54 (d, J = 4.7 Hz, 2H), 3.68 (s, 6H), 2.12 (br. s., 2H), 2.05-1.95 (m, 3H), 1.39-1.28 (m, 2H), 1.13-1.01 (m, 2H), 0.89 (d, J = 6.1 Hz, 6H), 0.65 (t, J = 7.2 Hz, 3H) | 1.99 C 485.1 | A |
| 175 | 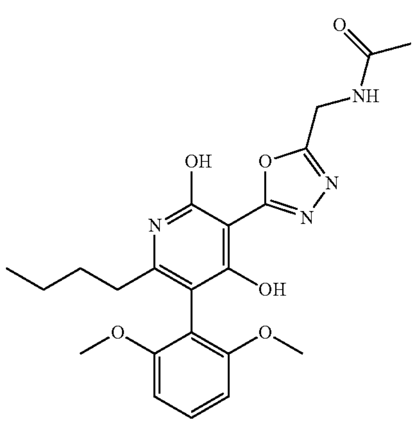 [SMILES: CCCCc1nc(O)c(-c2nnc(CNC(C)=O)o2)c(O)c1-c1c(OC)cccc1OC] | N-({5-[6-butyl-5-(2,6-dimethoxyphenyl)-2,4-dihydroxypyridin-3-yl]-1,3,4-oxadiazol-2-yl}methyl)acetamide | 1H NMR (500 MHz, DMSO-d6) δ 7.34 (t, J = 8.1 Hz, 1H), 6.71 (d, J = 8.5 Hz, 2H), 4.54 (d, J = 5.2 Hz, 2H), 3.68 (s, 6H), 2.13 (t, J = 7.0 Hz, 2H), 1.94-1.81 (m, 3H), 1.32 (t, J = 7.4 Hz, 2H), 1.14-0.96 (m, 2H), 0.65 (t, J = 7.0 Hz, 3H) | 1.81 C 443.1 | A |

-continued

| Ex # | Structure | Name | ¹H NMR | LC/MS Rt (min) Method M + H | hAPJ cAMP EC$_{50}$ Potency range (nM) |
|---|---|---|---|---|---|
| 176 | 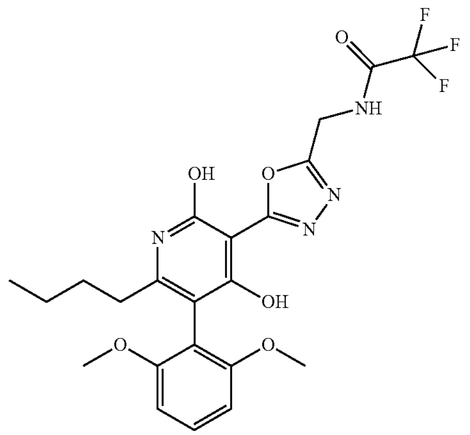 [SMILES: CCCCc1nc(O)c(-c2nnc(CNC(=O)C(F)(F)F)o2)c(O)c1-c1c(OC)cccc1OC] | N-({5-[6-butyl-5-(2,6-dimethoxyphenyl)-2,4-dihydroxypyridin-3-yl]-1,3,4-oxadiazol-2-yl}methyl)-2,2,2-trifluoroacetamide | 1H NMR (500 MHz, DMSO-d6) δ 7.35 (t, J = 8.4 Hz, 1H), 6.72 (d, J = 8.3 Hz, 2H), 4.75 (d, J = 5.8 Hz, 2H), 3.68 (s, 6H), 2.21-2.08 (m, 2H), 1.38-1.28 (m, 2H), 1.14-0.98 (m, 2H), 0.65 (t, J = 7.4 Hz, 3H) | 1.95 C 497.0 | B |
| 178 | 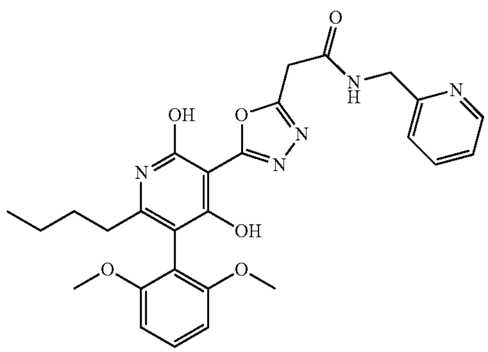 [SMILES: CCCCc1nc(O)c(-c2nnc(CC(=O)NCc3ccccn3)o2)c(O)c1-c1c(OC)cccc1OC] | 2-{5-[6-butyl-5-(2,6-dimethoxyphenyl)-2,4-dihydroxypyridin-3-yl]-1,3,4-oxadiazol-2-yl}-N-(pyridin-2-ylmethyl)acetamide | 1H NMR (500 MHz, DMSO-d6) δ 11.99 (s, 1H), 11.91 (s, 1H), 8.24 (d, J = 7.0 Hz, 1H), 7.54 (d, J = 9.2 Hz, 1H), 7.40-7.28 (m, 2H), 6.81-6.62 (m, 2H), 4.15 (s, 2H), 3.69 (s, 6H), 2.53-2.49 (m, 4H), 2.17 (t, J = 7.5 Hz, 2H), 1.44-1.21 (m, 2H), 1.14-1.04 (m, 2H), 0.66 (t, J = 7.2 Hz, 3H) | 1.80 A 520.0 | B |
| 179 | 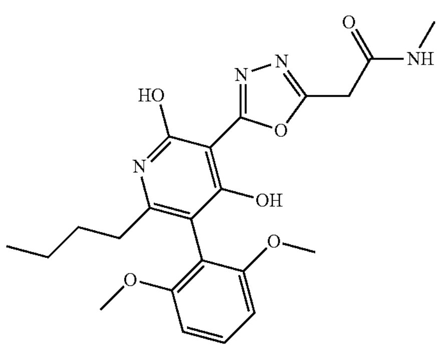 [SMILES: CCCCc1nc(O)c(-c2nnc(CC(=O)NC)o2)c(O)c1-c1c(OC)cccc1OC] | 2-{5-[6-butyl-5-(2,6-dimethoxyphenyl)-2,4-dihydroxypyridin-3-yl]-1,3,4-oxadiazol-2-yl}-N-methylacetamide | 1H NMR (500 MHz, DMSO-d6) δ 8.26 (d, J = 5.0 Hz, 1H), 7.37 (t, J = 8.3 Hz, 1H), 6.74 (d, J = 8.5 Hz, 2H), 3.94 (s, 2H), 3.70 (s, 6H), 2.66 (d, J = 4.7 Hz, 3H), 2.16 (t, J = 7.7 Hz, 2H), 1.41-1.30 (m, 2H), 1.15-1.03 (m, 2H), 0.67 (t, J = 7.4 Hz, 3H) | 0.97 D 443.4 | A |
| 180 | 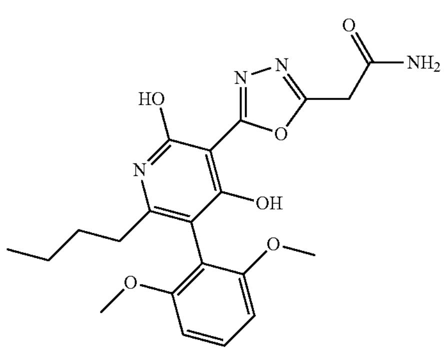 [SMILES: CCCCc1nc(O)c(-c2nnc(CC(N)=O)o2)c(O)c1-c1c(OC)cccc1OC] | 2-{5-[6-butyl-5-(2,6-dimethoxyphenyl)-2,4-dihydroxypyridin-3-yl]-1,3,4-oxadiazol-2-yl}acetamide | 1H NMR (500 MHz, DMSO-d6) δ 7.77 (br. s., 1H), 7.46-7.25 (m, 2H), 6.74 (d, J = 8.3 Hz, 1H), 3.93 (s, 2H), 3.70 (s, 6H), 2.16 (t, J = 7.7 Hz, 2H), 1.34 (quin, J = 7.4 Hz, 2H), 1.16-1.05 (m, 2H), 0.67 (t, J = 7.3 Hz, 3H) | 1.75 C 429.1 | B |

-continued

| Ex # | Structure | Name | ¹H NMR | LC/MS Rt (min) Method M + H | hAPJ cAMP EC$_{50}$ Potency range (nM) |
|---|---|---|---|---|---|
| 181 | 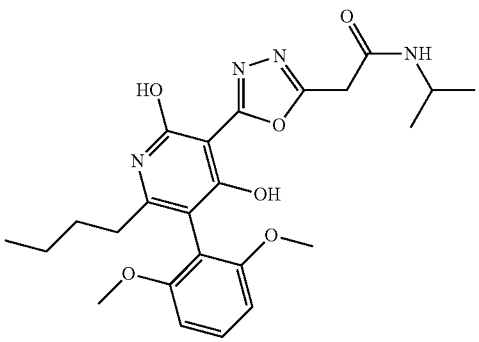 [SMILES: CCCCc1nc(O)c(-c2nnc(CC(=O)NC(C)C)o2)c(O)c1-c1c(OC)cccc1OC] | 2-{5-[6-butyl-5-(2,6-dimethoxyphenyl)-2,4-dihydroxypyridin-3-yl]-1,3,4-oxadiazol-2-yl}-N-(propan-2-yl)acetamide | 1H NMR (500 MHz, DMSO-d6) δ 8.23 (d, J = 7.7 Hz, 1H), 7.37 (t, J = 8.5 Hz, 1H), 6.74 (d, J = 8.3 Hz, 2H), 3.91 (s, 2H), 3.86 (dd, J = 13.3, 6.5 Hz, 1H), 3.71 (s, 6H), 2.16 (t, J = 7.7 Hz, 2H), 1.37-1.28 (m, 2H), 1.16-1.01 (m, 8H), 0.67 (t, J = 7.2 Hz, 3H) | 0.84 D 471.5 | A |
| 182 | 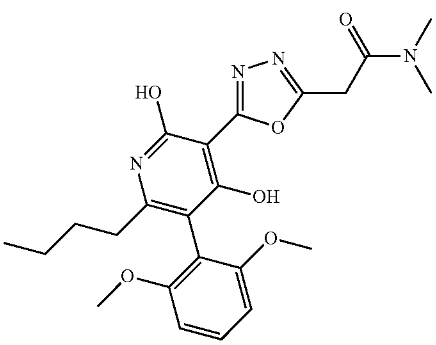 [SMILES: CCCCc1nc(O)c(-c2nnc(CC(=O)N(C)C)o2)c(O)c1-c1c(OC)cccc1OC] | 2-{5-[6-butyl-5-(2,6-dimethoxyphenyl)-2,4-dihydroxypyridin-3-yl]-1,3,4-oxadiazol-2-yl}-N,N-dimethylacetamide | 1H NMR (500 MHz, DMSO-d6) δ 7.37 (t, J = 8.5 Hz, 1H), 6.74 (d, J = 8.3 Hz, 2H), 4.29 (s, 2H), 3.71 (s, 6H), 3.09 (s, 3H), 2.89 (s, 3H), 2.16 (t, J = 7.4 Hz, 2H), 1.41-1.28 (m, 2H), 1.14-1.04 (m, 2H), 0.67 (t, J = 7.3 Hz, 3H) | 0.80 D 457.5 | A |
| 183 | 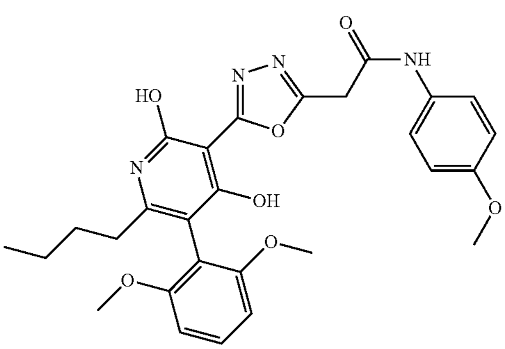 [SMILES: CCCCc1nc(O)c(-c2nnc(CC(=O)Nc3ccc(OC)cc3)o2)c(O)c1-c1c(OC)cccc1OC] | 2-{5-[6-butyl-5-(2,6-dimethoxyphenyl)-2,4-dihydroxypyridin-3-yl]-1,3,4-oxadiazol-2-yl}-N-(4-methoxyphenyl)acetamide | 1H NMR (500 MHz, DMSO-d6) δ 7.52 (d, J = 8.8 Hz, 2H), 7.36 (t, J = 8.4 Hz, 1H), 6.92 (d, J = 9.1 Hz, 2H), 6.73 (d, J = 8.5 Hz, 2H), 4.17 (s, 2H), 3.78-3.63 (m, 9H), 2.15 (t, J = 7.6 Hz, 2H), 1.38-1.27 (m, 2H), 1.16-1.02 (m, 2H), 0.67 (t, J = 7.3 Hz, 3H) | 0.88 D 535.4 | B |
| 184 | 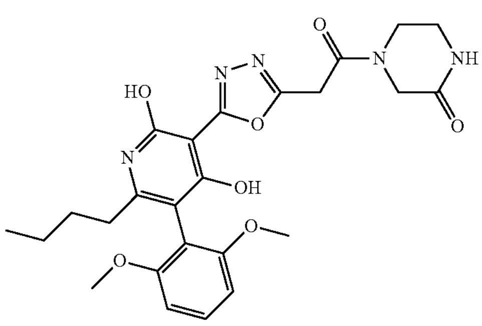 [SMILES: CCCCc1nc(O)c(-c2nnc(CC(=O)N3CCNC(=O)C3)o2)c(O)c1-c1c(OC)cccc1OC] | 4-(2-{5-[6-butyl-5-(2,6-dimethoxyphenyl)-2,4-dihydroxypyridin-3-yl]-1,3,4-oxadiazol-2-yl}acetyl)piperazin-2-one | 1H NMR (500 MHz, DMSO-d6) δ 7.35 (t, J = 8.3 Hz, 1H), 6.73 (d, J = 8.5 Hz, 2H), 4.36 (d, J = 19.3 Hz, 2H), 4.20 (s, 1H), 3.98 (s, 1H), 3.74 (t, J = 5.2 Hz, 1H), 3.70 (s, 6H), 3.64 (t, 1H), 3.22 (br. s., 2H), 2.15 (t, J = 7.7 Hz, 2H), 1.34 (quin, J = 7.5 Hz, 2H), 1.15-1.03 (m, 2H), 0.67 (t, J = 7.3 Hz, 3H) | 0.75 D 512.4 | A |

-continued

| Ex # | Structure | Name | ¹H NMR | LC/MS Rt (min) Method M + H | hAPJ cAMP EC₅₀ Potency range (nM) |
|---|---|---|---|---|---|
| 185 | 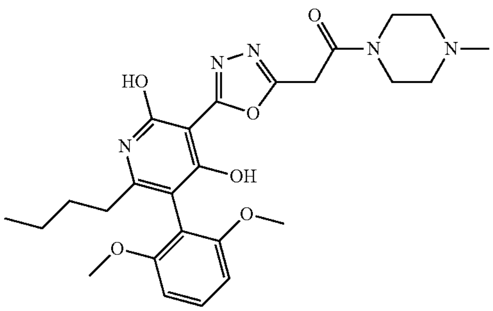 [SMILES: CCCCc1nc(O)c(-c2nnc(CC(=O)N3CCN(C)CC3)o2)c(O)c1-c1c(OC)cccc1OC] | 2-{5-[6-butyl-5-(2,6-dimethoxyphenyl)-2,4-dihydroxypyridin-3-yl]-1,3,4-oxadiazol-2-yl}-1-(4-methylpiperazin-1-yl)ethan-1-one | 1H NMR (500 MHz, DMSO-d6) δ 7.37 (t, J = 8.4 Hz, 1H), 6.74 (d, J = 8.3 Hz, 2H), 4.32 (s, 2H), 3.71 (s, 6H), 3.54 (d, J = 4.1 Hz, 4H), 2.42 (br. s., 2H), 2.33 (br. s., 2H), 2.23 (s, 3H), 2.16 (t, J = 7.6 Hz, 2H), 1.46-1.29 (m, 2H), 1.18-1.04 (m, 2H), 0.67 (t, J = 7.3 Hz, 3H) | 0.70 D 512.5 | B |
| 186 | 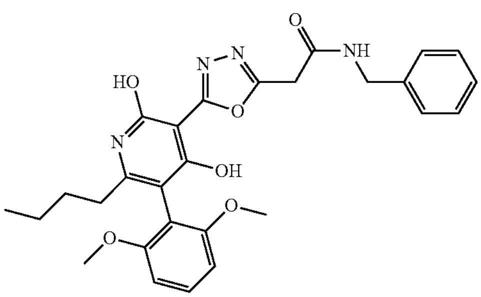 [SMILES: CCCCc1nc(O)c(-c2nnc(CC(=O)NCc3ccccc3)o2)c(O)c1-c1c(OC)cccc1OC] | N-benzyl-2-{5-[6-butyl-5-(2,6-dimethoxyphenyl)-2,4-dihydroxypyridin-3-yl]-1,3,4-oxadiazol-2-yl}acetamide | 1H NMR (500 MHz, DMSO-d6) δ 7.45-7.33 (m, 5H), 7.30-7.23 (m, 1H), 6.74 (d, J = 8.3 Hz, 2H), 4.35 (d, J = 5.5 Hz, 2H), 4.05 (s, 2H), 3.70 (s, 6H), 2.17 (t, J = 7.4 Hz, 2H), 1.40-1.29 (m, 2H), 1.16-1.03 (m, 2H), 0.67 (t, J = 7.3 Hz, 3H) | 0.89 D 519.4 | A |
| 187 | 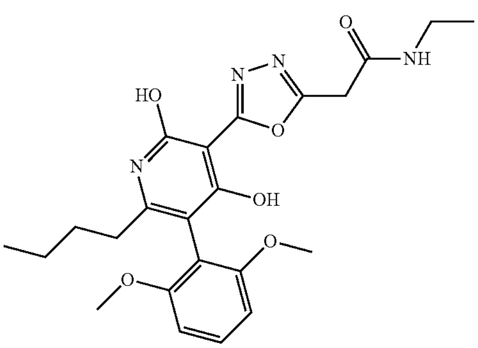 [SMILES: CCCCc1nc(O)c(-c2nnc(CC(=O)NCC)o2)c(O)c1-c1c(OC)cccc1OC] | 2-{5-[6-butyl-5-(2,6-dimethoxyphenyl)-2,4-dihydroxypyridin-3-yl]-1,3,4-oxadiazol-2-yl}-N-ethylacetamide | 1H NMR (500 MHz, DMSO-d6) δ 7.35 (t, J = 8.4 Hz, 1H), 6.72 (d, J = 8.5 Hz, 2H), 3.92 (s, 2H), 3.69 (s, 6H), 3.19-3.05 (m, 2H), 2.15 (t, J = 7.6 Hz, 2H), 1.43-1.27 (m, 2H), 1.14-0.96 (m, 5H), 0.65 (t, J = 7.3 Hz, 3H) | 0.83 D 457.5 | A |
| 188 | 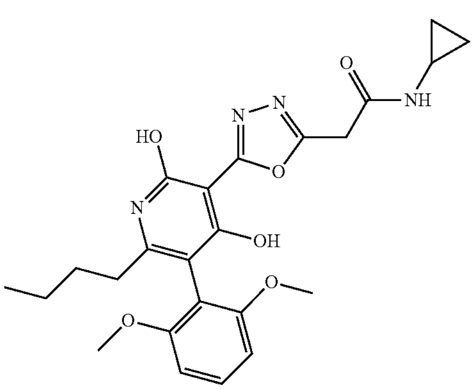 [SMILES: CCCCc1nc(O)c(-c2nnc(CC(=O)NC3CC3)o2)c(O)c1-c1c(OC)cccc1OC] | 2-{5-[6-butyl-5-(2,6-dimethoxyphenyl)-2,4-dihydroxypyridin-3-yl]-1,3,4-oxadiazol-2-yl}-N-cyclopropyl-acetamide | 1H NMR (500 MHz, DMSO-d6) δ 7.37 (t, J = 8.1 Hz, 1H), 6.75 (d, J = 8.3 Hz, 2H), 3.91 (s, 2H), 3.71 (s, 6H), 2.69 (br. s., 1H), 2.25-2.13 (m, 2H), 1.41-1.26 (m, 2H), 1.16-1.03 (m, 2H), 0.71-0.58 (m, 5H), 0.48 (br. s., 2H) | 0.83 D 469.5 | A |

-continued

| Ex # | Structure | Name | ¹H NMR | LC/MS Rt (min) Method M + H | hAPJ cAMP EC$_{50}$ Potency range (nM) |
|---|---|---|---|---|---|
| 189 | 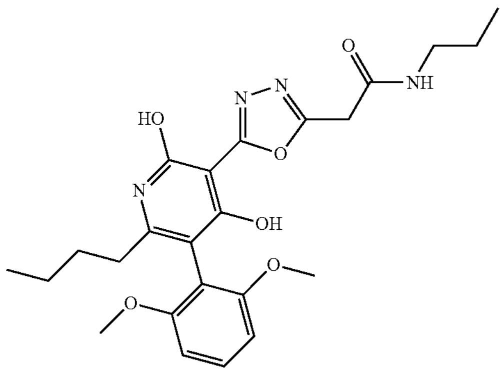 [SMILES: CCCCc1nc(O)c(-c2nnc(CC(=O)NCCC)o2)c(O)c1-c1c(OC)cccc1OC] | 2-{5-[6-butyl-5-(2,6-dimethoxyphenyl)-2,4-dihydroxypyridin-3-yl]-1,3,4-oxadiazol-2-yl}-N-propylacetamide | 1H NMR (500 MHz, DMSO-d6) δ 7.35 (t, J = 8.3 Hz, 1H), 6.72 (d, J = 8.3 Hz, 2H), 3.93 (s, 2H), 3.69 (s, 6H), 3.06 (q, J = 6.3 Hz, 2H), 2.15 (t, J = 7.4 Hz, 2H), 1.50-1.41 (m, 2H), 1.37-1.24 (m, 2H), 1.13-1.00 (m, 2H), 0.87 (t, J = 7.2 Hz, 3H), 0.65 (t, J = 7.3 Hz, 3H) | 0.85 D 471.5 | A |
| 190 | 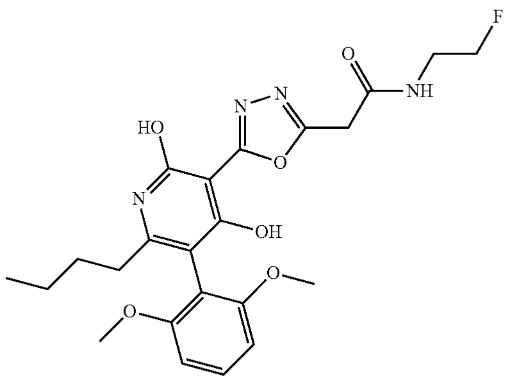 [SMILES: CCCCc1nc(O)c(-c2nnc(CC(=O)NCCF)o2)c(O)c1-c1c(OC)cccc1OC] | 2-{5-[6-butyl-5-(2,6-dimethoxyphenyl)-2,4-dihydroxypyridin-3-yl]-1,3,4-oxadiazol-2-yl}-N-(2-fluoroethyl)acetamide | 1H NMR (500 MHz, DMSO-d6) δ 7.34 (t, J = 8.3 Hz, 1H), 6.71 (d, J = 8.5 Hz, 2H), 4.56-4.39 (m, 2H), 3.98 (s, 2H), 3.68 (s, 6H), 3.49-3.37 (m, 2H), 2.13 (br. s., 2H), 1.43-1.27 (m, 2H), 1.13-1.02 (m, 2H), 0.65 (t, J = 7.2 Hz, 3H) | 0.82 D 475.4 | A |
| 191 | 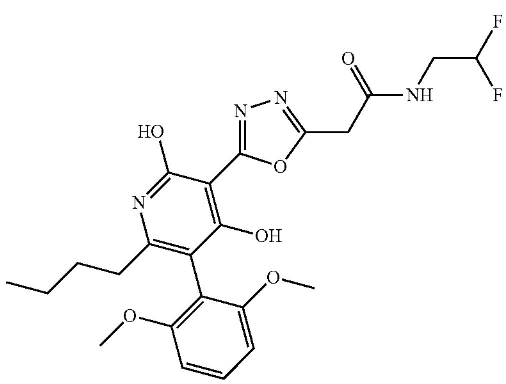 [SMILES: CCCCc1nc(O)c(-c2nnc(CC(=O)NCC(F)F)o2)c(O)c1-c1c(OC)cccc1OC] | 2-{5-[6-butyl-5-(2,6-dimethoxyphenyl)-2,4-dihydroxypyridin-3-yl]-1,3,4-oxadiazol-2-yl}-N-(2,2-difluoroethyl)acetamide | 1H NMR (500 MHz, DMSO-d6) δ 7.35 (t, J = 8.1 Hz, 1H), 6.72 (d, J = 8.5 Hz, 2H), 6.22-5.88 (m, 1H), 4.04 (s, 2H), 3.69 (s, 6H), 3.56 (t, J = 16.4 Hz, 2H), 2.15 (t, J = 7.6 Hz, 2H), 1.39-1.27 (m, 2H), 1.12-1.01 (m, 2H), 0.65 (t, J = 7.4 Hz, 3H) | 0.85 D 493.4 | A |
| 192 | 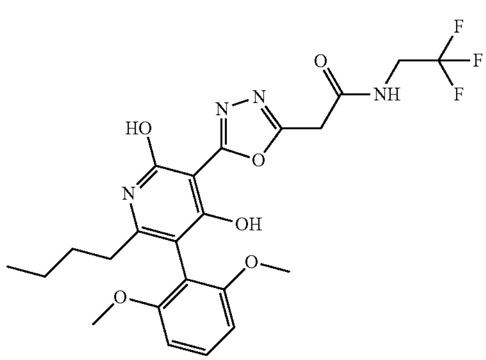 [SMILES: CCCCc1nc(O)c(-c2nnc(CC(=O)NCC(F)(F)F)o2)c(O)c1-c1c(OC)cccc1OC] | 2-{5-[6-butyl-5-(2,6-dimethoxyphenyl)-2,4-dihydroxypyridin-3-yl]-1,3,4-oxadiazol-2-yl}-N-(2,2,2-trifluoroethyl)acetamide | 1H NMR (500 MHz, DMSO-d6) δ 7.35 (t, J = 8.4 Hz, 1H), 6.72 (d, J = 8.3 Hz, 2H), 4.08 (s, 2H), 4.02-3.90 (m, 2H), 3.69 (s, 6H), 2.14 (t, J = 7.4 Hz, 2H), 1.33 (t, J = 7.4 Hz, 2H), 1.14-0.99 (m, 2H), 0.65 (t, J = 7.3 Hz, 3H) | 0.87 D 511.4 | A |

-continued

| Ex # | Structure | Name | ¹H NMR | LC/MS Rt (min) Method M + H | hAPJ cAMP EC₅₀ Potency range (nM) |
|---|---|---|---|---|---|
| 193 | 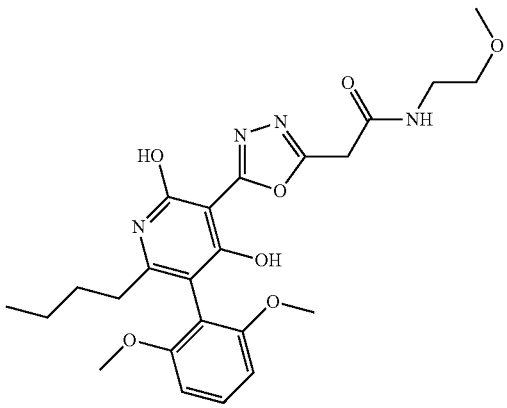 [SMILES: CCCCc1nc(O)c(-c2nnc(CC(=O)NCCOC)o2)c(O)c1-c1c(OC)cccc1OC] | 2-{5-[6-butyl-5-(2,6-dimethoxyphenyl)-2,4-dihydroxypyridin-3-yl]-1,3,4-oxadiazol-2-yl}-N-(2-methoxy-ethyl)acetamide | 1H NMR (500 MHz, DMSO-d6) δ 7.35 (t, J = 8.4 Hz, 1H), 6.72 (d, J = 8.3 Hz, 2H), 3.96 (s, 2H), 3.69 (s, 6H), 3.38 (d, J = 5.5 Hz, 4H), 3.27 (s, 3H), 2.15 (t, J = 7.3 Hz, 2H), 1.33 (t, J = 7.4 Hz, 2H), 1.15-1.03 (m, 2H), 0.65 (t, J = 6.9 Hz, 3H) | 0.81 D 487.5 | B |
| 194 | 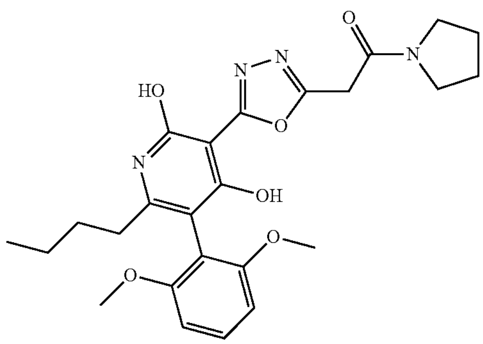 [SMILES: CCCCc1nc(O)c(-c2nnc(CC(=O)N3CCCC3)o2)c(O)c1-c1c(OC)cccc1OC] | 2-{5-[6-butyl-5-(2,6-dimethoxyphenyl)-2,4-dihydroxypyridin-3-yl]-1,3,4-oxadiazol-2-yl}-1-(pyrrolidin-1-yl)ethan-1-one | 1H NMR (500 MHz, DMSO-d6) δ 7.37 (t, J = 8.5 Hz, 1H), 6.74 (d, J = 8.5 Hz, 2H), 4.22 (s, 2H), 3.71 (s, 6H), 3.58 (t, J = 6.6 Hz, 2H), 2.16 (t, J = 7.4 Hz, 2H), 1.98-1.72 (m, 6H), 1.39-1.27 (m, 2H), 1.13-1.05 (m, 2H), 0.67 (t, J = 7.2 Hz, 3H) | 0.85 D 483.5 | A |
| 195 | 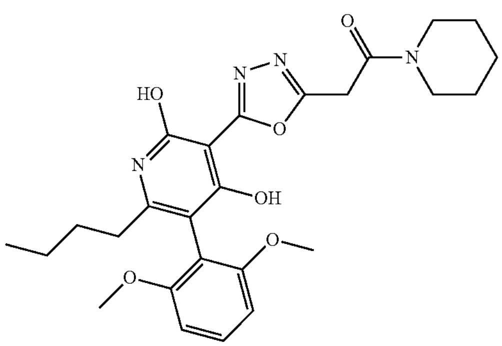 [SMILES: CCCCc1nc(O)c(-c2nnc(CC(=O)N3CCCCC3)o2)c(O)c1-c1c(OC)cccc1OC] | 2-{5-[6-butyl-5-(2,6-dimethoxyphenyl)-2,4-dihydroxypyridin-3-yl]-1,3,4-oxadiazol-2-yl}-1-(piperidin-1-yl)ethan-1-one | 1H NMR (500 MHz, DMSO-d6) δ 7.35 (t, J = 8.1 Hz, 1H), 6.73 (d, J = 8.3 Hz, 2H), 4.28 (s, 2H), 3.69 (s, 6H), 3.51-3.39 (m, 4H), 2.15 (t, J = 7.7 Hz, 2H), 1.59 (br. s., 4H), 1.47 (br. s., 2H), 1.36-1.25 (m, 2H), 1.14-1.01 (m, 2H), 0.65 (t, J = 7.3 Hz, 3H) | 0.89 D 497.5 | A |
| 196 | 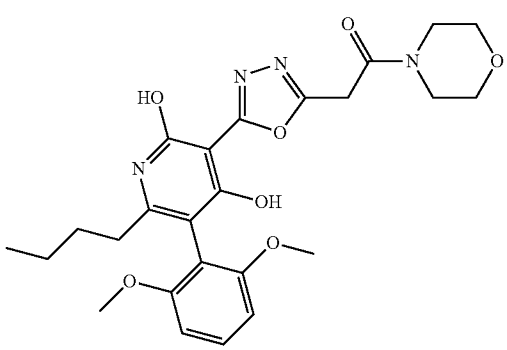 [SMILES: CCCCc1nc(O)c(-c2nnc(CC(=O)N3CCOCC3)o2)c(O)c1-c1c(OC)cccc1OC] | 2-{5-[6-butyl-5-(2,6-dimethoxyphenyl)-2,4-dihydroxypyridin-3-yl]-1,3,4-oxadiazol-2-yl}-1-(morpholin-4-yl)ethan-1-one | 1H NMR (500 MHz, DMSO-d6) δ 7.35 (t, J = 8.3 Hz, 1H), 6.73 (d, J = 8.0 Hz, 2H), 4.31 (s, 2H), 3.72-3.64 (m, 6H), 3.61-3.44 (m, 8H), 2.14 (t, J = 7.3 Hz, 2H), 1.38-1.27 (m, 2H), 1.14-1.01 (m, 2H), 0.65 (t, J = 7.2 Hz, 3H) | 0.82 D 499.4 | A |

| Ex # | Structure | Name | $^1$H NMR | LC/MS Rt (min) Method M + H | hAPJ cAMP EC$_{50}$ Potency range (nM) |
|---|---|---|---|---|---|
| 197 | 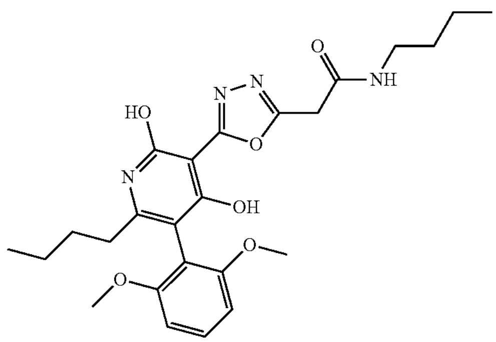 [SMILES: CCCCNC(=O)Cc1nnc(-c2c(O)nc(CCCC)c(-c3c(OC)cccc3OC)c2O)o1] | N-butyl-2-{5-[6-butyl-5-(2,6-dimethoxyphenyl)-2,4-dihydroxypyridin-3-yl]-1,3,4-oxadiazol-2-yl}acetamide | 1H NMR (500 MHz, DMSO-d6) δ 7.19 (t, J = 8.1 Hz, 1H), 6.61 (d, J = 8.3 Hz, 2H), 3.73 (s, 2H), 3.63 (s, 6H), 3.13-3.04 (m, 2H), 1.93 (t, J = 7.3 Hz, 2H), 1.42 (quin, J = 7.0 Hz, 2H), 1.36-1.23 (m, 6H), 1.14-1.02 (m, 2H), 0.89 (t, J = 7.2 Hz, 3H), 0.67 (t, J = 7.4 Hz, 3H) | 0.94 D 485.4 | A |
| 198 | 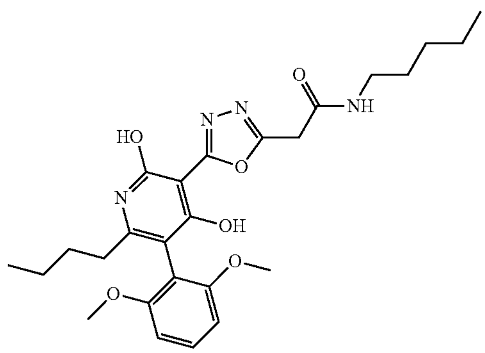 [SMILES: CCCCCNC(=O)Cc1nnc(-c2c(O)nc(CCCC)c(-c3c(OC)cccc3OC)c2O)o1] | 2-{5-[6-butyl-5-(2,6-dimethoxyphenyl)-2,4-dihydroxypyridin-3-yl]-1,3,4-oxadiazol-2-yl}-N-pentylacetamide | 1H NMR (500 MHz, DMSO-d6) δ 8.28 (br. s., 1H), 7.39-7.24 (m, 1H), 6.72 (d, J = 7.7 Hz, 2H), 3.92 (br. s., 2H), 3.68 (br. s., 6H), 3.09 (br. s., 2H), 2.14 (br. s., 2H), 1.43 (br. s., 2H), 1.36-1.20 (m, 6), 1.08 (d, J = 7.2 Hz, 2H), 0.86 (br. s., 3H), 0.73-0.59 (m, 3H) | 0.97 D 499.4 | B |
| 199 | 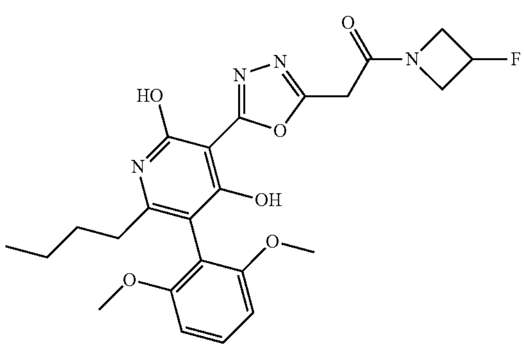 [SMILES: CCCCc1nc(O)c(-c2nnc(CC(=O)N3CC(F)C3)o2)c(O)c1-c1c(OC)cccc1OC] | 2-{5-[6-butyl-5-(2,6-dimethoxyphenyl)-2,4-dihydroxypyridin-3-yl]-1,3,4-oxadiazol-2-yl}-1-(3-fluoroazetidin-1-yl)ethan-1-one | 1H NMR (500 MHz, DMSO-d6) δ 7.35 (t, J = 8.3 Hz, 1H), 6.72 (d, J = 8.5 Hz, 2H), 5.53-5.33 (m, 1H), 4.66-4.55 (m, 1H), 4.45-4.33 (m, 1H), 4.24 (d, J = 14.6 Hz, 1H), 4.07 (d, J = 6.9 Hz, 2H), 4.03-3.90 (m, 1H), 3.68 (s, 6H), 2.20-2.08 (m, 2H), 1.32 (d, J = 7.2 Hz, 2H), 1.12-1.03 (m, 2H), 0.65 (t, J = 7.0 Hz, 3H) | 0.87 D 487.4 | A |
| 200 | 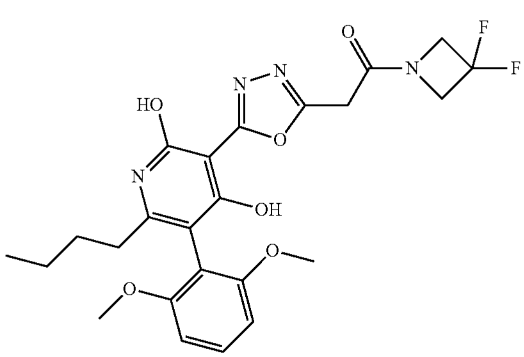 [SMILES: CCCCc1nc(O)c(-c2nnc(CC(=O)N3CC(F)(F)C3)o2)c(O)c1-c1c(OC)cccc1OC] | 2-{5-[6-butyl-5-(2,6-dimethoxyphenyl)-2,4-dihydroxypyridin-3-yl]-1,3,4-oxadiazol-2-yl}-1-(3,3-difluoroazetidin-1-yl)ethan-1-one | 1H NMR (500 MHz, DMSO-d6) δ 7.34 (t, J = 8.2 Hz, 1H), 6.71 (d, J = 8.5 Hz, 2H), 4.75 (t, J = 12.2 Hz, 2H), 4.34 (t, J = 12.4 Hz, 2H), 4.08 (s, 2H), 3.86 (br. s., 5H), 2.13 (t, J = 7.6 Hz, 2H), 1.29 (quin, J = 7.6 Hz, 2H), 1.11-0.96 (m, 2H), 0.61 (t, J = 7.3 Hz, 3H) | 0.91 D 505.3 | A |

-continued

| Ex # | Structure | Name | ¹H NMR | LC/MS Rt (min) Method M + H | hAPJ cAMP EC$_{50}$ Potency range (nM) |
|---|---|---|---|---|---|
| 201 | 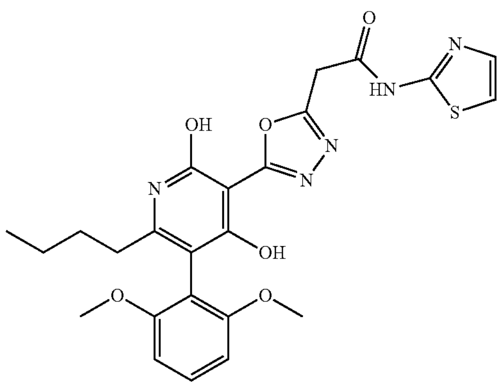 | 2-{5-[6-butyl-5-(2,6-dimethoxyphenyl)-2,4-dihydroxypyridin-3-yl]-1,3,4-oxadiazol-2-yl}-N-(1,3-thiazol-2-yl)acetamide | 1H NMR (500 MHz, DMSO-d6) δ 7.53 (d, J = 3.3 Hz, 1H), 7.37 (t, J = 8.4 Hz, 1H), 7.29 (d, J = 3.3 Hz, 1H), 6.74 (d, J = 8.5 Hz, 2H), 4.37 (s, 2H), 3.71 (s, 6H), 2.17 (t, J = 7.7 Hz, 2H), 1.42-1.29 (m, 2H), 1.14-1.05 (m, 2H), 0.67 (t, J = 7.3 Hz, 3H) | 1.94 C 512.1 | A |
| 203 | 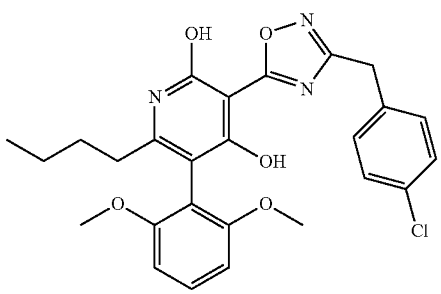 [SMILES: CCCCc1nc(O)c(-c2nc(Cc3ccc(Cl)cc3)no2)c(O)c1-c1c(OC)cccc1OC] | 6-butyl-3-{3-[(4-chlorophenyl)methyl]-1,2,4-oxadiazol-5-yl}-5-(2,6-dimethoxyphenyl)pyridine-2,4-diol | 1H NMR (500 MHz, DMSO-d6) δ 7.41-7.31 (m, 5H), 6.72 (d, J = 8.5 Hz, 2H), 4.14 (s, 2H), 2.15 (t, J = 7.3 Hz, 2H), 1.32 (t, J = 7.7 Hz, 2H), 1.08 (q, J = 7.0 Hz, 2H), 0.64 (t, J = 7.3 Hz, 3H) | 2.26 C 495.9 | B |
| 206 | 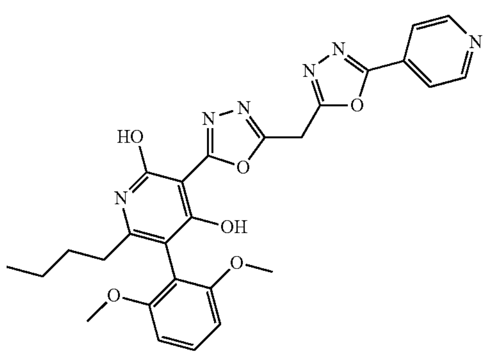 [SMILES: CCCCc1nc(O)c(-c2nnc(Cc3nnc(-c4ccncc4)o3)o2)c(O)c1-c1c(OC)cccc1OC] | 6-butyl-5-(2,6-dimethoxyphenyl)-3-(5-{[5-(pyridin-4-yl)-1,3,4-oxadiazol-2-yl]methyl}-1,3,4-oxadiazol-2-yl)pyridine-2,4-diol | 1H NMR (500 MHz, DMSO-d6) δ 8.85 (d, J = 5.2 Hz, 2H), 7.96 (d, J = 5.0 Hz, 2H), 7.34 (t, J = 8.1 Hz, 1H), 6.72 (d, J = 8.3 Hz, 2H), 4.99 (s, 2H), 3.69 (s, 6H), 2.12 (t, J = 7.6 Hz, 2H), 1.40-1.28 (m, 2H), 1.14-1.03 (m, 2H), 0.67 (t, J = 7.6 Hz, 3H) | 0.77 D 531.3 | A |
| 207 | 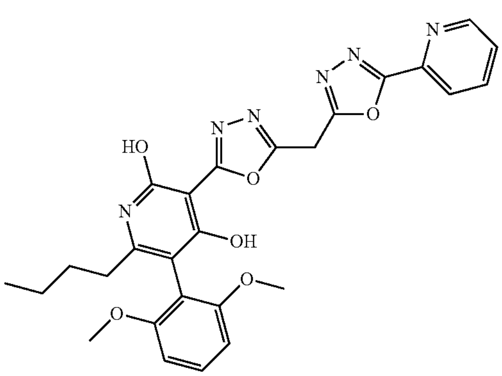 [SMILES: CCCCc1nc(O)c(-c2nnc(Cc3nnc(-c4ccccn4)o3)o2)c(O)c1-c1c(OC)cccc1OC] | 6-butyl-5-(2,6-dimethoxyphenyl)-3-(5-{[5-(pyridin-2-yl)-1,3,4-oxadiazol-2-yl]methyl}-1,3,4-oxadiazol-2-yl)pyridine-2,4-diol | 1H NMR (500 MHz, DMSO-d6) δ 8.79 (d, J = 4.4 Hz, 1H), 8.21 (d, J = 8.0 Hz, 1H), 8.08 (t, J = 7.7 Hz, 1H), 7.70-7.61 (m, 1H), 7.35 (t, J = 8.5 Hz, 1H), 6.72 (d, J = 8.3 Hz, 2H), 5.00 (s, 2H), 3.69 (s, 6H), 2.14 (t, J = 7.6 Hz, 2H), 1.45-1.29 (m, 2H), 1.11-1.04 (m, 2H), 0.67 (t, J = 7.4 Hz, 3H) | 0.84 D 531.3 | A |

| Ex # | Structure | Name | ¹H NMR | LC/MS Rt (min) Method M + H | hAPJ cAMP EC$_{50}$ Potency range (nM) |
|---|---|---|---|---|---|
| 208 | 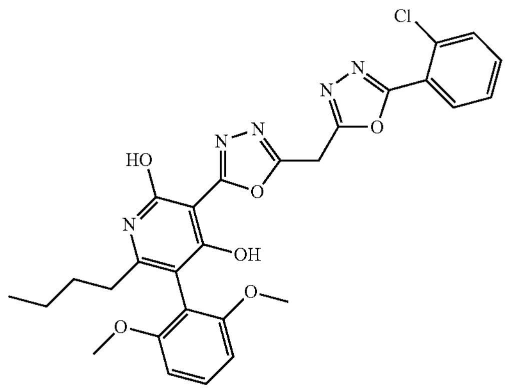 [SMILES: CCCCc1nc(O)c(-c2nnc(Cc3nnc(-c4ccccc4Cl)o3)o2)c(O)c1-c1c(OC)cccc1OC] | 6-butyl-3-(5-{[5-(2-chlorophenyl)-1,3,4-oxadiazol-2-yl]methyl}-1,3,4-oxadiazol-2-yl)-5-(2,6-dimethoxyphenyl)pyridine-2,4-diol | 1H NMR (500 MHz, DMSO-d6) δ 7.99 (d, J = 7.4 Hz, 1H), 7.79-7.73 (m, 1H), 7.68 (t, J = 7.8 Hz, 1H), 7.61-7.51 (m, 1H), 7.36 (t, J = 8.3 Hz, 1H), 6.73 (d, J = 8.5 Hz, 2H), 5.00 (s, 2H), 3.70 (s, 6H), 2.15 (t, J = 7.6 Hz, 2H), 1.39-1.26 (m, 2H), 1.17-1.03 (m, 2H), 0.67 (t, J = 7.3 Hz, 3H) | 0.94 D 564.3 | A |
| 209 | 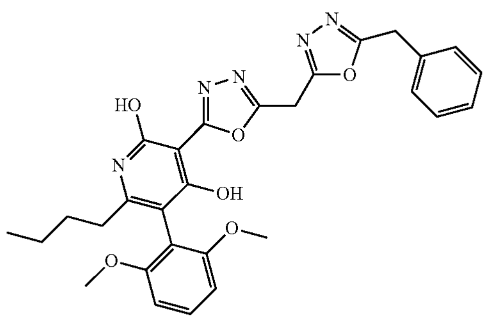 [SMILES: CCCCc1nc(O)c(-c2nnc(Cc3nnc(Cc4ccccc4)o3)o2)c(O)c1-c1c(OC)cccc1OC] | 3-{5-[(5-benzyl-1,3,4-oxadiazol-2-yl)methyl]-1,3,4-oxadiazol-2-yl}-6-butyl-5-(2,6-dimethoxyphenyl)pyridine-2,4-diol | 1H NMR (500 MHz, DMSO-d6) δ 7.41-7.25 (m, 6H), 6.74 (d, J = 8.5 Hz, 2H), 4.85 (s, 2H), 4.36-4.25 (m, 2H), 3.70 (s, 6H), 2.16 (t, J = 7.6 Hz, 2H), 1.35 (t, J = 7.4 Hz, 2H), 1.17-1.05 (m, 2H), 0.67 (t, J = 7.2 Hz, 3H) | 0.92 D 544.4 | A |
| 210 | 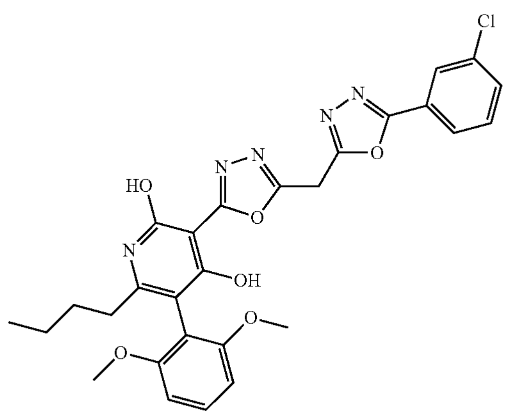 [SMILES: CCCCc1nc(O)c(-c2nnc(Cc3nnc(-c4cccc(Cl)c4)o3)o2)c(O)c1-c1c(OC)cccc1OC] | 6-butyl-3-(5-{[5-(3-chlorophenyl)-1,3,4-oxadiazol-2-yl]methyl}-1,3,4-oxadiazol-2-yl)-5-(2,6-dimethoxyphenyl)pyridine-2,4-diol | 1H NMR (500 MHz, DMSO-d6) δ 8.03-7.97 (m, 2H), 7.75 (d, J = 7.7 Hz, 1H), 7.69-7.63 (m, 1H), 7.36 (t, J = 8.3 Hz, 1H), 6.74 (d, J = 8.3 Hz, 2H), 4.98 (s, 2H), 3.70 (s, 6H), 2.16 (br. s, 2H), 1.39-1.29 (m, 2H), 1.16-1.04 (m, 2H), 0.67 (t, J = 7.2 Hz, 3H) | 2.17 C 564.1 | B |
| 211 | 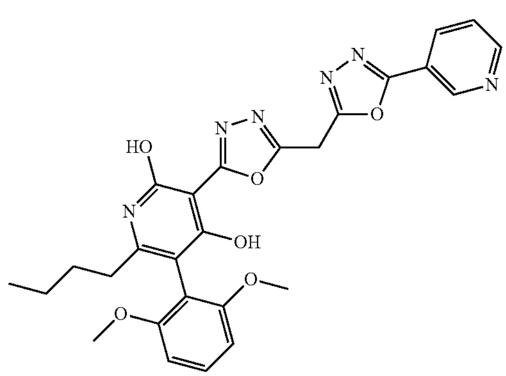 [SMILES: CCCCc1nc(O)c(-c2nnc(Cc3nnc(-c4cccnc4)o3)o2)c(O)c1-c1c(OC)cccc1OC] | 6-butyl-5-(2,6-dimethoxyphenyl)-3-(5-{[5-(pyridin-3-yl)-1,3,4-oxadiazol-2-yl]methyl}-1,3,4-oxadiazol-2-yl)pyridine-2,4-diol | 1H NMR (500 MHz, DMSO-d6) δ 9.19 (s, 1H), 8.83 (d, J = 5.0 Hz, 1H), 8.39 (d, J = 8.5 Hz, 1H), 7.71-7.62 (m, 1H), 7.36 (t, J = 8.3 Hz, 1H), 6.74 (d, J = 8.5 Hz, 2H), 5.00 (s, 2H), 3.70 (s, 6H), 2.16 (t, J = 7.6 Hz, 2H), 1.40-1.24 (m, 2H), 1.13-1.00 (m, 2H), 0.66 (t, J = 7.3 Hz, 3H) | 1.87 C 531.1 | B |

-continued

| Ex # | Structure | Name | ¹H NMR | LC/MS Rt (min) Method M + H | hAPJ cAMP EC₅₀ Potency range (nM) |
|---|---|---|---|---|---|
| 213 | 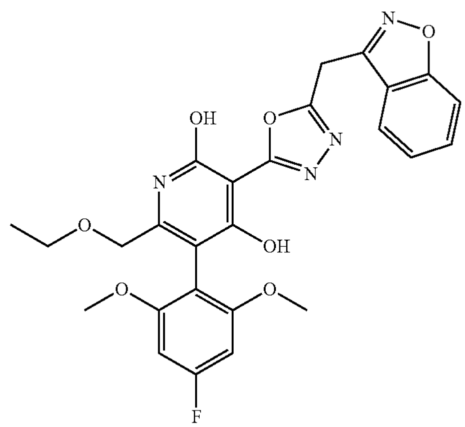 [SMILES: CCOCc1nc(O)c(-c2nnc(Cc3noc4ccccc34)o2)c(O)c1-c1c(OC)cc(F)cc1OC] | 3-[5-(1,2-benzoxazol-3-ylmethyl)-1,3,4-oxadiazol-2-yl]-6-(ethoxymethyl)-5-(4-fluoro-2,6-dimethoxyphenyl)pyridine-2,4-diol | 1H NMR (400 MHz, CDCl3) δ 7.92 (d, J = 7.9 Hz, 1H), 7.63-7.54 (m, 2H), 7.37 (m, 1H), 6.39 (s, 1H), 6.36 (s, 1H), 4.75 (s, 2H), 4.13 (s, 2H), 3.73 (s, 6H), 3.53 (m, 2H), 1.25 (t, J = 6.9 Hz, 3H) | 1.96 C 523.1 | A |
| 214 | 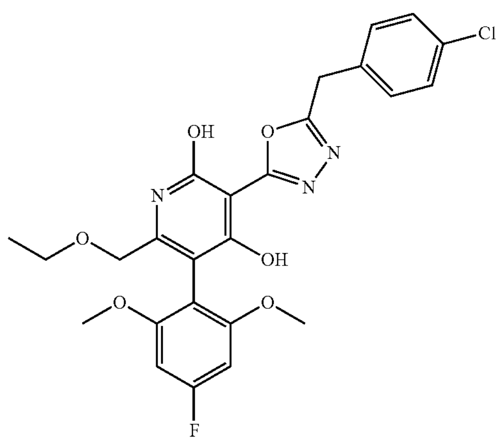 [SMILES: CCOCc1nc(O)c(-c2nnc(Cc3ccc(Cl)cc3)o2)c(O)c1-c1c(OC)cc(F)cc1OC] | 3-{5-[(4-chlorophenyl)methyl]-1,3,4-oxadiazol-2-yl}-6-(ethoxymethyl)-5-(4-fluoro-2,6-dimethoxyphenyl)pyridine-2,4-diol | 1H NMR (400 MHz, CDCl3) δ 7.33 (m, 4H), 6.39 (s, 1H), 6.37 (s, 1H), 4.29 (s, 2H), 4.14 (s, 2H), 3.73 (s, 6H), 3.53 (m, 2H), 1.25 (t, J = 6.9 Hz, 3H) | 2.10 C 516.1 | A |
| 215 | 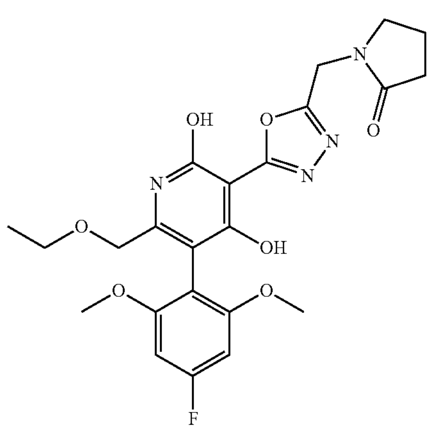 [SMILES: CCOCc1nc(O)c(-c2nnc(CN3CCCC3=O)o2)c(O)c1-c1c(OC)cc(F)cc1OC] | 1-({5-[6-(ethoxymethyl)-5-(4-fluoro-2,6-dimethoxyphenyl)-2,4-dihydroxypyridin-3-yl]-1,3,4-oxadiazol-2-yl}methyl)pyrrolidin-2-one | 1H NMR (400 MHz, CDCl3) δ 6.43 (s, 1H), 6.41 (s, 1H), 4.87 (s, 2H), 4.22 (s, 2H), 3.76 (s, 6H), 3.66 (m, 2H), 3.62-3.55 (m, 2H), 2.58-2.52 (m, 2H), 2.23-2.13 (m, 2H), 1.30 (t, J = 6.9 Hz, 3H) | 1.69 C 489.1 | B |

-continued

| Ex # | Structure | Name | ¹H NMR | LC/MS Rt (min) Method M + H | hAPJ cAMP EC₅₀ Potency range (nM) |
|---|---|---|---|---|---|
| 216 | 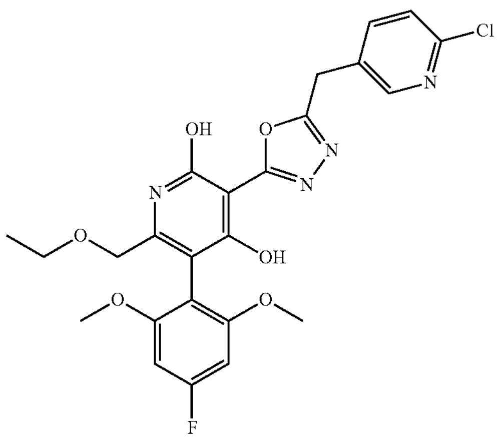 [SMILES: CCOCc1nc(O)c(-c2nnc(Cc3ccc(Cl)nc3)o2)c(O)c1-c1c(OC)cc(F)cc1OC] | 3-{5-[(6-chloropyridin-3-yl)methyl]-1,3,4-oxadiazol-2-yl}-6-(ethoxymethyl)-5-(4-fluoro-2,6-dimethoxyphenyl)pyridine-2,4-diol | 1H NMR (400 MHz, CDCl3) δ 8.46 (d, J = 2.2 Hz, 1H), 7.80 (m, 1H), 7.38 (d, J = 8.4 Hz, 1H), 6.43 (s, 1H), 6.40 (s, 1H), 4.35 (s, 2H), 4.20 (s, 2H), 3.75 (s, 6H), 3.58 (m, 2H), 1.29 (t, J = 7.0 Hz, 3H) | 1.89 C 517.1 | A |
| 220 | 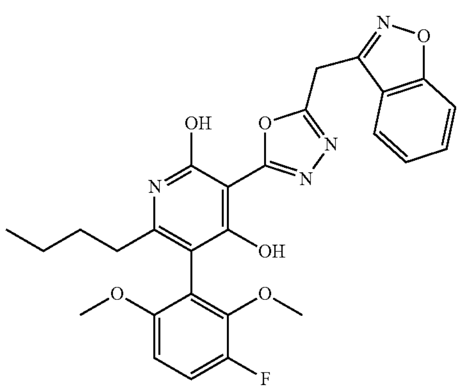 [SMILES: CCCCc1nc(O)c(-c2nnc(Cc3noc4ccccc34)o2)c(O)c1-c1c(OC)ccc(F)c1OC] | 3-[5-(1,2-benzoxazol-3-ylmethyl)-1,3,4-oxadiazol-2-yl]-6-butyl-5-(3-fluoro-2,6-dimethoxyphenyl)pyridine-2,4-diol (isomer 1) | 1H NMR (400 MHz, CDCl3) δ 7.78 (d, J = 7.9 Hz, 1H), 7.54-7.46 (m, 2H), 7.31-7.24 (m, 1H), 7.06 (m, 1H), 6.54 (m, 1H), 4.65 (s, 2H), 4.01-3.91 (m, 2H), 3.74 (m, 3H), 3.64 (s, 3H), 2.25 (m, 2H), 0.70 (t, J = 7.2 Hz, 3H) | 2.09 C 521.1 | B |
| 221 | 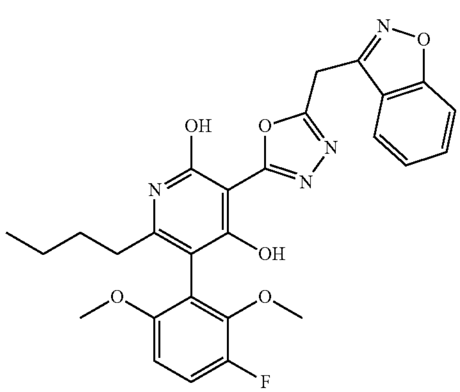 [SMILES: CCCCc1nc(O)c(-c2nnc(Cc3noc4ccccc34)o2)c(O)c1-c1c(OC)ccc(F)c1OC] | 3-[5-(1,2-benzoxazol-3-ylmethyl)-1,3,4-oxadiazol-2-yl]-6-butyl-5-(3-fluoro-2,6-dimethoxyphenyl)pyridine-2,4-diol (isomer 2) | 1H NMR (400 MHz, CDCl3) δ 7.78 (d, J = 7.9 Hz, 1H), 7.54-7.48 (m, 2H), 7.32-7.25 (m, 1H), 7.05 (m, 1H), 6.54 (m, 1H), 4.65 (s, 2H), 4.01-3.91 (m, 2H), 3.74 (m, 3H), 3.64 (s, 3H), 2.25 (m, 2H), 0.70 (t, J = 7.3 Hz, 3H) | 2.09 C 521.1 | A |

-continued

| Ex # | Structure | Name | ¹H NMR | LC/MS Rt (min) Method M + H | hAPJ cAMP EC₅₀ Potency range (nM) |
|---|---|---|---|---|---|
| 225 | 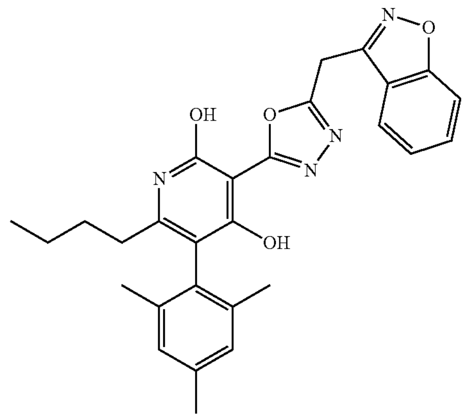 [SMILES: CCCCc1nc(O)c(-c2nnc(Cc3noc4ccccc34)o2)c(O)c1-c1c(C)cc(C)cc1C] | 3-[5-(1,2-benzoxazol-3-ylmethyl)-1,3,4-oxadiazol-2-yl]-6-butyl-5-(2,4,6-trimethylphenyl)pyridine-2,4-diol | 1H NMR (500 MHz, DMSO-d6) δ 11.86 (br. s., 1H), 7.99 (d, J = 7.9 Hz, 1H), 7.80 (d, J = 8.5 Hz, 1H), 7.74-7.68 (m, 1H), 7.44 (t, J = 7.3 Hz, 1H), 6.96 (s, 2H), 4.95 (s, 2H), 3.35 (br. s., 23H), 2.52 (br. s., 6H), 2.28 (s, 3H), 2.15 (t, J = 7.6 Hz, 2H), 1.40-1.31 (m, 2H), 1.18-1.08 (m, 2H), 0.71 (t, J = 7.2 Hz, 3H) | 2.29 A 485.3 | B |
| 226 | 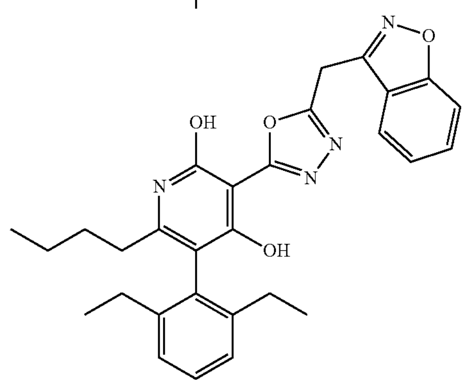 | 3-[5-(1,2-benzoxazol-3-ylmethyl)-1,3,4-oxadiazol-2-yl]-6-butyl-5-(2,6-diethylphenyl)pyridine-2,4-diol | 1H NMR (400 MHz, CDCl3) δ 12.34 (br. s., 1H), 10.84 (br. s., 1H), 7.86 (d, J = 7.9 Hz, 1H), 7.61-7.53 (m, 2H), 7.40-7.31 (m, 2H), 7.21 (d, J = 7.7 Hz, 2H), 4.71 (s, 2H), 2.38 (q, J = 7.6 Hz, 4H), 2.30-2.22 (m, 2H), 1.51 (dt, J = 15.6, 7.7 Hz, 2H), 1.28-1.20 (m, 2H), 1.11 (t, J = 7.6 Hz, 6H), 0.77 (t, J = 7.4 Hz, 3H) | 1.12 D 499.4 | A |
| 228 | 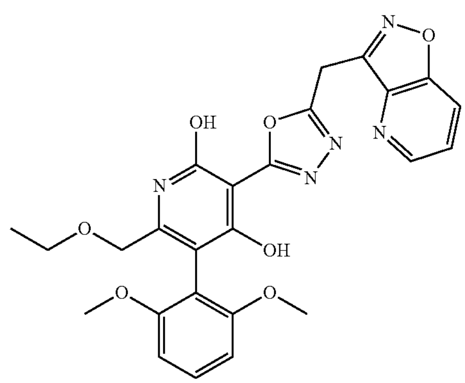 [SMILES: CCOCc1nc(O)c(-c2nnc(Cc3noc4cccnc34)o2)c(O)c1-c1c(OC)cccc1OC] | 5-(2,6-dimethoxyphenyl)-6-(ethoxymethyl)-3-(5-{[1,2]oxazolo[4,5-b]pyridin-3-ylmethyl}-1,3,4-oxadiazol-2-yl)pyridine-2,4-diol | 1H NMR (500 MHz, DMSO-d6) δ 8.77 (d, J = 4.3 Hz, 1H), 8.34 (d, J = 8.5 Hz, 1H), 7.75 (dd, J = 8.5, 4.3 Hz, 1H), 7.35 (t, J = 8.2 Hz, 1H), 6.72 (d, J = 8.2 Hz, 2H), 4.94 (s, 2H), 3.94 (s, 2H), 3.69 (s, 6H), 3.28 (q, J = 6.9 Hz, 2H), 1.00 (t, J = 6.9 Hz, 3H) | 1.21 A 506.2 | A |

Example 230

3-{5-[(5-chloropyridin-2-yl)methyl]-1,3,4-oxadiazol-2-yl}-5-(2,6-dimethoxyphenyl)-6-[(ethylamino)methyl]pyridine-2,4-diol

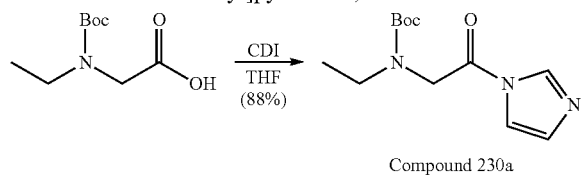

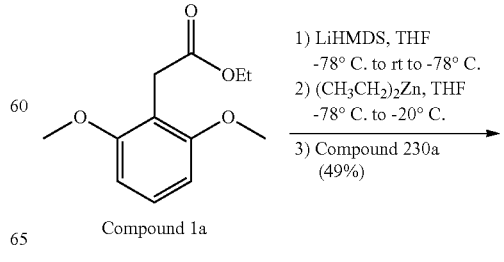

Compound 1a

1) LiHMDS, THF
 -78° C. to rt to -78° C.
2) (CH₃CH₂)₂Zn, THF
 -78° C. to -20° C.
3) Compound 230a
 (49%)

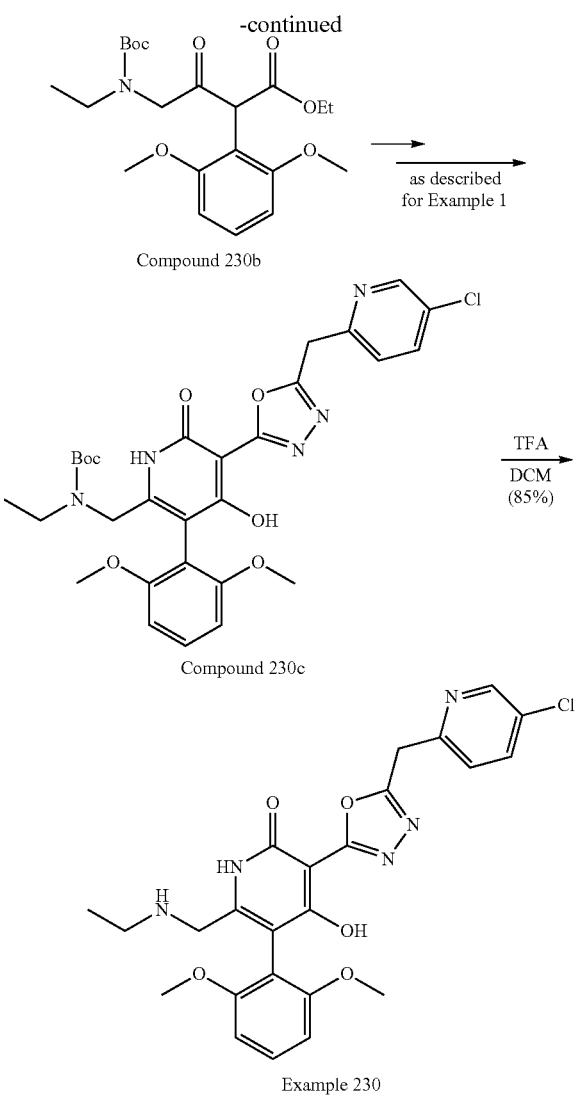

Compound 230a. tert-butyl (2-(1H-imidazol-1-yl)-2-oxoethyl)(ethyl)carbamate

To a solution of 2-((tert-butoxycarbonyl)(ethyl)amino)acetic acid (200 mg, 0.98 mmol) in THF (2 mL) was added CDI (180 mg, 1.1 mmol) and the reaction mixture stirred for 18 h. The reaction mixture was diluted with water and extracted with EtOAc (3×). The combined extracts were dried (MgSO$_4$) filtered and concentrated under reduced pressure to generate Compound 230a (220 mg, 0.87 mmol, 88% yield) as a yellow oil. LCMS (Method E) Rt=1.58 min, m/z=252.2 (M–H).

Compound 230b. ethyl 4-((tert-butoxycarbonyl)(ethyl)amino)-2-(2,6-dimethoxyphenyl)-3-oxobutanoate To a solution of Compound 1a (0.90 g, 4.0 mmol) in THF (5 mL) at −78° C. was added dropwise 1M LiHMDS in THF (5.6 mL, 5.6 mmol) and the reaction mixture stirred for 10 min then allowed to warm to room temperature and stirred for 1 h. The reaction mixture was cooled back to −78° C. then a 2M solution of diethylzinc in hexane (2.8 mL, 5.6 mmol) was added dropwise. The reaction mixture was stirred for 10 min then allowed to warm to −20° C. A solution of Compound 230a (1.2 g, 4.8 mmol) in THF (1 mL) was added dropwise, and the reaction mixture stirred at −20° C. for 20 min then quenched by the addition of 1N HCl. The reaction mixture was extracted with DCM (2×) and the organic extracts were dried (MgSO$_4$) filtered and concentrated under reduced pressure. The residue was purified by silica gel chromatography eluting with 0 to 30% EtOAc/hexanes to give Compound 230b (0.81 g, 2.0 mmol, 49% yield) as a white solid. LCMS (Method E) Rt=1.99 min, m/z=410.3 (M+H).

Compound 230c. tert-butyl N-[(5-{5-[(5-chloropyridin-2-yl)methyl]-1,3,4-oxadiazol-2-yl}-3-(2,6-dimethoxyphenyl)-4, 6-dihydroxypyridin-2-yl)methyl]-N-ethylcarbamate Compound 230c was prepared from Compound 230b as described in the general procedure given for Example 1 in 5% overall yield. LCMS (Method A) Rt=1.76 min, m/z=598.4 (M+H). $^1$H NMR (500 MHz, DMSO-d6) δ 8.53 (s, 1H), 8.03-7.87 (m, 1H), 7.54 (d, J=8.2 Hz, 1H), 7.33 (t, J=8.2 Hz, 1H), 6.70 (d, J=8.2 Hz, 2H), 4.54 (s, 2H), 3.95 (br. m, 1H), 3.72 (br. m., 2H), 2.78 (br. m., 2H), 2.51 (br. s., 6H), 1.26 (s, 4H), 1.30 (s, 5H), 0.77 (br. s., 3H).

Example 230

3-{5-[(5-chloropyridin-2-yl)methyl]-1,3,4-oxadiazol-2-yl}-5-(2,6-dimethoxyphenyl)-6-[(ethylamino)methyl]pyridine-2,4-diol To a solution of Compound 230b (13 mg, 0.022 mmol) in DCM (1 mL) was added TFA (0.1 mL) and the reaction mixture stirred for 24 h. The reaction mixture was concentrated under reduced pressure and the residue purified by preparative HPLC to give Example 230 (10 mg, 0.019 mmol, 85% yield) as a white solid. LCMS (Method A) Rt=0.95 min, m/z=498.1 (M+H). $^1$H NMR (500 MHz, DMSO-d6) δ 8.56 (s, 1H), 7.97 (d, J=6.8 Hz, 1H), 7.55 (d, J=8.3 Hz, 1H), 7.37 (t, J=8.3 Hz, 1H), 6.74 (d, J=8.3 Hz, 2H), 4.56 (s, 2H), 2.55 (m, 8H), 2.47 (br. s., 2H), 0.89 (t, J=6.7 Hz, 3H). Human APJ cAMP EC$_{50}$ potency range A.

Example 231

3-{5-[(1,2-benzoxazol-3-yl)methyl]-1,3,4-thiadiazol-2-yl}-5-(2,6-dimethoxyphenyl)-6-(ethoxymethyl)pyridine-2,4-diol

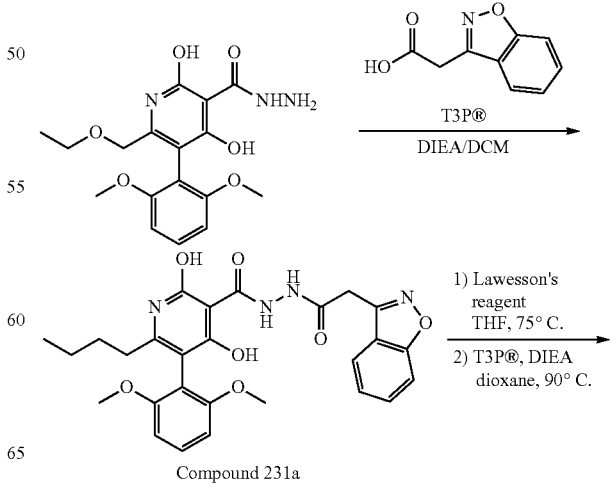

Compound 231a

-continued

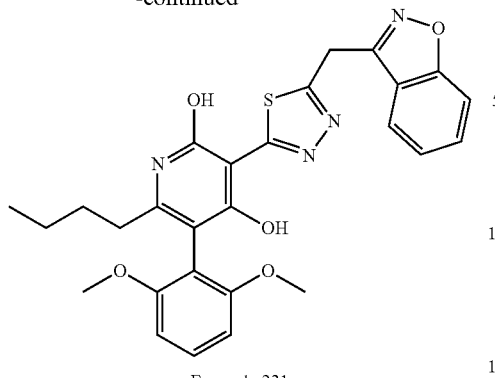

Example 231

Compound 231a. N'-(2-(benzo[d]isoxazol-3-yl)acetyl)-6-butyl-5-(2,6-dimethoxyphenyl)-2,4-dihydroxynicotinohydrazide To a mixture of 5-(2,6-dimethoxyphenyl)-6-(ethoxymethyl)-2,4-dihydroxynicotinohydrazide (80 mg, 0.22 mmol, prepared by the general procedures given for Example 1) and 2-(benzo[d]isoxazol-3-yl)acetic acid (47 mg, 0.26 mmol) in DCM (1 mL) was added and Hunig's base (0.058 mL, 0.33 mmol) followed by a 50% solution of T3P® in ethyl acetate (0.20 mL, 0.33 mmol) and the reaction mixture was stirred at room temperature for 1.5 h. The reaction mixture was concentrated under reduced pressure and the residue purified by preparative HPLC to give Compound 231a (82 mg, 0.16 mmol, 71% yield) as a white solid. LCMS (Method D) Rt=0.82 min, m/z=517.2 (M+H).

Example 231

3-{5-[(1,2-benzoxazol-3-yl)methyl]-1,3,4-thiadiazol-2-yl}-5-(2,6-dimethoxyphenyl)-6-(ethoxymethyl)pyridine-2,4-diol To a solution of Compound 231a (82 mg, 0.16 mmol) in THF (2 mL) was added Lawesson's reagent (64 mg, 0.16 mmol) and the mixture was heated at 75° C. for 1 h. The mixture was allowed to cool to room temperature then concentrated under reduced pressure. The residue was dissolved in dioxane (1 mL) then Hunig's base (0.069 mL, 0.39 mmol) was added followed by a 50% solution of T3P® in ethyl acetate (0.23 mL, 0.39 mmol) and the reaction mixture was heated at 90° C. for 0.5 h. The reaction mixture was allowed to cool to room temperature then concentrated under reduced pressure and the residue purified by preparative HPLC to give Example 231 (56 mg, 0.11 mmol, 69% yield) as a white solid. LCMS (Method A) Rt=2.013 min, m/z=521.0 (M+H). 1H NMR (500 MHz, DMSO-d6) δ 7.85 (d, J=7.9 Hz, 1H), 7.78 (d, J=8.2 Hz, 1H), 7.69 (t, J=7.6 Hz, 1H), 7.48-7.32 (m, 2H), 6.75 (d, J=8.5 Hz, 2H), 5.04 (s, 2H), 4.01 (s, 2H), 3.69 (s, 6H), 3.28 (q, J=6.9 Hz, 2H), 1.00 (t, J=7.0 Hz, 3H). Human APJ cAMP $EC_{50}$ potency range B.

Examples 232-235 were prepared by the general procedures given for Example 231.

Examples 236-245 were prepared by the general procedures given for Example 1.

Examples 246-251 were prepared by the general procedures given for Example 137.

Examples 252-273 were prepared by the general procedures given for Example 177.

Examples 274-276 were prepared by the general procedures given for Example 222.

| Ex # | Structure | Name | $^1$H NMR | LC/MS Rt (min) Method M + H | hAPJ cAMP $EC_{50}$ (nM) Potency range |
|---|---|---|---|---|---|
| 232 | 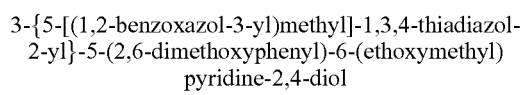 | 3-{5-[(5-chloropyridin-2-yl)methyl]-1,3,4-thiadiazol-2-yl}-5-(2,6-dimethoxyphenyl)-6-(ethoxymethyl)pyridine-2,4-diol | 1H NMR (500 MHz, DMSO-d6) δ 8.58 (s, 1H), 7.92 (dd, J = 8.3, 2.2 Hz, 1H), 7.53 (d, J = 8.4 Hz, 1H), 7.37 (t, J = 8.4 Hz, 1H), 6.73 (d, J = 8.4 Hz, 2H), 4.64 (s, 2H), 3.99 (s, 2H), 3.89-3.71 (m, 3H), 3.66 (s, 3H), 3.26 (q, J = 7.0 Hz, 2H), 0.97 (t, J = 6.9 Hz, 3H) | 1.909 A 515.2 | A |

-continued

| Ex # | Structure | Name | ¹H NMR | LC/MS Rt (min) Method M + H | hAPJ cAMP EC$_{50}$ (nM) Potency range |
|---|---|---|---|---|---|
| 233 | 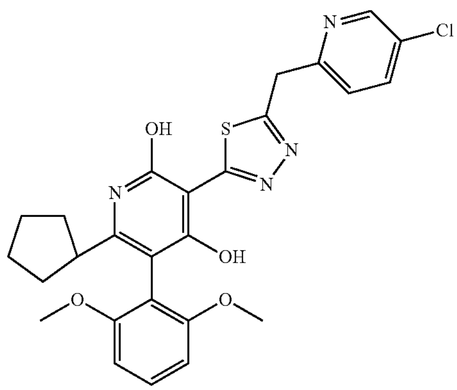 [SMILES: COc1cccc(OC)c1-c1c(C2CCCC2)nc(O)c(-c2nnc(Cc3ccc(Cl)cn3)s2)c1O] | 3-{5-[(5-chloropyridin-2-yl)methyl]-1,3,4-thiadiazol-2-yl}-6-cyclopentyl-5-(2,6-dimethoxyphenyl)pyridine-2,4-diol | 1H NMR (500 MHz, DMSO-d6) δ 8.62 (s, 1H), 7.95 (d, J = 6.3 Hz, 1H), 7.56 (d, J = 8.3 Hz, 1H), 7.35 (t, J = 8.3 Hz, 1H), 6.73 (d, J = 8.3 Hz, 2H), 4.66 (s, 2H), 3.67 (s, 6H), 2.55 (s, 9H), 1.73 (br. s., 6H), 1.66 (br. s, 3H), 1.38 (br. s., 3H) | 2.068 A 525.3 | B |
| 234 | 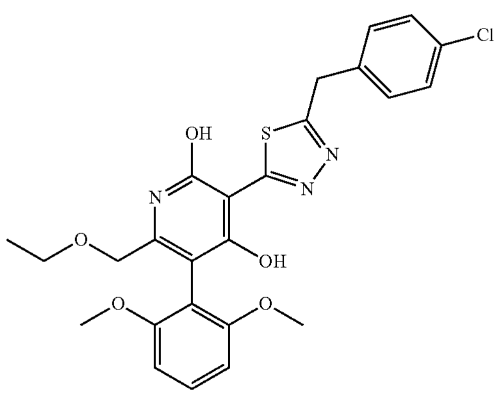 | 3-{5-[(4-chlorophenyl)methyl]-1,3,4-thiadiazol-2-yl}-5-(2,6-dimethoxyphenyl)-6-(ethoxymethyl)pyridine-2,4-diol | 1H NMR (500 MHz, DMSO-d6) δ 7.45-7.27 (m, 5H), 6.74 (d, J = 8.5 Hz, 2H), 4.49 (s, 2H), 3.99 (s, 2H), 3.68 (s, 6H), 3.26 (q, J = 6.6 Hz, 2H), 0.98 (t, J = 7.0 Hz, 3H) | 2.341 A 514.3 | B |
| 235 | 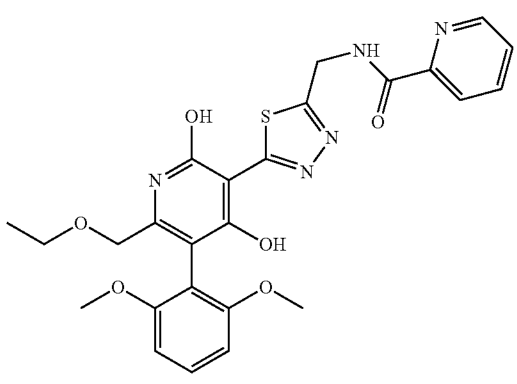 [SMILES: CCOCc1nc(O)c(-c2nnc(CNC(=O)c3ccccn3)s2)c(O)c1-c1c(OC)cccc1OC] | N-({5-[5-(2,6-dimethoxyphenyl)-6-(ethoxymethyl)-2,4-dihydroxypyridin-3-yl]-1,3,4-thiadiazol-2-yl}methyl)pyridine-2-carboxamide | 1H NMR (500 MHz, DMSO-d6) δ 9.79 (t, J = 6.0 Hz, 1H), 8.69 (d, J = 4.3 Hz, 1H), 8.14-7.95 (m, 2H), 7.76-7.53 (m, 1H), 7.37 (t, J = 8.3 Hz, 1H), 6.74 (d, J = 8.3 Hz, 2H), 4.91 (d, J = 6.0 Hz, 2H), 3.98 (s, 2H), 3.78-3.69 (m, 2H), 3.66 (s, 2H), 3.26 (q, J = 7.0 Hz, 2H), 3.16 (s, 2H), 0.97 (t, J = 6.9 Hz, 3H) | 1.656 A 524.1 | B |

| Ex # | Structure | Name | ¹H NMR | LC/MS Rt (min) Method M + H | hAPJ cAMP EC₅₀ (nM) Potency range |
|---|---|---|---|---|---|
| 236 | 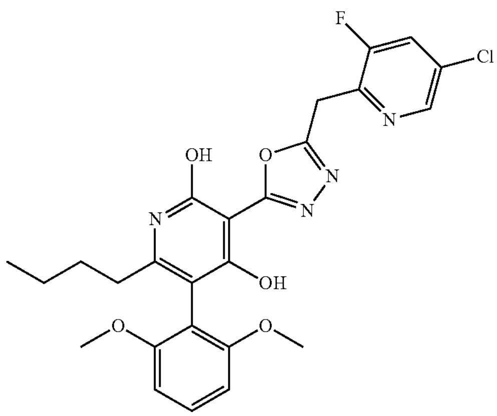 [SMILES: CCCCc1nc(O)c(-c2nnc(Cc3ncc(Cl)cc3F)o2)c(O)c1-c1c(OC)cccc1OC] | 6-butyl-3-{5-[(5-chloro-3-fluoropyridin-2-yl)methyl]-1,3,4-oxadiazol-2-yl}-5-(2,6-dimethoxyphenyl)pyridine-2,4-diol | 1H NMR (500 MHz, DMSO-d6) δ 8.49 (d, J = 1.2 Hz, 1H), 8.18 (dd, J = 9.5, 1.8 Hz, 1H), 7.36 (t, J = 8.4 Hz, 1H), 6.74 (d, J = 8.2 Hz, 2H), 4.63 (s, 2H), 3.70 (s, 6H), 2.15 (t, J = 7.6 Hz, 2H), 1.33 (quin, J = 7.5 Hz, 2H), 1.16-1.03 (m, 2H), 0.66 (t, J = 7.3 Hz, 3H) | 1.80 A 515.0 | A |
| 237 | 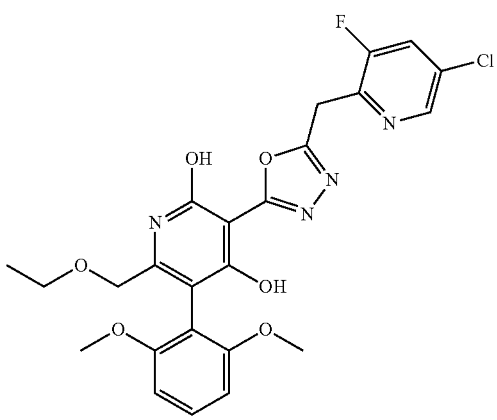 [SMILES: CCOCc1nc(O)c(-c2nnc(Cc3ncc(Cl)cc3F)o2)c(O)c1-c1c(OC)cccc1OC] | 3-{5-[(5-chloro-3-fluoropyridin-2-yl)methyl]-1,3,4-oxadiazol-2-yl}-5-(2,6-dimethoxyphenyl)-6-(ethoxymethyl)pyridine-2,4-diol | 1H NMR (500 MHz, DMSO-d6) δ 8.50 (d, J = 1.2 Hz, 1H), 8.19 (dd, J = 9.5, 1.8 Hz, 1H), 7.38 (t, J = 8.4 Hz, 1H), 6.74 (d, J = 8.5 Hz, 2H), 4.64 (s, 2H), 3.97 (s, 2H), 3.70 (s, 6H), 3.28 (q, J = 7.0 Hz, 2H), 1.00 (t, J = 7.0 Hz, 3H) | 1.69 A 517.1 | A |
| 238 | 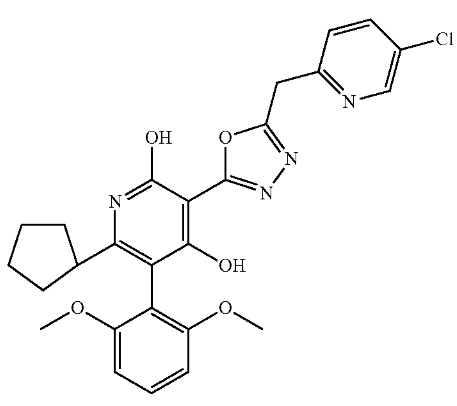 [SMILES: COc1cccc(OC)c1-c1c(C2CCCC2)nc(O)c(-c2nnc(Cc3ccc(Cl)cn3)o2)c1O] | 3-{5-[(5-chloropyridin-2-yl)methyl]-1,3,4-oxadiazol-2-yl}-6-cyclopentyl-5-(2,6-dimethoxyphenyl)pyridine-2,4-diol | 1H NMR (500 MHz, DMSO-d6) δ 8.60-8.51 (m, 1H), 7.97 (dd, J = 8.3, 2.1 Hz, 1H), 7.55 (d, J = 8.4 Hz, 1H), 7.34 (t, J = 8.4 Hz, 1H), 6.72 (d, J = 8.4 Hz, 2H), 4.58 (s, 2H), 3.68 (s, 6H), 1.71 (br. s., 6H), 1.63 (br. s., 3H), 1.37 (br. s., 2H) | 1.722 A 509.3 | A |

-continued

| Ex # | Structure | Name | ¹H NMR | LC/MS Rt (min) Method M + H | hAPJ cAMP EC₅₀ (nM) Potency range |
|---|---|---|---|---|---|
| 239 | 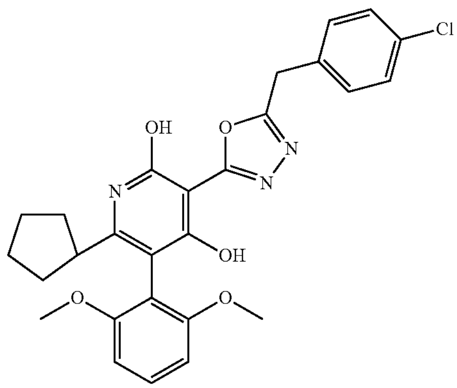 [SMILES: COc1cccc(OC)c1-c1c(C2CCCC2)nc(O)c(-c2nnc(Cc3ccc(Cl)cc3)o2)c1O] | 3-{5-[(4-chloro-phenyl)methyl]-1,3,4-oxadiazol-2-yl}-6-cyclopentyl-5-(2,6-dimethoxyphenyl)pyridine-2,4-diol | 1H NMR (500 MHz, DMSO-d6) δ 7.47-7.33 (m, 4H), 7.27 (t, J = 8.3 Hz, 1H), 6.67 (d, J = 8.2 Hz, 2H), 4.30 (br. s., 2H), 2.55 (s, 6H), 1.67 (br. s., 5H), 1.58 (br. s., 2H), 1.34 (br. s., 2H) | 1.983 A 508.1 | A |
| 240 | 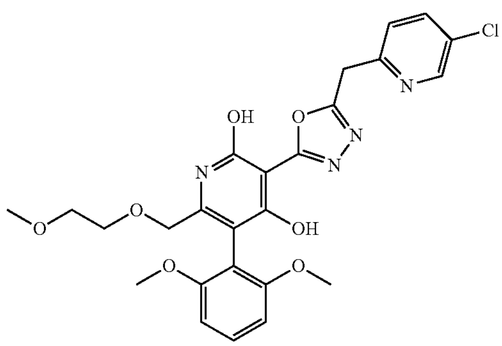 [SMILES: COCCOCc1nc(O)c(-c2nnc(Cc3ccc(Cl)cn3)o2)c(O)c1-c1c(OC)cccc1OC] | 3-{5-[(5-chloropyridin-2-yl)methyl]-1,3,4-oxadiazol-2-yl}-5-(2,6-dimethoxy-phenyl)-6-[(2-methoxyethoxy)methyl]pyridine-2,4-diol | 1H NMR (500 MHz, DMSO-d6) δ 11.37 (s, 1H), 8.57 (d, J = 2.5 Hz, 1H), 7.98 (dd, J = 8.4, 2.6 Hz, 1H), 7.56 (d, J = 8.3 Hz, 1H), 7.37 (t, J = 8.4 Hz, 1H), 6.74 (d, J = 8.5 Hz, 2H), 4.59 (s, 2H), 4.01 (s, 2H), 3.70 (s, 6H), 3.38 (dd, J = 6.5, 3.4 Hz, 2H), 3.36-3.32 (m, 2H), 3.19 (s, 3H) | 1.25 D 529.3 | A |
| 242 | 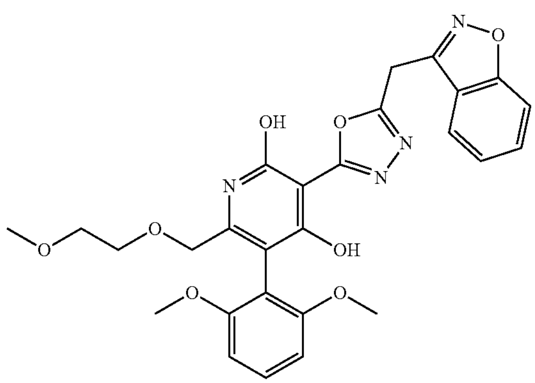 [SMILES: COCCOCc1nc(O)c(-c2nnc(Cc3noc4ccccc34)o2)c(O)c1-c1c(OC)cccc1OC] | 3-{5-[(1,2-benzoxazol-3-yl)methyl]-1,3,4-oxadiazol-2-yl}-5-(2,6-dimethoxy-phenyl)-6-[(2-methoxyethoxy)methyl]pyridine-2,4-diol | 1H NMR (500 MHz, DMSO-d6) δ 11.79 (br. s., 1H), 11.41 (s, 1H), 7.97 (d, J = 8.0 Hz, 1H), 7.80 (d, J = 8.8 Hz, 1H), 7.71 (d, J = 7.2 Hz, 1H), 7.43 (t, J = 7.3 Hz, 1H), 7.40-7.32 (m, 1H), 6.73 (d, J = 8.5 Hz, 2H), 4.94 (s, 2H), 4.01 (s, 2H), 3.69 (s, 6H), 3.38 (br. s., 4H), 3.19 (s, 3H) | 1.31 D 535.2 | B |
| 243 | 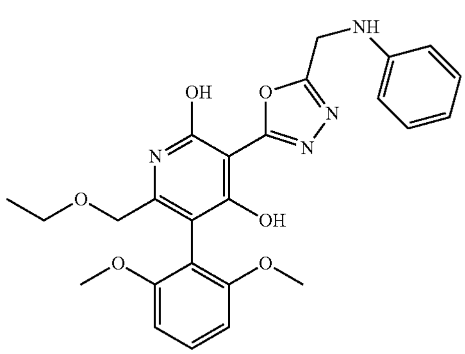 [SMILES: CCOCc1nc(O)c(-c2nnc(CNc3ccccc3)o2)c(O)c1-c1c(OC)cccc1OC] | 5-(2,6-dimethoxy-phenyl)-6-(ethoxymethyl)-3-{5-[(phenyl-amino)methyl]-1,3,4-oxadiazol-2-yl}pyridine-2,4-diol | 1H NMR (500 MHz, DMSO-d6) δ 7.35 (t, J = 8.2 Hz, 1H), 7.11 (t, J = 7.8 Hz, 2H), 6.77-6.66 (m, 4H), 6.61 (t, J = 7.2 Hz, 1H), 4.60 (br. s., 2H), 3.94 (s, 2H), 3.69 (s, 6H), 3.35-3.22 (m, 2H), 1.00 (t, J = 7.0 Hz, 3H) | 1.669 A 479.1 | B |

| Ex # | Structure | Name | ¹H NMR | LC/MS Rt (min) Method M + H | hAPJ cAMP EC$_{50}$ (nM) Potency range |
|---|---|---|---|---|---|
| 244 | 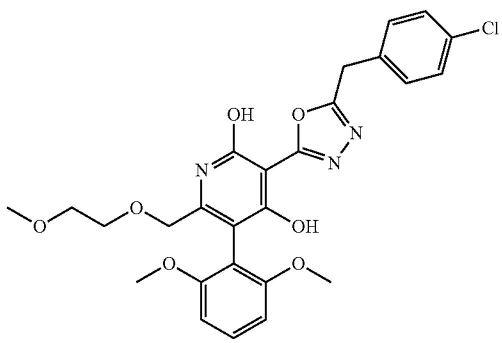 [SMILES: COCCOCc1nc(O)c(-c2nnc(Cc3ccc(Cl)cc3)o2)c(O)c1-c1c(OC)cccc1OC] | 3-{5-[(4-chloro-phenyl)methyl]-1,3,4-oxadiazol-2-yl}-5-(2,6-dimethoxy-phenyl)-6-[(2-methoxy-ethoxy)methyl]pyridine-2,4-diol | 1H NMR (500 MHz, DMSO-d6) δ 11.35 (s, 1H), 7.52-7.31 (m, 4H), 6.74 (d, J = 8.5 Hz, 2H), 4.40 (s, 2H), 4.01 (s, 3H), 3.70 (s, 6H), 3.41-3.30 (m, 4H), 3.19 (s, 3H) | 2.050 E 526.3 | B |
| 246 | 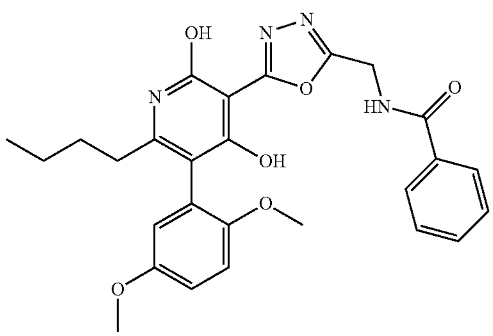 [SMILES: CCCCc1nc(O)c(-c2nnc(CNC(=O)c3ccccc3)o2)c(O)c1-c1cc(OC)ccc1OC] | N-({5-[6-butyl-5-(2,5-dimethoxy-phenyl)-2,4-dihydroxy-pyridin-3-yl]-1,3,4-oxadiazol-2-yl}methyl)benzamide | 1H NMR (500 MHz, DMSO-d6) δ 9.35 (br. s., 1H), 7.88 (d, J = 7.5 Hz, 2H), 7.64-7.41 (m, 3H), 6.97-6.81 (m, 2H), 6.63 (br, s., 1H), 4.71 (d, J = 4.5 Hz, 2H), 2.55 (s, 6H), 2.26-1.97 (m, 2H), 1.42-1.28 (m, 2H), 1.16-1.02 (m, 2H), 0.66 (t, J = 7.2 Hz, 3H) | 1.51 A 505.0 | A |
| 247 | 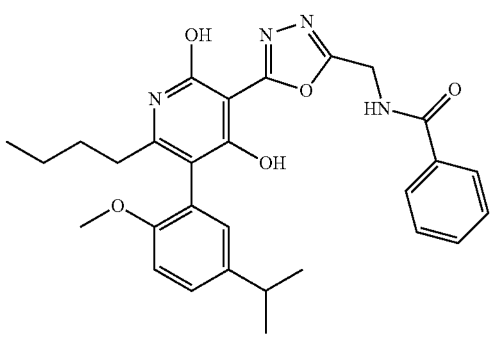 [SMILES: CCCCc1nc(O)c(-c2nnc(CNC(=O)c3ccccc3)o2)c(O)c1-c1cc(C(C)C)ccc1OC] | N-[(5-{6-butyl-2,4-dihydroxy-5-[2-methoxy-5-(propan-2-yl)phenyl]pyridin-3-yl}-1,3,4-oxadiazol-2-yl)methyl]benzamide | 1H NMR (500 MHz, DMSO-d6) δ 9.34 (t, J = 5.3 Hz, 1H), 7.90 (d, J = 7.6 Hz, 2H), 7.63-7.45 (m, 3H), 7.22 (d, J = 8.1 Hz, 1H), 7.07-6.90 (m, 2H), 4.78 (d, J = 5.2 Hz, 2H), 3.67 (s, 3H), 2.92-2.78 (m, 1H), 2.28-2.06 (m, 2H), 1.44-1.31 (m, 2H), 1.18 (t, J = 5.9 Hz, 6H), 1.12-1.02 (m, 2H), 0.65 (t, J = 7.2 Hz, 3H) | 2.09 A 517.1 | A |
| 248 | 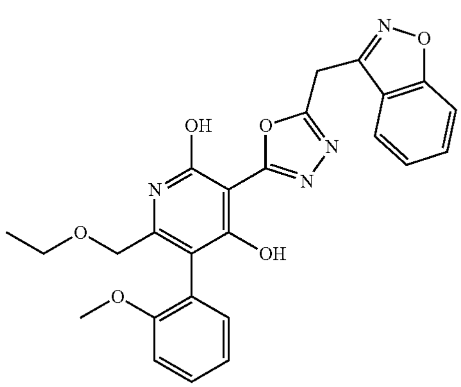 [SMILES: CCOCc1nc(O)c(-c2nnc(Cc3noc4ccccc34)o2)c(O)c1-c1ccccc1OC] | 3-{5-[(1,2-benzoxazol-3-yl)methyl]-1,3,4-oxadiazol-2-yl}-6-(ethoxymethyl)-5-(2-methoxyphenyl)pyridine-2,4-diol | 1H NMR (500 MHz, DMSO-d6) δ 7.95 (d, J = 7.9 Hz, 1H), 7.78 (d, J = 8.2 Hz, 1H), 7.74-7.65 (m, 1H), 7.46-7.35 (m, 2H), 7.19-7.12 (m, 1H), 7.08 (d, J = 8.5 Hz, 1H), 7.01-6.93 (m, 1H), 4.92 (s, 2H), 4.09-3.89 (m, 2H), 3.70 (s, 3H), 3.28 (quin, J = 6.7 Hz, 2H), 0.99 (t, J = 7.0 Hz, 4H) | 1.48 A 475.0 | A |

| Ex # | Structure | Name | ¹H NMR | LC/MS Rt (min) Method M + H | hAPJ cAMP EC₅₀ (nM) Potency range |
|---|---|---|---|---|---|
| 249 | 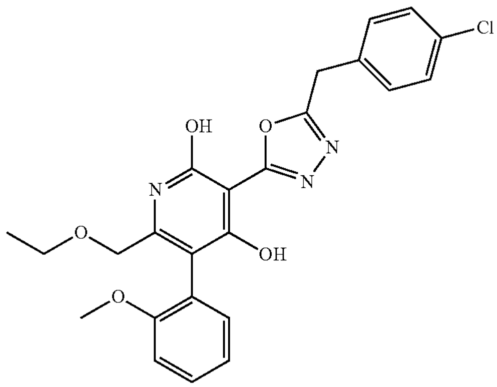 [SMILES: CCOCc1nc(O)c(-c2nnc(Cc3ccc(Cl)cc3)o2)c(O)c1-c1ccccc1OC] | 3-{5-[(4-chloro-phenyl)methyl]-1,3,4-oxadiazol-2-yl}-6-(ethoxy-methyl)-5-(2-methoxy-phenyl)pyridine-2,4-diol | 1H NMR (500 MHz, DMSO-d6) δ 7.50-7.31 (m, 5H), 7.18-6.89 (m, 3H), 4.36 (s, 2H), 4.09-3.88 (m, 2H), 3.70 (s, 3H), 3.34-3.11 (m, 2H), 0.99 (t, J = 6.9 Hz, 3H) | 1.71 A 468.2 | A |
| 250 | 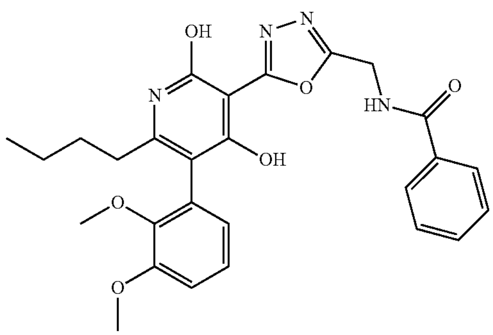 [SMILES: CCCCc1nc(O)c(-c2nnc(CNC(=O)c3ccccc3)o2)c(O)c1-c1cccc(OC)c1OC] | N-({5-[6-butyl-5-(2,3-dimethoxy-phenyl)-2,4-dihydroxy-pyridin-3-yl]-1,3,4-oxadiazol-2-yl}methyl)benzamide | 1H NMR (500 MHz, DMSO-d6) δ 9.33 (br. s., 1H), 7.90 (d, J = 7.4 Hz, 2H), 7.60-7.46 (m, 4H), 7.12-6.95 (m, 2H), 6.66 (d, J = 6.6 Hz, 1H), 4.72 (d, J = 5.0 Hz, 2H), 3.80 (s, 3H), 2.55 (s, 3H), 2.18-2.04 (m, 2H), 1.91 (s, 2H), 1.37 (d, J = 6.9 Hz, 2H), 1.15-1.03 (m, 3H) | 1.48 A 505.4 | A |
| 251 | 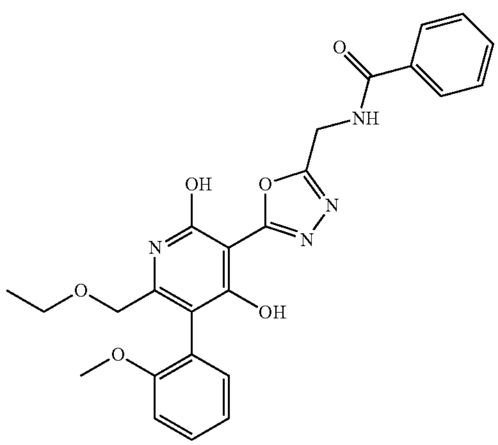 [SMILES: CCOCc1nc(O)c(-c2nnc(CNC(=O)c3ccccc3)o2)c(O)c1-c1ccccc1OC] | N-({5-[6-(ethoxy-methyl)-2,4-dihydroxy-5-(2-methoxyphenyl)pyridin-3-yl]-1,3,4-oxadiazol-2-yl}methyl)benzamide | 1H NMR (500 MHz, DMSO-d6) δ 9.26 (t, J = 5.5 Hz, 1H), 7.90 (d, J = 7.6 Hz, 2H), 7.58-7.45 (m, 4H), 7.30-7.21 (m, 1H), 7.06-6.87 (m, 3H), 4.68 (d, J = 5.5 Hz, 2H), 3.98-3.79 (m, 3H), 3.67 (s, 3H), 3.27 (q, J = 6.6 Hz, 2H), 1.07-0.90 (m, 3H) | 1.30 A 477.0 | A |
| 252 | 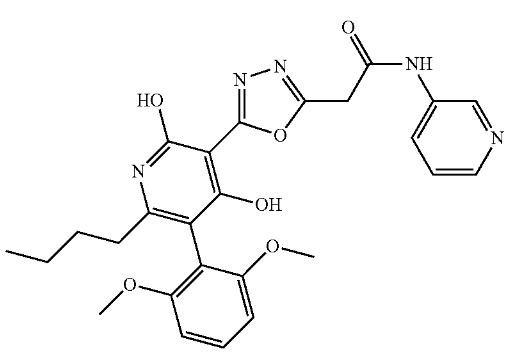 [SMILES: CCCCc1nc(O)c(-c2nnc(CC(=O)Nc3cccnc3)o2)c(O)c1-c1c(OC)cccc1OC] | 2-{5-[6-butyl-5-(2,6-dimethoxy-phenyl)-2,4-dihydroxy-pyridin-3-yl]-1,3,4-oxadiazol-2-yl}-N-(pyridin-3-yl)acetamide | 1H NMR (500 MHz, DMSO-d6) δ 10.78 (NH), 8.79 (br. s., 1H), 8.34 (br. s., 1H), 8.07 (d, J = 7.9 Hz, 1H), 7.48-7.41 (m, 1H), 7.37 (t, J = 8.5 Hz, 1H), 6.74 (d, J = 8.5 Hz, 2H), 4.28 (s, 2H), 3.70 (s, 6H), 2.16 (t, J = 7.2 Hz, 2H), 1.42-1.27 (m, 2H), 1.15-1.02 (m, 2H), 0.66 (t, J = 7.2 Hz, 3H) | 1.40 A 506.2 | A |

-continued

| Ex # | Structure | Name | ¹H NMR | LC/MS Rt (min) Method M + H | hAPJ cAMP EC$_{50}$ (nM) Potency range |
|---|---|---|---|---|---|
| 253 | 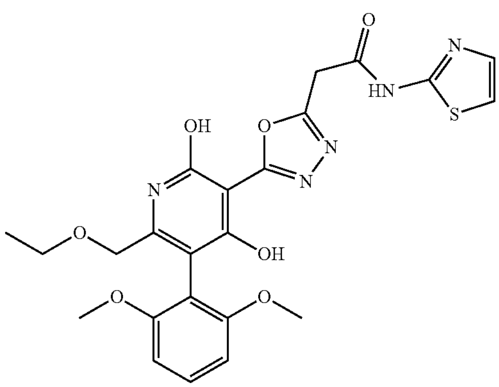 [SMILES: CCOCc1nc(O)c(-c2nnc(CC(=O)Nc3nccs3)o2)c(O)c1-c1c(OC)cccc1OC] | 2-{5-[5-(2,6-dimethoxyphenyl)-6-(ethoxymethyl)-2,4-dihydroxypyridin-3-yl]-1,3,4-oxadiazol-2-yl}-N-(1,3-thiazol-2-yl)acetamide | 1H NMR (500 MHz, DMSO-d6) δ 7.53 (d, J = 3.0 Hz, 1H), 7.38 (t, J = 8.4 Hz, 1H), 7.29 (d, J = 3.0 Hz, 1H), 6.75 (d, J = 8.3 Hz, 2H), 4.37 (s, 2H), 3.97 (s, 2H), 3.71 (s, 6H), 3.28 (q, J = 6.9 Hz, 2H), 1.00 (t, J = 7.0 Hz, 3H). | 1.18 C 514.1 | A |
| 254 | 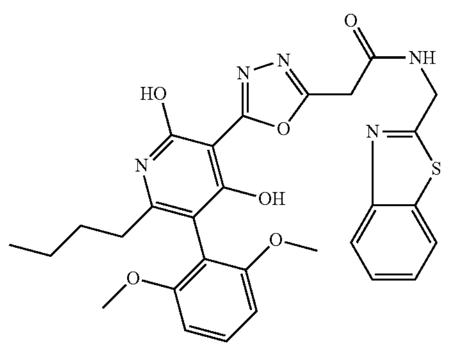 [SMILES: CCCCc1nc(O)c(-c2nnc(CC(=O)NCc3nc4ccccc4s3)o2)c(O)c1-c1c(OC)cccc1OC] | N-[(1,3-benzothiazol-2-yl)methyl]-2-{5-[6-butyl-5-(2,6-dimethoxyphenyl)-2,4-dihydroxypyridin-3-yl]-1,3,4-oxadiazol-2-yl}acetamide | 1H NMR (500 MHz, DMSO-d6) δ 9.43-9.30 (NH), 8.07 (d, J = 7.9 Hz, 1H), 7.97 (d, J = 7.9 Hz, 1H), 7.55-7.50 (m, 1H), 7.44 (t, J = 7.5 Hz, 1H), 7.36 (t, J = 8.2 Hz, 1H), 6.74 (d, J = 8.5 Hz, 2H), 4.76 (d, J = 5.8 Hz, 2H), 4.11 (s, 2H), 3.69 (s, 6H), 2.16 (t, J = 7.5 Hz, 2H), 1.44-1.29 (m, 2H), 1.16-1.03 (m, 2H), 0.67 (t, J = 7.3 Hz, 3H) | 1.617 A 576.2 | A |
| 255 | 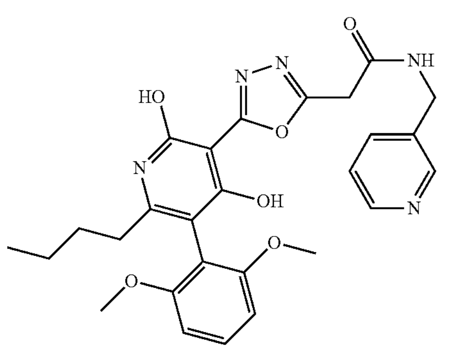 [SMILES: CCCCc1nc(O)c(-c2nnc(CC(=O)NCc3cccnc3)o2)c(O)c1-c1c(OC)cccc1OC] | 2-{5-[6-butyl-5-(2,6-dimethoxyphenyl)-2,4-dihydroxypyridin-3-yl]-1,3,4-oxadiazol-2-yl}-N-[(pyridin-3-yl)methyl]acetamide | 1H NMR (500 MHz, DMSO-d6) δ 8.92 (NH), 8.53 (s, 1H), 8.48 (d, J = 4.3 Hz, 1H), 7.74 (d, J = 7.3 Hz, 1H), 7.44-7.26 (m, 2H), 6.73 (d, J = 8.5 Hz, 2H), 4.38 (d, J = 5.5 Hz, 2H), 4.03 (s, 2H), 3.69 (s, 6H), 2.14 (d, J = 7.3 Hz, 2H), 1.41-1.27 (m, 2H), 1.13-1.04 (m, 2H), 0.67 (t, J = 7.2 Hz, 3H) | 1.358 A 520.2 | A |
| 256 | 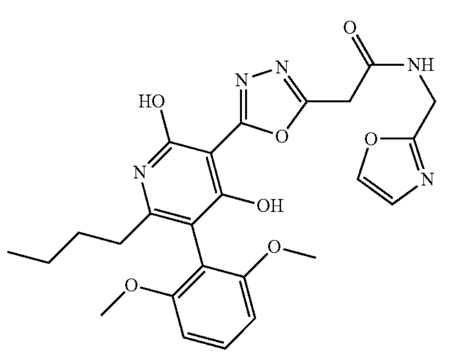 [SMILES: CCCCc1nc(O)c(-c2nnc(CC(=O)NCc3ncco3)o2)c(O)c1-c1c(OC)cccc1OC] | 2-{5-[6-butyl-5-(2,6-dimethoxyphenyl)-2,4-dihydroxypyridin-3-yl]-1,3,4-oxadiazol-2-yl}-N-[(1,3-oxazol-2-yl)methyl]acetamide | 1H NMR (500 MHz, DMSO-d6) δ 9.03 (NH), 8.06 (s, 1H), 7.36 (t, J = 8.4 Hz, 1H), 7.18 (s, 1H), 6.74 (d, J = 8.5 Hz, 2H), 4.46 (d, J = 5.8 Hz, 2H), 4.04 (s, 2H), 3.70 (s, 6H), 2.15 (br. s, 2H), 1.40-1.29 (m, 2H), 1.15-1.03 (m, 2H), 0.67 (t, J = 7.3 Hz, 3H) | 1.596 B 510.2 | A |

| Ex # | Structure | Name | ¹H NMR | LC/MS Rt (min) Method M + H | hAPJ cAMP EC$_{50}$ (nM) Potency range |
|---|---|---|---|---|---|
| 257 | 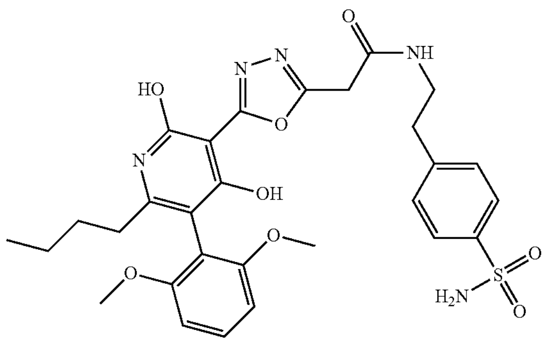 [SMILES: CCCCc1nc(O)c(-c2nnc(CC(=O)NCCc3ccc(S(N)(=O)=O)cc3)o2)c(O)c1-c1c(OC)cccc1OC] | 2-{5-[6-butyl-5-(2,6-dimethoxy-phenyl)-2,4-dihydroxy-pyridin-3-yl]-1,3,4-oxadiazol-2-yl}-N-[2-(4-sulfamoyl-phenyl)ethyl]acetamide | 1H NMR (500 MHz, DMSO-d6) δ 8.47 (NH), 7.77 (d, J = 7.9 Hz, 2H), 7.45 (d, J = 7.6 Hz, 2H), 7.39-7.28 (m, 1H), 6.78-6.63 (m, 2H), 3.93 (s, 2H), 3.75-3.64 (m, 6H), 3.54-3.32 (m, 2H), 2.85 (t, J = 7.0 Hz, 2H), 2.23-2.11 (m, 2H), 1.41-1.25 (m, 2H), 1.16-1.01 (m, 2H), 0.66 (t, J = 7.2 Hz, 3H) | 1.862 A 612.1 | A |
| 258 | 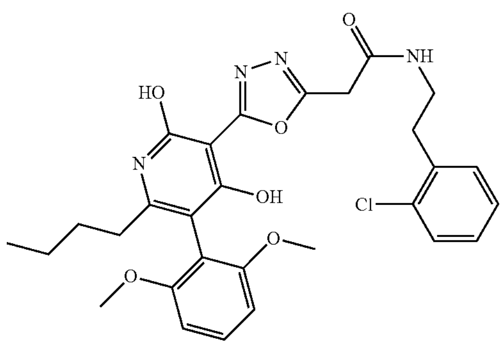 [SMILES: CCCCc1nc(O)c(-c2nnc(CC(=O)NCCc3ccccc3Cl)o2)c(O)c1-c1c(OC)cccc1OC] | 2-{5-[6-butyl-5-(2,6-dimethoxy-phenyl)-2,4-dihydroxy-pyridin-3-yl]-1,3,4-oxadiazol-2-yl}-N-[2-(2-chlorophenyl)ethyl]acetamide | 1H NMR (500 MHz, DMSO-d6) δ 8.48 (NH), 7.43 (d, J = 7.6 Hz, 1H), 7.35 (d, J = 5.2 Hz, 2H), 7.32-7.23 (m, 2H), 6.74 (d, J = 8.2 Hz, 2H), 3.92 (s, 2H), 3.70 (s, 6H), 3.36 (d, J = 6.4 Hz, 2H), 2.89 (t, J = 6.9 Hz, 2H), 2.15 (t, J = 7.3 Hz, 2H), 1.40-1.27 (m, 2H), 1.19-1.02 (m, 2H), 0.67 (t, J = 7.2 Hz, 3H) | 1.806 A 567.1 | A |
| 259 | 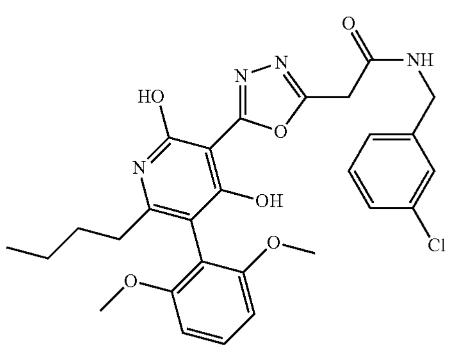 [SMILES: CCCCc1nc(O)c(-c2nnc(CC(=O)NCc3cccc(Cl)c3)o2)c(O)c1-c1c(OC)cccc1OC] | 2-{5-[6-butyl-5-(2,6-dimethoxy-phenyl)-2,4-dihydroxy-pyridin-3-yl]-1,3,4-oxadiazol-2-yl}-N-[(3-chlorophenyl)methyl]acetamide | 1H NMR (500 MHz, DMSO-d6) δ 8.90 (NH), 7.43-7.21 (m, 5H), 6.73 (d, J = 8.5 Hz, 2H), 4.35 (d, J = 5.5 Hz, 2H), 4.05 (s, 2H), 3.69 (s, 6H), 2.15 (t, J = 7.0 Hz, 2H), 1.43-1.27 (m, 2H), 1.18-0.99 (m, 2H), 0.67 (t, J = 7.2 Hz, 3H) | 1.749 A 553.1 | A |
| 260 | 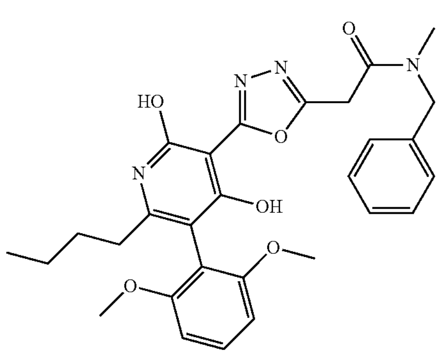 [SMILES: CCCCc1nc(O)c(-c2nnc(CC(=O)N(C)Cc3ccccc3)o2)c(O)c1-c1c(OC)cccc1OC] | N-benzyl-2-{5-[6-butyl-5-(2,6-dimethoxy-phenyl)-2,4-dihydroxy-pyridin-3-yl]-1,3,4-oxadiazol-2-yl}-N-methylacetamide | 1H NMR (500 MHz, DMSO-d6) δ 7.57-7.23 (m, 6H), 6.72 (d, J = 8.2 Hz, 2H), 4.55 (s, 2H), 4.35 (s, 2H), 3.69 (s, 6H), 2.12 (t, J = 7.3 Hz, 2H), 1.92 (s, 3H), 1.39-1.26 (m, 2H), 1.14-1.00 (m, 2H), 0.67 (t, J = 7.2 Hz, 3H) | 1.701 A 533.2 | A |

| Ex # | Structure | Name | ¹H NMR | LC/MS Rt (min) Method M + H | hAPJ cAMP EC₅₀ (nM) Potency range |
|---|---|---|---|---|---|
| 261 | 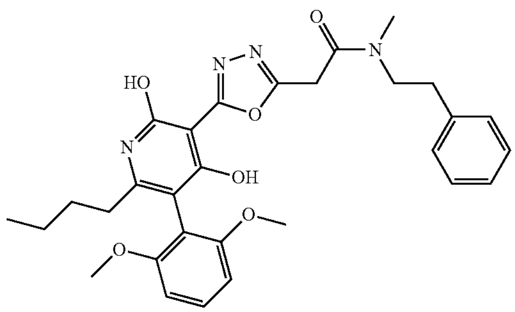 [SMILES: CCCCc1nc(O)c(-c2nnc(CC(=O)N(C)CCc3ccccc3)o2)c(O)c1-c1c(OC)cccc1OC] | 2-{5-[6-butyl-5-(2,6-dimethoxy-phenyl)-2,4-dihydroxy-pyridin-3-yl]-1,3,4-oxadiazol-2-yl}-N-methyl-N-(2-phenyl-ethyl)acetamide | 1H NMR (500 MHz, DMSO-d6) δ 7.43-7.15 (m, 6H), 6.74 (d, J = 7.6 Hz, 2H), 4.04 (s, 2H), 3.70 (br. S., 6H), 2.93 (t, J = 7.3 Hz, 2H), 2.79 (t, J = 7.3 Hz, 2H), 2.17 (m, 2H), 1.34 (m, 2H), 1.09 (d, J = 6.7 Hz, 2H), 0.66 (t, J = 7.2 Hz, 3H) | 1.778 A 546.9 | A |
| 262 | 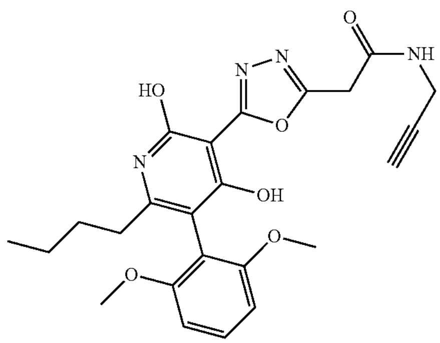 [SMILES: C#CCNC(=O)Cc1nnc(-c2c(O)nc(CCCC)c(-c3c(OC)cccc3OC)c2O)o1] | 2-{5-[6-butyl-5-(2,6-dimethoxy-phenyl)-2,4-dihydroxy-pyridin-3-yl]-1,3,4-oxadiazol-2-yl}-N-(prop-2-yn-1-yl)acetamide | 1H NMR (500 MHz, DMSO-d6) δ 8.81 (NH), 7.37 (t, J = 8.2 Hz, 1H), 6.74 (d, J = 8.5 Hz, 2H), 4.00 (d, J = 1.0 Hz, 2H), 3.93 (s, 2H), 3.70 (s, 6H), 3.18 (s, 1H), 2.16 (t, J = 7.5 Hz, 2H), 1.40-1.28 (m, 2H), 1.14-1.04 (m, 2H), 0.67 (t, J = 7.2 Hz, 3H) | 1.729 A 467.1 | A |
| 263 | 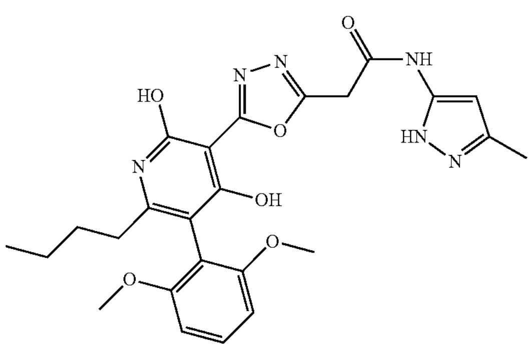 [SMILES: CCCCc1nc(O)c(-c2nnc(CC(=O)Nc3cc(C)n[nH]3)o2)c(O)c1-c1c(OC)cccc1OC] | 2-{5-[6-butyl-5-(2,6-dimethoxy-phenyl)-2,4-dihydroxy-pyridin-3-yl]-1,3,4-oxadiazol-2-yl}-N-(3-methyl-1H-pyrazol-5-yl)acetamide | 1H NMR (500 MHz, DMSO-d6) δ 7.36 (t, J = 8.3 Hz, 1H), 6.73 (d, J = 8.3 Hz, 2H), 6.24 (br. s., 1H), 4.15 (s, 2H), 3.70 (s, 6H), 2.20 (s, 3H), 2.15 (t, J = 1.0 Hz, 2H), 1.36-1.27 (m, 2H), 1.10-1.01 (m, 2H), 0.66 (t, J = 7.3 Hz, 3H) | 1.736 A 509.1 | A |
| 264 | 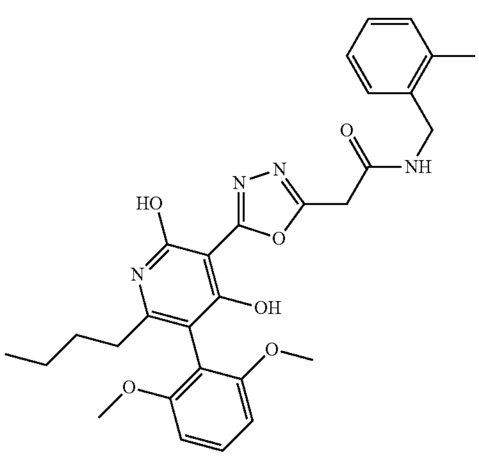 [SMILES: CCCCc1nc(O)c(-c2nnc(CC(=O)NCc3ccccc3C)o2)c(O)c1-c1c(OC)cccc1OC] | 2-{5-[6-butyl-5-(2,6-dimethoxy-phenyl)-2,4-dihydroxy-pyridin-3-yl]-1,3,4-oxadiazol-2-yl}-N-[(2-methylphenyl)methyl]acetamide | 1H NMR (500 MHz, DMSO-d6) δ 8.73 (NH), 7.37 (t, J = 8.2 Hz, 1H), 7.32-7.27 (m, 1H), 7.23-7.12 (m, 3H), 6.74 (d, J = 8.5 Hz, 2H), 4.32 (d, J = 5.2 Hz, 2H), 4.04 (s, 2H), 3.70 (s, 6H), 2.29 (s, 3H), 2.16 (t, J = 7.5 Hz, 2H), 1.37-1.26 (m, 2H), 1.17-0.98 (m, 2H), 0.67 (t, J = 7.2 Hz, 3H) | 1.743 A 533.2 | A |

| Ex # | Structure | Name | ¹H NMR | LC/MS Rt (min) Method M + H | hAPJ cAMP EC$_{50}$ (nM) Potency range |
|---|---|---|---|---|---|
| 265 | 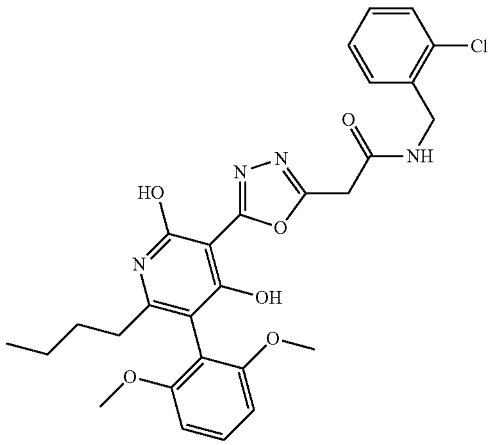 [SMILES: CCCCc1nc(O)c(-c2nnc(CC(=O)NCc3ccccc3Cl)o2)c(O)c1-c1c(OC)cccc1OC] | 2-{5-[6-butyl-5-(2,6-dimethoxy-phenyl)-2,4-dihydroxy-pyridin-3-yl]-1,3,4-oxadiazol-2-yl}-N-[(2-chlorophenyl)methyl]acetamide | 1H NMR (500 MHz, DMSO-d6) δ 8.90 (NH), 7.46 (d, J = 7.6 Hz, 2H), 7.40-7.25 (m, 3H), 6.74 (d, J = 8.2 Hz, 2H), 4.41 (d, J = 5.8 Hz, 2H), 4.08 (s, 2H), 3.70 (s, 5H), 2.16 (t, J = 7.5 Hz, 2H), 1.39-1.28 (m, 2H), 1.15-0.99 (m, 2H), 0.67 (t, J = 7.2 Hz, 3H) | 2.009 A 553.1 | A |
| 266 | 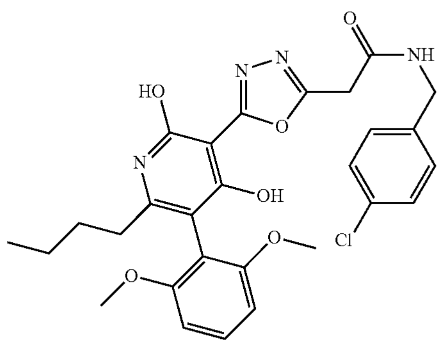 [SMILES: CCCCc1nc(O)c(-c2nnc(CC(=O)NCc3ccc(Cl)cc3)o2)c(O)c1-c1c(OC)cccc1OC] | 2-{5-[6-butyl-5-(2,6-dimethoxy-phenyl)-2,4-dihydroxypyridin-3-yl]-1,3,4-oxadiazol-2-yl}-N-[(4-chloro-phenyl)methyl]acetamide | 1H NMR (500 MHz, DMSO-d6) δ 8.90 (NH), 7.49-7.30 (m, 5H), 6.74 (d, J = 8.2 Hz, 2H), 4.33 (d, J = 5.5 Hz, 2H), 4.04 (s, 2H), 3.70 (s, 6H), 2.18 (t, J = 1.0 Hz, 2H), 1.43-1.28 (m, J = 7.0 Hz, 2H), 1.15-1.03 (m, J = 7.0 Hz, 2H), 0.67 (t, J = 7.2 Hz, 3H) | 1.750 A 553.3 | A |
| 267 | 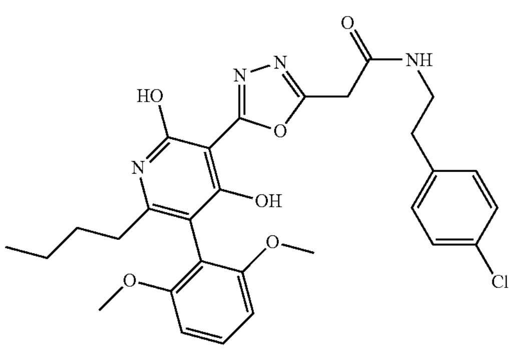 [SMILES: CCCCc1nc(O)c(-c2nnc(CC(=O)NCCc3ccc(Cl)cc3)o2)c(O)c1-c1c(OC)cccc1OC] | 2-{5-[6-butyl-5-(2,6-dimethoxy-phenyl)-2,4-dihydroxy-pyridin-3-yl]-1,3,4-oxadiazol-2-yl}-N-[2-(4-chlorophenyl)ethyl]acetamide | 1H NMR (500 MHz, DMSO-d6) δ 8.41 (NH), 7.35 (d, J = 7.9 Hz, 3H), 7.27 (d, J = 7.9 Hz, 2H), 6.74 (d, J = 8.5 Hz, 2H), 3.92 (br. s., 2H), 3.70 (s, 6H), 3.33 (q, J = 6.1 Hz, 2H), 2.75 (t, J = 6.7 Hz, 2H), 2.16 (t, J = 7.2 Hz, 2H), 1.59-1.49 (m, J = 10.7 Hz, 2H), 1.39-1.30 (m, 2H), 0.66 (t, J = 7.3 Hz, 3H) | 1.834 A 567.1 | A |
| 268 | 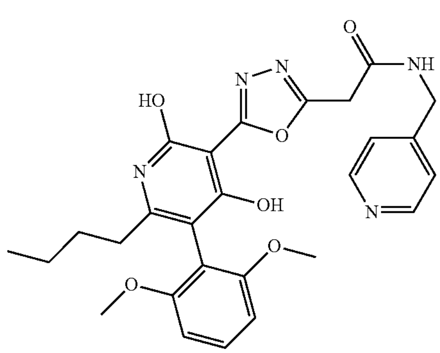 [SMILES: CCCCc1nc(O)c(-c2nnc(CC(=O)NCc3ccncc3)o2)c(O)c1-c1c(OC)cccc1OC] | 2-{5-[6-butyl-5-(2,6-dimethoxy-phenyl)-2,4-dihydroxypyridin-3-yl]-1,3,4-oxadiazol-2-yl}-N-[(pyridin-4-yl)methyl]acetamide | 1H NMR (500 MHz, DMSO-d6) δ 8.99 (NH), 8.51 (d, J = 4.9 Hz, 2H), 7.40-7.23 (m, 3H), 6.71 (d, J = 8.2 Hz, 2H), 4.37 (d, J = 5.8 Hz, 2H), 4.04 (s, 2H), 3.68 (s, 6H), 2.11 (t, J = 7.0 Hz, 2H), 1.38-1.27 (m, J = 7.5, 7.5 Hz, 2H), 1.16-1.03 (m, 2H), 0.66 (t, J = 7.2 Hz, 3H) | 1.337 A 520.2 | A |

-continued

| Ex # | Structure | Name | ¹H NMR | LC/MS Rt (min) Method M + H | hAPJ cAMP EC$_{50}$ (nM) Potency range |
|---|---|---|---|---|---|
| 269 | 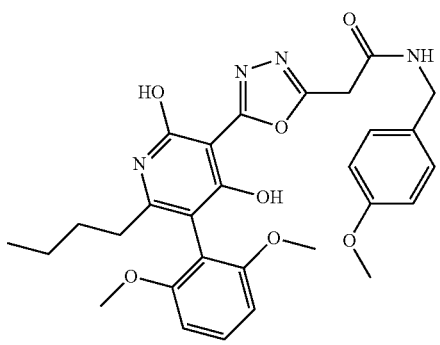 [SMILES: CCCCc1nc(O)c(-c2nnc(CC(=O)NCc3ccc(OC)cc3)o2)c(O)c1-c1c(OC)cccc1OC] | 2-{5-[6-butyl-5-(2,6-dimethoxy-phenyl)-2,4-dihydroxy-pyridin-3-yl]-1,3,4-oxadiazol-2-yl}-N-[(4-methoxyphenyl)methyl]acetamide | 1H NMR (500 MHz, DMSO-d6) δ 8.77 (NH), 7.37 (t, J = 8.2 Hz, 1H), 7.24 (d, J = 8.2 Hz, 2H), 6.91 (d, J = 8.2 Hz, 2H), 6.74 (d, J = 8.2 Hz, 2H), 4.27 (d, J = 5 5 Hz, 2H), 4.05-3.96 (m, 2H), 3.74 (s, 3H), 3.70 (s, 6H), 2.16 (t, J = 7.5 Hz, 2H), 1.43-1.29 (m, J = 7.3, 7.3 Hz, 2H), 1.14-1.04 (m, 2H), 0.67 (t, J = 7.3 Hz, 3H) | 1.701 A 549.1 | A |
| 270 | 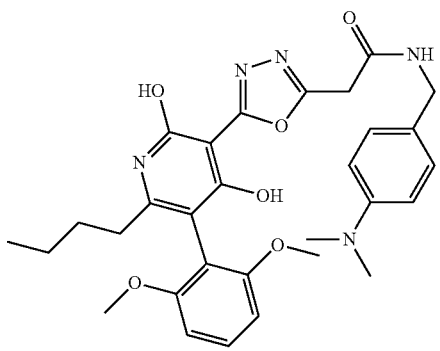 [SMILES: CCCCc1nc(O)c(-c2nnc(CC(=O)NCc3ccc(N(C)C)cc3)o2)c(O)c1-c1c(OC)cccc1OC] | 2-{5-[6-butyl-5-(2,6-dimethoxy-phenyl)-2,4-dihydroxy-pyridin-3-yl]-1,3,4-oxadiazol-2-yl}-N-{[4-(dimethylamino)phenyl]methyl}acetamide | 1H NMR (500 MHz, DMSO-d6) δ 8.68 (NH), 7.36 (t, J = 8.4 Hz, 1H), 7.13 (d, J = 7.9 Hz, 2H), 6.80-6.61 (m, J = 17.2, 8.1 Hz, 4H), 4.21 (d, J = 5.2 Hz, 2H), 3.98 (s, 2H), 3.70 (s, 6H), 2.87 (s, 6H), 2.16 (t, J = 7.3 Hz, 2H), 1.38-1.28 (m, 2H), 1.14-1.05 (m, 2H), 0.67 (t, J = 7.2 Hz, 3H) | 1.694 A 562.2 | A |
| 271 | 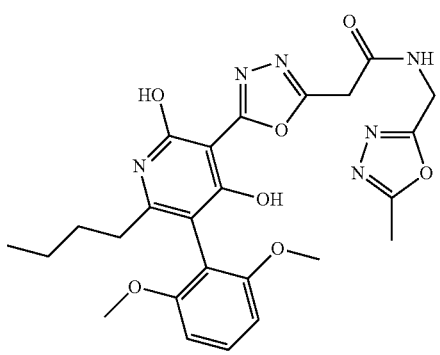 [SMILES: CCCCc1nc(O)c(-c2nnc(CC(=O)NCc3nnc(C)o3)o2)c(O)c1-c1c(OC)cccc1OC] | 2-{5-[6-butyl-5-(2,6-dimethoxy-phenyl)-2,4-dihydroxy-pyridin-3-yl]-1,3,4-oxadiazol-2-yl}-N-[(5-methyl-1,3,4-oxadiazol-2-yl)methyl]acetamide | 1H NMR (500 MHz, DMSO-d6) δ 9.10 (NH), 7.37 (t, J = 8.2 Hz, 1H), 6.74 (d, J = 8.2 Hz, 2H), 4.54 (d, J = 5.5 Hz, 2H), 4.05 (s, 2H), 3.69 (s, 6H), 2.48 (s, 3H), 2.16 (t, J = 7.5 Hz, 2H), 1.38-1.27 (m, 2H), 1.15-0.99 (m, 3H), 0.66 (t, J = 7.2 Hz, 4H) | 1.652 A 525.2 | A |
| 272 | 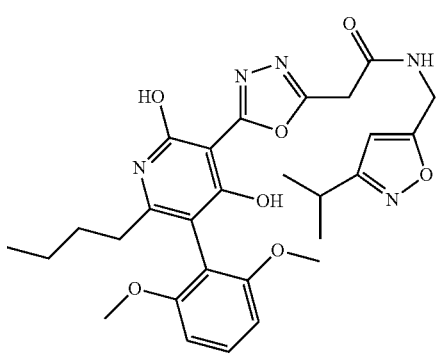 [SMILES: CCCCc1nc(O)c(-c2nnc(CC(=O)NCc3cc(C(C)C)no3)o2)c(O)c1-c1c(OC)cccc1OC] | 2-{5-[6-butyl-5-(2,6-dimethoxy-phenyl)-2,4-dihydroxy-pyridin-3-yl]-1,3,4-oxadiazol-2-yl}-N-{[3-(propan-2-yl)-1,2-oxazol-5-yl]methyl}acetamide | 1H NMR (500 MHz, DMSO-d6) δ 9.02 (t, J = 5.5 Hz, 1H), 7.35 (t, J = 8.2 Hz, 1H), 6.73 (d, J = 8.2 Hz, 2H), 6.35 (s, 1H), 4.43 (d, J = 5.5 Hz, 2H), 4.04 (s, 2H), 2.97 (dt, J = 14.0, 7.2 Hz, 1H), 2.15 (t, J = 7.5 Hz, 2H), 1.38-1.29 (m, 2H), 1.21 (s, 3H), 1.20 (s, 3H), 1.14-1.03 (m, 2H), 0.66 (t, J = 7.3 Hz, 3H) | 1.603 A 552.2 | A |

| Ex # | Structure | Name | ¹H NMR | LC/MS Rt (min) Method M + H | hAPJ cAMP EC₅₀ (nM) Potency range |
|---|---|---|---|---|---|
| 273 | 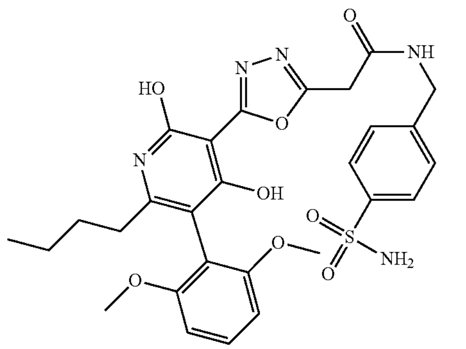 [SMILES: CCCCc1nc(O)c(-c2nnc(CC(=O)NCc3ccc(S(N)(=O)=O)cc3)o2)c(O)c1-c1c(OC)cccc1OC] | 2-{5-[6-butyl-5-(2,6-dimethoxy-phenyl)-2,4-dihydroxy-pyridin-3-yl]-1,3,4-oxadiazol-2-yl}-N-[(4-sulfamoylphenyl)methyl]acetamide | 1H NMR (500 MHz, DMSO-d6) δ 8.95 (NH), 7.80 (d, J = 7.9 Hz, 2H), 7.50 (d, J = 7.9 Hz, 2H), 7.35 (t, J = 1.0 Hz, 1H), 6.73 (d, J = 8.5 Hz, 2H), 4.41 (d, J = 5.8 Hz, 2H), 4.05 (s, 2H), 3.69 (s, 6H), 2.15 (t, J = 7.6 Hz, 2H), 1.38-1.27 (m, J = 7.3, 7.3 Hz, 2H), 1.13-1.03 (m, 2H), 0.67 (t, J = 7.3 Hz, 3H) | 1.463 A 598.3 | B |
| 274 | 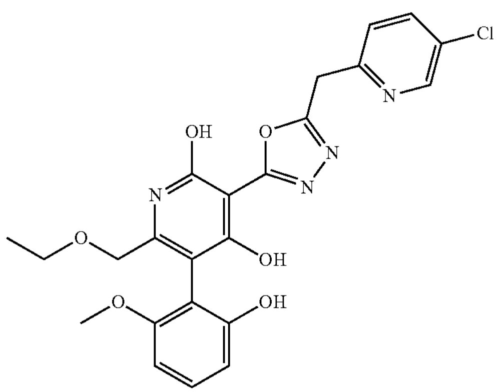 [SMILES: CCOCc1nc(O)c(-c2nnc(Cc3ccc(Cl)cn3)o2)c(O)c1-c1c(O)cccc1OC] | 3-{5-[(5-chloropyridin-2-yl)methyl]-1,3,4-oxadiazol-2-yl}-6-(ethoxymethyl)-5-(2-hydroxy-6-methoxyphenyl)pyridine-2,4-diol | 1H NMR (400 MHz, CDCl₃) δ 8.62-8.37 (m, 1H), 7.73-7.55 (m, 1H), 7.27 (m, 2H), 6.79-6.63 (m, 1H), 6.56-6.38 (m, 1H), 4.40-4.26 (m, 2H), 4.20-4.12 (m, 2H), 3.70 (s, 3H), 3.62-3.39 (m, 2H), 1.38-1.26 (m, 3H) | 0.80 D 485.0 | A |
| 275 | 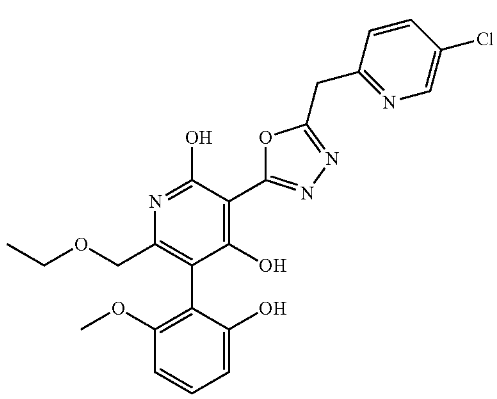 [SMILES: CCOCc1nc(O)c(-c2nnc(Cc3ccc(Cl)cn3)o2)c(O)c1-c1c(O)cccc1OC] | 3-{5-[(5-chloropyridin-2-yl)methyl]-1,3,4-oxadiazol-2-yl}-6-(ethoxymethyl)-5-(2-hydroxy-6-methoxyphenyl)pyridine-2,4-diol | 1H NMR (400 MHz, CDCl₃) δ 8.40 (br. s., 1H), 7.53 (br. s., 1H), 7.36-7.09 (m, 2H), 6.59 (d, J = 8.4 Hz, 1H), 6.43 (d, J = 8.1 Hz, 1H), 4.28 (br. s., 2H), 4.14 (q, J = 15.3 Hz, 2H), 3.53-3.38 (m, 2H), 2.75 (br. s., 2H), 1.22-1.15 (m, 3H) | 0.80 D 485.0 | B |

| Ex # | Structure | Name | ¹H NMR | LC/MS Rt (min) Method M + H | hAPJ cAMP EC$_{50}$ (nM) Potency range |
|---|---|---|---|---|---|
| 276 | 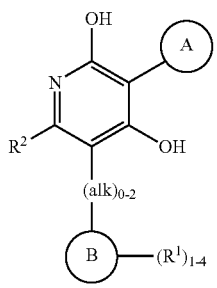 | 3-{5-[(5-chloropyridin-2-yl)methyl]-1,3,4-oxadiazol-2-yl}-5-(2,6-dihydroxyphenyl)-6-(ethoxymethyl)pyridine-2,4-diol | 1H NMR (500 MHz, DMSO-d6) δ 12.06-11.78 (m, 1H), 11.40-11.21 (m, 1H), 9.26-9.05 (m, 2H), 8.69-8.45 (m, 1H), 8.11-7.82 (m, 1H), 7.64-7.49 (m, 1H), 7.04-6.90 (m, 1H), 6.37 (d, J = 8.0 Hz, 2H), 4.60 (s, 2H), 4.04 (s, 2H), 3.33 (d, J = 6.9 Hz, 2H), 1.03 (t, J = 6.9 Hz, 3H) | 0.71 D 471.0 | B |

What is claimed is:

1. A compound of Formula (I):

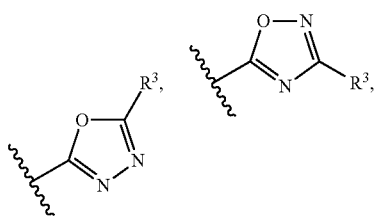

(I)

or a stereoisomer, a tautomer, or a pharmaceutically acceptable salt thereof, wherein:

alk is $C_{1-6}$ alkyl substituted with 0-5 $R^e$;

ring A is independently selected from the group consisting of:

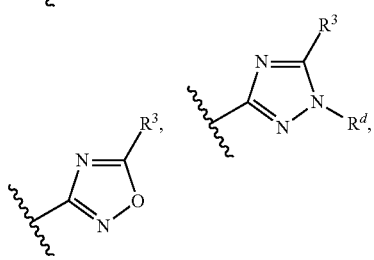

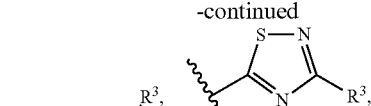

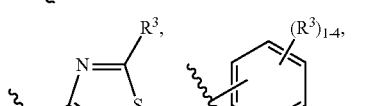

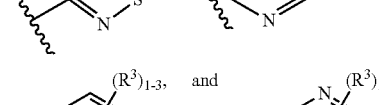

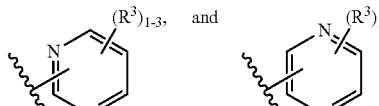

ring B is independently selected from the group consisting of:

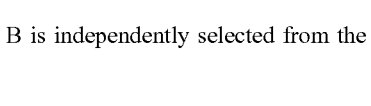

and 6-membered heteroaryl;

$R^1$ is independently selected from the group consisting of: H, halogen, $NO_2$, $-(CH_2)_nOR^b$, $-(CH_2)_nS(O)_pR^c$, $-(CH_2)_nC(=O)R^b$, $-(CH_2)_nNR^aR^a$, $-(CH_2)_nCN$, $-(CH_2)_nC(=O)NR^aR^a$, $-(CH_2)_nNR^aC(=O)R^b$, $-(CH_2)_nNR^aC(=O)NR^aR^a$, $-(CH_2)_nNR^aC(=O)OR^b$, $-(CH_2)_nOC(=O)NR^aR^a$, $-(CH_2)_nC(=O)OR^b$, $-(CH_2)_nS(O)_pNR^aR^a$, $-(CH_2)_nNR^aS(O)_pNR^aR^a$, $-(CH_2)_nNR^aS(O)_pR^c$, $C_{1-4}$ alkyl substituted with 0-3 $R^e$, —(CH$_2$)$_n$—C$_{3-6}$ carbocyclyl substituted with 0-3 $R^e$, and —(CH$_2$)$_n$-heterocyclyl substituted with 0-3 $R^e$;

$R^2$ is independently selected from the group consisting of: C$_{1-5}$ alkyl substituted with 0-3 $R^e$, C$_{1-5}$ alkenyl substituted with 0-3 $R^e$, and C$_{1-6}$ cycloalkyl substituted with 0-3 $R^e$; provided when $R^2$ is C$_{1-5}$ alkyl, the carbon atom except the one attached directly to the pyridine ring may be replaced by O, N, and S;

$R^3$ is independently selected from the group consisting of:
(1) —(CR$^4$R$^4$)$_r$C(=O)OC$_{1-4}$ alkyl substituted with 0-5 $R^e$,
(2) —(CR$^4$R$^4$)$_r$NR$^a$R$^a$,
(3) —(CR$^4$R$^4$)$_r$C(=O)NR$^a$R$^a$,
(4) —(CR$^4$R$^4$)$_r$NR$^a$C(=O)C$_{1-4}$alkyl substituted with 0-5 $R^e$,
(5) —(CR$^4$R$^4$)$_r$NR$^a$C(=O)(CR$^4$R$^4$)$_n$OC$_{1-4}$alkyl substituted with 0-5 $R^e$,
(6) —(CR$^4$R$^4$)$_r$—R$^5$,
(7) —(CR$^4$R$^4$)$_r$—OR$^5$,
(8) —(CR$^4$R$^4$)$_r$NR$^a$C(=O)(CR$^4$R$^4$)$_n$R$^5$, and
(9) (CR$^4$R$^4$)$_r$C(=O)NR$^a$(CR$^4$R$^4$)$_n$R$^5$;

$R^4$ is independently selected from the group consisting of: H, halogen, NR$^a$R$^a$, OC$_{1-4}$ alkyl, and C$_{1-4}$ alkyl; or $R^4$ and $R^4$ together with the carbon atom to which they are both attached form C$_{3-6}$ cycloalkyl substituted with 0-5 $R^e$;

$R^5$ is independently selected from the group consisting of: —(CH$_2$)$_n$—C$_{3-10}$ carbocycle and —(CH$_2$)$_n$-heterocycle, each substituted with 0-3 $R^6$;

$R^6$ is independently selected from: H, halogen, =O, —(CH$_2$)$_n$OR$^b$, (CH$_2$)$_n$S(O)$_p$R$_c$, —(CH$_2$)$_n$C(=O)R$^b$, —(CH$_2$)$_n$NR$^a$R$^a$, —(CH$_2$)$_n$CN, —(CH$_2$)$_n$C(=O)NR$^a$R$^a$, —(CH$_2$)$_n$NR$^a$C(=O)R$^b$, —(CH$_2$)$_n$NR$^a$C(=O)NR$^a$R$^a$, —(CH$_2$)$_n$NR$^a$C(=O)OR$^b$, —(CH$_2$)$_n$OC(=O)NR$^a$R$^a$, —(CH$_2$)$_n$C(=O)OR$^b$, —(CH$_2$)$_n$S(O)$_p$NR$^a$R$^a$, —(CH$_2$)$_n$NR$^a$S(O)$_p$NR$^a$R$^a$, —(CH$_2$)$_n$NR$^a$S(O)$_p$R$^c$, C$_{1-5}$ alkyl substituted with 0-3 $R^e$, (CH$_2$)$_n$—C$_{3-6}$ carbocyclyl substituted with 0-3 $R^e$, and —(CH$_2$)$_n$-heterocyclyl substituted with 0-3 $R^e$;

$R^a$ is independently selected from the group consisting of: H, C$_{1-6}$ alkyl substituted with 0-5 $R^e$, C$_{2-6}$ alkenyl substituted with 0-5 $R^e$, C$_{2-6}$ alkynyl substituted with 0-5 $R^e$, —(CH$_2$)$_n$—C$_{3-10}$carbocyclyl substituted with 0-5 $R^e$, and —(CH$_2$)$_n$-heterocyclyl substituted with 0-5 $R^e$; or $R^a$ and $R^a$ together with the nitrogen atom to which they are both attached form a heterocyclic ring substituted with 0-5 $R^e$;

$R^b$ is independently selected from the group consisting of: H, C$_{1-6}$ alkyl substituted with 0-5 $R^e$, C$_{2-6}$ alkenyl substituted with 0-5 $R^e$, C$_{2-6}$ alkynyl substituted with 0-5 $R^e$, —(CH$_2$)$_n$—C$_{3-10}$carbocyclyl substituted with 0-5 $R^e$, and —(CH$_2$)$_n$-heterocyclyl substituted with 0-5 $R^e$;

$R^c$ is independently selected from the group consisting of: C$_{1-6}$ alkyl substituted with 0-5 $R^e$, C$_{2-6}$alkenyl substituted with 0-5 $R^e$, C$_{2-6}$alkynyl substituted with 0-5 $R^e$, C$_{3-6}$carbocyclyl, and heterocyclyl;

$R^d$ is independently selected from the group consisting of: H and C$_{1-4}$alkyl substituted with 0-5 $R^e$;

$R^e$ is independently selected from the group consisting of: C$_{1-6}$ alkyl substituted with 0-5 R$_f$, C$_{2-6}$ alkenyl, C$_{2-6}$ alkynyl, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, CO$_2$H, —(CH$_2$)$_n$OR$_f$, S(O)$_p$R$^f$, C(=O)NR$^f$R$^f$, NR$^f$C(=O)R$^f$, S(O)$_p$NR$^f$R$^f$, NR$^f$S(O)$_p$R$^f$, NR$^f$C(=O)OR$^f$, OC(=O)NR$^f$R$^f$, and —(CH$_2$)$_n$NR$^f$R$^f$;

$R^f$ is independently selected from the group consisting of: H, F, Cl, Br, CN, OH, C$_{1-5}$alkyl (optimally substituted with halogen and OH), C$_{3-6}$ cycloalkyl, and phenyl, or $R^f$ and $R^f$ together with the nitrogen atom to which they are both attached form a heterocyclic ring optionally substituted with C$_{1-4}$alkyl;

n is independently selected from zero, 1, 2, and 3;
r is independently selected from zero, 1, 2, and 3; and
p is independently selected from zero, 1, and 2.

2. The compound according to claim 1, having Formula (II):

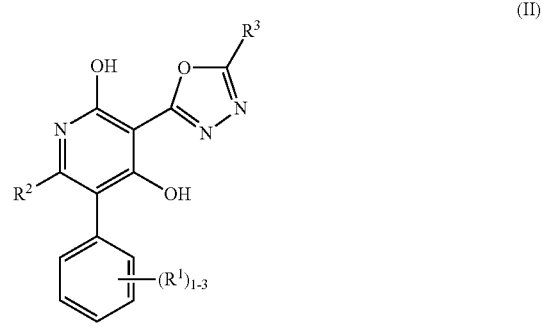

or a stereoisomer, a tautomer, or a pharmaceutically acceptable salt thereof, wherein:

$R^1$ is independently selected from the group consisting of: F, Cl, Br, NO$_2$, —(CH$_2$)$_n$OR$^b$, —(CH$_2$)$_n$C(=O)R$^b$, —(CH$_2$)$_n$NR$^a$R$^a$, —(CH$_2$)$_n$C(=O)NR$^a$R$^a$, —(CH$_2$)$_n$NR$^a$C(=O) R$^b$, C$_{1-4}$ alkyl substituted with 0-3 $R^e$, and C$_{3-6}$ cycloalkyl substituted with 0-3 $R^e$;

$R^2$ is independently selected from the group consisting of: C$_{1-5}$ alkyl substituted with 0-3 $R^e$, C$_{1-5}$ alkenyl, and C$_{1-6}$ cycloalkyl; provided when $R^2$ is C$_{1-5}$ alkyl, the carbon atom except the one attached directly to the pyridine ring may be replaced by O and S;

$R^3$ is independently selected from the group consisting of:
(1) —(CR$^4$R$^4$)$_r$C(=O)OC$_{1-4}$ alkyl substituted with 0-5 $R^e$,
(2) —(CR$^4$R$^4$)$_r$NR$^a$R$^a$,
(3) —(CR$^4$R$^4$)$_r$C(=O)NR$^a$R$^a$,
(4) —(CR$^4$R$^4$)$_r$NR$^a$C(=O)C$_{1-4}$alkyl substituted with 0-5 $R^e$,
(5) —(CR$^4$R$^4$)$_r$NR$^a$C(=O)(CR$^4$R$^4$)$_n$OC$_{1-4}$alkyl substituted with 0-5 $R^e$,
(6) —(CR$^4$R$^4$)$_r$—R$^5$,
(7) —(CR$^4$R$^4$)$_r$—OR$^5$,
(8) —(CR$^4$R$^4$)$_r$NR$^a$C(=O)(CR$^4$R$^4$)$_n$R$^5$, and
(9) —(CR$^4$R$^4$)$_r$C(=O)NR$^a$(CR$^4$R$^4$)$_n$R$^5$;

$R^4$ is independently selected from the group consisting of: H, F, Cl, NR$^a$R$^a$, OC$_{1-4}$ alkyl, and C$_{1-4}$ alkyl; or $R^4$ and $R^4$ together with the carbon atom to which they are both attached form C$_{3-6}$ cycloalkyl substituted with 0-5 $R^e$;

$R^5$ is independently selected from the group consisting of: —(CH$_2$)$_n$-aryl, —(CH$_2$)$_n$—C$_{3-6}$ cycloalkyl, and —(CH$_2$)$_n$-heterocycle, each substituted with 0-3 $R^6$;

$R^6$ is independently selected from the group consisting of: H, F, Cl, Br, —OR$^b$, =O, —(CH$_2$)$_n$C(=O)R$^b$, —(CH$_2$)$_n$C(=O)OR$^b$, —(CH$_2$)$_n$NR$^a$R$^a$, CN, —(CH$_2$)$_n$C(=O)NR$^a$R$^a$, —(CH$_2$)$_n$S(O)$_p$NR$^a$R$^a$, C$_{1-4}$ alkyl substituted with 0-3 $R^e$, $(CH_2)_n$—$C_{3-6}$ carbocyclyl substituted with 0-3 $R^e$, and —$(CH_2)_n$-heterocyclyl substituted with 0-3 $R^e$;

$R^a$ is independently selected from the group consisting of: H, $C_{1-6}$ alkyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$ is independently selected from the group consisting of: H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$;

$R^e$ is independently selected from the group consisting of: $C_{1-6}$ alkyl substituted with 0-5 $R^f$, $C_{2-6}$ alkenyl, $C_{2-6}$ alkynyl, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, $NO_2$, =O, $CO_2H$, —$(CH_2)_nOR^f$, $S(O)_pR^f$, $C(=O)NR^fR^f$, $NR^fC(=O)R^f$, $S(O)_pNR^fR^f$, $NR^fS(O)_pR^f$, $NR^fC(=O)OR^f$, $OC(=O)NR^fR^f$, and —$(CH_2)_nNR^fR^f$;

$R^f$ is independently selected from the group consisting of: H, F, Cl, Br, CN, OH, $C_{1-5}$alkyl (optimally substituted with halogen and OH), $C_{3-6}$ cycloalkyl, and phenyl;

n is independently selected from zero, 1, 2, and 3;
r is independently selected from 1, 2, and 3; and
p is independently selected from zero, 1, and 2.

3. The compound according to claim 2, having Formula (III):

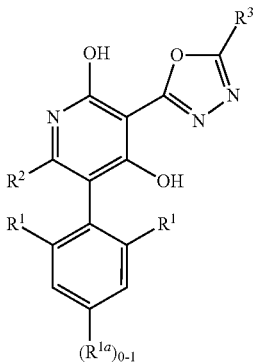

(III)

or a stereoisomer, a tautomer, or a pharmaceutically acceptable salt thereof, wherein:

$R^1$ is independently selected from the group consisting of: F, Cl, OH, and $OC_{1-4}$ alkyl;

$R^{1a}$ is independently selected from the group consisting of: F, Cl, and $C_{1-2}$ alkyl;

$R^2$ is independently selected from the group consisting of: $C_{1-5}$ alkyl substituted with 0-3 $R^e$, $C_{1-5}$ alkenyl, $C_{1-6}$ cycloalkyl, and $CH_2O(CH_2)_{1-3}CH_3$;

$R^3$ is independently selected from the group consisting of:
(1) —$(CR^4R^4)_rC(=O)OC_{1-4}$ alkyl substituted with 0-5 $R^e$,
(2) —$(CR^4R^4)_rNR^aR^a$,
(3) —$(CR^4R^4)_rC(=O)NR^aR^a$,
(4) —$(CR^4R^4)_rNR^aC(=O)$ $C_{1-4}$alkyl substituted with 0-5 $R^e$,
(5) $(CR^4R^4)_rNR^aC(=O)(CR^4R^4)_nOC_{1-4}$alkyl substituted with 0-5 $R^e$,
(6) —$(CR^4R^4)_r$—$R^5$,
(7) —$(CR^4R^4)_r$—$OR^5$,
(8) —$(CR^4R^4)_rNR^aC(=O)(CR^4R^4)_nR^5$, and
(9) —$(CR^4R^4)_rC(=O)NR^a(CR^4R^4)_nR^5$;

$R^4$ is independently selected from the group consisting of: H, F, Cl, $NR^aR^a$, $OC_{1-4}$ alkyl, and $C_{1-4}$ alkyl; or $R^4$ and $R^4$ together with the carbon atom to which they are both attached form $C_{3-6}$ cycloalkyl substituted with 0-5 $R^e$;

$R^5$ is independently elected from the group consisting of: —$(CH_2)_n$-aryl, —$(CH_2)_n$—$C_{3-6}$ cycloalkyl, and —$(CH_2)_n$-heterocycle, each substituted with 0-3 $R^6$;

$R^6$ is independently selected from the group consisting of: H, F, Cl, Br, —$OR^b$, =O, —$(CH_2)_nC(=O)R^b$, —$(CH_2)_nC(=O)OR^b$, —$(CH_2)_nNR^aR^a$, CN, —$(CH_2)_nC(=O)NR^aR^a$, —$(CH_2)_nS(O)_pNR^aR^a$, $C_{1-4}$ alkyl substituted with 0-3 $R^e$, $(CH_2)_n$—$C_{3-6}$ carbocyclyl substituted with 0-3 $R^e$, and —$(CH_2)_n$-heterocyclyl substituted with 0-3 $R^e$;

$R^a$ is independently selected from the group consisting of: H, $C_{1-6}$ alkyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$ is independently selected from the group consisting of: H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$;

$R^e$ is independently selected from the group consisting of: $C_{1-6}$ alkyl (optionally substituted with F and Cl), OH, $OCH_3$, $OCF_3$, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, $NO_2$, =O, and $CO_2H$;

n is independently selected from zero, 1, 2, and 3; and
r is independently selected from 1, 2, and 3.

4. The compound according to claim 3, or a stereoisomer, a tautomer, or a pharmaceutically acceptable salt thereof, wherein:

$R^3$ is independently selected from the group consisting of:
(1) —$(CR^4R^4)_r$—$R^5$,
(2) —$(CR^4R^4)_r$—$OR^5$,
(3) —$(CR^4R^4)_rNR^aC(=O)(CR^4R^4)_nR^5$, and
(4) —$(CR^4R^4)_rC(=O)NR^a(CR^4R^4)_nR^5$;

$R^4$ is independently selected from the group consisting of: H, F, Cl, $N(CH_3)_2$, $OCH_3$, and $CH_3$; or $R^4$ and $R^4$ together with the carbon atom to which they are both attached form cyclopropyl;

$R^5$ is independently selected from the group consisting of:

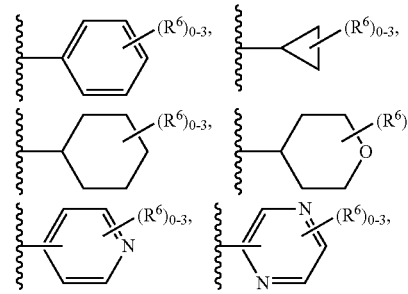

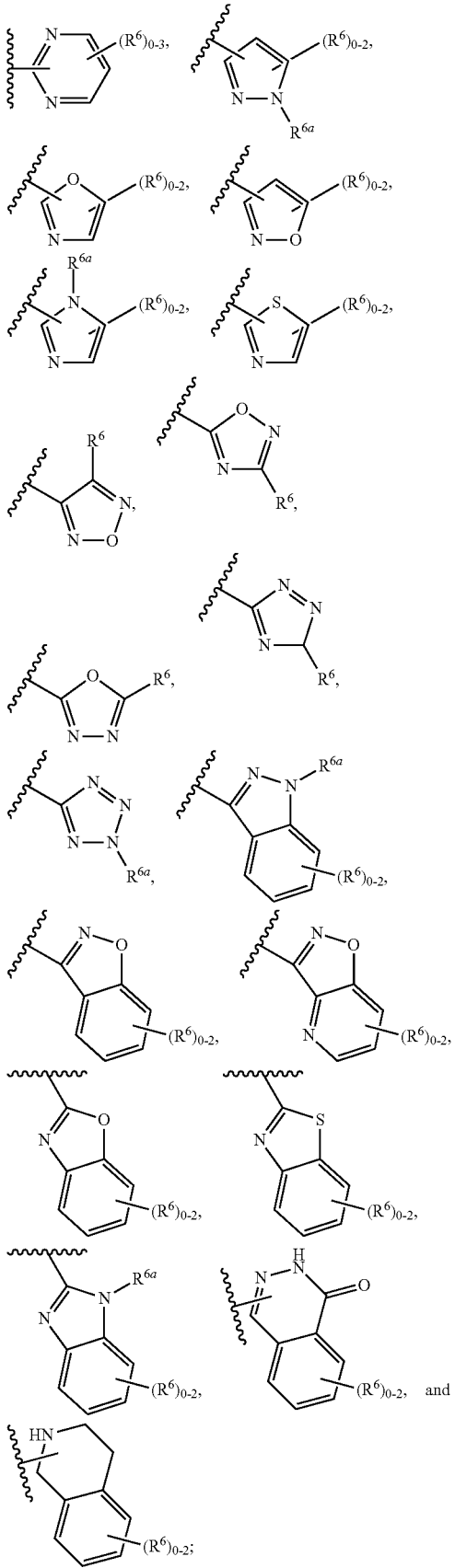

$R^6$ is independently selected from the group consisting of: H, F, Cl, Br, —OCH$_3$, —OCF$_3$, =O, —NR$^a$R$^a$, CN, —S(O)$_2$NH$_2$, CH$_3$, CF$_3$ —(CH$_2$)$_n$-aryl, —(CH$_2$)$_n$—C$_{3-6}$ cycloalkyl substituted with 0-3 R$^e$, and —(CH$_2$)$_n$-heterocyclyl substituted with 0-3 R$^e$;

$R^{6a}$ is independently selected from the group consisting of: H, CH$_3$, aryl substituted with 0-3 R$^e$, and heterocyclyl substituted with 0-3 R$^e$;

$R^a$ is independently selected from the group consisting of: H, C$_{1-6}$ alkyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$;

$R^e$ is independently selected from the group consisting of: C$_{1-6}$ alkyl (optionally substituted with F and Cl), OH, OCH$_3$, OCF$_3$, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, and CO$_2$H;

n is independently selected from zero, 1, 2, and 3; and r is independently selected from 1, 2, and 3.

5. The compound according to claim 1, or a stereoisomer, a tautomer, or a pharmaceutically acceptable salt thereof, wherein:

$R^3$ is independently selected from the group consisting of:
(1) —(CR$^4$R$^4$)$_r$NR$^a$R$^a$, and
(2) —(CR$^4$R$^4$)$_r$C(=O)NR$^a$R$^a$, $R^4$ is independently selected from the group consisting of: H, F, Cl, N(CH$_3$)$_2$, OCH$_3$, and CH$_3$; or R$^4$ and R$^4$ together with the carbon atom to which they are both attached form C$_{3-6}$ cycloalkyl substituted with 0-5 R$^e$;

$R^6$ is independently selected from the group consisting of: H, F, Cl, Br, —OCH$_3$, —OCF$_3$, =O, CN, —NR$^a$R$^a$, —S(O)$_2$NH$_2$, —CH$_3$, CF$_3$—(CH$_2$)$_n$-aryl, —(CH$_2$)$_n$—C$_{3-6}$ cycloalkyl substituted with 0-3 R$^e$, and —(CH$_2$)$_n$-heterocyclyl substituted with 0-3 R$^e$;

$R^{6a}$ is independently selected from the group consisting of: H, CH$_3$, aryl substituted with 0-3 R$^e$, and heterocyclyl substituted with 0-3 R$^e$;

$R^a$ and $R^a$ together with the nitrogen atom to which they are both attached form a heterocyclic ring substituted with 0-5 R$^e$, wherein the heterocyclic ring is selected from the group consisting of:

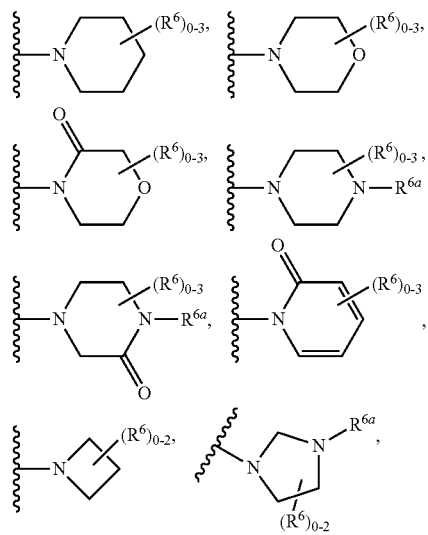

-continued $R^e$ is independently selected from the group consisting of:
C$_{1-6}$ alkyl (optionally substituted with F and Cl), OH, OCH$_3$, OCF$_3$, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, and CO$_2$H;

n is independently selected from zero, 1, 2, and 3; and
r is independently selected from 1, 2, and 3.

6. The compound according to claim 1, or a stereoisomer, a tautomer, or a pharmaceutically acceptable salt thereof, wherein:

$R^1$ is independently selected from the group consisting of:
F, Cl, OH, and OC$_{1-4}$ alkyl;

$R^{1a}$ is independently selected from the group consisting of: F, Cl, and C$_{1-2}$ alkyl;

$R^2$ is independently selected from the group consisting of:
C$_{1-5}$ alkyl substituted with 0-3 R$^e$, C$_{1-5}$ alkenyl, C$_{1-6}$ cycloalkyl, and CH$_2$O(CH$_2$)$_{1-3}$CH$_3$;

$R^3$ is independently selected from the group consisting of:
(1) —(CH$_2$)$_r$C(=O)OC$_{1-4}$ alkyl substituted with 0-3 R$^e$,
(2) —(CH$_2$)$_r$NR$^a$R$^a$,
(3) —(CH$_2$)$_r$C(=O)NR$^a$R$^a$,
(4) —(CH$_2$)$_r$NR$^a$C(=O)C$_{1-4}$alkyl substituted with 0-3 R$^e$, and
(5) —(CH$_2$)$_r$NR$^a$C(=O)(CR$^4$R$^4$)$_n$OC$_{1-4}$alkyl substituted with 0-3 R$^e$;

$R^4$ is independently selected from the group consisting of:
H, F, Cl, NR$^a$R$^a$, OC$_{1-4}$ alkyl, and C$_{1-4}$ alkyl;

$R^5$ is independently selected from the group consisting of:
—(CH$_2$)$_n$-aryl, —(CH$_2$)$_n$—C$_{3-6}$ cycloalkyl and —(CH$_2$)$_n$-heterocycle, each substituted with 0-3 R$^6$;

$R^6$ is independently selected from the group consisting of:
H, F, Cl, Br, —OCH$_3$, —OCF$_3$, =O, CN, —NR$^a$R$^a$, —S(O)$_2$NH$_2$, CH$_3$, CF$_3$—(CH$_2$)$_n$-aryl, —(CH$_2$)$_n$—C$_{3-6}$ cycloalkyl substituted with 0-3 R$^e$, and —(CH$_2$)$_n$-heterocyclyl substituted with 0-3 R$^e$;

$R^a$ is independently selected from the group consisting of:
H, C$_{1-6}$ alkyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$;

$R^e$ is independently selected from the group consisting of:
C$_{1-6}$ alkyl (optionally substituted with F and Cl), OH, OCH$_3$, OCF$_3$, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, and CO$_2$H;

n is independently selected from zero, 1, 2, and 3; and
r is independently selected from 1, 2, and 3.

7. The compound according to claim 1, having Formula (IVa):

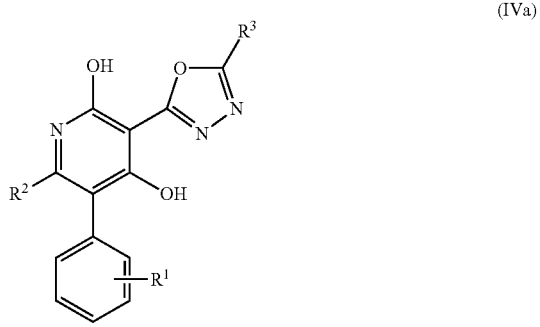

(IVa)

or a stereoisomer, a tautomer, or a pharmaceutically acceptable salt thereof, wherein:

$R^1$ is independently selected from the group consisting of:
—CH$_2$OH, —OCH$_3$, —OCF$_3$, OCH$_2$Ph, —C(=O)NR$^a$R$^a$, —NR$^a$R$^a$, CH$_3$, CH$_2$CH$_3$, CH(CH$_3$)$_2$, and cyclopropyl;

$R^2$ is independently selected from the group consisting of:
C$_{1-4}$ alkyl substituted with 0-3 R$^e$, C$_{2-4}$ alkenyl, C$_{1-6}$ cycloalkyl, and CH$_2$O(CH$_2$)$_{1-3}$CH$_3$;

$R^3$ is independently selected from the group consisting of:
(1) —(CR$^4$R$^4$)$_r$C(=O)OC$_{1-4}$ alkyl substituted with 0-3 R$^e$,
(2) —(CR$^4$R$^4$)$_r$NR$^a$R$^a$,
(3) —(CR$^4$R$^4$)$_r$C(=O)NR$^a$R$^a$,
(4) —(CR$^4$R$^4$)$_r$NR$^a$C(=O)C$_{1-4}$alkyl substituted with 0-3 R$^e$,
(5) —(CR$^4$R$^4$)$_r$NR$^a$C(=O)(CR$^4$R$^4$)$_n$OC$_{1-4}$alkyl substituted with 0-3 R$^e$,
(6) —(CR$^4$R$^4$)$_r$—R$^5$,
(7) —(CR$^4$R$^4$)$_r$—OR$^5$,
(8) —(CR$^4$R$^4$)$_r$NR$^a$C(=O)(CR$^4$R$^4$)$_n$R$^5$, and
(9) —(CR$^4$R$^4$)$_r$C(=O)NR$^a$(CR$^4$R$^4$)$_n$R$^5$;

$R^4$ is independently selected from the group consisting of:
H, F, Cl, NR$^a$R$^a$, OC$_{1-4}$ alkyl, and C$_{1-4}$ alkyl;

$R^5$ is independently selected from the group consisting of:
aryl, C$_{3-6}$ cycloalkyl, and heterocycle, each substituted with 0-3 R$^6$;

$R^6$ is independently selected from the group consisting of:
H, F, Cl, Br, —OR$^b$, =O, —(CH$_2$)$_n$C(=O)R$^b$, —(CH$_2$)$_n$C(=O)OR$^b$, —(CH$_2$)$_n$NR$^a$R$^a$, CN, —(CH$_2$)$_n$C(=O)NR$^a$R$^a$, C$_{1-4}$ alkyl substituted with 0-3 R$^e$, (CH$_2$)$_n$—C$_{3-6}$ carbocyclyl substituted with 0-3 R$^e$, and —(CH$_2$)$_n$-heterocyclyl substituted with 0-3 R$^e$;

$R^a$ is independently selected from the group consisting of:
H, C$_{1-6}$ alkyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$; or R$^a$ and R$^a$ together with the nitrogen atom to which they are both attached form a heterocyclic ring substituted with 0-5 R$^e$;

R$^b$ is independently selected from the group consisting of: H, C$_{1-6}$ alkyl substituted with 0-5 R$^e$, C$_{2-6}$ alkenyl substituted with 0-5 R$^e$, C$_{2-6}$ alkynyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$;

R$^e$ is independently selected from the group consisting of: C$_{1-6}$ alkyl (optionally substituted with F and Cl), OH, OCH$_3$, OCF$_3$, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, and CO$_2$H;

n is independently selected from zero, 1, 2, and 3; and r is independently selected from 1, 2, and 3.

8. The compound according to claim 1, having Formula (V):

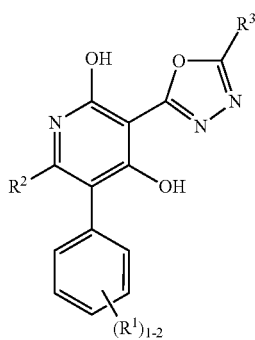

(V)

or a stereoisomer, a tautomer, or a pharmaceutically acceptable salt thereof, wherein:

R$^1$ is independently selected from the group consisting of: —CH$_2$OH, —OCH$_3$, —OCF$_3$, CH$_3$, CH$_2$CH$_3$, CH(CH$_3$)$_2$, and cyclopropyl;

R$^2$ is independently selected from the group consisting of: C$_{1-4}$ alkyl substituted with 0-3 R$^e$, C$_{2-4}$ alkenyl, C$_{1-6}$ cycloalkyl, and CH$_2$O(CH$_2$)$_{1-3}$CH$_3$;

R$^3$ is independently selected from the group consisting of:
(1) —CH$_2$C(=O)OC$_{1-4}$ alkyl substituted with 0-3 R$^e$,
(2) —CH$_2$NR$^a$R$^a$,
(3) —CH$_2$C(=O)NR$^a$R$^a$,
(4) —CH$_2$NHC(=O)C$_{1-4}$alkyl substituted with 0-3 R$^e$,
(5) —CH$_2$NR$^a$C(=O)(CH$_2$)$_{0-2}$OC$_{1-4}$alkyl substituted with 0-3 R$^e$,
(6) —CH$_2$—R$^5$,
(7) —CH$_2$—OR$^5$,
(8) —CH$_2$NR$^a$C(=O)(CH$_2$)$_{0-2}$R$^5$, and
(9) —CH$_2$C(=O)NR$^a$(CH$_2$)$_{0-2}$R$^5$;

R$^5$ is independently selected from the group consisting of: aryl, C$_{3-6}$ cycloalkyl, and heterocycle, each substituted with 0-3 R$^6$;

R$^6$ is independently selected from the group consisting of: H, F, Cl, Br, —OR$^b$, =O, —(CH$_2$)$_n$C(=O)R$^b$, —(CH$_2$)$_n$C(=O)OR$^b$, —(CH$_2$)NR$^a$R$^a$, CN, —(CH$_2$)$_n$C(=O)NR$^a$R$^a$, —S(O)$_2$NH$_2$, C$_{1-4}$ alkyl substituted with 0-3 R$^e$, (CH$_2$)$_n$—C$_{3-6}$ carbocyclyl substituted with 0-3 R$^e$, and —(CH$_2$)$_n$-heterocyclyl substituted with 0-3 R$^e$;

R$^a$ is independently selected from the group consisting of: H, C$_{1-6}$ alkyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$; or R$^a$ and R$^a$ together with the nitrogen atom to which they are both attached form a heterocyclic ring substituted with 0-5 R$^e$;

R$^b$ is independently selected from the group consisting of: H, C$_{1-6}$ alkyl substituted with 0-5 R$^e$, C$_{2-6}$ alkenyl substituted with 0-5 R$^e$, C$_{2-6}$ alkynyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$;

R$^e$ is independently selected from the group consisting of: C$_{1-6}$ alkyl (optionally substituted with F and Cl), OH, OCH$_3$, OCF$_3$, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, and CO$_2$H; and n is independently selected from zero, 1, 2, and 3.

9. The compound according to claim 8, or a stereoisomer, a tautomer, or a pharmaceutically acceptable salt thereof, wherein:

R$^3$ is independently selected from the group consisting of:
(1) —CH$_2$—R$^5$,
(2) —CH$_2$—OR$^5$,
(3) —CH$_2$—NHC(=O)(CH$_2$)$_{0-1}$R$^5$, and
(4) —CH$_2$—C(=O)NH(CH$_2$)$_{0-1}$R$^5$;

R$^5$ is independently selected from:

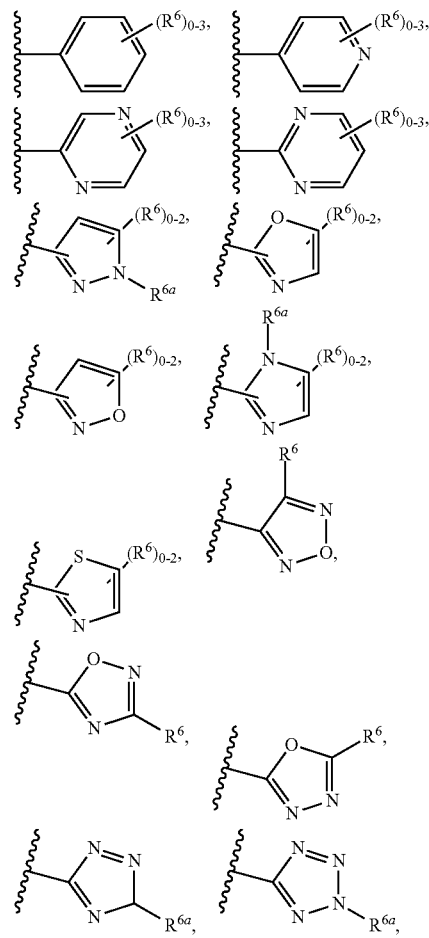

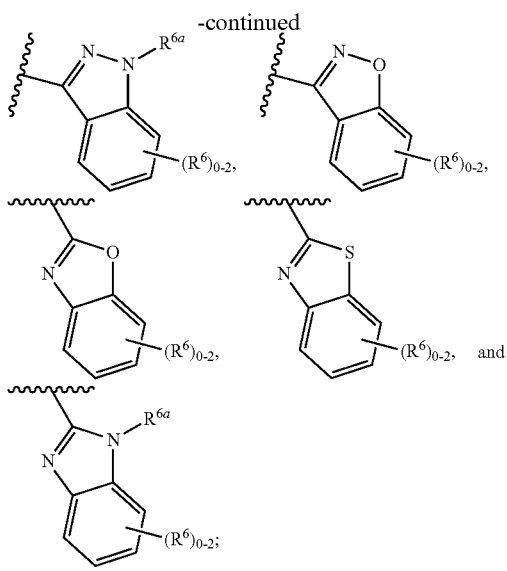

$R^6$ is independently selected from the group consisting of: H, F, Cl, Br, —OCH$_3$, —OCF$_3$, =O, CN, CH$_3$, CF$_3$— (CH$_2$)$_n$-aryl, —(CH$_2$)$_n$—C$_{3-6}$ cycloalkyl substituted with 0-3 R$^e$, and —(CH$_2$)$_n$-heterocyclyl substituted with 0-3 R$^e$;

$R^{6a}$ is independently selected from the group consisting of: H, CH$_3$, aryl substituted with 0-3 R$^e$, and heterocyclyl substituted with 0-3 R$^e$;

$R^a$ is independently selected from the group consisting of: H, C$_{1-6}$ alkyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$;

$R^e$ is independently selected from the group consisting of: C$_{1-6}$ alkyl (optionally substituted with F and Cl), OH, OCH$_3$, OCF$_3$, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, and CO$_2$H; and n is independently selected from zero, 1, 2, and 3.

10. The compound according to claim 1, having Formula (VI):

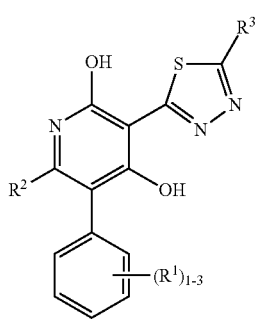

(VI)

or a stereoisomer, a tautomer, or a pharmaceutically acceptable salt thereof, wherein:

$R^1$ is independently selected from the group consisting of: F, Cl, Br, NO$_2$, —(CH$_2$)$_n$OR$^b$, —(CH$_2$)$_n$C(=O)R$^b$, —(CH$_2$)$_n$NR$^a$R$^a$, —(CH$_2$)$_n$C(=O)NR$^a$R$^a$, —(CH$_2$)$_n$NR$^a$C(=O) R$^b$, C$_{1-4}$ alkyl substituted with 0-3 R$^e$ and C$_{3-6}$ cycloalkyl substituted with 0-3 R$^e$;

$R^2$ is independently selected from the group consisting of: C$_{1-5}$ alkyl substituted with 0-3 R$^e$, C$_{1-5}$ alkenyl, and C$_{1-6}$ cycloalkyl; provided when R$^2$ is C$_{1-5}$ alkyl, the carbon atom except the one attached directly to the pyridine ring may be replaced by O, N, and S;

$R^3$ is independently selected from the group consisting of:
(1) —CH$_2$C(=O)OC$_{1-4}$ alkyl substituted with 0-5 R$^e$,
(2) —CH$_2$NR$^a$R$^a$,
(3) —CH$_2$C(=O)NR$^a$R$^a$,
(4) —CH$_2$NR$^a$C(=O)C$_{1-4}$alkyl substituted with 0-5 R$^e$,
(5) —CH$_2$NR$^a$C(=O)(CH$_2$)$_n$OC$_{1-4}$alkyl substituted with 0-5 R$^e$,
(6) —CH$_2$—R$^5$,
(7) —CH$_2$—OR$^5$,
(8) —CH$_2$NR$^a$C(=O)(CH$_2$)$_n$R$^5$, and
(9) —CH$_2$C(=O)NR$^a$(CH$_2$)$_n$R$^5$;

$R^5$ is independently selected from the group consisting of: —(CH$_2$)$_n$-aryl, —(CH$_2$)$_n$—C$_{3-6}$ cycloalkyl and —(CH$_2$)$_n$-heterocycle, each substituted with 0-3 R$^6$;

$R^6$ is independently selected from the group consisting of: H, F, Cl, Br, —OR$^b$, =O, —(CH$_2$)$_n$C(=O)R$^b$, —(CH$_2$)$_n$C(=O)OR$^b$, —(CH$_2$)$_n$NR$^a$R$^a$, CN, —(CH$_2$)$_n$C(=O)NR$^a$R$^a$, C$_{1-4}$ alkyl substituted with 0-3 R$^e$, (CH$_2$)$_n$—C$_{3-6}$ carbocyclyl substituted with 0-3 R$^e$, and —(CH$_2$)$_n$-heterocyclyl substituted with 0-3 R$^e$;

$R^a$ is independently selected from the group consisting of: H, C$_{1-6}$ alkyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$; or R$^a$ and R$^a$ together with the nitrogen atom to which they are both attached form a heterocyclic ring substituted with 0-5 W;

$R^b$ is independently selected from the group consisting of: H, C$_{1-6}$ alkyl substituted with 0-5 R$^e$, C$_{2-6}$ alkenyl substituted with 0-5 R$^e$, C$_{2-6}$ alkynyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$;

$R^e$ is independently selected from the group consisting of: C$_{1-6}$ alkyl substituted with 0-5 R$_f$, C$_{2-6}$ alkenyl, C$_{2-6}$ alkynyl, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, CO$_2$H, —(CH$_2$)$_n$OR$^f$, S(O)$_p$R$^f$, C(=O)NR$^f$R$^f$, NR$^f$C(=O)R$^f$, S(O)$_p$NR$^f$R$^f$, NR$^f$S(O)$_p$R$^f$, NR$^f$C(=O)OR$^f$, OC(=O)NR$^f$R$^f$, and —(CH$_2$)$_p$NR$^f$R$^f$;

$R^f$ is independently selected from H, F, Cl, Br, CN, OH, C$_{1-5}$alkyl (optimally substituted with halogen and OH), C$_{3-6}$ cycloalkyl, and phenyl;

n is independently selected from zero, 1, 2, and 3; and
p is independently selected from zero, 1, and 2.

11. The compound according to claim 1 selected from the group consisting of:
3-(5-benzyl-1,3,4-oxadiazol-2-yl)-6-butyl-5-(2,6-dimethoxyphenyl)pyridine-2,4-diol,
3-(5-benzyl-1,3,4-oxadiazol-2-yl)-6-butyl-5-(2,6-dimethoxy-4-methylphenyl)pyridine-2,4-diol,
6-butyl-5-(2,6-dimethoxyphenyl)-3-[5-(pyridin-4-ylmethyl)-1,3,4-oxadiazol-2-yl]pyridine-2,4-diol,
6-butyl-5-(2,6-dimethoxyphenyl)-3-[5-(2-phenylethyl)-1,3,4-oxadiazol-2-yl]pyridine-2,4-diol,
6-butyl-3-{5-[(2-chlorophenyl)methyl]-1,3,4-oxadiazol-2-yl}-5-(2,6-dimethoxyphenyl)pyridine-2,4-diol,
6-butyl-5-(2,6-dimethoxyphenyl)-3-{5-[(2-methoxyphenyl)methyl]-1,3,4-oxadiazol-2-yl}pyridine-2,4-diol, 6-butyl-5-(2,6-dimethoxyphenyl)-3-{5-[(3-methoxyphenyl)methyl]-1,3,4-oxadiazol-2-yl}pyridine-2,4-diol,
6-butyl-3-{5-[(4-chlorophenyl)methyl]-1,3,4-oxadiazol-2-yl}-5-(2,6-dimethoxyphenyl)pyridine-2,4-diol,
6-butyl-5-(2,6-dimethoxyphenyl)-3-{5-[(4-methoxyphenyl)methyl]-1,3,4-oxadiazol-2-yl}pyridine-2,4-diol,
6-butyl-3-[5-(3-chlorophenyl)-1,3,4-oxadiazol-2-yl]-5-(2,6-dimethoxyphenyl)pyridine-2,4-diol,
6-butyl-3-[5-(2-chlorophenyl)-1,3,4-oxadiazol-2-yl]-5-(2,6-dimethoxyphenyl)pyridine-2,4-diol,
6-butyl-5-(2,6-dimethoxyphenyl)-3-[5-(pyrazin-2-yl)-1,3,4-oxadiazol-2-yl]pyridine-2,4-diol,
6-butyl-5-(2,6-dimethoxyphenyl)-3-[5-(1-phenylcyclopropyl)-1,3,4-oxadiazol-2-yl]pyridine-2,4-diol,
6-butyl-3-(5-cyclopropyl-1,3,4-oxadiazol-2-yl)-5-(2,6-dimethoxyphenyl)pyridine-2,4-diol,
6-butyl-5-(2,6-dimethoxyphenyl)-3-[5-(2-phenylpropan-2-yl)-1,3,4-oxadiazol-2-yl]pyridine-2,4-diol,
6-butyl-5-(2,6-dimethoxyphenyl)-3-[5-(pyridin-3-yl)-1,3,4-oxadiazol-2-yl]pyridine-2,4-diol,
6-butyl-5-(2,6-dimethoxyphenyl)-3-[5-(phenoxymethyl)-1,3,4-oxadiazol-2-yl]pyridine-2,4-diol,
3-(5-benzyl-1,3,4-oxadiazol-2-yl)-6-(but-3-en-1-yl)-5-(2,6-dimethoxyphenyl)pyridine-2,4-diol,
6-butyl-5-(2,6-dimethoxyphenyl)-3-[5-(5-methyl-1H-pyrazol-3-yl)-1,3,4-oxadiazol-2-yl]pyridine-2,4-diol,
3-[5-(1,2-benzoxazol-3-ylmethyl)-1,3,4-oxadiazol-2-yl]-6-butyl-5-(2,6-dimethoxyphenyl)pyridine-2,4-diol,
6-butyl-5-(2,6-dimethoxyphenyl)-3-[5-(pyrazin-2-ylmethyl)-1,3,4-oxadiazol-2-yl]pyridine-2,4-diol,
6-butyl-5-(2,6-dimethoxyphenyl)-3-[5-(pyrimidin-5-ylmethyl)-1,3,4-oxadiazol-2-yl]pyridine-2,4-diol,
6-butyl-3-{5-[(3-chlorophenyl)methyl]-1,3,4-oxadiazol-2-yl}-5-(2,6-dimethoxyphenyl)pyridine-2,4-diol,
6-butyl-3-{5-[difluoro(phenyl)methyl]-1,3,4-oxadiazol-2-yl}-5-(2,6-dimethoxyphenyl)pyridine-2,4-diol,
3-[5-(1,3-benzoxazol-2-ylmethyl)-1,3,4-oxadiazol-2-yl]-6-butyl-5-(2,6-dimethoxyphenyl)pyridine-2,4-diol,
3-[5-(1,2-benzoxazol-3-ylmethyl)-1,3,4-oxadiazol-2-yl]-6-butyl-5-(2,6-dimethoxy-4-methylphenyl)pyridine-2,4-diol,
3-[5-(1,2-benzoxazol-3-ylmethyl)-1,3,4-oxadiazol-2-yl]-6-(but-3-en-1-yl)-5-(2,6-dimethoxyphenyl)pyridine-2,4-diol,
6-butyl-5-(2,6-dimethoxyphenyl)-3-{5-[2-(5-phenyl-1,3-oxazol-2-yl)ethyl]-1,3,4-oxadiazol-2-yl}pyridine-2,4-diol,
6-butyl-5-(2,6-dimethoxyphenyl)-3-{5-[2-(1-methyl-1H-imidazol-2-yl)ethyl]-1,3,4-oxadiazol-2-yl}pyridine-2,4-diol,
6-butyl-3-{5-[(6-chloropyridin-3-yl)methyl]-1,3,4-oxadiazol-2-yl}-5-(2,6-dimethoxyphenyl)pyridine-2,4-diol,
6-butyl-3-{5-[2-(4-chlorophenyl)propan-2-yl]-1,3,4-oxadiazol-2-yl}-5-(2,6-dimethoxyphenyl)pyridine-2,4-diol,
6-butyl-5-(2,6-dimethoxyphenyl)-3-{5-[(4-fluorophenyl)methyl]-1,3,4-oxadiazol-2-yl}pyridine-2,4-diol,
6-butyl-3-{5-[(3,4-dichlorophenyl)methyl]-1,3,4-oxadiazol-2-yl}-5-(2,6-dimethoxyphenyl)pyridine-2,4-diol,
6-butyl-5-(2,6-dimethoxyphenyl)-3-(5-{[4-fluoro-3-(trifluoromethyl)phenyl]methyl}-1,3,4-oxadiazol-2-yl)pyridine-2,4-diol,
6-butyl-3-{5-[(2,4-dichlorophenyl)methyl]-1,3,4-oxadiazol-2-yl}-5-(2,6-dimethoxyphenyl)pyridine-2,4-diol,
6-butyl-5-(2,6-dimethoxyphenyl)-3-{5-[(3,5-dimethyl-1H-pyrazol-4-yl)methyl]-1,3,4-oxadiazol-2-yl}pyridine-2,4-diol,
4-({5-[6-butyl-5-(2,6-dimethoxyphenyl)-2,4-dihydroxypyridin-3-yl]-1,3,4-oxadiazol-2-yl}methyl)benzonitrile,
6-butyl-3-{5-[(3,4-difluorophenyl)methyl]-1,3,4-oxadiazol-2-yl}-5-(2,6-dimethoxyphenyl)pyridine-2,4-diol,
6-butyl-3-(5-{[2-(4-chlorophenyl)-1,3-thiazol-4-yl]methyl}-1,3,4-oxadiazol-2-yl)-5-(2,6-dimethoxyphenyl)pyridine-2,4-diol,
6-butyl-3-{5-[1-(4-chlorophenyl)ethyl]-1,3,4-oxadiazol-2-yl}-5-(2,6-dimethoxyphenyl)pyridine-2,4-diol,
6-butyl-5-(2,6-dimethoxyphenyl)-3-{5-[(4-methyl-1,2,5-oxadiazol-3-yl)methyl]-1,3,4-oxadiazol-2-yl}pyridine-2,4-diol,
6-butyl-5-(2,6-dimethoxyphenyl)-3-[5-(4-fluorophenoxymethyl)-1,3,4-oxadiazol-2-yl]pyridine-2,4-diol,
6-butyl-5-(2,6-dimethoxyphenyl)-3-[5-(1H-indazol-3-ylmethyl)-1,3,4-oxadiazol-2-yl]pyridine-2,4-diol,
4-({5-[6-butyl-5-(2,6-dimethoxyphenyl)-2,4-dihydroxypyridin-3-yl]-1,3,4-oxadiazol-2-yl}methyl)-1,2-dihydrophthalazin-1-one,
6-butyl-5-(2,6-dimethoxyphenyl)-3-{5-[methoxy(phenyl)methyl]-1,3,4-oxadiazol-2-yl}pyridine-2,4-diol,
6-butyl-5-(2,6-dimethoxyphenyl)-3-{5-[(2-phenyl-1,3-thiazol-4-yl)methyl]-1,3,4-oxadiazol-2-yl}pyridine-2,4-diol,
3-{5-[2-(1,3-benzoxazol-2-yl)ethyl]-1,3,4-oxadiazol-2-yl}-6-butyl-5-(2,6-dimethoxyphenyl)pyridine-2,4-diol,
6-butyl-5-(2,6-dimethoxyphenyl)-3-{5-[(4-fluoro-3-methoxyphenyl)methyl]-1,3,4-oxadiazol-2-yl}pyridine-2,4-diol,
6-butyl-5-(2,6-dimethoxyphenyl)-3-[5-(1,3-thiazol-5-ylmethyl)-1,3,4-oxadiazol-2-yl]pyridine-2,4-diol,
6-butyl-3-[5-(3,4-dichlorophenoxymethyl)-1,3,4-oxadiazol-2-yl]-5-(2,6-dimethoxyphenyl)pyridine-2,4-diol,
6-butyl-5-(2,6-dimethoxyphenyl)-3-{5-[(3-methyl-1,2-oxazol-5-yl)methyl]-1,3,4-oxadiazol-2-yl}pyridine-2,4-diol,
6-butyl-5-(2,6-dimethoxyphenyl)-3-(5-{2-[3-(pyrazin-2-yl)-1,2,4-oxadiazol-5-yl]ethyl}-1,3,4-oxadiazol-2-yl)pyridine-2,4-diol,
6-butyl-3-[5-(4-chlorophenoxymethyl)-1,3,4-oxadiazol-2-yl]-5-(2,6-dimethoxyphenyl)pyridine-2,4-diol,
6-butyl-3-{5-[2-(4-chlorophenyl)-2-methylpropyl]-1,3,4-oxadiazol-2-yl}-5-(2,6-dimethoxyphenyl)pyridine-2,4-diol,
6-butyl-5-(2,6-dimethoxyphenyl)-3-(5-{[3-(pyridin-2-yl)-1,2,4-oxadiazol-5-yl]methyl}-1,3,4-oxadiazol-2-yl)pyridine-2,4-diol,
6-butyl-5-(2,6-dimethoxyphenyl)-3-(5-{[4-(trifluoromethoxy)phenyl]methyl}-1,3,4-oxadiazol-2-yl)pyridine-2,4-diol,
6-butyl-5-(2,6-dimethoxyphenyl)-3-(5-{[3-fluoro-5-(trifluoromethyl)phenyl]methyl}-1,3,4-oxadiazol-2-yl)pyridine-2,4-diol,
6-butyl-5-(2,6-dimethoxyphenyl)-3-{5-[2-(1-methyl-1H-1,3-benzodiazol-2-yl)ethyl]-1,3,4-oxadiazol-2-yl}pyridine-2,4-diol,
6-butyl-3-{5-[(2-chloropyridin-4-yl)methyl]-1,3,4-oxadiazol-2-yl}-5-(2,6-dimethoxyphenyl)pyridine-2,4-diol,
6-butyl-5-(2,6-dimethoxyphenyl)-3-(5-{2-[3-(4-methoxyphenyl)-1,2,4-oxadiazol-5-yl]ethyl}-1,3,4-oxadiazol-2-yl)pyridine-2,4-diol,
6-butyl-5-(2,6-dimethoxyphenyl)-3-[5-(1,2,3,4-tetrahydroisoquinolin-1-yl)-1,3,4-oxadiazol-2-yl]pyridine-2,4-diol, 6-butyl-3-{5-[2-(3,4-dichlorophenyl)propan-2-yl]-1,3,4-oxadiazol-2-yl}-5-(2,6-dimethoxyphenyl)pyridine-2,4-diol, 6-butyl-5-(2,6-dimethoxyphenyl)-3-{5-[(2-methyl-2H-1,2,3,4-tetrazol-5-yl)methyl]-1,3,4-oxadiazol-2-yl}pyridine-2,4-diol, 6-butyl-5-(2,6-dimethoxyphenyl)-3-[5-(2-methyl-1-phenylpropan-2-yl)-1,3,4-oxadiazol-2-yl]pyridine-2,4-diol, 6-butyl-5-(2,6-dimethoxyphenyl)-3-{5-[4-(trifluoromethyl)phenoxymethyl]-1,3,4-oxadiazol-2-yl}pyridine-2,4-diol, 6-butyl-5-(2,6-dimethoxyphenyl)-3-{5-[(5-phenyl-4H-1,2,4-triazol-3-yl)methyl]-1,3,4-oxadiazol-2-yl}pyridine-2,4-diol, 6-butyl-3-[5-(cyclohexylmethyl)-1,3,4-oxadiazol-2-yl]-5-(2,6-dimethoxyphenyl)pyridine-2,4-diol, 6-butyl-3-{5-[2-(4-chlorophenyl)ethyl]-1,3,4-oxadiazol-2-yl}-5-(2,6-dimethoxyphenyl)pyridine-2,4-diol, 6-butyl-5-(2,6-dimethoxyphenyl)-3-[5-(oxan-4-ylmethyl)-1,3,4-oxadiazol-2-yl]pyridine-2,4-diol, 6-butyl-3-{5-[(3-chloro-4-fluorophenyl)methyl]-1,3,4-oxadiazol-2-yl}-5-(2,6-dimethoxyphenyl)pyridine-2,4-diol, 6-butyl-3-{5-[(4-chloro-3-fluorophenyl)methyl]-1,3,4-oxadiazol-2-yl}-5-(2,6-dimethoxyphenyl)pyridine-2,4-diol, 6-butyl-5-(2,6-dimethoxyphenyl)-3-{5-[2-(1,3-thiazol-2-yl)ethyl]-1,3,4-oxadiazol-2-yl}pyridine-2,4-diol, 6-butyl-5-(2,6-dimethoxyphenyl)-3-(5-{[3-(trifluoromethyl)phenyl]methyl}-1,3,4-oxadiazol-2-yl)pyridine-2,4-diol, 6-butyl-3-{5-[2-(3,4-difluorophenyl)ethyl]-1,3,4-oxadiazol-2-yl}-5-(2,6-dimethoxyphenyl)pyridine-2,4-diol, 6-butyl-5-(2,6-dimethoxyphenyl)-3-(5-{2-[4-(trifluoromethyl)phenyl]ethyl}-1,3,4-oxadiazol-2-yl)pyridine-2,4-diol, 6-butyl-3-[5-(3,4-difluorophenoxymethyl)-1,3,4-oxadiazol-2-yl]-5-(2,6-dimethoxyphenyl)pyridine-2,4-diol, 6-butyl-5-(2,6-dimethoxyphenyl)-3-{5-[2-(3-phenyl-1,2,4-oxadiazol-5-yl)ethyl]-1,3,4-oxadiazol-2-yl}pyridine-2,4-diol, 6-butyl-5-(2,6-dimethoxyphenyl)-3-{5-[(1-phenyl-1H-pyrazol-4-yl)methyl]-1,3,4-oxadiazol-2-yl}pyridine-2,4-diol, 6-butyl-5-(2,6-dimethoxyphenyl)-3-{5-[(2-methyl-1,3-thiazol-4-yl)methyl]-1,3,4-oxadiazol-2-yl}pyridine-2,4-diol, 6-butyl-5-(2,6-dimethoxyphenyl)-3-(5-{[4-(trifluoromethyl)phenyl]methyl}-1,3,4-oxadiazol-2-yl)pyridine-2,4-diol, 6-butyl-5-(2,6-dimethoxyphenyl)-3-{5-[2-(pyrimidin-2-yl)ethyl]-1,3,4-oxadiazol-2-yl}pyridine-2,4-diol, 3-{5-[2-(1,3-benzothiazol-2-yl)ethyl]-1,3,4-oxadiazol-2-yl}-6-butyl-5-(2,6-dimethoxyphenyl)pyridine-2,4-diol, 6-butyl-5-(2,6-dimethoxyphenyl)-3-(5-{2-[3-(pyridin-2-yl)-1,2,4-oxadiazol-5-yl]ethyl}-1,3,4-oxadiazol-2-yl)pyridine-2,4-diol, 6-butyl-5-(2,6-dimethoxyphenyl)-3-{5-[(5-methyl-2-phenyl-1,3-thiazol-4-yl)methyl]-1,3,4-oxadiazol-2-yl}pyridine-2,4-diol, 6-butyl-3-{5-[2-(3,4-dichlorophenyl)ethyl]-1,3,4-oxadiazol-2-yl}-5-(2,6-dimethoxyphenyl)pyridine-2,4-diol, 3-[5-(1,2-benzoxazol-3-ylmethyl)-1,3,4-oxadiazol-2-yl]-6-butyl-5-(2,6-dichlorophenyl)pyridine-2,4-diol, 6-butyl-3-{5-[(4-chlorophenyl)methyl]-1,3,4-oxadiazol-2-yl}-5-(2,6-dichlorophenyl)pyridine-2,4-diol, 6-butyl-5-(2,6-dimethoxyphenyl)-3-{5-[(dimethylamino)(4-fluorophenyl)methyl]-1,3,4-oxadiazol-2-yl}pyridine-2,4-diol, 3-[5-(1,2-benzoxazol-3-ylmethyl)-1,3,4-oxadiazol-2-yl]-5-(2,6-dimethoxyphenyl)-6-(ethoxymethyl)pyridine-2,4-diol, 3-{5-[(4-chlorophenyl)methyl]-1,3,4-oxadiazol-2-yl}-5-(2,6-dimethoxyphenyl)-6-(ethoxymethyl)pyridine-2,4-diol, 6-butyl-5-(2,6-dimethoxyphenyl)-3-{5-[(5-methyl-2-phenyl-1,3-oxazol-4-yl)methyl]-1,3,4-oxadiazol-2-yl}pyridine-2,4-diol, 3-[5-(1,2-benzoxazol-3-ylmethyl)-1,3,4-oxadiazol-2-yl]-6-cyclopropyl-5-(2,6-dimethoxyphenyl)pyridine-2,4-diol, 3-{5-[(4-chlorophenyl)methyl]-1,3,4-oxadiazol-2-yl}-6-cyclopropyl-5-(2,6-dimethoxyphenyl)pyridine-2,4-diol, 6-cyclopropyl-5-(2,6-dimethoxyphenyl)-3-{5-[(2-methyl-1,3-thiazol-4-yl)methyl]-1,3,4-oxadiazol-2-yl}pyridine-2,4-diol, 6-cyclopropyl-5-(2,6-dimethoxyphenyl)-3-(5-{[3-(pyridin-2-yl)-1,2,4-oxadiazol-5-yl]methyl}-1,3,4-oxadiazol-2-yl)pyridine-2,4-diol, ethyl 2-{5-[6-butyl-5-(2,6-dimethoxyphenyl)-2,4-dihydroxypyridin-3-yl]-1,3,4-oxadiazol-2-yl}acetate, 6-butyl-5-(2,6-dimethoxyphenyl)-3-{5-[(1,3-dimethyl-1H-pyrazol-5-yl)methyl]-1,3,4-oxadiazol-2-yl}pyridine-2,4-diol, 3-({5-[6-butyl-5-(2,6-dimethoxyphenyl)-2,4-dihydroxypyridin-3-yl]-1,3,4-oxadiazol-2-yl}methyl)-1-methylimidazolidine-2,4-dione, 6-butyl-5-(2,6-dimethoxyphenyl)-3-{5-[(3-fluorophenyl)methyl]-1,3,4-oxadiazol-2-yl}pyridine-2,4-diol, 6-butyl-5-(2,6-dimethoxyphenyl)-3-[5-(piperidin-1-ylmethyl)-1,3,4-oxadiazol-2-yl]pyridine-2,4-diol, 6-butyl-5-(2,6-dimethoxyphenyl)-3-(5-{[3-(pyridin-3-yl)-1,2,4-oxadiazol-5-yl]methyl}-1,3,4-oxadiazol-2-yl)pyridine-2,4-diol, 6-butyl-5-(2,6-dimethoxyphenyl)-3-{5-[(1-methyl-1H-pyrazol-4-yl)methyl]-1,3,4-oxadiazol-2-yl}pyridine-2,4-diol, 6-butyl-3-{5-[(4-chloro-2-fluorophenyl)methyl]-1,3,4-oxadiazol-2-yl}-5-(2,6-dimethoxyphenyl)pyridine-2,4-diol, 6-butyl-5-(2,6-dimethoxyphenyl)-3-(5-{[3-(pyridin-4-yl)-1,2,4-oxadiazol-5-yl]methyl}-1,3,4-oxadiazol-2-yl)pyridine-2,4-diol, 1-({5-[6-butyl-5-(2,6-dimethoxyphenyl)-2,4-dihydroxypyridin-3-yl]-1,3,4-oxadiazol-2-yl}methyl)pyrrolidin-2-one, 5-(2,6-dimethoxyphenyl)-6-(ethoxymethyl)-3-{5-[(2-methyl-1,3-thiazol-4-yl)methyl]-1,3,4-oxadiazol-2-yl}pyridine-2,4-diol, 5-(2,6-dimethoxyphenyl)-6-(ethoxymethyl)-3-(5-{[5-(pyridin-2-yl)-1,2,4-oxadiazol-3-yl]methyl}-1,3,4-oxadiazol-2-yl)pyridine-2,4-diol, 3-{5-[(3-benzyl-1,2,4-oxadiazol-5-yl)methyl]-1,3,4-oxadiazol-2-yl}-6-butyl-5-(2,6-dimethoxyphenyl)pyridine-2,4-diol, 6-butyl-3-{5-[(3-cyclopropyl-1,2,4-oxadiazol-5-yl)methyl]-1,3,4-oxadiazol-2-yl}-5-(2,6-dimethoxyphenyl)pyridine-2,4-diol, 3-{5-[(6-chloropyridin-3-yl)methyl]-1,3,4-oxadiazol-2-yl}-5-(2,6-dimethoxyphenyl)-6-(ethoxymethyl)pyridine-2,4-diol, 6-butyl-5-(2,6-dimethoxyphenyl)-3-{5-[(3-phenyl-1,2,4-oxadiazol-5-yl)methyl]-1,3,4-oxadiazol-2-yl}pyridine-2,4-diol, 1-({545-(2,6-dimethoxyphenyl)-6-(ethoxymethyl)-2,4-dihydroxypyridin-3-yl]-1,3,4-oxadiazol-2-yl}methyl)pyrrolidin-2-one, 3-({5-[6-butyl-5-(2,6-dimethoxyphenyl)-2,4-dihydroxypyridin-3-yl]-1,3,4-oxadiazol-2-yl}methyl)imidazolidine-2,4-dione, 1-({5-[6-butyl-5-(2,6-dimethoxyphenyl)-2,4-dihydroxypyridin-3-yl]-1,3,4-oxadiazol-2-yl}methyl)-1,2-dihydropyridin-2-one, 6-butyl-5-(2,6-dimethoxyphenyl)-3-[5-(1H-imidazol-1-ylmethyl)-1,3,4-oxadiazol-2-yl]pyridine-2,4-diol, 3-({5-[6-butyl-5-(2,6-dimethoxyphenyl)-2,4-dihydroxypyridin-3-yl]-1,3,4-oxadiazol-2-yl}methyl)-1,3-oxazolidin-2-one, 4-({5-[6-butyl-5-(2,6-dimethoxyphenyl)-2,4-dihydroxypyridin-3-yl]-1,3,4-oxadiazol-2-yl}methyl)morpholin-3-one, tert-butyl 2-{5-[6-butyl-5-(2,6-dimethoxyphenyl)-2,4-dihydroxypyridin-3-yl]-1,3,4-oxadiazol-2-yl}acetate, 1-({545-(2,6-dimethoxyphenyl)-6-(ethoxymethyl)-2,4-dihydroxypyridin-3-yl]-1,3,4-oxadiazol-2-yl}methyl)-1,2-dihydropyridin-2-one, tert-butyl N-({5-[6-butyl-5-(2,6-dimethoxyphenyl)-2,4-dihydroxypyridin-3-yl]-1,3,4-oxadiazol-2-yl}methyl)carbamate, tert-butyl N-({5-[6-butyl-5-(2,6-dimethoxyphenyl)-2,4-dihydroxypyridin-3-yl]-1,3,4-oxadiazol-2-yl}methyl)-N-methylcarbamate, 3-{5-[(4-chloro-3-fluorophenyl)methyl]-1,3,4-oxadiazol-2-yl}-5-(2,6-dimethoxyphenyl)-6-(ethoxymethyl)pyridine-2,4-diol, 3-{5-[(4-chloro-2-fluorophenyl)methyl]-1,3,4-oxadiazol-2-yl}-5-(2,6-dimethoxyphenyl)-6-(ethoxymethyl)pyridine-2,4-diol, 5-(2,6-dimethoxyphenyl)-6-(ethoxymethyl)-3-{5-[(5-fluoropyridin-2-yl)methyl]-1,3,4-oxadiazol-2-yl}pyridine-2,4-diol, 5-(2,6-dimethoxyphenyl)-6-(ethoxymethyl)-3-[5-(1H-imidazol-1-ylmethyl)-1,3,4-oxadiazol-2-yl]pyridine-2,4-diol, 5-(2,6-dimethoxyphenyl)-6-(ethoxymethyl)-3-{5-[(3-fluoro-4-methylphenyl)methyl]-1,3,4-oxadiazol-2-yl}pyridine-2,4-diol, 3-{5-[(5-chloropyridin-2-yl)methyl]-1,3,4-oxadiazol-2-yl}-5-(2,6-dimethoxyphenyl)-6-(ethoxymethyl)pyridine-2,4-diol, 5-(2,6-dimethoxyphenyl)-6-(ethoxymethyl)-3-{5-[(3-phenyl-1H-pyrazol-1-yl)methyl]-1,3,4-oxadiazol-2-yl}pyridine-2,4-diol, 5-(2,6-dimethoxyphenyl)-6-(ethoxymethyl)-3-(5-{[3-(trifluoromethyl)-1H-pyrazol-1-yl]methyl}-1,3,4-oxadiazol-2-yl)pyridine-2,4-diol, 5-(2,6-dimethoxyphenyl)-6-(ethoxymethyl)-3-{5-[(1-methyl-1H-pyrazol-4-yl)methyl]-1,3,4-oxadiazol-2-yl}pyridine-2,4-diol, 5-(2,6-dimethoxyphenyl)-6-(ethoxymethyl)-3-{5-[(6-fluoropyridin-3-yl)methyl]-1,3,4-oxadiazol-2-yl}pyridine-2,4-diol, 5-(2,6-dimethoxyphenyl)-6-(ethoxymethyl)-3-[5-(1H-indazol-3-ylmethyl)-1,3,4-oxadiazol-2-yl]pyridine-2,4-diol, 3-[5-(1H-1,2,3-benzotriazol-1-ylmethyl)-1,3,4-oxadiazol-2-yl]-5-(2,6-dimethoxyphenyl)-6-(ethoxymethyl)pyridine-2,4-diol, 5-(2,6-dimethoxyphenyl)-6-(ethoxymethyl)-3-[5-(1H-indazol-1-ylmethyl)-1,3,4-oxadiazol-2-yl]pyridine-2,4-diol, 5-(2,6-dimethoxyphenyl)-6-(ethoxymethyl)-3-{5-[(4-fluorophenyl)methyl]-1,3,4-oxadiazol-2-yl}pyridine-2,4-diol, 5-(2,6-dimethoxyphenyl)-6-(ethoxymethyl)-3-[5-(1H-indol-1-ylmethyl)-1,3,4-oxadiazol-2-yl]pyridine-2,4-diol, 6-butyl-5-(3-ethylphenyl)-4-hydroxy-3-{5-[(2-methyl-1,3-thiazol-4-yl)methyl]-1,3,4-oxadiazol-2-yl}-1,2-dihydropyridin-2-one, 3-[5-(1,2-benzoxazol-3-ylmethyl)-1,3,4-oxadiazol-2-yl]-6-butyl-5-phenylpyridine-2,4-diol, 6-butyl-3-{5-[(3,4-difluorophenyl)methyl]-1,3,4-oxadiazol-2-yl}-5-(3-methoxyphenyl)pyridine-2,4-diol, 6-butyl-3-{5-[(3,4-difluorophenyl)methyl]-1,3,4-oxadiazol-2-yl}-5-(3-ethylphenyl)pyridine-2,4-diol, 6-butyl-3-{5-[(3,4-difluorophenyl)methyl]-1,3,4-oxadiazol-2-yl}-5-[3-(trifluoromethoxy)phenyl]pyridine-2,4-diol, 5-[3-(benzyloxy)phenyl]-6-butyl-3-{5-[(3,4-difluorophenyl)methyl]-1,3,4-oxadiazol-2-yl}pyridine-2,4-diol, 6-butyl-3-{5-[(3,4-difluorophenyl)methyl]-1,3,4-oxadiazol-2-yl}-5-[3-(hydroxymethyl)phenyl]pyridine-2,4-diol, 6-butyl-5-(cyclohex-1-en-1-yl)-3-{5-[(3,4-difluorophenyl)methyl]-1,3,4-oxadiazol-2-yl}pyridine-2,4-diol, 6-butyl-3-{5-[(3,4-difluorophenyl)methyl]-1,3,4-oxadiazol-2-yl}-5-[3-(propan-2-yl)phenyl]pyridine-2,4-diol, 6-butyl-3-{5-[(3,4-difluorophenyl)methyl]-1,3,4-oxadiazol-2-yl}-5-[3-(methoxymethyl)phenyl]pyridine-2,4-diol, 3-(2-butyl-5-{5-[(3,4-difluorophenyl)methyl]-1,3,4-oxadiazol-2-yl}-4,6-dihydroxypyridin-3-yl)-N-(propan-2-yl)benzamide, 6-butyl-4-hydroxy-3-{5-[(2-methyl-1,3-thiazol-4-yl)methyl]-1,3,4-oxadiazol-2-yl}-5-[3-(propan-2-yl)phenyl]-1,2-dihydropyridin-2-one, 3-(2-butyl-4-hydroxy-5-{5-[(2-methyl-1,3-thiazol-4-yl)methyl]-1,3,4-oxadiazol-2-yl}-6-oxo-1,6-dihydropyridin-3-O—N-(propan-2-yl)benzamide, 6-butyl-5-(3-cyclopropylphenyl)-4-hydroxy-3-{5-[(2-methyl-1,3-thiazol-4-yl)methyl]-1,3,4-oxadiazol-2-yl}-1,2-dihydropyridin-2-one, 6-butyl-4-hydroxy-5-(3-methoxyphenyl)-3-{5-[(2-methyl-1,3-thiazol-4-yl)methyl]-1,3,4-oxadiazol-2-yl}-1,2-dihydropyridin-2-one, 6-butyl-4-hydroxy-5-[3-(hydroxymethyl)phenyl]-3-{5-[(2-methyl-1,3-thiazol-4-yl)methyl]-1,3,4-oxadiazol-2-yl}-1,2-dihydropyridin-2-one, 6-butyl-4-hydroxy-3-{5-[(2-methyl-1,3-thiazol-4-yl)methyl]-1,3,4-oxadiazol-2-yl}-5-[3-(pyrrolidin-1-yl)phenyl]-1,2-dihydropyridin-2-one, 6-butyl-5-(2,6-dimethoxyphenyl)-3-{5-[(methylamino)methyl]-1,3,4-oxadiazol-2-yl}pyridine-2,4-diol, N-({5-[6-butyl-5-(2,6-dimethoxyphenyl)-2,4-dihydroxypyridin-3-yl]-1,3,4-oxadiazol-2-yl}methyl)-N-methyl-2-phenylacetamide, N-({5-[6-butyl-5-(2,6-dimethoxyphenyl)-2,4-dihydroxypyridin-3-yl]-1,3,4-oxadiazol-2-yl}methyl)-3-chloro-N-methylbenzamide, N-({5-[6-butyl-5-(2,6-dimethoxyphenyl)-2,4-dihydroxypyridin-3-yl]-1,3,4-oxadiazol-2-yl}methyl)-N-methylpyridine-2-carboxamide, N-({5-[6-butyl-5-(2,6-dimethoxyphenyl)-2,4-dihydroxypyridin-3-yl]-1,3,4-oxadiazol-2-yl}methyl)-2-methoxyacetamide,
N-({5-[6-butyl-5-(2,6-dimethoxyphenyl)-2,4-dihydroxypyridin-3-yl]-1,3,4-oxadiazol-2-yl}methyl)-N-methylpyridine-4-carboxamide,
N-({5-[6-butyl-5-(2,6-dimethoxyphenyl)-2,4-dihydroxypyridin-3-yl]-1,3,4-oxadiazol-2-yl}methyl)pyridine-3-carboxamide,
N-({5-[6-butyl-5-(2,6-dimethoxyphenyl)-2,4-dihydroxypyridin-3-yl]-1,3,4-oxadiazol-2-yl}methyl)-2-chloro-N-methylbenzamide,
N-({5-[6-butyl-5-(2,6-dimethoxyphenyl)-2,4-dihydroxypyridin-3-yl]-1,3,4-oxadiazol-2-yl}methyl)-3-chlorobenzamide,
N-({5-[6-butyl-5-(2,6-dimethoxyphenyl)-2,4-dihydroxypyridin-3-yl]-1,3,4-oxadiazol-2-yl}methyl)-4-chlorobenzamide,
N-({5-[6-butyl-5-(2,6-dimethoxyphenyl)-2,4-dihydroxypyridin-3-yl]-1,3,4-oxadiazol-2-yl}methyl)pyridine-4-carboxamide,
N-({5-[6-butyl-5-(2,6-dimethoxyphenyl)-2,4-dihydroxypyridin-3-yl]-1,3,4-oxadiazol-2-yl}methyl)-N-methylpyridine-3-carboxamide,
N-({5-[6-butyl-5-(2,6-dimethoxyphenyl)-2,4-dihydroxypyridin-3-yl]-1,3,4-oxadiazol-2-yl}methyl)-2-phenylacetamide,
N-({5-[6-butyl-5-(2,6-dimethoxyphenyl)-2,4-dihydroxypyridin-3-yl]-1,3,4-oxadiazol-2-yl}methyl)-2,2-dimethylpropanamide,
N-({5-[6-butyl-5-(2,6-dimethoxyphenyl)-2,4-dihydroxypyridin-3-yl]-1,3,4-oxadiazol-2-yl}methyl)pyridine-2-carboxamide,
N-({5-[6-butyl-5-(2,6-dimethoxyphenyl)-2,4-dihydroxypyridin-3-yl]-1,3,4-oxadiazol-2-yl}methyl)-N,2,2-trimethylpropanamide,
3-[5-(aminomethyl)-1,3,4-oxadiazol-2-yl]-6-butyl-5-(2,6-dimethoxyphenyl)pyridine-2,4-diol,
N-({5-[6-butyl-5-(2,6-dimethoxyphenyl)-2,4-dihydroxypyridin-3-yl]-1,3,4-oxadiazol-2-yl}methyl)benzamide,
N-({5-[6-butyl-5-(2,6-dimethoxyphenyl)-2,4-dihydroxypyridin-3-yl]-1,3,4-oxadiazol-2-yl}methyl)-N-methylbenzamide,
N-({5-[5-(2,6-dimethoxyphenyl)-6-(ethoxymethyl)-2,4-dihydroxypyridin-3-yl]-1,3,4-oxadiazol-2-yl}methyl)benzamide,
N-({5-[6-butyl-5-(2,6-dimethoxyphenyl)-2,4-dihydroxypyridin-3-yl]-1,3,4-oxadiazol-2-yl}methyl)-3-methylbutanamide,
N-({5-[6-butyl-5-(2,6-dimethoxyphenyl)-2,4-dihydroxypyridin-3-yl]-1,3,4-oxadiazol-2-yl}methyl)acetamide,
N-({5-[6-butyl-5-(2,6-dimethoxyphenyl)-2,4-dihydroxypyridin-3-yl]-1,3,4-oxadiazol-2-yl}methyl)-2,2,2-trifluoroacetamide,
2-{5-[6-butyl-5-(2,6-dimethoxyphenyl)-2,4-dihydroxypyridin-3-yl]-1,3,4-oxadiazol-2-yl}-N,N-diethylacetamide,
2-{5-[6-butyl-5-(2,6-dimethoxyphenyl)-2,4-dihydroxypyridin-3-yl]-1,3,4-oxadiazol-2-yl}-N-(pyridin-2-ylmethyl)acetamide,
2-{5-[6-butyl-5-(2,6-dimethoxyphenyl)-2,4-dihydroxypyridin-3-yl]-1,3,4-oxadiazol-2-yl}-N-methylacetamide,
2-{5-[6-butyl-5-(2,6-dimethoxyphenyl)-2,4-dihydroxypyridin-3-yl]-1,3,4-oxadiazol-2-yl}acetamide,
2-{5-[6-butyl-5-(2,6-dimethoxyphenyl)-2,4-dihydroxypyridin-3-yl]-1,3,4-oxadiazol-2-yl}-N-(propan-2-yl)acetamide,
2-{5-[6-butyl-5-(2,6-dimethoxyphenyl)-2,4-dihydroxypyridin-3-yl]-1,3,4-oxadiazol-2-yl}-N,N-dimethylacetamide,
2-{5-[6-butyl-5-(2,6-dimethoxyphenyl)-2,4-dihydroxypyridin-3-yl]-1,3,4-oxadiazol-2-yl}-N-(4-methoxyphenyl)acetamide,
4-(2-{5-[6-butyl-5-(2,6-dimethoxyphenyl)-2,4-dihydroxypyridin-3-yl]-1,3,4-oxadiazol-2-yl}acetyl)piperazin-2-one,
2-{5-[6-butyl-5-(2,6-dimethoxyphenyl)-2,4-dihydroxypyridin-3-yl]-1,3,4-oxadiazol-2-yl}-1-(4-methylpiperazin-1-yl)ethan-1-one,
N-benzyl-2-{5-[6-butyl-5-(2,6-dimethoxyphenyl)-2,4-dihydroxypyridin-3-yl]-1,3,4-oxadiazol-2-yl}acetamide,
2-{5-[6-butyl-5-(2,6-dimethoxyphenyl)-2,4-dihydroxypyridin-3-yl]-1,3,4-oxadiazol-2-yl}-N-ethylacetamide,
2-{5-[6-butyl-5-(2,6-dimethoxyphenyl)-2,4-dihydroxypyridin-3-yl]-1,3,4-oxadiazol-2-yl}-N-cyclopropylacetamide,
2-{5-[6-butyl-5-(2,6-dimethoxyphenyl)-2,4-dihydroxypyridin-3-yl]-1,3,4-oxadiazol-2-yl}-N-propylacetamide,
2-{5-[6-butyl-5-(2,6-dimethoxyphenyl)-2,4-dihydroxypyridin-3-yl]-1,3,4-oxadiazol-2-yl}-N-(2-fluoroethyl)acetamide,
2-{5-[6-butyl-5-(2,6-dimethoxyphenyl)-2,4-dihydroxypyridin-3-yl]-1,3,4-oxadiazol-2-yl}-N-(2,2-difluoroethyl)acetamide,
2-{5-[6-butyl-5-(2,6-dimethoxyphenyl)-2,4-dihydroxypyridin-3-yl]-1,3,4-oxadiazol-2-yl}-N-(2,2,2-trifluoroethyl)acetamide,
2-{5-[6-butyl-5-(2,6-dimethoxyphenyl)-2,4-dihydroxypyridin-3-yl]-1,3,4-oxadiazol-2-yl}-N-(2-methoxyethyl)acetamide,
2-{5-[6-butyl-5-(2,6-dimethoxyphenyl)-2,4-dihydroxypyridin-3-yl]-1,3,4-oxadiazol-2-yl}-1-(pyrrolidin-1-yl)ethan-1-one,
2-{5-[6-butyl-5-(2,6-dimethoxyphenyl)-2,4-dihydroxypyridin-3-yl]-1,3,4-oxadiazol-2-yl}-1-(piperidin-1-yl)ethan-1-one,
2-{5-[6-butyl-5-(2,6-dimethoxyphenyl)-2,4-dihydroxypyridin-3-yl]-1,3,4-oxadiazol-2-yl}-1-(morpholin-4-yl)ethan-1-one,
N-butyl-2-{5-[6-butyl-5-(2,6-dimethoxyphenyl)-2,4-dihydroxypyridin-3-yl]-1,3,4-oxadiazol-2-yl}acetamide,
2-{5-[6-butyl-5-(2,6-dimethoxyphenyl)-2,4-dihydroxypyridin-3-yl]-1,3,4-oxadiazol-2-yl}-N-pentylacetamide,
2-{5-[6-butyl-5-(2,6-dimethoxyphenyl)-2,4-dihydroxypyridin-3-yl]-1,3,4-oxadiazol-2-yl}-1-(3-fluoroazetidin-1-yl)ethan-1-one,
2-{5-[6-butyl-5-(2,6-dimethoxyphenyl)-2,4-dihydroxypyridin-3-yl]-1,3,4-oxadiazol-2-yl}-1-(3,3-difluoroazetidin-1-yl)ethan-1-one,
2-{5-[6-butyl-5-(2,6-dimethoxyphenyl)-2,4-dihydroxypyridin-3-yl]-1,3,4-oxadiazol-2-yl}-N-(1,3-thiazol-2-yl)acetamide,
3-(3-benzyl-1,2,4-oxadiazol-5-yl)-6-butyl-5-(2,6-dimethoxyphenyl)pyridine-2,4-diol,
6-butyl-3-{3-[(4-chlorophenyl)methyl]-1,2,4-oxadiazol-5-yl}-5-(2,6-dimethoxyphenyl)pyridine-2,4-diol,
3-(5-benzyl-4H-1,2,4-triazol-3-yl)-6-butyl-5-(2,6-dimethoxyphenyl)pyridine-2,4-diol, 6-butyl-3-(5-{[5-(4-chlorophenyl)-1,3,4-oxadiazol-2-yl]methyl}-1,3,4-oxadiazol-2-yl)-5-(2,6-dimethoxyphenyl)pyridine-2,4-diol,
6-butyl-5-(2,6-dimethoxyphenyl)-3-(5-{[5-(pyridin-4-yl)-1,3,4-oxadiazol-2-yl]methyl}-1,3,4-oxadiazol-2-yl)pyridine-2,4-diol,
6-butyl-5-(2,6-dimethoxyphenyl)-3-(5-{[5-(pyridin-2-yl)-1,3,4-oxadiazol-2-yl]methyl}-1,3,4-oxadiazol-2-yl)pyridine-2,4-diol,
6-butyl-3-(5-{[5-(2-chlorophenyl)-1,3,4-oxadiazol-2-yl]methyl}-1,3,4-oxadiazol-2-yl)-5-(2,6-dimethoxyphenyl)pyridine-2,4-diol,
3-{5-[(5-benzyl-1,3,4-oxadiazol-2-yl)methyl]-1,3,4-oxadiazol-2-yl}-6-butyl-5-(2,6-dimethoxyphenyl)pyridine-2,4-diol,
6-butyl-3-(5-{[5-(3-chlorophenyl)-1,3,4-oxadiazol-2-yl]methyl}-1,3,4-oxadiazol-2-yl)-5-(2,6-dimethoxyphenyl)pyridine-2,4-diol,
6-butyl-5-(2,6-dimethoxyphenyl)-3-(5-{[5-(pyridin-3-yl)-1,3,4-oxadiazol-2-yl]methyl}-1,3,4-oxadiazol-2-yl)pyridine-2,4-diol,
1-({5-[6-(ethoxymethyl)-5-(4-fluoro-2,6-dimethoxyphenyl)-2,4-dihydroxypyridin-3-yl]-1,3,4-oxadiazol-2-yl}methyl)-1,2-dihydropyridin-2-one,
3-[5-(1,2-benzoxazol-3-ylmethyl)-1,3,4-oxadiazol-2-yl]-6-(ethoxymethyl)-5-(4-fluoro-2,6-dimethoxyphenyl)pyridine-2,4-diol,
3-{5-[(4-chlorophenyl)methyl]-1,3,4-oxadiazol-2-yl}-6-(ethoxymethyl)-5-(4-fluoro-2,6-dimethoxyphenyl)pyridine-2,4-diol,
1-({5-[6-(ethoxymethyl)-5-(4-fluoro-2,6-dimethoxyphenyl)-2,4-dihydroxypyridin-3-yl]-1,3,4-oxadiazol-2-yl}methyl)pyrrolidin-2-one,
3-{5-[(6-chloropyridin-3-yl)methyl]-1,3,4-oxadiazol-2-yl}-6-(ethoxymethyl)-5-(4-fluoro-2,6-dimethoxyphenyl)pyridine-2,4-diol,
3-{5-[(4-chlorophenyl)methyl]-1,3,4-oxadiazol-2-yl}-5-(3,5-dimethoxypyridin-4-yl)-6-(ethoxymethyl)pyridine-2,4-diol,
6-butyl-3-{5-[(4-chlorophenyl)methyl]-1,3,4-oxadiazol-2-yl}-5-(3-fluoro-2,6-dimethoxyphenyl)pyridine-2,4-diol,
3-[5-(1,2-benzoxazol-3-ylmethyl)-1,3,4-oxadiazol-2-yl]-6-butyl-5-(3-fluoro-2,6-dimethoxyphenyl)pyridine-2,4-diol,
3-{5-[(4-chlorophenyl)methyl]-1,3,4-oxadiazol-2-yl}-6-(ethoxymethyl)-5-(2-hydroxy-6-methoxyphenyl)pyridine-2,4-diol,
3-[5-(1,2-benzoxazol-3-ylmethyl)-1,3,4-oxadiazol-2-yl]-6-butyl-5-(2,6-dimethylphenyl)pyridine-2,4-diol,
3-[5-(1,2-benzoxazol-3-ylmethyl)-1,3,4-oxadiazol-2-yl]-6-butyl-5-(2,4,6-trimethylphenyl)pyridine-2,4-diol,
3-[5-(1,2-benzoxazol-3-ylmethyl)-1,3,4-oxadiazol-2-yl]-6-butyl-5-(2,6-diethylphenyl)pyridine-2,4-diol,
6-butyl-5-(2,6-dimethoxyphenyl)-3-(5-{[1,2]oxazolo[4,5-b]pyridin-3-ylmethyl}-1,3,4-oxadiazol-2-yl)pyridine-2,4-diol,
5-(2,6-dimethoxyphenyl)-6-(ethoxymethyl)-3-(5-{[1,2]oxazolo[4,5-b]pyridin-3-ylmethyl}-1,3,4-oxadiazol-2-yl)pyridine-2,4-diol,
3-{5-[(4-chlorophenyl)methyl]-1,3,4-oxadiazol-2-yl}-5-(2,6-dihydroxyphenyl)-6-(ethoxymethyl)pyridine-2,4-diol,
3-{5-[(5-chloropyridin-2-yl)methyl]-1,3,4-oxadiazol-2-yl}-5-(2,6-dimethoxyphenyl)-6-[(ethylamino)methyl]pyridine-2,4-diol,
3-{5-[(1,2-benzoxazol-3-yl)methyl]-1,3,4-thiadiazol-2-yl}-5-(2,6-dimethoxyphenyl)-6-(ethoxymethyl)pyridine-2,4-diol,
3-{5-[(5-chloropyridin-2-yl)methyl]-1,3,4-thiadiazol-2-yl}-5-(2,6-dimethoxyphenyl)-6-(ethoxymethyl)pyridine-2,4-diol,
3-{5-[(5-chloropyridin-2-yl)methyl]-1,3,4-thiadiazol-2-yl}-6-cyclopentyl-5-(2,6-dimethoxyphenyl)pyridine-2,4-diol,
3-{5-[(4-chlorophenyl)methyl]-1,3,4-thiadiazol-2-yl}-5-(2,6-dimethoxyphenyl)-6-(ethoxymethyl)pyridine-2,4-diol,
N-({5-[5-(2,6-dimethoxyphenyl)-6-(ethoxymethyl)-2,4-dihydroxypyridin-3-yl]-1,3,4-thiadiazol-2-yl}methyl)pyridine-2-carboxamide,
6-butyl-3-{5-[(5-chloro-3-fluoropyridin-2-yl)methyl]-1,3,4-oxadiazol-2-yl}-5-(2,6-dimethoxyphenyl)pyridine-2,4-diol,
3-{5-[(5-chloro-3-fluoropyridin-2-yl)methyl]-1,3,4-oxadiazol-2-yl}-5-(2,6-dimethoxyphenyl)-6-(ethoxymethyl)pyridine-2,4-diol,
3-{5-[(5-chloropyridin-2-yl)methyl]-1,3,4-oxadiazol-2-yl}-6-cyclopentyl-5-(2,6-dimethoxyphenyl)pyridine-2,4-diol,
3-{5-[(4-chlorophenyl)methyl]-1,3,4-oxadiazol-2-yl}-6-cyclopentyl-5-(2,6-dimethoxyphenyl)pyridine-2,4-diol,
3-{5-[(5-chloropyridin-2-yl)methyl]-1,3,4-oxadiazol-2-yl}-5-(2,6-dimethoxyphenyl)-6-[(2-methoxyethoxy)methyl]pyridine-2,4-diol,
3-{5-[(1,2-benzoxazol-3-yl)methyl]-1,3,4-oxadiazol-2-yl}-5-(2,6-dimethoxyphenyl)-6-[(2-methoxyethoxy)methyl]pyridine-2,4-diol,
5-(2,6-dimethoxyphenyl)-6-(ethoxymethyl)-3-{5-[(phenylamino)methyl]-1,3,4-oxadiazol-2-yl}pyridine-2,4-diol,
3-{5-[(4-chlorophenyl)methyl]-1,3,4-oxadiazol-2-yl}-5-(2,6-dimethoxyphenyl)-6-[(2-methoxyethoxy)methyl]pyridine-2,4-diol,
N-({5-[6-butyl-5-(2,5-dimethoxyphenyl)-2,4-dihydroxypyridin-3-yl]-1,3,4-oxadiazol-2-yl}methyl)benzamide,
N-[(5-{6-butyl-2,4-dihydroxy-5-[2-methoxy-5-(propan-2-yl)phenyl]pyridin-3-yl}-1,3,4-oxadiazol-2-yl)methyl]benzamide,
3-{5-[(1,2-benzoxazol-3-yl)methyl]-1,3,4-oxadiazol-2-yl}-6-(ethoxymethyl)-5-(2-methoxyphenyl)pyridine-2,4-diol,
3-{5-[(4-chlorophenyl)methyl]-1,3,4-oxadiazol-2-yl}-6-(ethoxymethyl)-5-(2-methoxyphenyl)pyridine-2,4-diol,
N-({5-[6-butyl-5-(2,3-dimethoxyphenyl)-2,4-dihydroxypyridin-3-yl]-1,3,4-oxadiazol-2-yl}methyl)benzamide,
N-({5-[6-(ethoxymethyl)-2,4-dihydroxy-5-(2-methoxyphenyl)pyridin-3-yl]-1,3,4-oxadiazol-2-yl}methyl)benzamide,
2-{5-[6-butyl-5-(2,6-dimethoxyphenyl)-2,4-dihydroxypyridin-3-yl]-1,3,4-oxadiazol-2-yl}-N-(pyridin-3-yl)acetamide,
2-{5-[5-(2,6-dimethoxyphenyl)-6-(ethoxymethyl)-2,4-dihydroxypyridin-3-yl]-1,3,4-oxadiazol-2-yl}-N-(1,3-thiazol-2-yl)acetamide,
N-[(1,3-benzothiazol-2-yl)methyl]-2-{5-[6-butyl-5-(2,6-dimethoxyphenyl)-2,4-dihydroxypyridin-3-yl]-1,3,4-oxadiazol-2-yl}acetamide,
2-{5-[6-butyl-5-(2,6-dimethoxyphenyl)-2,4-dihydroxypyridin-3-yl]-1,3,4-oxadiazol-2-yl}-N-[(pyridin-3-yl)methyl]acetamide, 2-{5-[6-butyl-5-(2,6-dimethoxyphenyl)-2,4-dihydroxy-pyridin-3-yl]-1,3,4-oxadiazol-2-yl}-N-[(1,3-oxazol-2-yl)methyl]acetamide,
2-{5-[6-butyl-5-(2,6-dimethoxyphenyl)-2,4-dihydroxy-pyridin-3-yl]-1,3,4-oxadiazol-2-yl}-N-[2-(4-sulfamoylphenyl)ethyl]acetamide,
2-{5-[6-butyl-5-(2,6-dimethoxyphenyl)-2,4-dihydroxy-pyridin-3-yl]-1,3,4-oxadiazol-2-yl}-N-[2-(2-chlorophenyl)ethyl]acetamide,
2-{5-[6-butyl-5-(2,6-dimethoxyphenyl)-2,4-dihydroxy-pyridin-3-yl]-1,3,4-oxadiazol-2-yl}-N-[(3-chlorophenyl)methyl]acetamide,
N-benzyl-2-{5-[6-butyl-5-(2,6-dimethoxyphenyl)-2,4-dihydroxypyridin-3-yl]-1,3,4-oxadiazol-2-yl}-N-methylacetamide,
2-{5-[6-butyl-5-(2,6-dimethoxyphenyl)-2,4-dihydroxy-pyridin-3-yl]-1,3,4-oxadiazol-2-yl}-N-methyl-N-(2-phenylethyl)acetamide,
2-{5-[6-butyl-5-(2,6-dimethoxyphenyl)-2,4-dihydroxy-pyridin-3-yl]-1,3,4-oxadiazol-2-yl}-N-(prop-2-yn-1-yl)acetamide,
2-{5-[6-butyl-5-(2,6-dimethoxyphenyl)-2,4-dihydroxy-pyridin-3-yl]-1,3,4-oxadiazol-2-yl}-N-(3-methyl-1H-pyrazol-5-yl)acetamide,
2-{5-[6-butyl-5-(2,6-dimethoxyphenyl)-2,4-dihydroxy-pyridin-3-yl]-1,3,4-oxadiazol-2-yl}-N-[(2-methylphenyl)methyl]acetamide,
2-{5-[6-butyl-5-(2,6-dimethoxyphenyl)-2,4-dihydroxy-pyridin-3-yl]-1,3,4-oxadiazol-2-yl}-N-[(2-chlorophenyl)methyl]acetamide,
2-{5-[6-butyl-5-(2,6-dimethoxyphenyl)-2,4-dihydroxy-pyridin-3-yl]-1,3,4-oxadiazol-2-yl}-N-[(4-chlorophenyl)methyl]acetamide,
2-{5-[6-butyl-5-(2,6-dimethoxyphenyl)-2,4-dihydroxy-pyridin-3-yl]-1,3,4-oxadiazol-2-yl}-N-[2-(4-chlorophenyl)ethyl]acetamide,
2-{5-[6-butyl-5-(2,6-dimethoxyphenyl)-2,4-dihydroxy-pyridin-3-yl]-1,3,4-oxadiazol-2-yl}-N-[(pyridin-4-yl)methyl]acetamide,
2-{5-[6-butyl-5-(2,6-dimethoxyphenyl)-2,4-dihydroxy-pyridin-3-yl]-1,3,4-oxadiazol-2-yl}-N-[(4-methoxyphenyl)methyl]acetamide,
2-{5-[6-butyl-5-(2,6-dimethoxyphenyl)-2,4-dihydroxy-pyridin-3-yl]-1,3,4-oxadiazol-2-yl}-N-{[4-(dimethylamino)phenyl]methyl}acetamide,
2-{5-[6-butyl-5-(2,6-dimethoxyphenyl)-2,4-dihydroxy-pyridin-3-yl]-1,3,4-oxadiazol-2-yl}-N-[(5-methyl-1,3,4-oxadiazol-2-yl)methyl]acetamide,
2-{5-[6-butyl-5-(2,6-dimethoxyphenyl)-2,4-dihydroxy-pyridin-3-yl]-1,3,4-oxadiazol-2-yl}-N-{[3-(propan-2-yl)-1,2-oxazol-5-yl]methyl}acetamide,
2-{5-[6-butyl-5-(2,6-dimethoxyphenyl)-2,4-dihydroxy-pyridin-3-yl]-1,3,4-oxadiazol-2-yl}-N-[(4-sulfamoylphenyl)methyl]acetamide,
3-{5-[(5-chloropyridin-2-yl)methyl]-1,3,4-oxadiazol-2-yl}-6-(ethoxymethyl)-5-(2-hydroxy-6-methoxyphenyl)pyridine-2,4-diol,
3-{5-[(5-chloropyridin-2-yl)methyl]-1,3,4-oxadiazol-2-yl}-6-(ethoxymethyl)-5-(2-hydroxy-6-methoxyphenyl)pyridine-2,4-diol, and
3-{5-[(5-chloropyridin-2-yl)methyl]-1,3,4-oxadiazol-2-yl}-5-(2,6-dihydroxyphenyl)-6-(ethoxymethyl)pyridine-2,4-diol.

12. A pharmaceutical composition, comprising a pharmaceutically acceptable carrier and a compound of claim 1, or a stereoisomer, a tautomer, or a pharmaceutically acceptable salt thereof.

13. A compound having the structure:

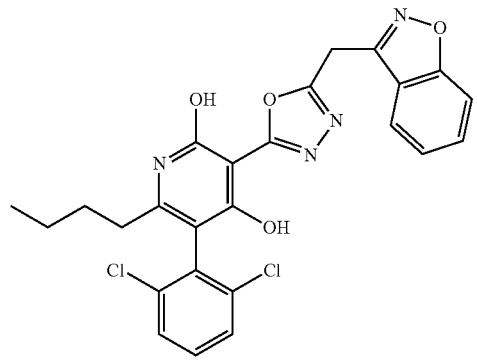 [SMILES: CCCCc1nc(O)c(-c2nnc(Cc3noc4ccccc34)o2)c(O)c1-c1c(Cl)cccc1Cl]

or a stereoisomer, a tautomer, or a pharmaceutically acceptable salt thereof.

14. A compound having the structure:

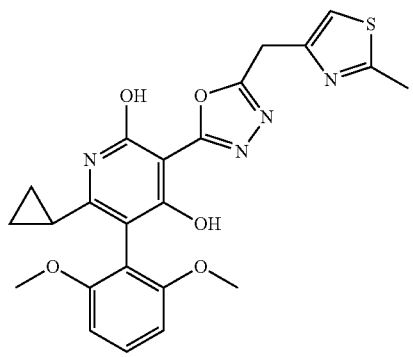 [SMILES: COc1cccc(OC)c1-c1c(C2CC2)nc(O)c(-c2nnc(Cc3csc(C)n3)o2)c1O]

or a stereoisomer, a tautomer, or a pharmaceutically acceptable salt thereof.

15. A compound having the structure:

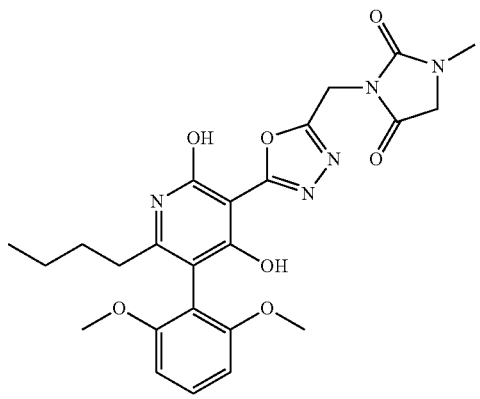 [SMILES: CCCCc1nc(O)c(-c2nnc(CN3C(=O)CN(C)C3=O)o2)c(O)c1-c1c(OC)cccc1OC]

or a stereoisomer, a tautomer, or a pharmaceutically acceptable salt thereof.

16. A compound having the structure:

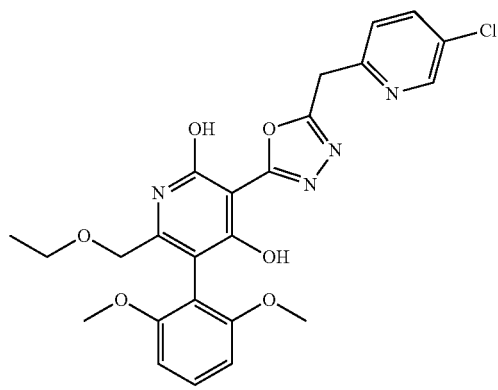 [SMILES: CCOCc1nc(O)c(-c2nnc(Cc3ccc(Cl)cn3)o2)c(O)c1-c1c(OC)cccc1OC]

or a stereoisomer, a tautomer, or a pharmaceutically acceptable salt thereof.

17. A compound having the structure:

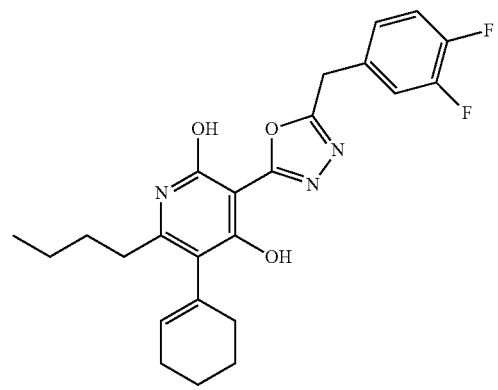 [SMILES: CCCCc1nc(O)c(-c2nnc(Cc3ccc(F)c(F)c3)o2)c(O)c1C1=CCCCC1]

or a stereoisomer, a tautomer, or a pharmaceutically acceptable salt thereof.

18. A compound having the structure:

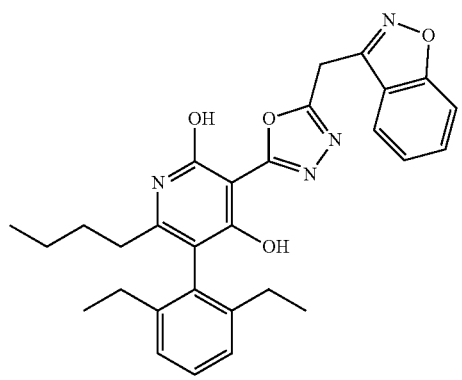 [SMILES: CCCCc1nc(O)c(-c2nnc(Cc3noc4ccccc34)o2)c(O)c1-c1c(CC)cccc1CC]

or a stereoisomer, a tautomer, or a pharmaceutically acceptable salt thereof.

19. A pharmaceutical composition comprising a pharmaceutically acceptable carrier and a compound according to claim 13, or a stereoisomer, a tautomer, or a pharmaceutically acceptable salt thereof.

20. A pharmaceutical composition comprising a pharmaceutically acceptable carrier and a compound according to claim 14, or a stereoisomer, a tautomer, or a pharmaceutically acceptable salt thereof.

21. A pharmaceutical composition comprising a pharmaceutically acceptable carrier and a compound according to claim 15, or a stereoisomer, a tautomer, or a pharmaceutically acceptable salt thereof.

22. A pharmaceutical composition comprising a pharmaceutically acceptable carrier and a compound according to claim 18, or a stereoisomer, a tautomer, or a pharmaceutically acceptable salt thereof.

23. A pharmaceutical composition comprising a pharmaceutically acceptable carrier and a compound according to claim 19, or a stereoisomer, a tautomer, or a pharmaceutically acceptable salt thereof.

24. A pharmaceutical composition comprising a pharmaceutically acceptable carrier and a compound according to claim 20, or a stereoisomer, a tautomer, or a pharmaceutically acceptable salt thereof.

25. A compound having the structure:

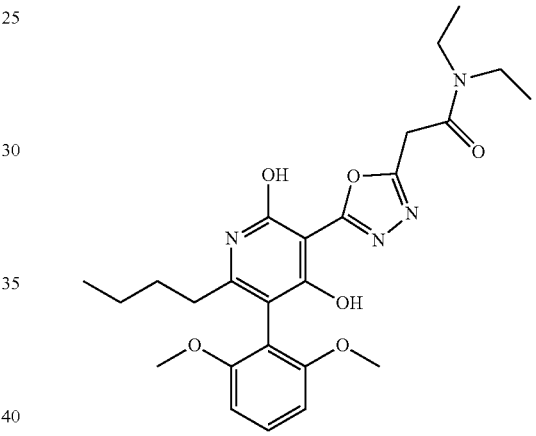

or a stereoisomer, a tautomer, or a pharmaceutically acceptable salt thereof.

26. A pharmaceutical composition comprising a pharmaceutically acceptable carrier and a compound according to claim 25, or a stereoisomer, a tautomer, or a pharmaceutically acceptable salt thereof.

27. A compound having the structure:

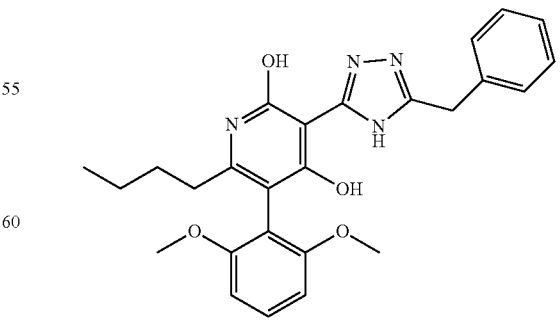

or a stereoisomer, a tautomer, or a pharmaceutically acceptable salt thereof.

28. A pharmaceutical composition comprising a pharmaceutically acceptable carrier and a compound according to claim 27, or a stereoisomer, a tautomer, or a pharmaceutically acceptable salt thereof.

29. A compound having the structure:

or a stereoisomer, a tautomer, or a pharmaceutically acceptable salt thereof.

30. A pharmaceutical composition comprising a pharmaceutically acceptable carrier and a compound according to claim 29, or a stereoisomer, a tautomer, or a pharmaceutically acceptable salt thereof.

* * * * *

UNITED STATES PATENT AND TRADEMARK OFFICE
CERTIFICATE OF CORRECTION

PATENT NO.       : 10,011,594 B2
APPLICATION NO.  : 15/171276
DATED            : July 3, 2018
INVENTOR(S)      : James Johnson et al.

Page 1 of 3

It is certified that error appears in the above-identified patent and that said Letters Patent is hereby corrected as shown below:

In the Claims

In Claim 1, Column 248, Line 41-45:

Delete " 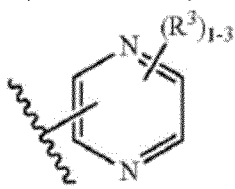 " and

Insert -- 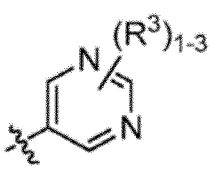 ;--, therefor.

In Claim 1, Column 249, Line 23:
Delete "(C" and
Insert -- —(C --, therefor.

In Claim 2, Column 250, Line 37:
Delete "=O) $R^b$," and
Insert -- =O)$R^b$, --, therefor.

In Claim 3, Column 252, Line 1:
Delete "(C" and
Insert -- —(C --, therefor.

In Claim 4, Column 254, Line 3:
Delete "$CF_3$" and
Insert -- $CF_3$, --, therefor.

Signed and Sealed this
Ninth Day of June, 2020

Andrei Iancu
*Director of the United States Patent and Trademark Office*

CERTIFICATE OF CORRECTION (continued)
U.S. Pat. No. 10,011,594 B2

In Claim 5, Column 254, Line 34:
Delete "CF₃" and
Insert -- CF$_3$, --, therefor.

In Claim 8, Column 257, Line 61:
Delete "—(CH₂)N" and
Insert -- —(CH$_2$)$_n$N --, therefor.

In Claim 9, Column 259, Line 25:
Delete "CF₃" and
Insert -- CF$_3$, --, therefor.

In Claim 10, Column 259, Line 66:
Delete "=O) R$^b$," and
Insert -- =O)R$^b$, --, therefor.

In Claim 10, Column 260, Line 34:
Delete "W;" and
Insert -- R$^e$; --, therefor.

In Claim 10, Column 260, Line 48:
Delete "—(CH₂)$_p$" and
Insert -- —(CH$_2$)$_n$ --, therefor.

In Claim 11, Column 264, Line 1-2:
Delete "(dimethylamino) (4-" and
Insert -- (dimethylamino)(4- --, therefor.

In Claim 11, Column 265, Line 4:
Delete "1-({545-(" and
Insert -- 1-({5-[5-( --, therefor.

In Claim 11, Column 265, Line 23:
Delete "1-({545-(" and
Insert -- 1-({5-[5-( --, therefor.

In Claim 11, Column 266, Line 44:
Delete "-3-O—" and
Insert -- -3-yl)- --, therefor.

In Claim 12, Column 271, Line 64:
Delete "composition," and
Insert -- composition --, therefor.

CERTIFICATE OF CORRECTION (continued)
U.S. Pat. No. 10,011,594 B2

In Claim 12, Column 271, Line 65:
Delete "of" and
Insert -- according to --, therefor.

In Claim 22, Column 274, Line 12 (Approx.):
Delete "Claim 18," and
Insert -- Claim 20, --, therefor.

In Claim 29, Column 275, Line 7-21:

Delete " 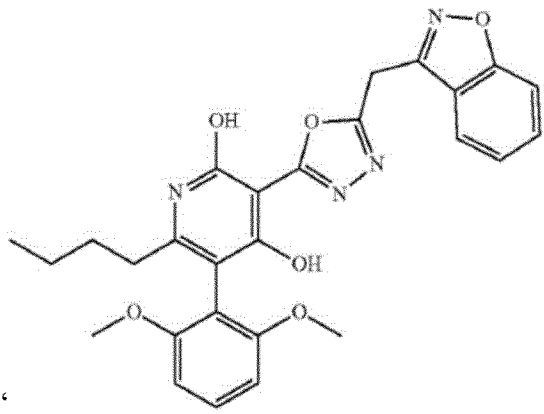 " and

Insert -- 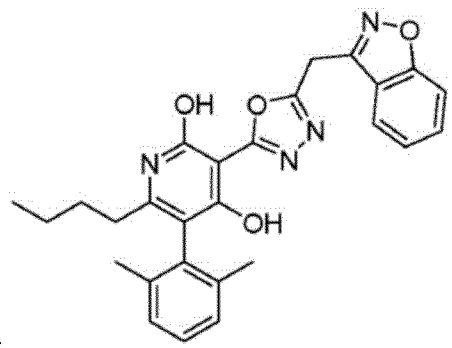 --, therefor.